US012590325B2

(12) United States Patent
Ting et al.

(10) Patent No.: US 12,590,325 B2
(45) Date of Patent: Mar. 31, 2026

(54) DIRECTED EVOLUTION FOR OBTAINING IMPROVED VARIANTS OF TEV PROTEASE FOR BIOTECHNOLOGICAL APPLICATIONS

(71) Applicants: CZ Biohub SF, LLC, San Francisco, CA (US); The Board of Trustees of the Leland Stanford Junior University, Stanford, CA (US)

(72) Inventors: Alice Y. Ting, Palo Alto, CA (US); Mateo Isidro Sanchez Lopez, Menlo Park, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 751 days.

(21) Appl. No.: 17/642,635

(22) PCT Filed: Sep. 24, 2020

(86) PCT No.: PCT/US2020/052590
§ 371 (c)(1),
(2) Date: Mar. 11, 2022

(87) PCT Pub. No.: WO2021/062063
PCT Pub. Date: Apr. 1, 2021

(65) Prior Publication Data
US 2023/0067225 A1      Mar. 2, 2023

Related U.S. Application Data

(60) Provisional application No. 62/906,373, filed on Sep. 26, 2019.

(51) Int. Cl.
*C12P 21/02*      (2006.01)
*C12N 9/50*      (2006.01)
(Continued)

(52) U.S. Cl.
CPC .............. *C12P 21/02* (2013.01); *C12N 9/506* (2013.01); *C12N 15/1086* (2013.01); *C12N 15/625* (2013.01); *C12Y 304/22044* (2013.01)

(58) Field of Classification Search
CPC ..... C12P 21/02; C12N 9/506; C12N 15/1086; C12N 15/625; C12N 15/81; C12Y 304/22044
See application file for complete search history.

(56) References Cited

U.S. PATENT DOCUMENTS 8,945,855 B2 * 2/2015 Iverson ................. C12N 15/81
435/254.2
2015/0203834 A1      7/2015 Iverson et al.
(Continued)

FOREIGN PATENT DOCUMENTS

WO      9303769 A1      3/1993
WO      9309239 A1      5/1993
(Continued)

OTHER PUBLICATIONS

Kennedy et al. "Rapid blue-light-mediated induction of protein interactions in living cells." Nature methods vol. 7,12 (2010): 973-975, (on IDS filed Jan. 23, 2025). (Year: 2010).*
(Continued)

*Primary Examiner* — Aaron J Kosar
*Assistant Examiner* — Andrew T Moehlman
(74) *Attorney, Agent, or Firm* — Kilpatrick Townsend & Stockton LLP

(57) ABSTRACT

Tobacco etch virus protease (TEV) is one of the most widely used proteases in biotechnology because of its exquisite sequence-specificity. A limitation of TEV is its slow catalytic rate, which limits product generation and therefore signal output. Provided is a generalizable yeast-based platform for directed evolution of protease catalytic properties.
(Continued)

Protease activity is determined via proteolytic release of a membrane-anchored transcription factor, and access to TEV's cleavage site is temporally regulated using a photosensory LOV domain. By gradually decreasing light exposure time, faster variants of TEV were selected over multiple rounds of selection. The mutant TEV proteases and the directed evolution platform are useful in a wide range of biotechnology applications, such as FLARE and SPARK tools.

20 Claims, 62 Drawing Sheets

Specification includes a Sequence Listing.

(51) Int. Cl.
*C12N 15/10* (2006.01)
*C12N 15/62* (2006.01)

(56) References Cited

U.S. PATENT DOCUMENTS

| | | | | |
|---|---|---|---|---|
| 2016/0319265 | A1 | 11/2016 | Ghanshani et al. | |
| 2018/0201657 | A1* | 7/2018 | Ting ................. | C07K 14/70514 |
| 2018/0203017 | A1 | 7/2018 | Ting et al. | |

FOREIGN PATENT DOCUMENTS

| | | | | |
|---|---|---|---|---|
| WO | 9319191 | A1 | 9/1993 | |
| WO | 9412649 | A2 | 6/1994 | |
| WO | 9428938 | A1 | 12/1994 | |
| WO | 9500655 | A1 | 1/1995 | |
| WO | 9511984 | A2 | 5/1995 | |
| WO | WO-2017144620 | A1 * | 8/2017 | ......... A61K 49/0047 |

OTHER PUBLICATIONS

Kawada et al., "The yeast Arf-GAP Glo3p is required for the endocytic recycling of cell surface proteins." Biochimica et biophysica acta vol. 1853,1 (2015): 144-56. doi:10.1016/j.bbamcr.2014.10.009 (on IDS filed Jan. 23, 2025) (Year: 2015).*

Branon, T.C., "Directed evolution of TurboID for efficient proximity labeling in living cells and organisms", Appendix Part II. Thesis: Ph.D., MIT, Department of Chemistry, 2018. URL: http://hdl.handle.net/1721.1/120909. Date available: Mar. 11, 2019. pp. 1-12 and 151-167 included (29 pages total) (Year: 2019).*

Ali et al., Adeno-Associated Virus Gene Transfer to Mouse Retina, Human Gene Therapy, vol. 9, No. 1, Jan. 1, 1998, pp. 81-86.

Ali et al., Gene Transfer into the Mouse Retina Mediated by an Adeno-Associated Viral Vector, Human Molecular Genetics, vol. 5, No. 5, Feb. 26, 1996, pp. 591-594.

Altschul et al., Basic Local Alignment Search Tool, Journal of Molecular Biology, vol. 215, No. 3, Oct. 5, 1990, pp. 403-410.

Altschul et al., Gapped BLAST and PSI-BLAST: A New Generation of Protein Database Search Programs, Nucleic Acids Research, vol. 25, No. 17, Sep. 1, 1997, pp. 3389-3402.

Barnea et al., The Genetic Design of Signaling Cascades to Record Receptor Activation, Proceedings of the National Academy of Sciences, vol. 105, No. 1, Jan. 8, 2008, pp. 64-69.

Bennett et al., Real-time, Noninvasive in Vivo Assessment of Adeno-associated Virus-mediated Retinal Transduction, Investigative Ophthalmology & Visual Science, vol. 38, No. 13, Dec. 1, 1997, pp. 2857-2863.

Bitter et al., Expression and Secretion Vectors for Yeast, Methods in Enzymology, vol. 153, Jan. 1, 1987, pp. 516-544.

Borras et al., Adenoviral Reporter Gene Transfer to the Human Trabecular Meshwork Does Not Alter Aqueous Humor Outflow. Relevance for Potential Gene Therapy of Glaucoma, Gene Therapy, vol. 6, No. 4, May 1999, pp. 515-524.

Branon et al., Efficient Proximity Labeling in Living Cells and Organisms with TurboID, Nature Biotechnology, vol. 36, No. 9, Oct. 2018, pp. 880-887.

Copeland et al., A Transcription Activator-like Effector Induction System Mediated by Proteolysis, Nature Chemical Biology, vol. 12, No. 4, Apr. 2016, pp. 254-260.

Curran et al., Use of Expression-enhancing Terminators in *Saccharomyces cerevisiae* to Increase mRNA Half-life and Improve Gene Expression Control for Metabolic Engineering Applications, Metabolic Engineering, vol. 19, Jul. 3, 2013, pp. 88-97.

Estell et al., Engineering an Enzyme by Site-directed Mutagenesis to be Resistant to Chemical Oxidation, Journal of Biological Chemistry, vol. 260, No. 11, Jun. 10, 1985, pp. 6518-6521.

Evnin et al., Substrate Specificity of Trypsin Investigated by Using a Genetic Selection, Proceedings of the National Academy of Sciences, vol. 87, No. 17, Sep. 1990, pp. 6659-6663.

Fink et al., Design of Fast Proteolysis-Based Signaling and Logic Circuits in Mammalian Cells, Nature Chemical Biology, vol. 15, No. 2, Feb. 1, 2019, pp. 115-122.

Flannery et al., Efficient Photoreceptor-targeted Gene Expression in Vivo by Recombinant Adeno-associated Virus, Proceedings of the National Academy of Sciences, vol. 94, No. 13, Jun. 24, 1997, pp. 6916-6921.

Flotte et al., Stable in Vivo Expression of the Cystic Fibrosis Transmembrane Conductance Regulator with an Adeno-Associated Virus Vector, Proceedings of the National Academy of Sciences, vol. 90, No. 22, Nov. 15, 1993, pp. 10613-10617.

Forler et al., An Efficient Protein Complex Purification Method for Functional Proteomics in Higher Eukaryotes, Nature Biotechnology, vol. 21, No. 1, Jan. 1, 2003, pp. 89-92.

Gao et al., Programmable Protein Circuits in Living Cells, Science, vol. 361, No. 6408, Sep. 21, 2018, pp. 1252-1258.

Han et al., Directed Evolution of Split APEX2 Peroxidase, American Chemical Society Chemical Biology, vol. 14, No. 4, Apr. 19, 2019, pp. 619-635.

Henikoff et al., Amino Acid Substitution Matrices from Protein Blocks, Proceedings of the National Academy of Sciences of the United States of America, vol. 89, No. 22, Nov. 15, 1992, pp. 10915-10919.

Jomary et al., Rescue of Photoreceptor Function by AAV-mediated Gene Transfer in a Mouse Model of Inherited Retinal Degeneration, Gene Therapy, vol. 4, No. 7, Aug. 1997, pp. 683-690.

Kapust et al., The P1′ Specificity of Tobacco Etch Virus Protease, Biochemical and Biophysical Research Communications, vol. 294, No. 5, Jun. 28, 2002, pp. 949-955.

Kapust et al., Tobacco Etch Virus Protease: Mechanism of Autolysis and Rational Design of Stable Mutants with Wild-type Catalytic Proficiency, Protein Engineering, vol. 14, No. 12, Dec. 1, 2001, pp. 993-1000.

Kawada et al., The Yeast Arf-GAP Glo3p is Required for the Endocytic Recycling of Cell Surface Proteins, Biochimica et Biophysica Acta, vol. 1853, No. 1, Jan. 1, 2015, pp. 144-156.

Kennedy et al., Rapid Blue-Light-Mediated Induction of Protein Interactions in Living Cells, Nature Methods, vol. 7, No. 12, Dec. 2010, pp. 973-975.

Kim et al., High Cleavage Efficiency of a 2A Peptide Derived from Porcine Teschovirus-1 in Human Cell Lines, Zebrafish and Mice, Public Library of Science One, vol. 6, No. 4, e18556, Apr. 29, 2011, pp. 1-8.

Kim et al., Time-gated Detection of Protein-protein Interactions with Transcriptional Readout, eLIFE, Nov. 30, 2017, pp. 1-24.

Kostallas et al., Substrate Profiling of Tobacco Etch Virus Protease Using a Novel Fluorescence-assisted Whole-cell Assay, Public Library of Science One, vol. 6, No. 1, Jan. 18, 2011, pp. 1-10.

Lam et al., Directed Evolution of APEX2 for Electron Microscopy and Proximity, Nature Methods, vol. 12, No. 1, Jan. 2015, pp. 51-54.

Lee et al., A Calcium-and Light-gated Switch to Induce Gene Expression in Activated Neurons, Nature Biotechnology, vol. 35, No. 9, May 17, 2017, 9 pages.

Li et al., In Vivo Transfer of a Reporter Gene to the Retina Mediated by an Adenoviral Vector, Investigative Ophthalmology & Visual Science, vol. 35, No. 5, Apr. 1, 1994, pp. 2543-2549.

(56)                References Cited

OTHER PUBLICATIONS

Li et al., Phenotype Correction in Retinal Pigment Epithelium in Murine Mucopolysaccharidosis VII by Adenovirus-mediated Gene Transfer, Proceedings of the National Academy of Sciences of the United States of America, vol. 92, No. 17, Aug. 1995, pp. 7700-7704.

Li et al., Profiling Protease Specificity: Combining Yeast ER Sequestration Screening (YESS) with Next Generation Sequencing, American Chemical Society Chemical Biology, vol. 12, No. 2, Dec. 15, 2016, pp. 510-518.

Lin et al., A Drug-controllable Tag for Visualizing Newly Synthesized Proteins in Cells and Whole Animals, Proceedings of the National Academy of Sciences, vol. 105, No. 22, Jun. 3, 2008, pp. 7744-7749.

Liu et al., A Photoactivatable Botulinum Neurotoxin for Inducible Control of Neurotransmission, Neuron, vol. 101, No. 5, Mar. 6, 2019, pp. 863-875.

Loh et al., Proteomic Analysis of Unbounded Cellular Compartments: Synaptic Clefts, Cell, vol. 166, No. 5, Aug. 25, 2016, pp. 1295-1307.

Martell et al., A Split Horseradish Peroxidase for the Detection of Intercellular Protein-Protein Interactions and Sensitive Visualization of Synapses, Nature Biotechnology, vol. 34, No. 7, Jul. 2016, pp. 774-780.

Matz et al., Fluorescent Proteins from Nonbioluminescent Anthozoa Species, Nature Biotechnology, vol. 17, No. 10, Oct. 1999, pp. 969-973.

Mendelson et al., Expression and Rescue of a Nonselected Marker from an Integrated AAV Vector, Virology, vol. 166, No. 1, May 22, 1988, pp. 154-165.

Miyoshi et al., Stable and Efficient Gene Transfer into the Retina Using an HIV-based Lentiviral Vector, Proceedings of the National Academy of Sciences, vol. 94, No. 19, Sep. 16, 1997, pp. 10319-10323.

Ottoz et al., Inducible, Tightly Regulated and Growth Condition-Independent Transcription Factor in *Saccharomyces cerevisiae*, Nucleic Acids Research, vol. 42, No. 17, Jun. 25, 2014, pp. 1-11.

Packer et al., Phage-assisted Continuous Evolution of Proteases with Altered Substrate Specificity, Nature Communications, vol. 8, No. 1, Oct. 16, 2017, pp. 1-11.

Parks et al., Expression and Purification of a Recombinant Tobacco Etch Virus Nia Proteinase: Biochemical Analyses of the Full-length and a Naturally Occurring Truncated Proteinase Form, Virology, vol. 210, No. 1, Apr. 18, 1995, pp. 194-201.

Partow et al., Characterization of Different Promoters for Designing a New Expression Vector in *Saccharomyces cerevisiae*, Yeast, vol. 27, No. 11, May 31, 2010, pp. 955-964.

Peng et al., Controlling Heterologous Gene Expression in Yeast Cell Factories on Different Carbon Substrates and Across the Diauxic Shift: a Comparison of Yeast Promoter Activities, Microbial Cell Factories, vol. 14, Dec. 2015, pp. 1-11.

Phan et al., Structural Basis for the Substrate Specificity of Tobacco Etch Virus Protease, Journal of Biological Chemistry, vol. 277, No. 52, Dec. 27, 2002, pp. 50564-50572.

Raran-Kurussi et al., Differential Temperature Dependence of Tobacco Etch Virus and Rhinovirus 3C Proteases, Analytical Biochemistry, vol. 436, No. 2, May 15, 2013, pp. 142-144.

Rolling et al., Evaluation of Adeno-associated Virus-mediated Gene Transfer into the Rat Retina by Clinical Fluorescence Photography, Human Gene Therapy, vol. 10, No. 4, Mar. 1, 1999, pp. 641-648.

Sakamoto et al., A Vitrectomy Improves the Transfection Efficiency of Adenoviral Vector-mediated Gene Transfer to Muller Cells, Gene Therapy, vol. 5, No. 8, Mar. 11, 1998, pp. 1088-1097.

Samulski et al., Helper-free Stocks of Recombinant Adeno-associated Viruses: Normal Integration Does Not Require Viral Gene Expression, Journal of Virology, vol. 63, No. 9, Sep. 1989, pp. 3822-3828.

Schuster et al., Controllable Protein Phase Separation and Modular Recruitment to Form Responsive Membraneless Organelles, Nature Communications, vol. 9, No. 1, Jul. 30, 2018, pp. 1-12.

Seifert et al., LOV Domains in the Design of Photoresponsive Enzymes, American Chemical Society Chemical Biology, vol. 13, No. 8, Jun. 15, 2018, pp. 1914-1920.

Sente et al., Molecular Mechanism of Modulating Arrestin Conformation by GPCR Phosphorylation, Nature Structural & Molecular Biology, vol. 25, No. 6, Jun. 2018, pp. 538-545.

Shaner et al., A Guide to Choosing Fluorescent Proteins, Nature Methods, vol. 2, No. 12, Dec. 2005, pp. 905-909.

Smart et al., Engineering a Light-activated Caspase-3 for Precise Ablation of Neurons in Vivo, Proceedings of the National Academy of Sciences, vol. 114, No. 39, Sep. 11, 2017, pp. E8174-E8183.

Swiech et al., In Vivo Interrogation of Gene Function in the Mammalian Brain Using CRISPR-Cas9, Nature Biotechnology, vol. 33, Oct. 19, 2014, pp. 1-5.

Takahashi et al., Rescue from Photoreceptor Degeneration in the rd Mouse by Human Immunodeficiency Virus Vector-mediated Gene Transfer, Journal of Virology, vol. 73, No. 9, Sep. 1, 1999, pp. 7812-7816.

Thomsen et al., Seq2Logo: a Method for Construction and Visualization of Amino Acid Binding Motifs and Sequence Profiles Including Sequence Weighting, Pseudo Counts and Two-sided Representation of Amino Acid Enrichment and Depletion, Nucleic Acids Research, vol. 40, No. W1, May 2, 2012, pp. W281-W287.

Tropea et al., Expression and Purification of Soluble His 6-tagged TEV Protease, High Throughput Protein Expression and Purification: Methods and Protocols, Jan. 2009, pp. 297-307.

Turk et al., Determination of Protease Cleavage Site Motifs Using Mixture-based Oriented Peptide Libraries, Nature Biotechnology, vol. 19, No. 7, Jul. 2001, pp. 661-667.

Wang et al., A Light-and Calcium-Gated Transcription Factor for Imaging and Manipulating Activated Neurons, Nature Biotechnology, vol. 35, No. 9, Sep. 2017, pp. 864-871.

Wiita et al., Global Analysis of Cellular Proteolysis by Selective Enzymatic Labeling of Protein N-termini, In Methods in Enzymology, vol. 544, Jan. 1, 2014, pp. 327-358.

Yi et al., Engineering of TEV Protease Variants by Yeast ER Sequestration Screening (YESS) of Combinatorial Libraries, Proceedings of the National Academy of Sciences, vol. 110, No. 18, Apr. 30, 2013, pp. 7229-7234.

PCT Application No. PCT/US2020/052590, International Search Report and Written Opinion mailed on Feb. 1, 2021, 12 pages.

Sellamuthu et al., An Engineered Viral Protease Exhibiting Substrate Specifically for Polyglutamine Stretch Prevents Polyglutamine-induced Neuronal Cell Death, PLoS One, vol. 6, No. 7, Jul. 20, 2011, pp. 1-9.

International Application No. PCT/US2020/052590, International Preliminary Report on Patentability mailed on Apr. 7, 2022, 9 pages.

* cited by examiner

Citrine signal (% cells in Q1+Q2)

|  | CRY-TEVΔ | | TEVΔ | |
|---|---|---|---|---|
| | Light | Dark | Light | Dark |
| 5 | | 1 | 0 | 0 |
| 0 | | 0 | 0 | 0 |
| 2 | | 0 | 0 | 0 |
| 25 | | 0 | 0 | 0 |
| 38 | | 0 | 0 | 0 |
| 51 | | 0 | 0 | 0 |

Membrane-anchored transcription factor

P-ACT1:STE2-CIBN-TEVcs-VP16

P-ACT1:STE2-BFP-CIBN-TEVcs-VP16

P-ACT1:STE2Δ-CIBN-TEVcs-VP16

P-ACT1:STE2Δ-BFP-CIBN-TEVcs-VP16

P-TDH3:STE2Δ-CIBN-TEVcs-VP16-tCYC1

P-TDH3:STE2Δ-BFP-CIBN-TEVcs-VP16-tCYC1

Light time:

No TEV
5, 10, 15, 25, 40 min
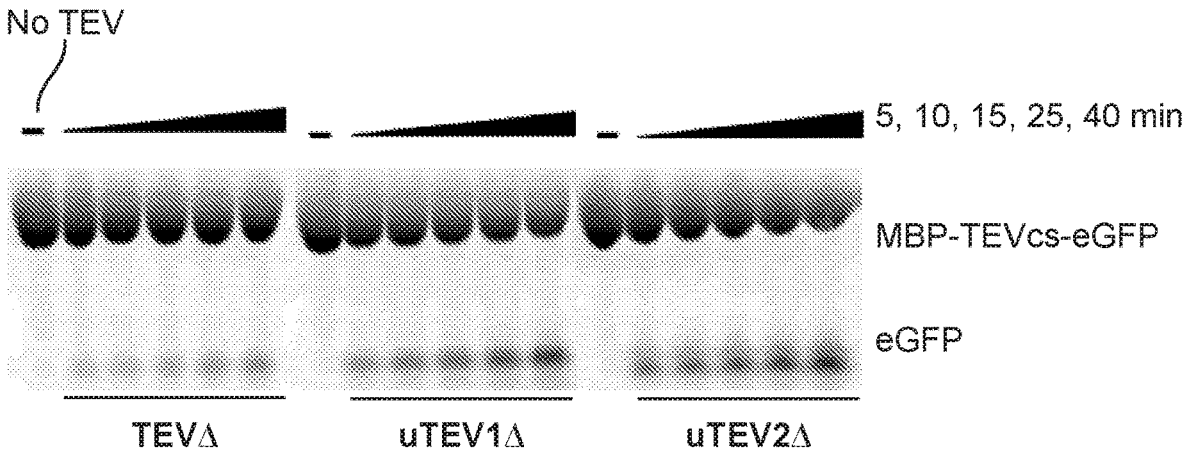
MBP-TEVcs-eGFP
eGFP
TEVΔ          uTEV1Δ          uTEV2Δ
FIG. 2C
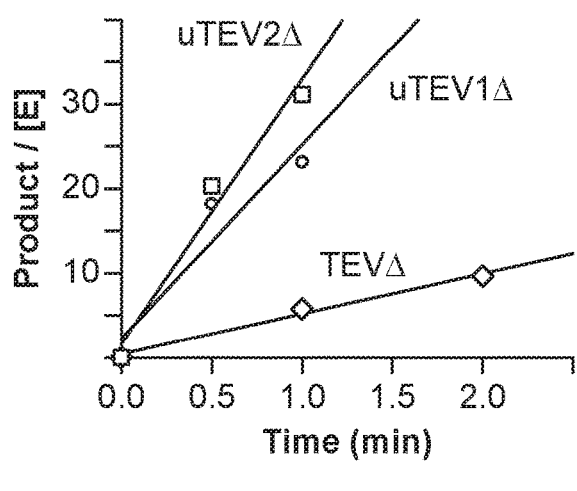
FIG. 2D
| | *Apparent k* |
|---|---|
| TEVΔ | 0.010 ± 0.0016 s-1 |
| uTEV1Δ | 0.054 ± 0.013 s-1 |
| uTEV2Δ | 0.062 ± 0.01 s-1 |
FIG. 2E 1- original TEV(S219V)    5- uTEV1-T180A
2- uTEV1    6- uTEV1-S135F/T180A
3- uTEV1-S135F    7- uTEV1-I138T/T180A = uTEV3
4- uTEV-I138T    8- uTEV1-S135F/I138T/180A

|  | $K\,cat$ (sec$^{-1}$) | $K_m$ (mM) | $K\,cat\,/$ $K_m$ |
|---|---|---|---|
| TEV | 0.17 ± 0.02 | 0.072 ± 12 | 2.42 |
| uTEV3 | 0.15 ± 0.01 | 0.022 ± 4 | 6.82 |

FIG. 4A                    FIG. 4B

FLARE TF: TM(CD4)-MKII-hLOV-TEVcs-TF(Gal4)
FLARE protease: eGFP-Calmodulin-TEVΔ
FLARE reporter: UAS-mCherry

FLARE TF: TM(NRX)-MKII-hLOV-TEVcs-TF(tTA)
FLARE protease: eGFP-Calmodulin-TEVΔ
FLARE reporter: TRE-mCherry

SPARK TF: GPCR(β2AR)-hLOV-TEVcs-TF(Gal4)
SPARK protease: GFP-p2A-Arrestin-TEVΔ
SPARK reporter: UAS-mCherry

|  | | | | | | | | | | | |
|---|---|---|---|---|---|---|---|---|---|---|---|
| #1 | | S31W | | | | | | | | | |
| #2 | T30A | | | | | | | | | S153N | N177Y |
| #3 | K67E | | | | | | | | | | N177Y |
| #4 | K89E | | | L56S | | | | | | | N177Y |
| #5 | | | | | | | | | | | N177Y |
| #6 | | | | | | | | | | | |
| #7 | | S31W | T54A | | | | | | | | N177Y |
| #8 | | S31W | | | | | | | | | |
| #9 | | | | F64L | | | | | | | N177Y |
| #10 | | S31W | | | | | | | | | |
| #11 | S16I | | R50G | | D90G | | | | | | N177Y |
| #12 | T30A | | | | | | | | | S153N | |
| #13 | T30I | | | | | | | | | S153N | N177Y |
| #14 | | | | | | | | | | | |
| #15 | | | | | | | D136V | | | | N177Y |
| #16 | | | | | | | | | | | |
| #17 | | | | | 100V | | | | | | |
| #18 | | | | | | | | | | | |
| #19 | | | | | | | | | | S153N | N177Y |
| #20 | | | | | | S135F | | | | | N177Y |
| #21 | | | | | | | | I138T | | | |
| #22 | | S31W | | | | C101R T114A | | | | | N177Y |
| #23 | S3F | T30A | | | | | | | | S153N | N177Y |
| #24 | | | | | | | | | | | |

FIG. 7B

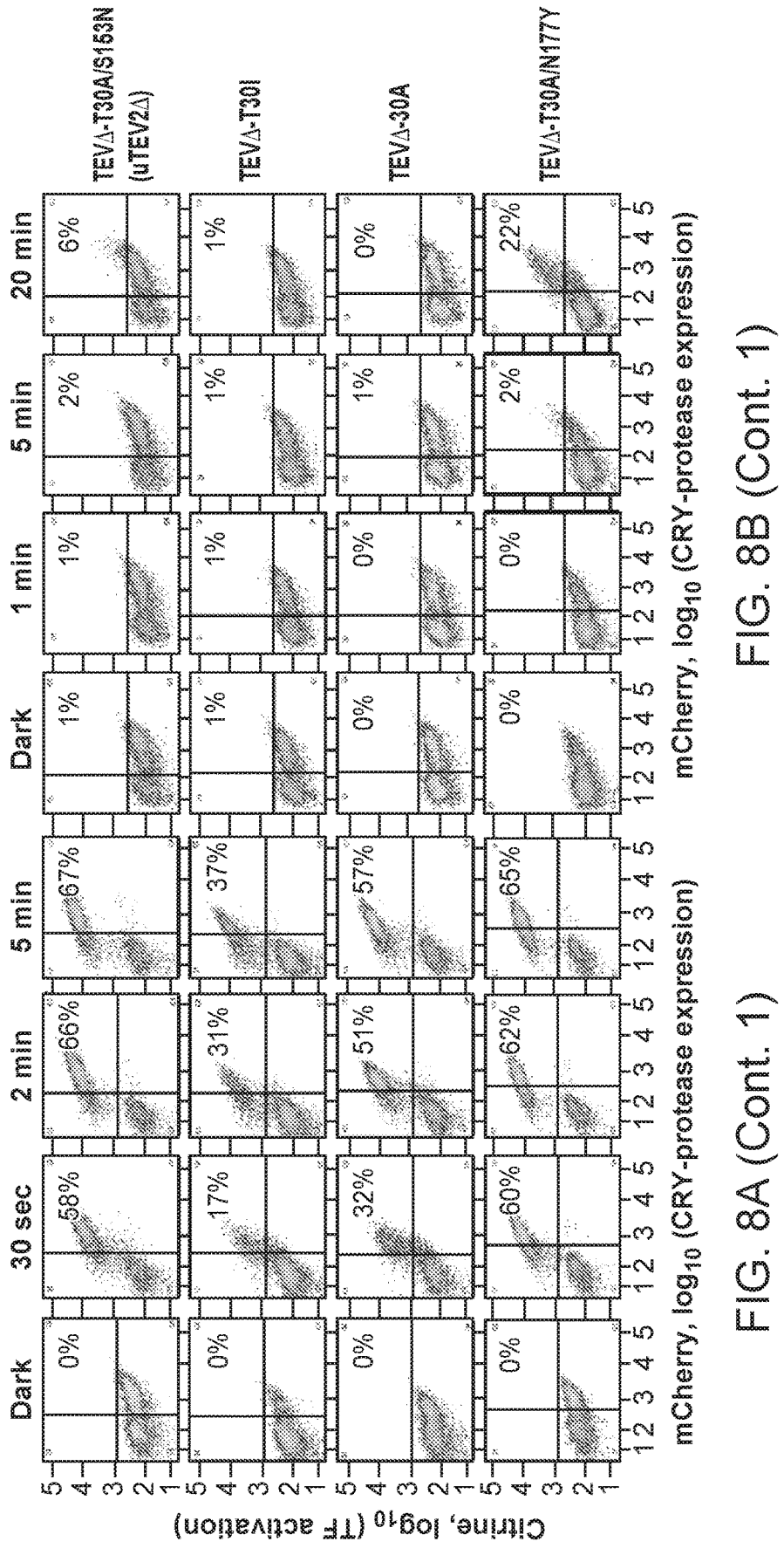
FIG. 8B (Cont. 1)
FIG. 8A (Cont. 1)

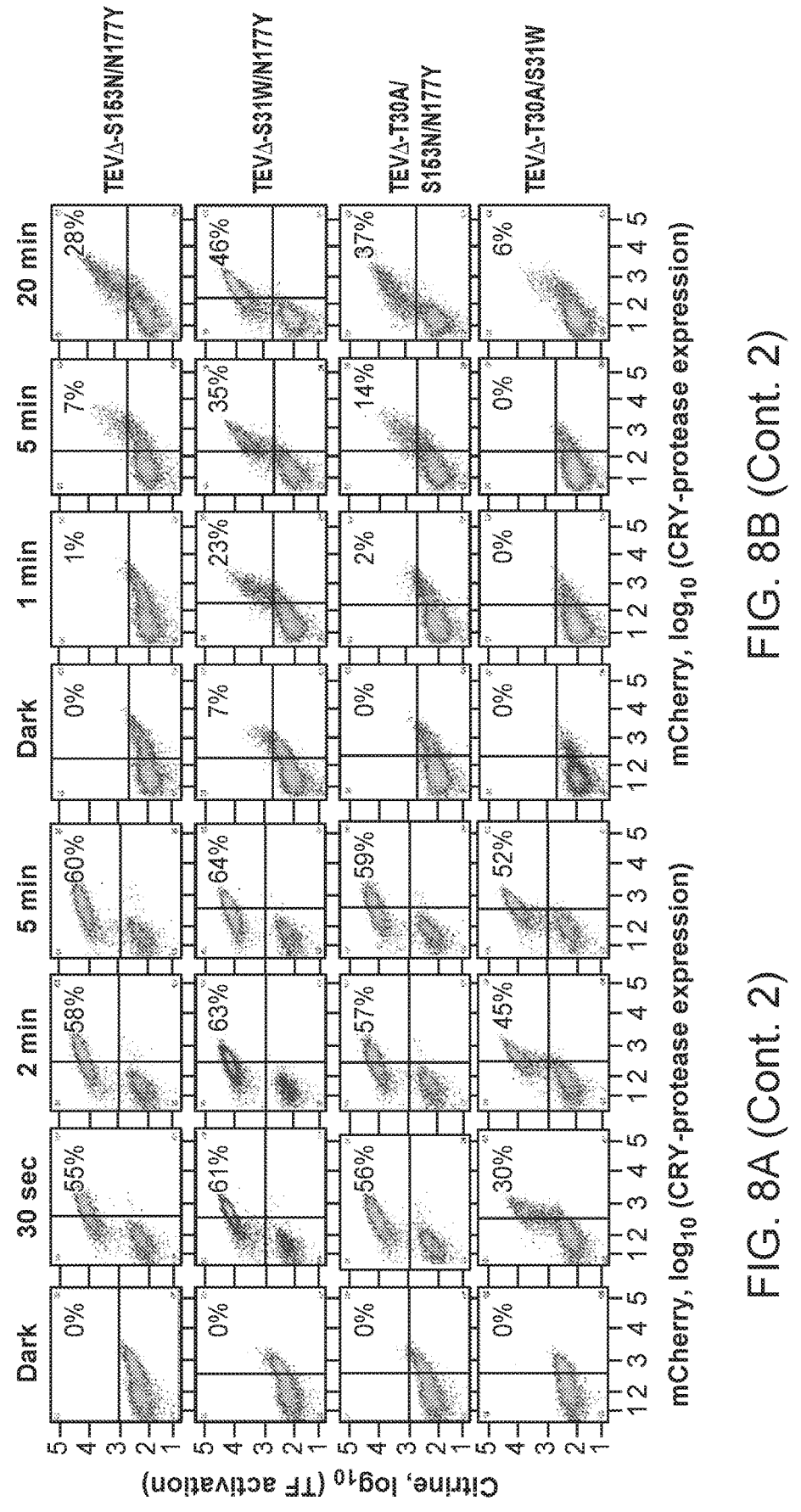
FIG. 8B (Cont. 2)
FIG. 8A (Cont. 2)

LexA-mCherry-TA

TEVcs = ENLHFQ/S

| | H28Y | M87T | D90G | k97R | P103L | F125L | D127G | I138T | Y140H | K141R | N177Y | T180A | M235T | V239A |
|---|---|---|---|---|---|---|---|---|---|---|---|---|---|---|
| #1 | | | | | | | | | | | N177Y | | | |
| #2 | | | | k97R | | | | I138T | | | N177Y | | | V239A |
| #3 | | | | | | | | I138T | | | N177Y | | | |
| #4 | | | D90G | | | | | | | | N177Y | | | |
| #5 | | | | | | | | | Y140H | K141R | N177Y | | | |
| #6 | | | | | | | D127G | | | | N177Y | | | |
| #7 | Template | | | | | | | | | | | | | |
| #8 | | | | k97R | | | | I138T | | | N177Y | | | V239A |
| #9 | | | | k97R | | | | I138T | | | N177Y | | | V239A |
| #10 | | | | | | | | | | | N177Y | | | |
| #11 | | | | | | F125L | | | | | N177Y | | | |
| #12 | | | | k97R | | | D127G | I138T | | | N177Y | | | V239A |
| #13 | | | | | | | | | | | N177Y | | | |
| #14 | | | | | | | | | | | N177Y | | | |
| #15 | | | | | | | | | | K141R | N177Y | T180A | | |
| #16 | | M87T | | | | | | I138T | | | N177Y | | | |
| #17 | | | | | | | | | | | N177Y | | | |
| #18 | | | | | | | | | | | N177Y | | | |
| #19 | | | | | | | | | | | N177Y | T180A | | |
| #20 | H28Y | | | | | | | | | | N177Y | | | |
| #21 | | | | | | | | | | K141R | N177Y | T180A | | |
| #22 | | | | | | | | | | | N177Y | | | |
| #23 | | | | | P103L | | | | | | N177Y | | M235T | |
| #24 | | | | | | | | | | K141R | N177Y | T180A | | |

FIG. 21A

TEVcs=ENLWFQ/S

| | | | | | | | | | | |
|---|---|---|---|---|---|---|---|---|---|---|
| #1 | | | | | | | | | | |
| #2 | N177Y | N192D | | | | | | | | |
| #3 | N177Y | | | | | | | | | |
| #4 | N177Y | | | | | | | | | |
| #5 | F132S | N177Y | | | | | | | | |
| #6 | N177Y | | N215D | | | | | | | |
| #7 | N177Y | | | | | | | | | |
| #8 | N177Y | | | | | | | | | |
| #9 | N177Y | | | | | | | | | |
| #10 | N177Y | | | S219G | | | | | | |
| #11 | N177Y | | | | | | | | | |
| #12 | N177Y | | | | P224L | | | | | |
| #13 | F40S | N177Y | | | | | | | | |
| #14 | Empty Vector | | | | | | | | | |
| #15 | N177Y | | | | | | | | | |
| #16 | Q117R | N177Y | | | | | | | | |
| #17 | N177Y | | | | | | | | | |
| #18 | N177Y | | | | | | | | | |
| #19 | N177Y | | | | | | | | | |
| #20 | S120G | N177Y | K184R | | | | | | | |
| #21 | S16N | N177Y | | | | | | | | |
| #22 | N177Y | | | P221S | | L238S | Y240D | | | |
| #23 | N177Y | | | E222G | | | | | | |
| #24 | N177Y | | | | | Y240N | | | | |

FIG. 21B (+): Electrical Stimulation  (++): Media Change Stimulation

SPARK expression (eGFP-p2A-arrestin-TEV1Δ)

SPARK activation (mCherry expression)

DIRECTED EVOLUTION FOR OBTAINING IMPROVED VARIANTS OF TEV PROTEASE FOR BIOTECHNOLOGICAL APPLICATIONS

REFERENCE TO RELATED APPLICATION

This application claims benefit and is a 371 application of PCT Application No. PCT/US2020/052590, filed Sep. 24, 2020, which claims the priority benefit of U.S. Provisional Application No. 62/906,373, filed Sep. 26, 2019. The priority application is hereby incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Sep. 23, 2020, is named 103182-1201936-002410WO_SL.txt and is 100,754 bytes in size.

BACKGROUND OF THE INVENTION

Proteases are ubiquitous in biology, frequently initiating or terminating endogenous signaling cascades. Their peptide bond cleavage activities have been harnessed for a wide range of biotechnological applications, including bottom-up mass spectrometry (MS)-based proteomics (e.g., digestion of proteins to peptides using trypsin and chymotrypsin prior to MS analysis), affinity purification (e.g., TAP tag [1]), neuronal silencing (e.g., tetanus toxin and botulinum toxin [2], light-regulated apoptosis [3], tagging of newly synthesized proteins (e.g., TimeSTAMP [4]), assembly/disassembly of protein droplets [5], construction of protease-based synthetic circuits [6,7], and transcriptional readout of elevated cytosolic calcium (e.g., FLARE [8] and Cal-Light [9]), protein-protein interactions (e.g., Tango [10] and SPARK [11]), and TALEN activity [12].

One of the most frequently-used proteases in biotechnology is TEV, the 27 kD cysteine protease from tobacco etch virus. TEV is appealing for a number of reasons: it is active in the mammalian cytosol, has no required cofactors, recognizes a 7-amino acid consensus peptide substrate (TEV cleavage sequence, or TEVcs), and most importantly, is highly sequence-specific, exhibiting negligible activity towards endogenous mammalian proteomes, thus minimizing toxicity and interference with endogenous signaling pathways. Consequently, TEV has been harnessed for sequence-specific transcription factor release in response to calcium and light in FLARE [8], GPCR activation in Tango [10], and GPCR activation and light in SPARK [11]. In the recently reported CHOMP [6] and SPOC [7] tools, TEV is activated by inputs such as rapamycin or abscisic acid, and in turn proteolytically turns on an infrared fluorescent protein reporter.

Despite the exquisite sequence-specificity of TEV, a major limitation of this protease is its slow catalysis. With a kcat of 0.15 s-1 (for its best TEVcs sequence, ENLYFQS (SEQ ID NO: 5)[13]), TEV is considerably slower than other proteases used for biotechnology, such as trypsin (kcat 75 s-1 [14]) and subtilisin (kcat 50 s-1 [15]). This slow catalytic turnover fundamentally limits the performance of technologies that rely on TEV, such as FLARE. In vivo, FLARE requires calcium and light stimulation for at least 30 minutes to give TEV sufficient time to release detectable quantities of membrane-anchored transcription factor [8]. Yet for the neuronal activity integration applications for which FLARE is designed, a temporal resolution of just a few minutes, or even seconds, is desired—a goal that was impossible to achieve using wild-type TEV (vide infra).

There have not been previous systematic efforts to improve the catalytic rate of TEV, apart from optimization of its substrate sequence (TEVcs). Directed evolution has previously been applied to alter TEV's sequence specificity, producing variants that have either similar [16] or depressed [17] catalytic efficiency compared to wild-type TEV. The instant disclosure provides methods for producing proteases with increased catalytic efficiency using directed evolution, and improved proteases produced by the methods.

BRIEF SUMMARY OF THE INVENTION

This disclosure provides fusion proteins, nucleic acids that encode the fusion proteins, recombinant host cells that express the fusion proteins, and methods of using the fusion proteins for selecting proteases with increased catalytic activity using directed evolution. Also provided are modified proteases with increased catalytic rates compared to control or wild-type proteases.

In one aspect, a yeast strain is provided, the yeast comprising: (a) a first fusion protein comprising: (i) a first member of a photoinducible protein binding pair; (ii) a TEV protease that cleaves the proteolytically cleavable linker, wherein the TEV protease is a low affinity protease having a Km of greater than 300 microMolar; (b) a second fusion protein comprising: (i) a transmembrane domain, (ii) a second member of a photoinducible protein binding pair; (iii) a light-oxygen-voltage-sensing (LOV) domain sequence; (iv) a proteolytically cleavable linker comprising a TEV cleavage sequence (TEVcs); and (iv) a transcription factor; and (c) a reporter gene that is transcribed by the transcription factor.

In some embodiments, the first member of the photoinducible protein binding pair is a cryptochrome (CRY) and the second member of the photoinducible protein binding pair is a cryptochrome-interacting basic-helix-loop-helix protein (CIB).

In some embodiments, the C-terminal of the LOV domain comprises an alpha helix fused to the TEV cleavage sequence.

In some embodiments, the transmembrane domain comprises an amino acid sequence from pheromone alpha factor receptor (STE2) or a truncated STE2.

In some embodiments, the first fusion protein, the second fusion protein, or both further comprise a fluorescent protein. In some embodiments, the fluorescent protein is mCherry or blue fluorescent protein (BFP).

In some embodiments, the protease is a C-terminally truncated TEV. In some embodiments, the C-terminally truncated TEV comprises the amino acid sequence of SEQ ID NO:2. (GESLFKGPRDYNPISSTICHLTNESDGHTTS-LYGIGFGPFIITNKHLFRRNNGTLL-VQSLHGVFKVKNTTTLQQHL IDGRDMIIIRM-PKDFPPFPQKLKFREPQREERICLVTTNFQTKSMSSM VSDTSCTFPSSDGIFWKHWIQTKDGQ CGSPLVSTRDGFIVGIHSASNFTNTN-NYFTSVPKNFMELLTNQEA-QQWVSGWRLNADSVLWGGHKVFMV)

In some embodiments, the linker comprises a BFP linker.

In some embodiments, the transcription factor comprises Transactivating tegument protein VP16.

In some embodiments, the reporter gene encodes a fluorescent protein.

In another aspect, a yeast strain comprising a nucleic acid encoding a fusion protein is provided. In some embodiments, the yeast strain comprises a first nucleic acid encoding a first fusion protein and a second nucleic acid encoding a second fusion protein. In some embodiments, the second nucleic acid comprises a promoter or a terminator that increases expression of a transcription factor encoded by the second nucleic acid.

In another aspect, a method for producing a modified protease having increased catalytic efficiency is described, the method comprising:
  a) expressing a first fusion protein in the cytosol of a yeast cell, wherein the first fusion protein comprises a TEV protease linked to a first member of a photoinducible protein binding pair
  wherein the yeast cell comprises
  a second fusion protein comprising:
    (i) a transmembrane domain,
    (ii) a second member of a photoinducible protein binding pair;
    (iii) a light-oxygen-voltage-sensing (LOV) domain sequence;
    (iv) a proteolytically cleavable linker; and
    (iv) a transcription factor;
    and
  a reporter gene that is transcribed by the transcription factor;
  b) irradiating the yeast cells with light;
  c) selecting yeast cells that express the reporter gene; and
  d) detecting increased catalytic activity compared to a control protease, thereby producing the modified protease.

In some embodiments, the irradiation produces an intermolecular complex between the first and second members of the photoinducible protein binding pair and induces a conformational change in the LOV domain sequence to expose the protease substrate cleavage sequence to the protease.

In some embodiments, the first member of the photoinducible protein binding pair is a cryptochrome (CRY) and the second member of the photoinducible protein binding pair is a cryptochrome-interacting basic-helix-loop-helix protein (CIB).

In some embodiments, the selecting step (c) comprises selecting yeast cells that express the reporter gene at levels at least one order of magnitude greater than non-irradiated yeast cells.

The irradiating step (b) and selecting of step (c) can be repeated one or more times to select for proteases having increased catalytic activity. For example, the period of time of irradiating step (b) can be decreased each time step (b) is repeated, which selects for protease mutations with higher proximity-dependent protease activity. In some embodiments, the percentage of cells expressing the reporter gene increases each time the period of time in step (b) is decreased In some embodiments, the step of detecting increased catalytic activity is performed by flow cytometry.

In some embodiments, the first or second fusion protein further comprises a fluorescent label.

In some embodiments, the selecting step (c) comprises detecting expression of the reporter gene, expression of the fluorescent label, or both.

In some embodiments, the catalytic activity is detected by contacting the protease with a substrate and determining the amount of substrate cleaved by the protease.

In another aspect, provided are modified TEV proteases having increased catalytic activity compared to a wild-type or unmodified TEV protease. In some embodiments, the modified TEV protease comprises an amino acid sequence differing from wild-type TEV (SEQ ID NO:1) at one or more positions corresponding to positions T30, S31, and S153. In some embodiments, the modified TEV protease comprises a sequence having at least 90% sequence identity to wild-type TEV (SEQ ID NO:1), and one or more mutations selected from T30A, T301, S31W, S153N, and T30A/S153N, wherein the positions are numbered with reference to SEQ ID NO:1.

In some embodiments, the modified TEV protease has a substrate specificity substantially similar to wild-type TEV protease (SEQ ID NO:1). In some embodiments, the catalytic activity is determined by incubating the modified TEV protease with increasing concentrations of a substrate sequence for increasing amounts of time and quantifying the amount of substrate cleaved. In some embodiments, the protease substrate amino acid sequence comprises ENLYFQS (SEQ ID NO: 5).

In another aspect, provided herein are composition comprising a modified TEV protease described herein. In some embodiments, the composition comprises a protein linked or fused to the modified TEV protease. In some embodiments, the protein is linked to the modified TEV protease by a peptide bond.

In another aspect, provided herein are improved FLARE and SPARK reporter tools. In some embodiments, the improved FLARE tool comprises a modified TEV protease linked or fused to calmodulin. In some embodiments, the improved FLARE tool further comprises a fusion protein comprising a transcription factor linked to a protease substrate amino acid sequence, a LOV domain sequence, a calmodulin binding peptide (MKII), and a transmembrane domain. In some embodiments, the transcription factor is Gal4.

In some embodiments, the improved SPARK tool comprises a modified TEV protease linked or fused to a G protein-coupled receptor (GPCR) ligand. In some embodiments, the improved SPARK tool further comprises a fusion protein comprising a transcription factor linked to a protease substrate amino acid sequence, a LOV domain sequence, a GPCR, and a transmembrane domain. In some embodiments, the ligand is an arrestin or beta-arrestin2, and the GPCR is a beta-2-adrenergic receptor. In some embodiments, the transcription factor is Gal4.

Also provided are kits comprising a modified TEV protease described herein. In some embodiments, the kit comprises a fusion protein described herein. In some embodiments, the kit comprises a nucleic acid comprising a reporter gene nucleotide sequence described herein.

Also provided are host cells comprising a modified TEV protease described herein. In some embodiments, the host cell comprises a fusion protein described herein. In some embodiments, the host cell comprises a nucleic acid comprising a reporter gene nucleotide sequence described herein. In some embodiments, the host cell is a eukaryotic cell. In some embodiments, the host cell is a yeast cell. In some embodiments, the host cell is a mammalian cell.

BRIEF DESCRIPTION OF THE DRAWINGS

FIG. 1A shows a schematic of evolution platform in the yeast cytosol. A library of truncated TEV protease (TEVA) variants is fused to CRY and mCherry. A transcription factor (TF) is tethered to the plasma membrane via a TEV cleavage site (TEVcs), a LOV domain, and CIBN. Upon exposure of cells to blue 450 nm light, the CRY-349 CIBN interaction brings the TEV protease into proximity of TEVcs, and the LOV domain changes conformation to expose TEVcs. Proteolysis releases the TF, which translocates to the nucleus and drives expression of the reporter gene Citrine. Selection stringency can be increased by decreasing the light exposure time (allowing less time for TEV-catalyzed TF release).

FIG. 1B shows a sample FACS analysis of yeast cells 6 hours after 8-minute blue light exposure. A subpopulation of cells exhibit Citrine fluorescence above background, indicating that they contain active TEV that can catalyze TF release during the 8-minute light window. mCherry fused to the protease is used to quantify protease expression levels. A gate is drawn to collect cells with the highest Citrine/mCherry intensity ratios.

FIG. 1C shows optimization of membrane-anchored transcription factor component of the evolution platform. For each construct, FACS analysis was performed as shown in (D), 6 hours after 45-minute blue light exposure. Controls are shown with light omitted (columns 2 and 4) or CRY omitted (columns 3-4). Table values reflect the fraction of cells with high Citrine intensity, i.e., cells in the upper FACS quadrants Q1 and Q2 (quadrants defined in panel B).

FIG. 1D shows FACS plots corresponding to the last row of the table in (C). All other FACS plots are shown in FIG. 5B. This experiment was performed twice with similar results.

FIG. 1E shows Citrine signal scales with light irradiation time. As the 450 nm light exposure time is increased from 0 min to 25 min, the resulting Citrine expression 6 hours later increases. Values in each plot reflect the percentage of cells within the red polygonal gate shown. This experiment was performed twice with similar results.

FIG. 1F shows FACS plots summarizing the progress of the selections. Re-amplified yeast pools were analyzed side by side under the three conditions shown (three columns). Values reflect the fraction of Citrine-positive cells, i.e. cells in upper quadrants Q1 and Q2. Additional FACS plots and summary graph are shown in FIG. 7A.

FIG. 1G shows mutations enriched by the evolution, highlighted on a ribbon structure of wild-type TEV protease in complex with its peptide substrate (PDB: 1LVM [26]). uTEV1A contains only the mutation S153N relative to wild-type TEV, while uTEVA2 has both S153N and T30A mutations. From our high-affinity TEV evolution (see FIG. 14B), we enriched the mutations S135F, T138I and T180A (in purple). uTEV3 has three mutations (I138T. S153N and T180). Mutation N177Y (cyan) arise from our evolution against altered TEV substrates (see FIG. 21).

FIGS. 2A to 2G show the characterization of evolved proteases in yeast and in vitro.

FIG. 2A shows a Comparison of evolved single, double, and triple TEVA mutants in yeast, with CRY present (top) and with CRY omitted (bottom, to test proximity-dependence of cleavage). Experiment was performed as in FIG. 1A and FACS plots quantified as in FIG. 1C. For each clone, three irradiation times were tested (0.5, 2, and 5 min) in addition to the dark state (D). The two clones with the highest proximity-dependent activity are highlighted yellow. Additional time points and FACS plots shown in FIG. 8.

FIG. 2B shows FACS plots for the two best clones in FIG. 2(A). Additional time points and data are shown in FIG. 8. Percentages show the fraction of Citrine-positive cells in Q1+Q2.

FIG. 2C shows fluorescence gel assay for measuring kinetics of purified TEV proteases. The substrate protein MBP-TEVcs-eGFP was incubated with the indicated TEV mutants (MBP=maltose binding protein; TEVcs=ENLYFQ/M (SEQ ID NO: 6)). At various time points, the reaction was quenched and run on SDS-PAGE. Reaction products were quantified by in-gel fluorescence imaging and compared to reference standards of known concentration (see Methods). Here, [MBP-TEVcs-eGFP] was 0.36 mM and all proteases were at 0.75 μM.

FIG. 2D shows quantitation of protease reaction rates. Product was quantified using the assay in FIG. 2(C). Product formed as a function of time, normalized by enzyme concentration.

FIG. 2E Apparent rate constants based on initial velocity measurements in (D). Because protein solubility limited substrate concentration to 360 uM, which is much lower than the expected Km, these values represent lower bounds to the actual kcat. Three technical replicates.

FIG. 2F shows profiling protease sequence specificity in yeast. Setup was the same as FIG. 1A, except the TEVcs sequence is randomized, and mCherry is fused to TEVcs rather than TEV to quantify its expression level. The FACS plots show the cleavage extent of various TEVcs test substrates, 6 hours after 30-minute blue light irradiation. Forward slash indicates proteolysis site. Mutations at the −6, −3, and −1 positions of TEVcs greatly reduce cleavage activity for wild-type TEVA. Figure discloses SEQ ID NOS 6, 66, 67, and 68 in order of appearance.

FIG. 2G shows the sequence specificity profiles of wild-type TEVA, uTEV1A, and uTEV2A obtained via sequencing following FACS enrichment from seven TEVcs libraries each. Associated FACS plots and sequencing data are shown in FIG. 10.

FIG. 3A shows a representative selection scheme in yeast cytosol. A library of full-length TEV variants is expressed as a fusion to mCherry. The transcription factor (TF) is anchored to the plasma membrane via a protease-sensitive linker. FACS is used to enrich cells with high Citrine/mCherry intensity ratio.

FIG. 3B shows tuning the dynamic range of the evolution platform. By decreasing the number of LexA boxes in the promoter recognized by the LexA-VP16 TF, we reduced the sensitivity of the readout (i.e., lower Citrine expression in response to protease activity). Corresponding FACS data is shown in FIGS. 12 and 13.

FIG. 3C shows the results of selection on a library of full-length uTEV1 variants, using the high-affinity TEVcs ENLYFQ/S (SEQ ID NO: 5). Percentages represent fraction of Citrine-positive cells in Q1+Q2. Additional FACS plots and conditions are shown in FIG. 14A.

FIG. 3D. shows analysis of individual clones enriched by selection. Activities were quantified in yeast by Citrine expression level, as in FIG. 1F. Additional characterization in yeast is shown in FIG. 16.

FIG. 3E shows a fluorescence gel assay for measuring the kinetics of purified proteases. The protein substrate MBP-TEVcs-GFP (72 kDa, 28 uM, TEVcs=ENLYFQ/S (SEQ ID NO: 5)) was incubated with the indicated proteases (all full-length, 125 nM) for 10, 20, or 45 min before analysis by SDS-PAGE.

FIG. 3F shows kinetic parameters for wild-type TEV and uTEV3 (containing the mutations I138T, S153N, and T180A), obtained via the fluorescence gel assay shown in FIG. 3E. The MBP-TEVcs-eGFP substrate concentration was varied from 7.5 to 320 μM to obtain the Km. Michaelis-Menten plots are shown in FIG. 9. Three technical replicates were performed.

FIG. 3G shows fluorescence gel assay for measuring the efficiency of uTEV3 to remove affinity tags. The protein substrate MBP-TEVcs-GFP (72 kDa, 10 uM, TEVcs=ENLYFQ/S (SEQ ID NO: 5)) was incubated with the indicated proteases (all full-length, 60 nM) at different times (0, 0,5, 1, 2 and 4 h). Reaction aliquots were incubated with amylose resin for 10 min, and the supernatant was analyzed by SDS-PAGE, as shown in FIG. 19.

FIG. 3H shows altering substrate specificity of TEV. Instead of the TEVcs used in FIG. 3C (ENLYFQ/S (SEQ ID NO: 5)), we used a mutated TEVcs (ENLHFQ/S (SEQ ID NO: 7)) that is not recognized by wild-type TEV. Three rounds of evolution produced a population of TEV variants with high activity against this new sequence. Each re-amplified cell population is shown under three different conditions (three columns). The most active mutant we isolated is also shown on the bottom row. Percentages reflect the fraction of Citrine-positive cells in Q1+Q2. FIGS. 20-22 show a similar evolution experiment against a different mutated TEVcs sequence, ENLWFQ/S (SEQ ID NO: 8).

FIGS. 4A to 4H show characterization of evolved low-affinity TEVA proteases in mammalian cells and incorporation into FLARE and SPARK tools.

FIG. 4A shows the FLARE tool used to integrate cytosolic calcium activity. FLARE is a coincidence detector of blue light and high calcium, with gene expression as the readout [8]. High calcium drives intermolecular complexation between calmodulin and its binding peptide (MKII), which brings TEVA protease close to its peptide substrate TEVcs. Blue light is also required to uncage TEVcs. Released TF translocates to the nucleus and drives mCherry expression.

FIG. 4B shows the SPARK tool used to integrate GPCR activity. SPARK is a coincidence detector of light and GPCR activity, with gene expression as the readout. Activated GPCR recruits the effector beta-arrestin, which brings TEVA protease close to its peptide substrate TEVcs. Blue light is also required to uncage TEVcs. Released TF translocates to the nucleus and drives mCherry expression.

FIG. 4C shows the genetic constructs used for FLARE and SPARK experiments. The first and third set are for HEK293T cells and the second set is for expression in neurons. hLOV is an improved LOV domain described in [11]. p2A is a self-cleaving peptide [37].

FIG. 4D shows the testing of protease mutants using FLARE in HEK293T cells. The indicated protease was incorporated into FLARE as shown in FIG. 4A and FIG. 4C. After transient transfection into HEK293T cells, cells were stimulated with 5 mM $CaCl_2$) and ionomycin for 30 sec in the presence or absence of blue light. Eight hours later, mCherry was imaged. Quantification was performed across 10 fields of view per condition (see FIG. 23). For uTEV1A, the light/dark signal ratio is 15, and the high/low Ca+2 signal ratio is 12. This experiment was performed two times with similar results.

FIG. 4E shows sample confocal fluorescence images from the first 8 columns in FIG. 4D. mCherry reflects FLARE turn-on. GFP reflects FLARE expression level. Scale bar, 20 μm.

FIG. 4F shows that uTEV1A improves FLARE performance in cultured neurons. Rat cortical neurons were transduced on day 12 with FLARE AAV1/2 viruses. 7 days later (at DIV19), we stimulated the neurons either electrically (3-s trains consisting of 32 1-ms 50 mA pulses at 20 Hz for a total of 1 or 5 min) or mechanically (via replacement of spent media with fresh media of identical composition). The light source was 467 nm, 60 mW/cm², 10% duty cycle (0.5s light every 5s). 18 hours later, cells were imaged by confocal microscopy (see FIG. 25). This experiment was replicated 3 times.

FIG. 4G shows that uTEV1A improves SPARK performance in HEK293T cells. SPARK constructs as shown in FIG. 4C containing either wild-type TEVA or uTEV1A were transiently expressed in HEK, and cells were stimulated with 10 μM isoproterenol for 1 min in the presence or absence of blue light. Nine hours later, mCherry was imaged. GFP reflects SPARK expression level. Scale bar, 10 μm.

FIG. 4H shows quantification of the experiment in FIG. 4G, across 10 fields of view per condition (see FIG. 26). For uTEV1A, light/dark signal ratio is 22.1, and the +/−agonist signal ratio is 20.7. This experiment was performed two times with similar results.

FIG. 5A shows fluorescence images of BY4741 yeast constitutively expressing STE2-citrine or STE2A-citrine and shows that the latter has much better surface localization. FIGS. 5B and 5C: Left: Sample FACS plots showing yeast cells 6 hours after 45-minute blue light stimulation. Percentage values reflect the fraction of cells with Citrine signal, i.e., cells that release TF to drive reporter gene expression.

FIG. 5B, Right: Control cells without light exposure. Each plot represents two replicates, n=10,000 cells. Scale bars, 10 μm.

FIG. 6A shows optimization of the LexA transcriptional activator fused to the LexA DNA-binding domain. In this embodiment, yeast are co-expressing mCherry-CRY-TEVA. Sample FACS plots 6 hours after variable amounts of blue light exposure. Percentages reflect the fraction of Citrine-positive cells. FIG. 6B shows sample FACS plots collected at various time points after 45-min blue light exposure to induce TF release. Percentage values reflect the fraction of cells with high Citrine intensity, i.e., cells in the upper FACS quadrants Q1+Q2 (quadrants defined in panel FIG. 1B). Each plot represents two replicates, n=20,000 cells.

FIGS. 7A and 7B show FACS plots summarizing the progress of the selections. Analysis of TEVA libraries after 3rd round of sorting (Related to FIG. 1F). FIG. 7A shows sample FACS plots 6 hours after blue light exposure for the indicated times. Percentages reflect the fraction of Citrine-positive cells. Each plot represents two replicates, n=10,000 cells. FIG. 7B shows sequencing analysis of yeast clones after the 3rd round of sorting from TEV directed evolution experiment.

FIG. 8A shows sample FACS plots collected 6 hours after blue light exposure for the indicated times (0.5, 2, and 5 min). FIG. 8B is the same as FIG. 8A but with CRY omitted to test for proximity-dependence of TEV-TEVcs interaction (cells express TEV-mCherry instead of CRY-TEV-mCherry). Each plot represents two replicates, n=10,000 cells.

FIG. 9A shows SDS-PAGE (9%) gel electrophoresis of purified TEV proteases. FIG. 9B shows TEV protease kinetics. Plots of initial rates of TEV protease vs. concentration of recombinant fusion protein substrate MBP-ENLYFGS-eGFP. (SEQ ID NO:5). Reactions at different substrate concentrations [0.0075-0.32 mM] were incubated with purified protease [100 nM] in 50 mM Tris-HCl buffer (pH 8.0), 10% Glycerol containing 1 mM EDTA and 2 mM of DTT at 30° C. A reaction aliquot was taken at different time points and terminated by the addition of sodium dodecyl sulfate-polyacrylamide gel electrophoresis (SDS-PAGE) sample buffer and immediately flash-frozen. The reaction products were separated by SDS-PAGE at 4° C. The band intensities of the product were quantified by in-gel fluorescence with a Thyphoon 9410. Quantitation of gels was performed using ImageJ on raw images under non-saturating conditions. Initial velocities were calculated under conditions of less than 25% substrate hydrolysis. Peak integrations were tabulated, converted into product concentrations using the standard curves. Data was fit to a Michaelis-Menten enzyme kinetics model with center values representing the mean and error bars representing the standard deviation of three technical replicates. Truncated TEV proteases were subcloned and expressed in the vector pRK793 (backbone pMal-C2). When full length proteases were expressed in the same vector, the higher affinity of TEV proteases for its product inhibited TEV purification. MBP-TEV proteases (TEVcs was deleted) were cloned and expressed into pYFJ16 vector.

FIG. 10A shows TEVA fused to CRY and BFP is expressed cytosolically. LexA-VP16 TF is tethered to the plasma membrane via a TEV cleavage site (TEVcs), a LOV domain to cage the TEVcs, mCherry as an expression marker and a CIBN binding partner for CRY. Upon exposure of cells to blue 450 nm light, the CRY-CIBN interaction brings the TEV protease proximal to TEVcs, and the LOV domain changes conformation to expose TEVcs. Sequences sensitive to TEV proteolysis will release the TF, which translocates to the nucleus and drives expression of the reporter gene Citrine. As a control, full length protease was fused to the BFP omitting the CRY module. FIG. 10B shows sequence profile of the seven TEVcs libraries with randomized nucleotides before sorting. FIG. 10C shows analysis of single randomized positions in the TEV cleavage site. Sample FACS plots 6 hours after blue light exposure. Each plot represents one replicate, n=10,000 cells. FIG. 10C includes SEQ ID NOS:69, 70, 71, 72, 73, 75, and 30 in order of appearance.

FIG. 12A shows the LexA DNA-binding domain was fused to different transcription activators (TAs), VP16, B42 and Gal4 with mCherry. Constructs were expressed in yeast strains with different numbers of LexA boxes upstream of the Citrine gene. FIG. 12B shows FACS data showing the effect of varying the number of LexA boxes in the promoter with different TAs. FACS data collected 12 hours following induction. Each plot represents two replicates, n=20,000 cells.

FIG. 14A shows FACS analyses of re-amplified yeast pools, 6 hours after various amounts of blue light exposure. Percentages reflect the fraction of Citrine-positive cells. FIG. 14B shows sequencing analysis of yeast clones after the 3rd round of selection. FIG. 14B discloses SEQ ID NO: 75. This experiment was performed once.

FIG. 18A shows side by side comparison of full-length uTEV proteases with the high-affinity TEVcs (ENLYFQ/S (SEQ ID NO: 5)). Sample FACS plots 12 hours after galactose induction. FIG. 18B shows side by side comparison of truncated uTEV proteases with the low-affinity TEVcs (ENLYFQ/M (SEQ ID NO: 6)). Sample FACS plots 6 hours after blue light exposure for the indicated times. Each plot represents two replicates, n=20,000 cells for (A) and 10,000 for (B). FIG. 18C shows side-by-side comparison in yeast, with full-length proteases and the high-affinity TEVcs (ENLYFQ/S (SEQ ID NO: 5)). First four columns show yeast induced with galactose in the dark for 6.5 to 18 hours before FACS analysis. The last two columns were irradiated with light before FACS analysis 6 hours later.

(B) The same aliquots were incubated with 100 µL of Amylose Resin® and after 10 min of binding, the supernatant was analyzed by in-gel fluorescence imaging.

Figure 20:
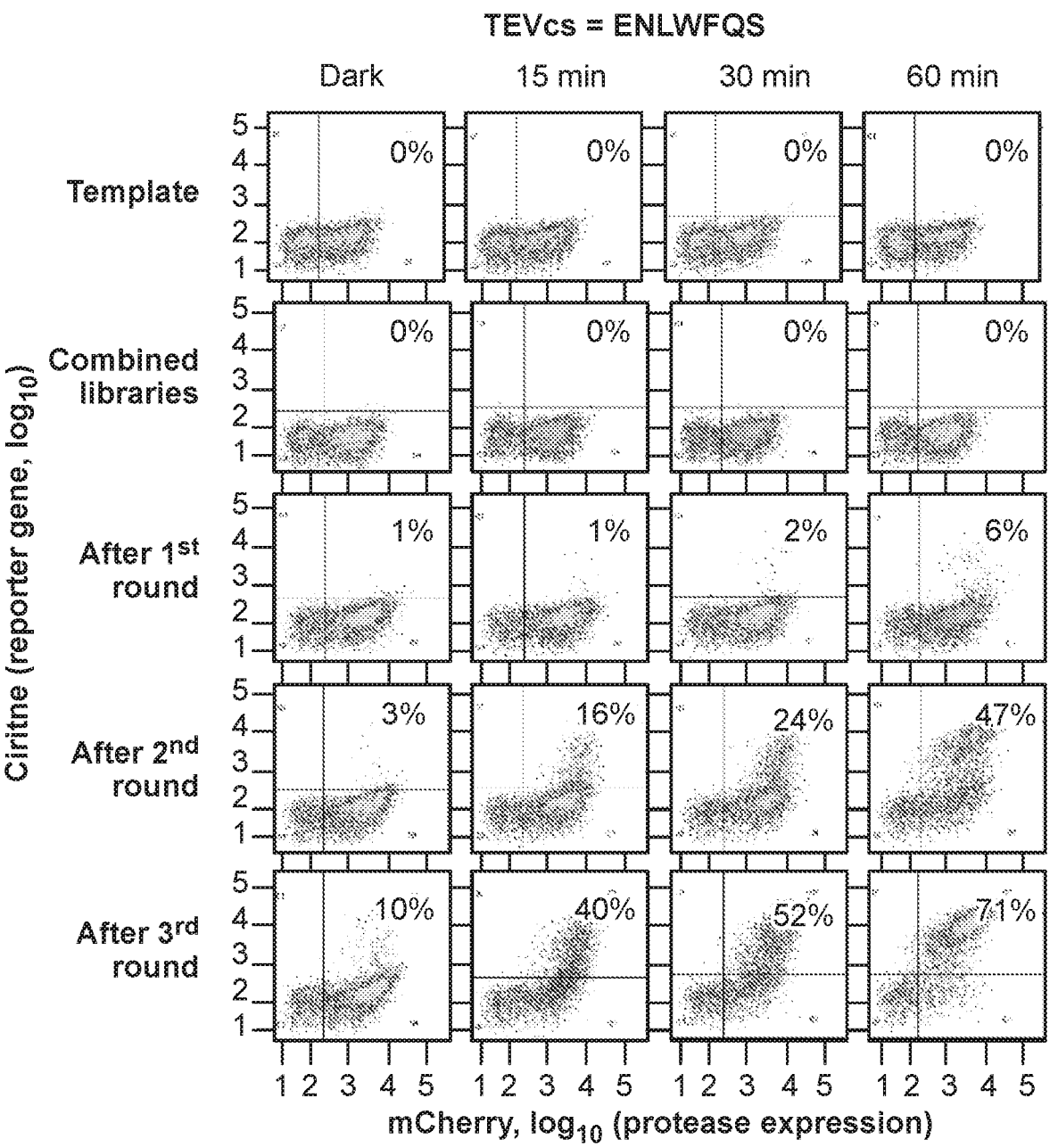

FIG. 20 shows FACS plots summarizing the progress of the selections. Analysis of full-length TEV libraries after 3 rounds of sorting (Related to FIG. 3H). Sample FACS plots 6 hours after blue light exposure for the indicated times. Percentages reflect the fraction of Citrine-positive cells. Each plot represents two replicates, n=10,000 cells. Figure discloses SEQ ID NO: 8.

FIGS. 21A and 21B show sequencing analysis of yeast clones after the 3rd round of selection. Related to FIG. 3H. (A) TEV libraries evolved against TEVcs (ENLHFQ/S (SEQ ID NO: 7)). (B) TEV libraries evolved against TEVcs (ENLWFQ/S (SEQ ID NO: 8)).

Figure 22A:
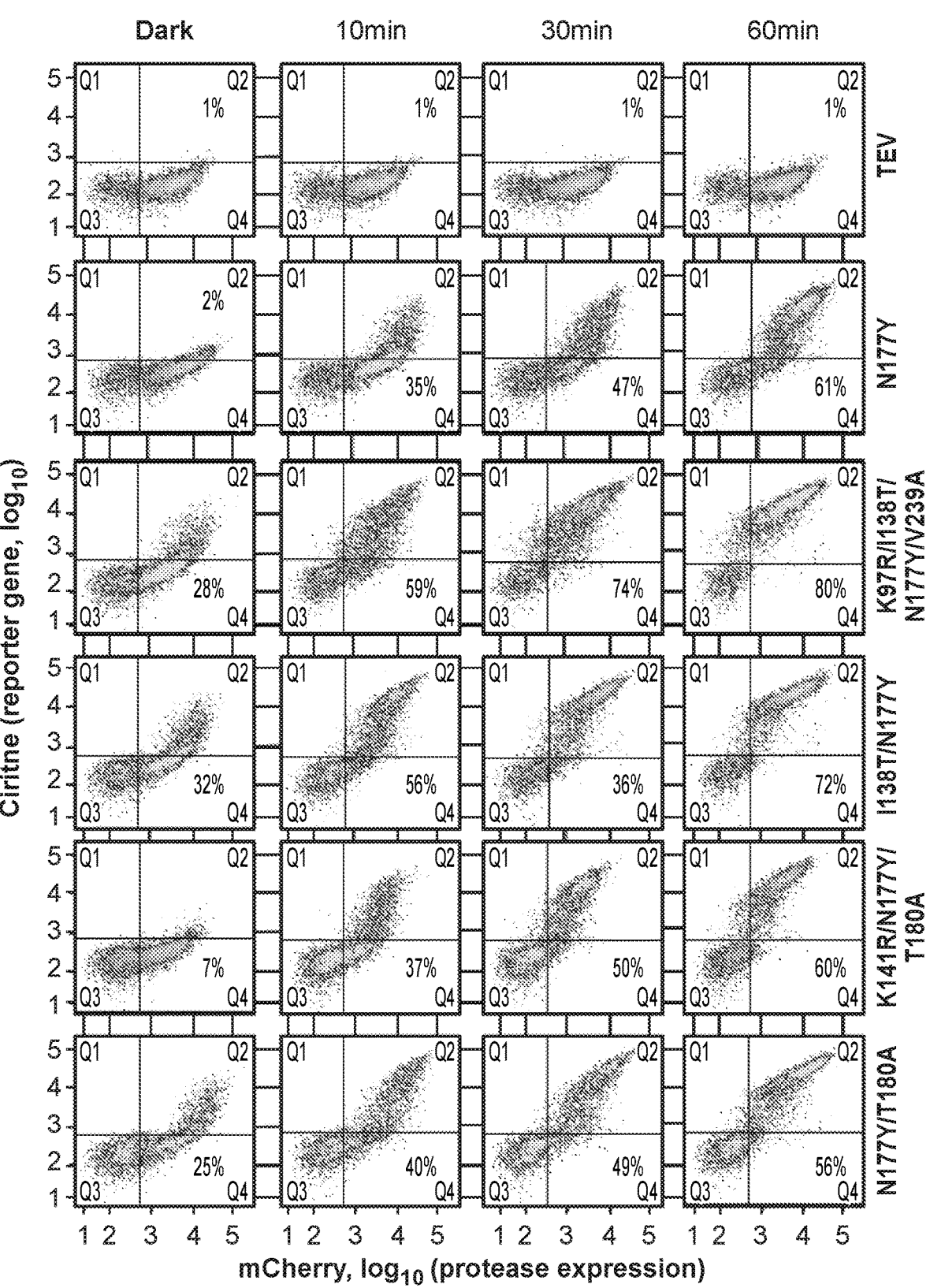
Figure 22B:
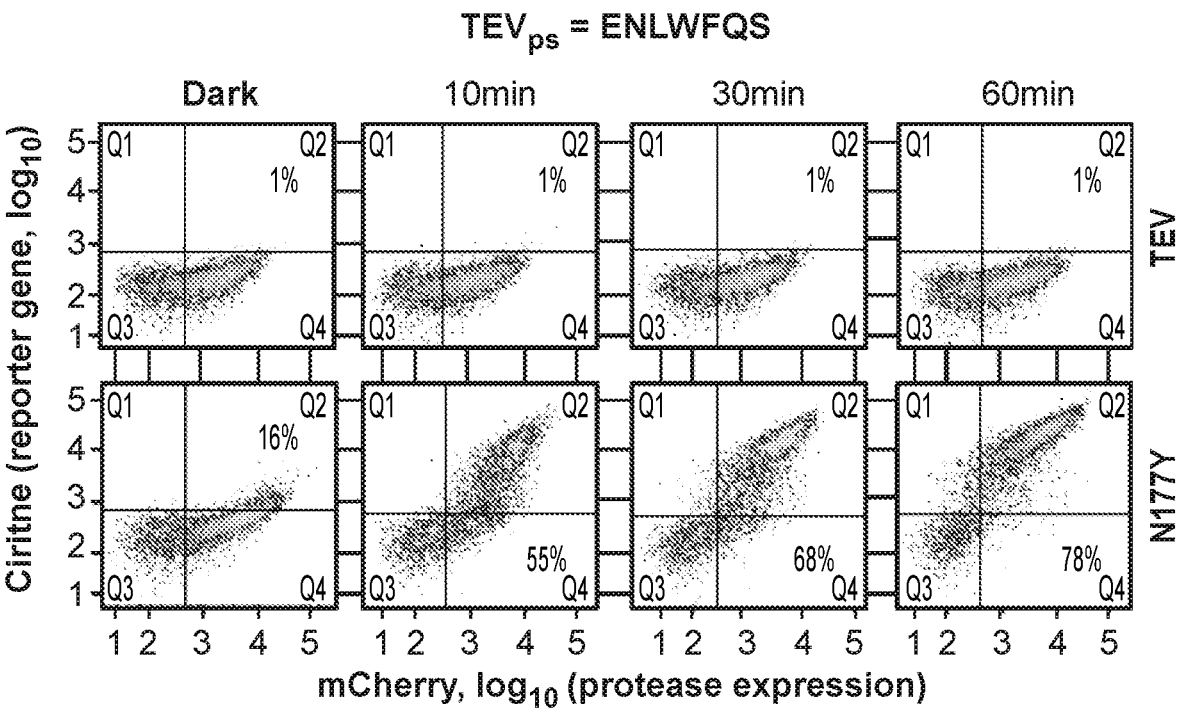
Figure 23A:
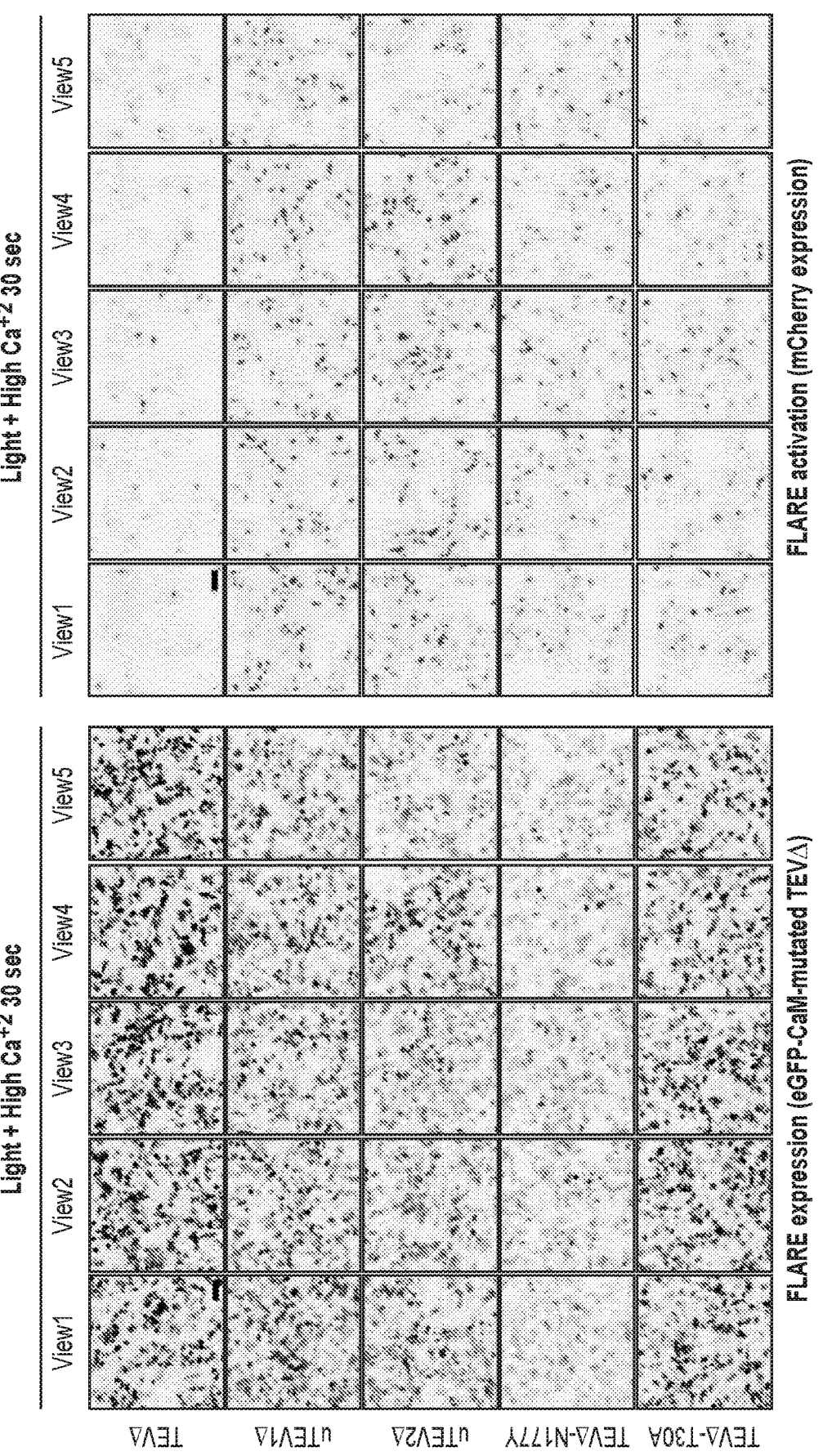
Figure 23B:
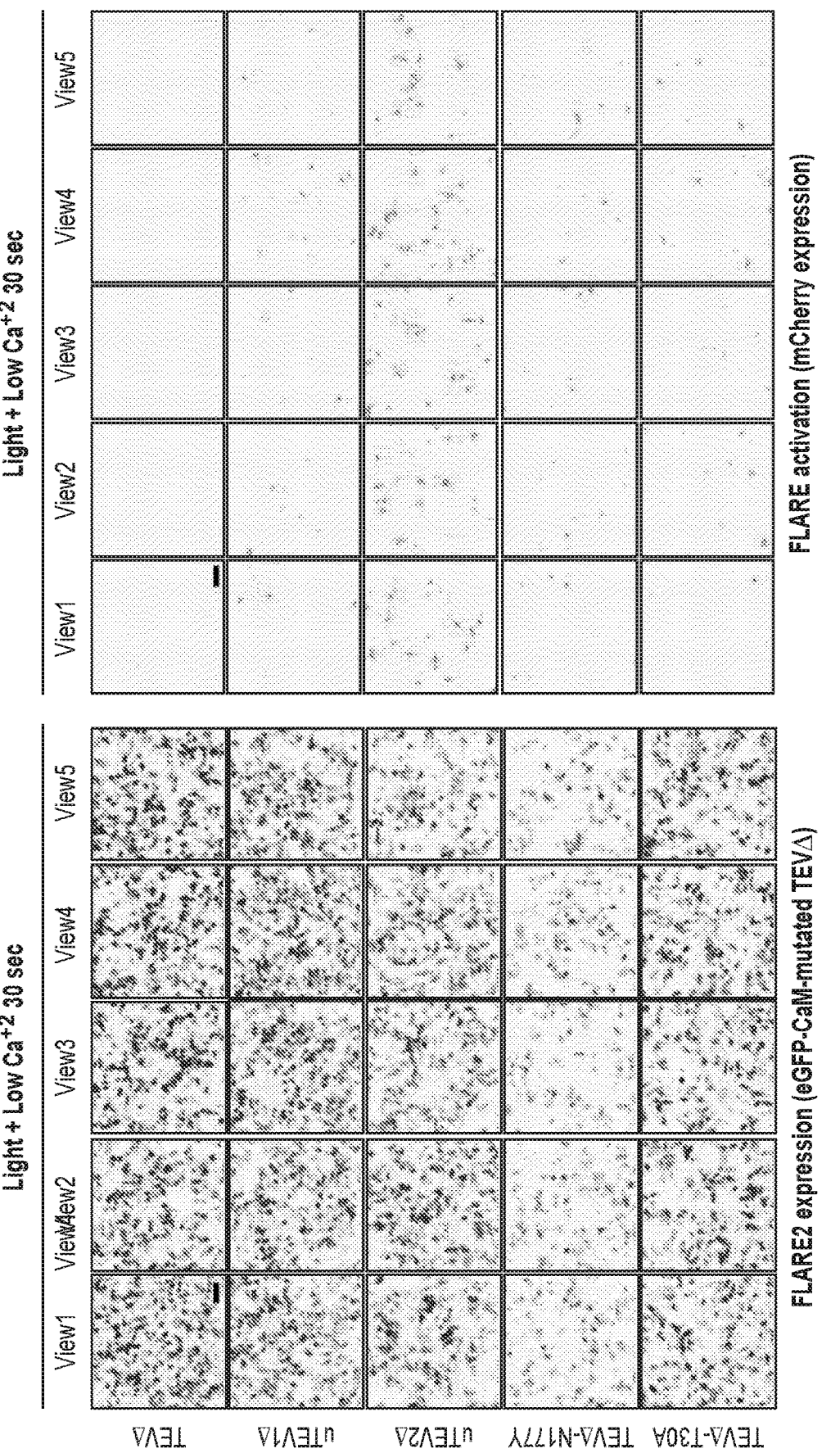
Figure 23C:
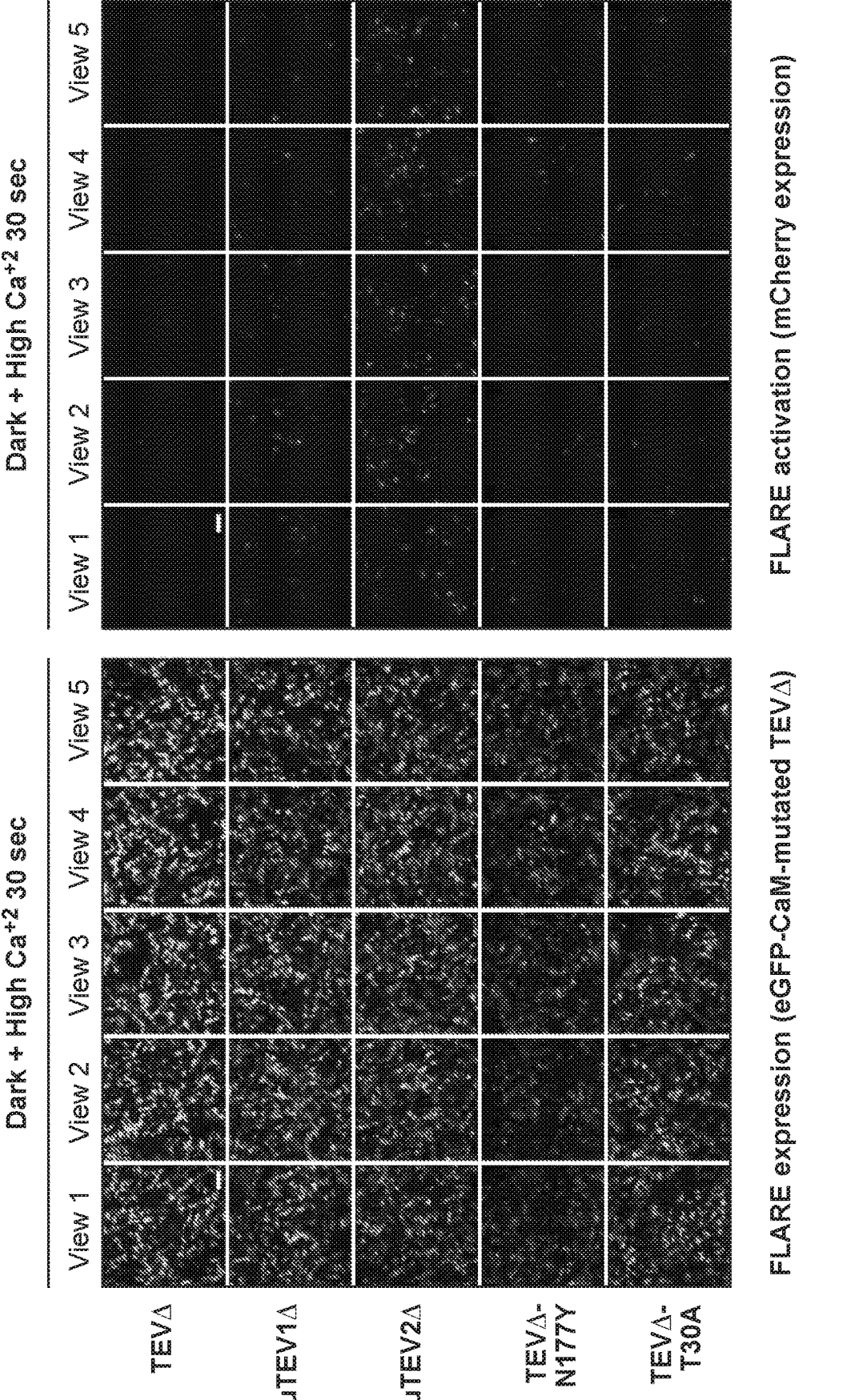
Figure 23D:
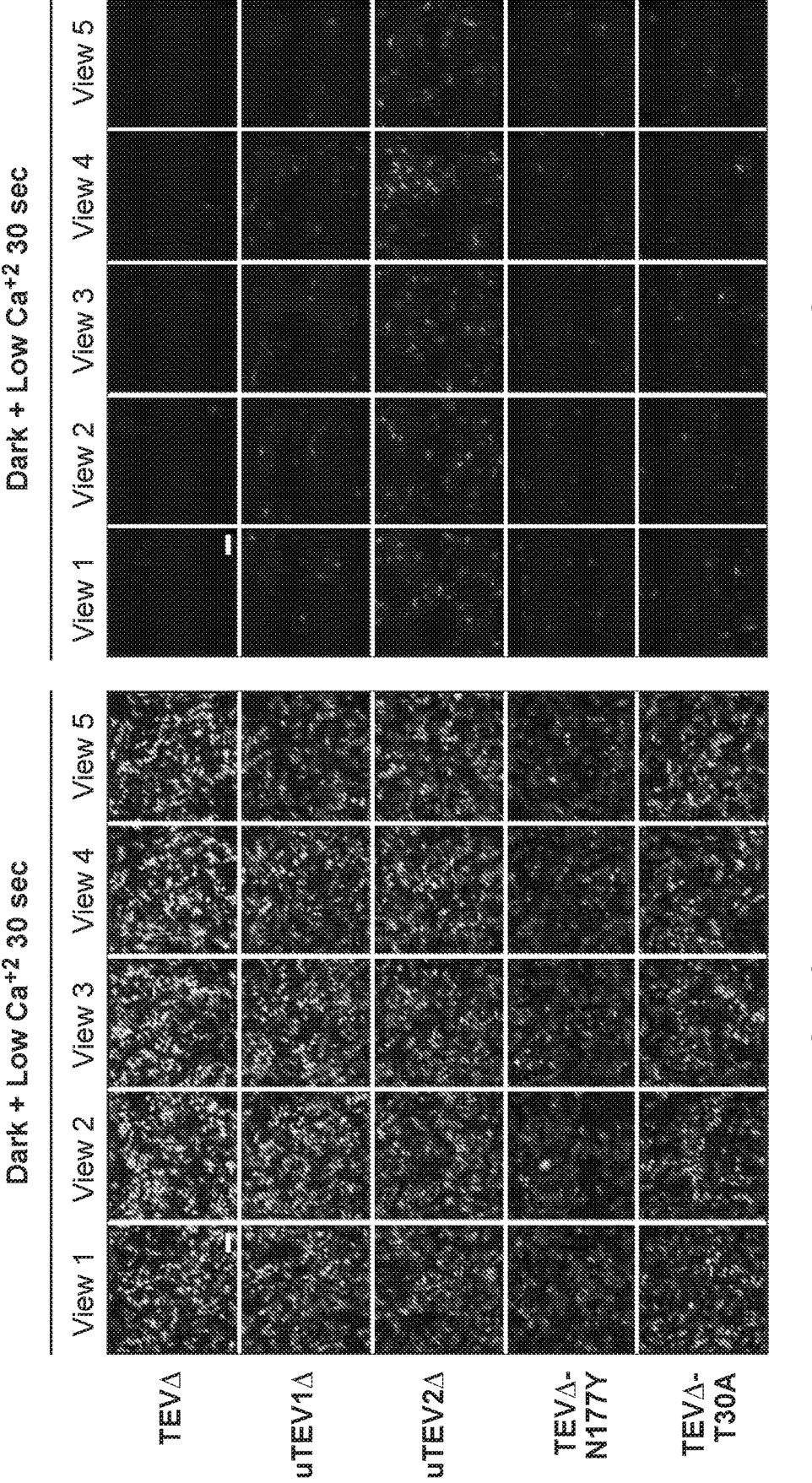

FIGS. 22A and 22B show shows characterization of evolved single and double mutants with altered recognition sequence. Related to FIG. 3H. Sample FACS plots 6 hours after blue light exposure for the indicated times. (A) TEVcs (ENLHFQ/S (SEQ ID NO: 7)) (B) TEVcs (ENLWFQ/S (SEQ ID NO: 8)). Percentages reflect the fraction of Citrine-positive cells. Each plot represents two replicates, n=10,000 cells.

Figure 4C:
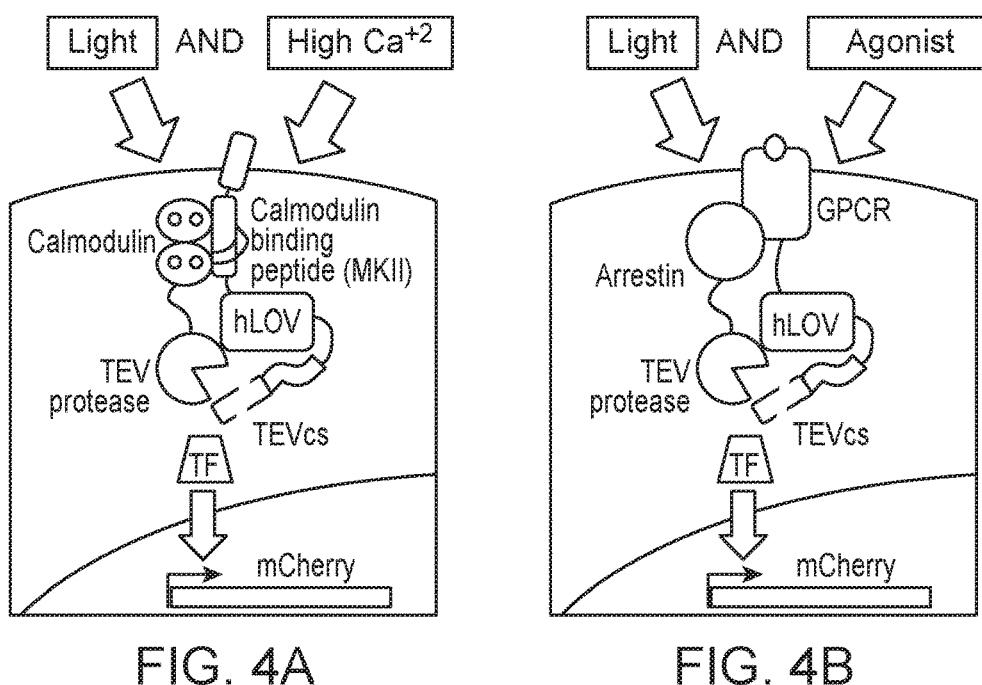

FIGS. 23A, 23B, 23C, and 23D show the evaluation of additional TEV mutants in the context of FLARE. (Summary of results in FIG. 4E with additional fields of view). HEK293T cells were transiently transfected with FLARE constructs (FIG. 4A) incorporating the indicated TEV mutant. Three FLARE constructs were introduced by transient transfection into HEK293T cells. Stimulation was performed using 5 mM CaCl$_2$) and 2 µM ionomycin for 30 sec in the presence or absence of blue light. Light source was 467 nm, 60 mW/cm2, 10% duty cycle (0.5s light every 5s). Nine hours later, cells were fixed and imaged. (Summary of results in FIG. 4D). 5 fields of view per condition. Scale bars, 10 µm.

Figure 24A:
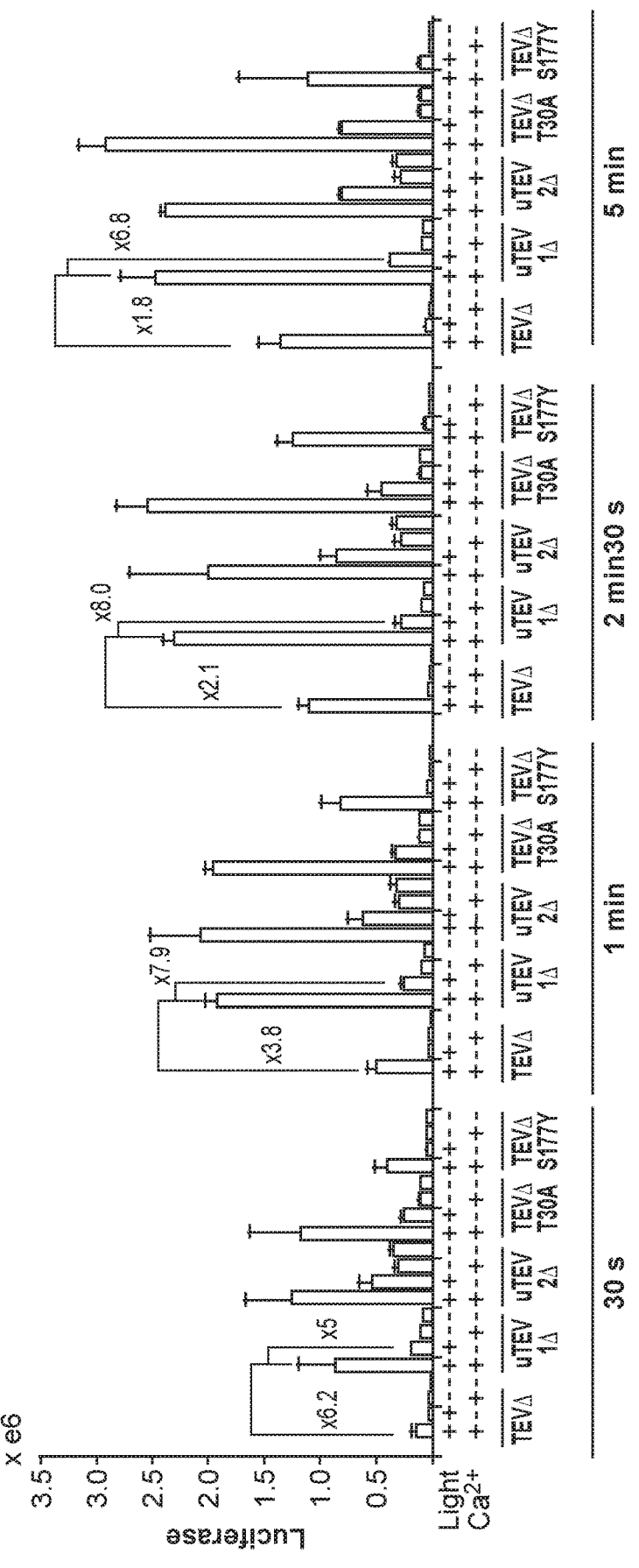
Figures 24B, 24C:
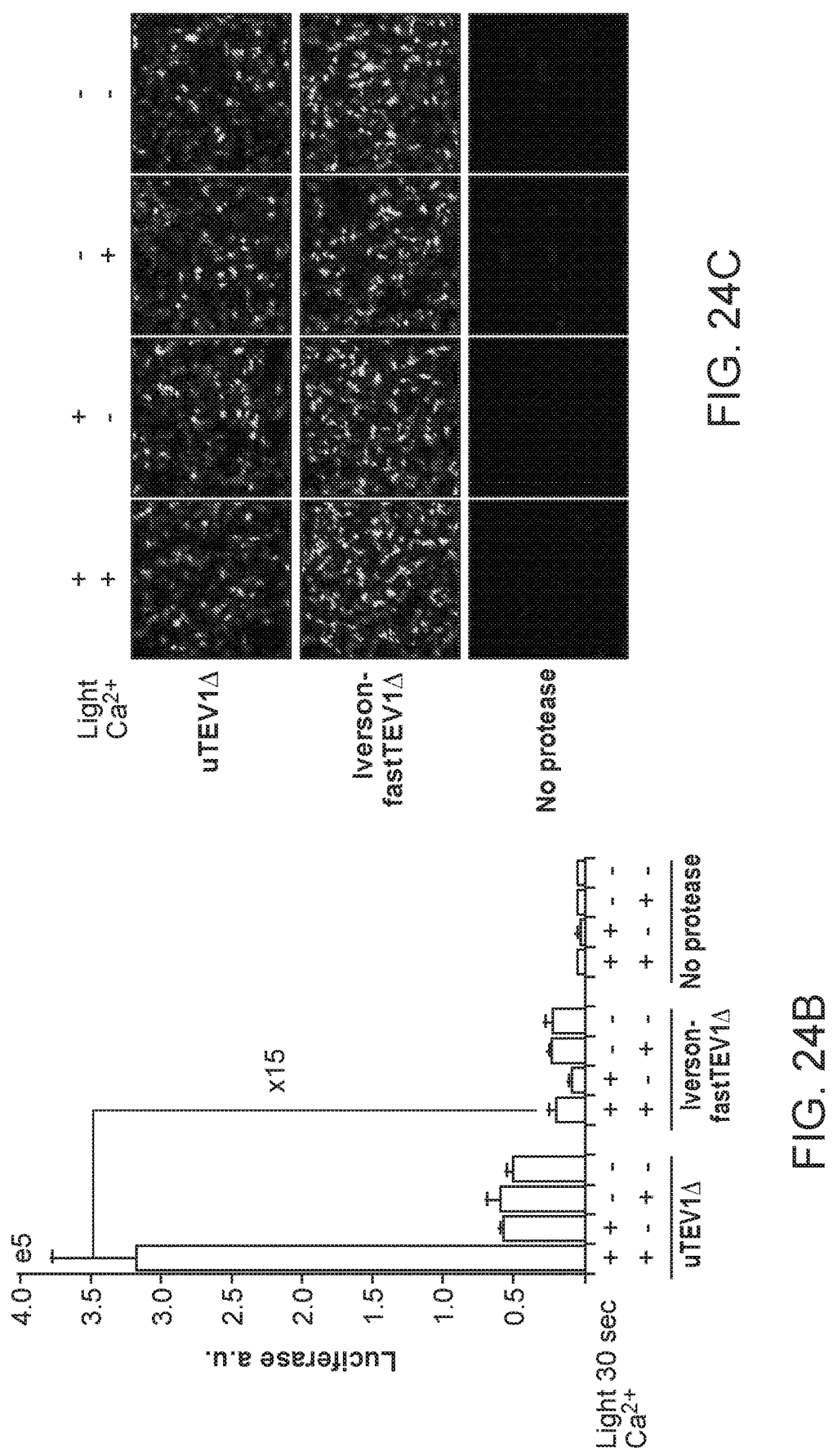

FIGS. 24A, 24B, and 24C show evaluation of TEV mutants in the context of FLARE. Related to FIG. 4C. (A) HEK293T cells were transiently transfected with FLARE constructs (UAS-Luciferase as reporter gene, FIG. 4A) incorporating the indicated TEV mutant. Stimulation was performed using 5 mM CaCl$_2$) and ionomycin at different time points in the presence or absence of blue light. Light source was 467 nm, 60 mW/cm2, 10% duty cycle (0.5s light every 5s). Eight hours later, cells were treated with Nano-Glo® Luciferase according to manufacturer's instructions and luciferase activity measured in a plate-reader. (B) Comparison of uTEV1A with the truncated version of Iverson's TEV in the context of FLARE. Cells were stimulated and treated same as (A). (C) Confocal microscopy imaging of cells expression uTEV1Δ and Iverson's TEVA.

Figure 25A:
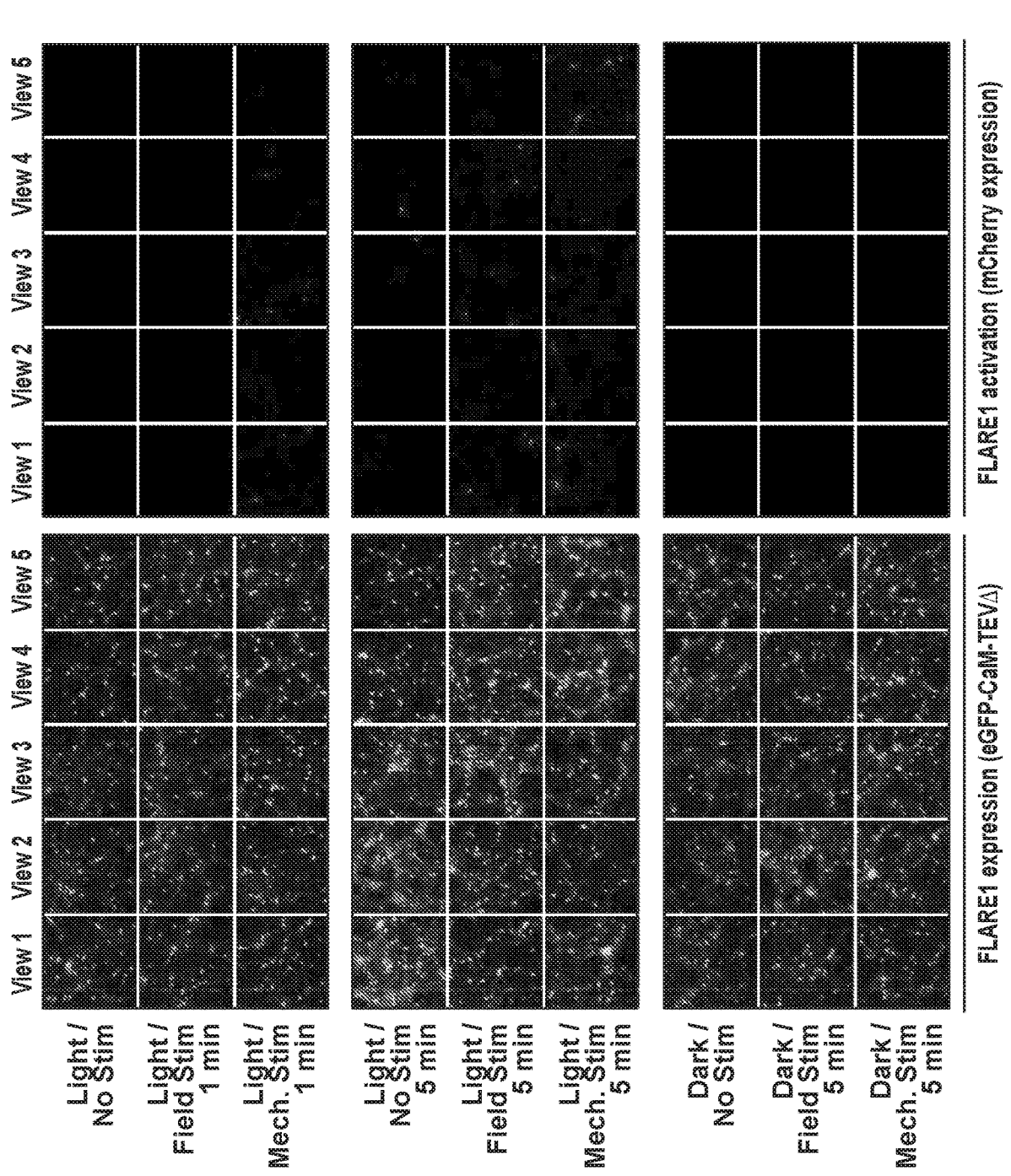
Figure 25B:
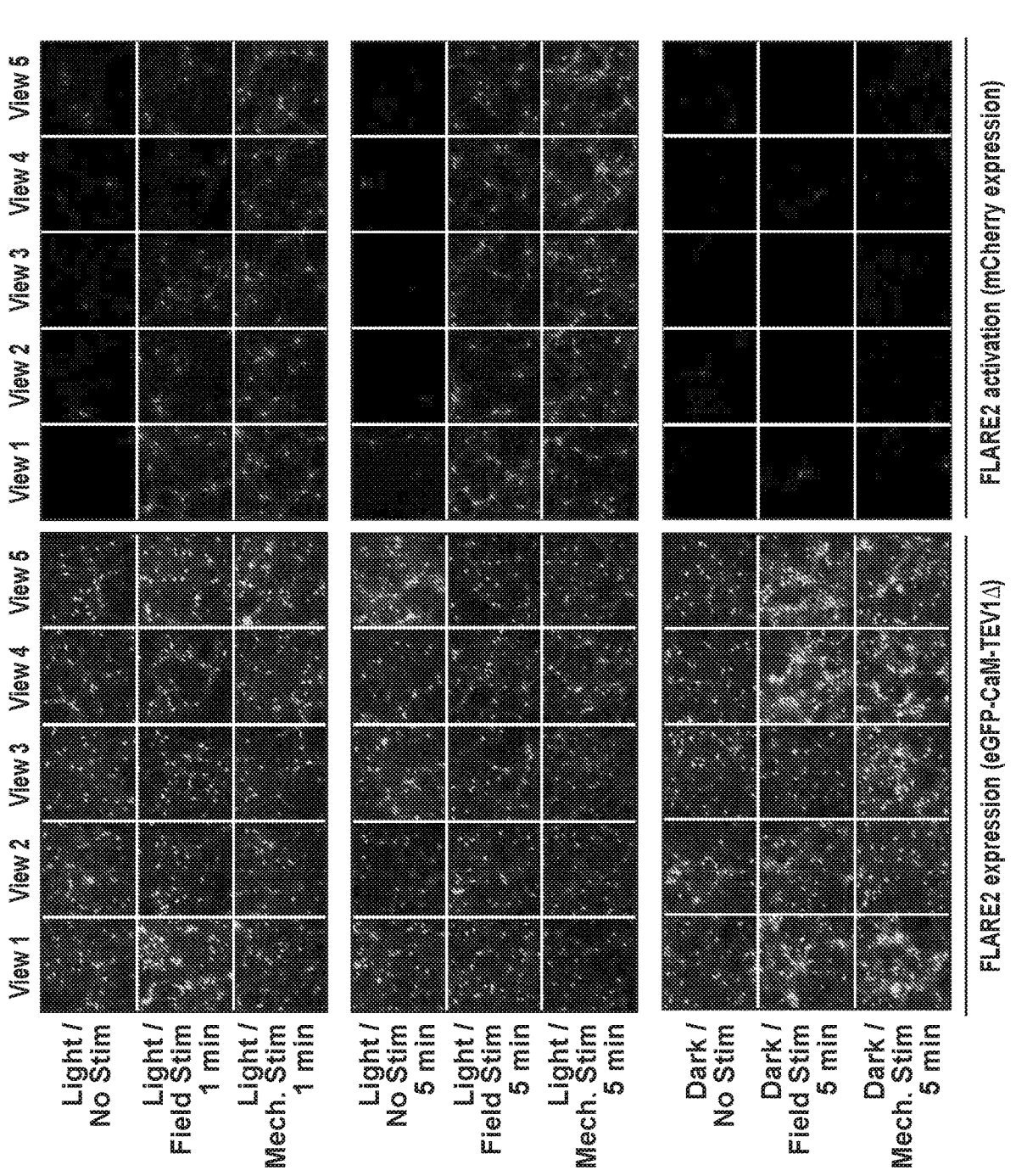
Figure 25C:
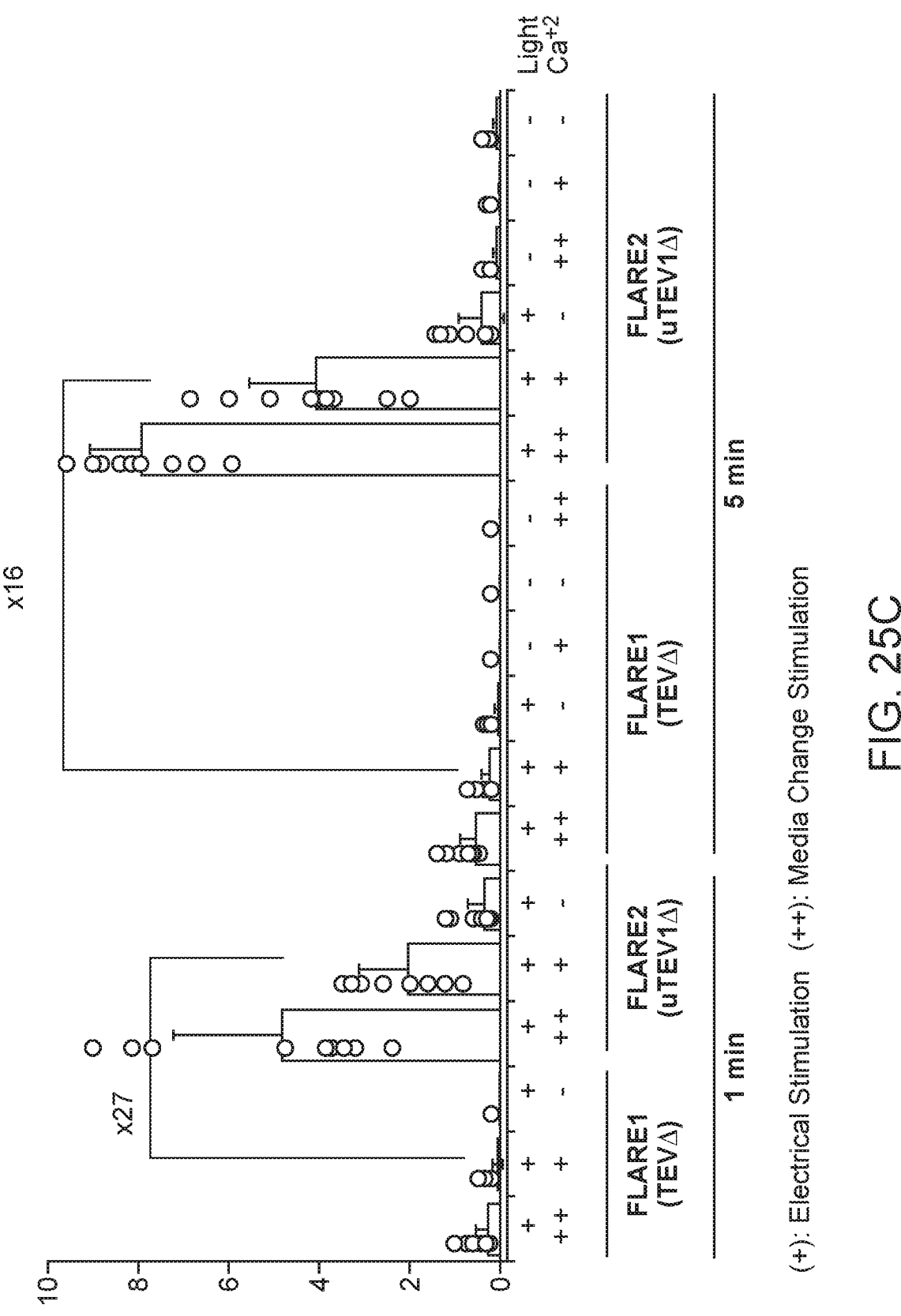

FIGS. 25A, 25B, and 25C show the evaluation of uTEV1Δ in the context of FLARE in neurons. (Summary of results in FIG. 4F but with additional field of views). Rat cortical neurons were transduced at day 12 with FLARE constructs (packaged into AAV1/2 viruses [44]) containing (A) the original TEVA protease or (B) evolved TEV1Δ-protease. At day 19 in vitro (DIV19), we stimulated the neurons using either field stimulation (3-s trains consisting of 32 1-ms 50 mA pulses at 20 Hz for a total of 1 or 5 min), or via replacement of culture media (with media of identical composition; this mechanically stimulates the cultures and also provides a fresh source of glutamate). Light source was 467 nm, 60 mW/cm2, 10% duty cycle (0.5s light every 5s). Imaging was performed 18 hours later. This experiment was replicated 3 times. For each condition, 5 fields of view are shown. Scale bars, 10 µm. (C) Signal ratios were based on mean mCherry intensity relative to eGFP signal across >100 cells from 10 fields of view per condition. White dots indicate quantitation of mCherry signal intensity from different fields of view, colored bars indicate mean signal intensity calculated from these fields of view.

Figure 26A:
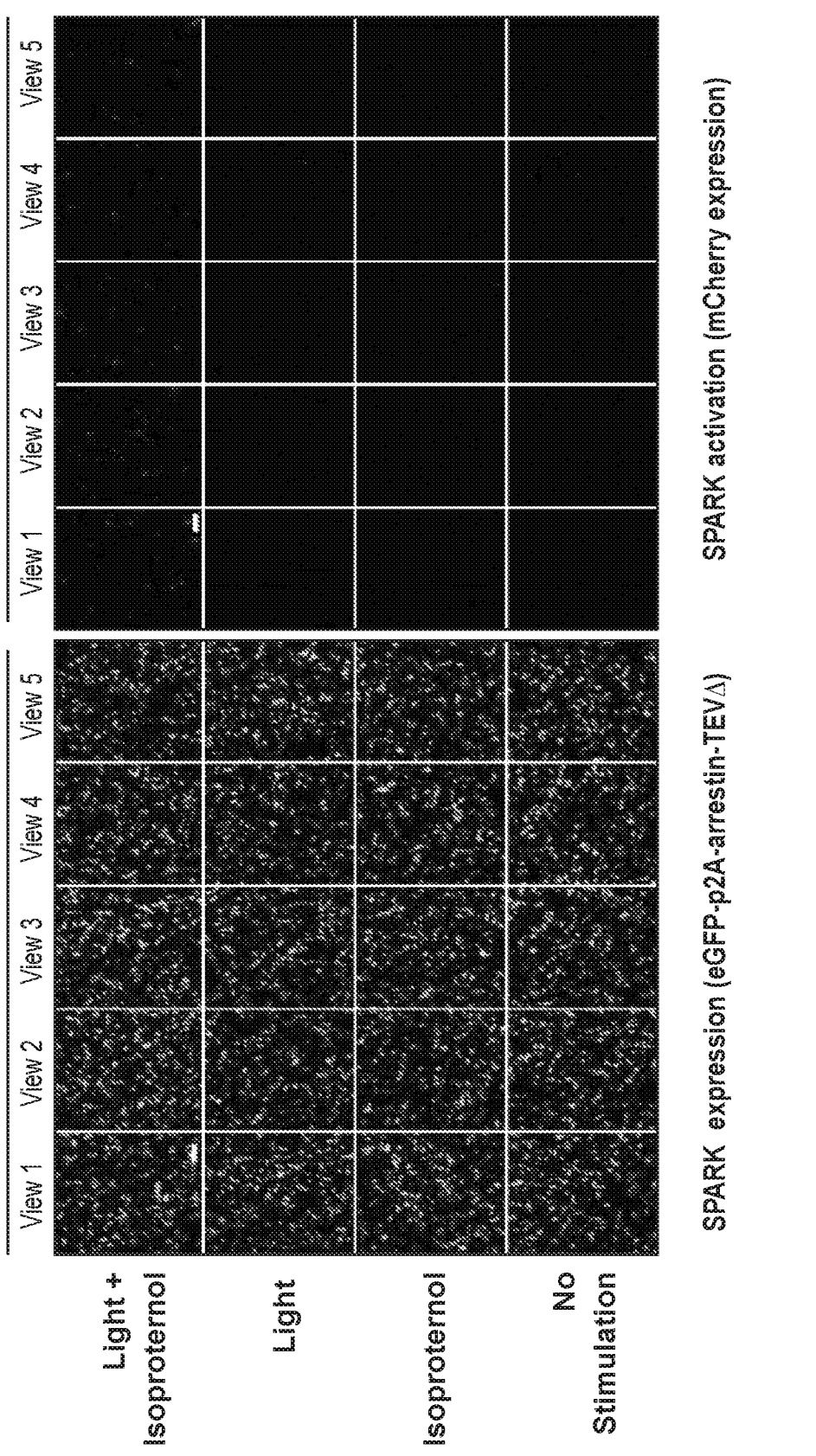
Figure 26B:
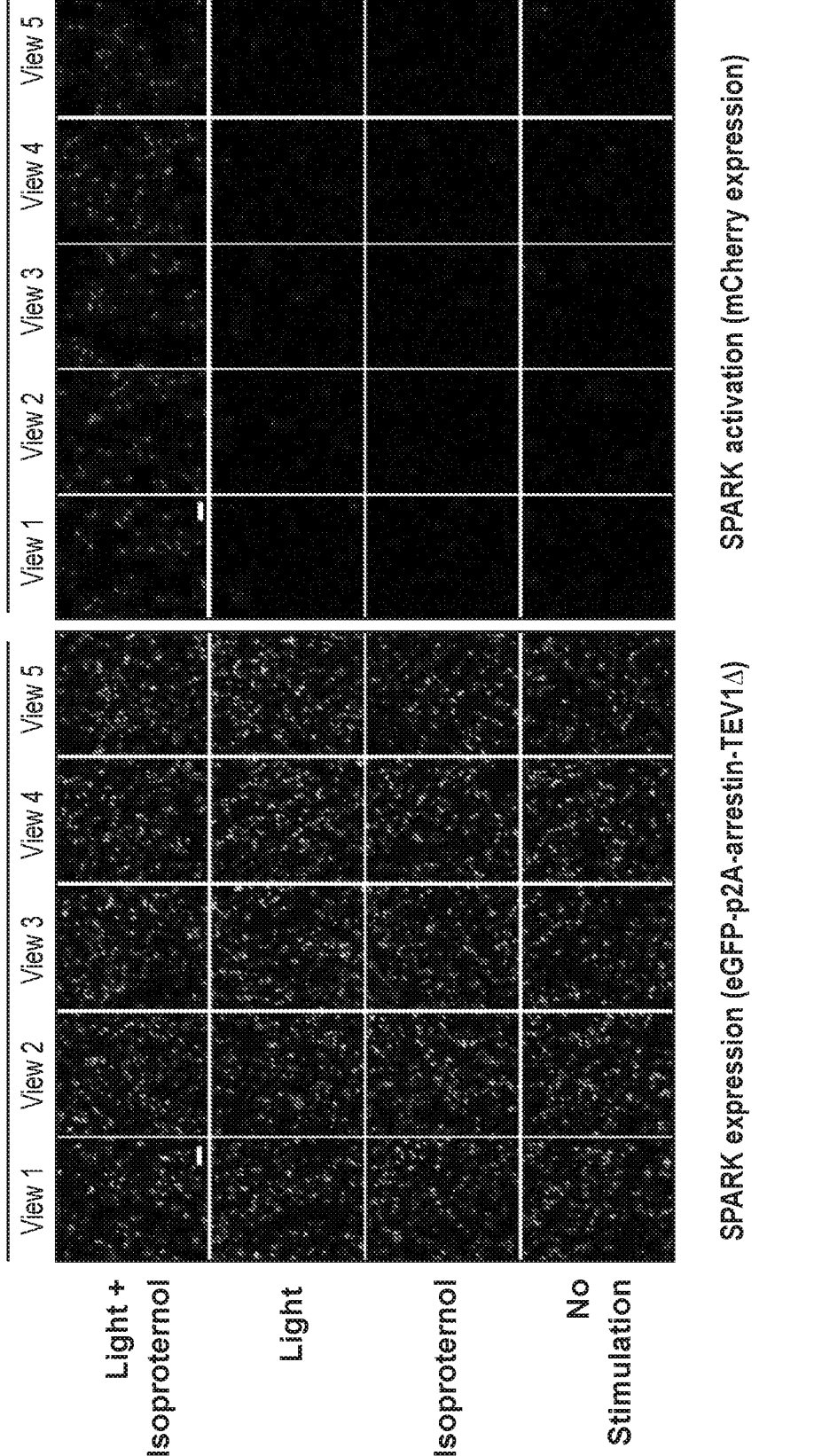

FIGS. 26A and 26B show evaluation of evolved protease uTEV1Δ using SPARK in HEK293T cells. (Summary of results in FIG. 4G but with additional field of views). HEK293T cells were transiently transfected with SPARK constructs (FIG. 4B) containing the indicated protease variant. Cells were stimulated with 10 µM isoproterenol for 60 sec in the presence or absence of blue light (467 nm, 60 mW/cm2, 10% duty cycle (0.5 s light every 5s)). Nine hours later, cells were imaged. This experiment was replicated two times. Scale bars, 10 µm.

Figure 27:
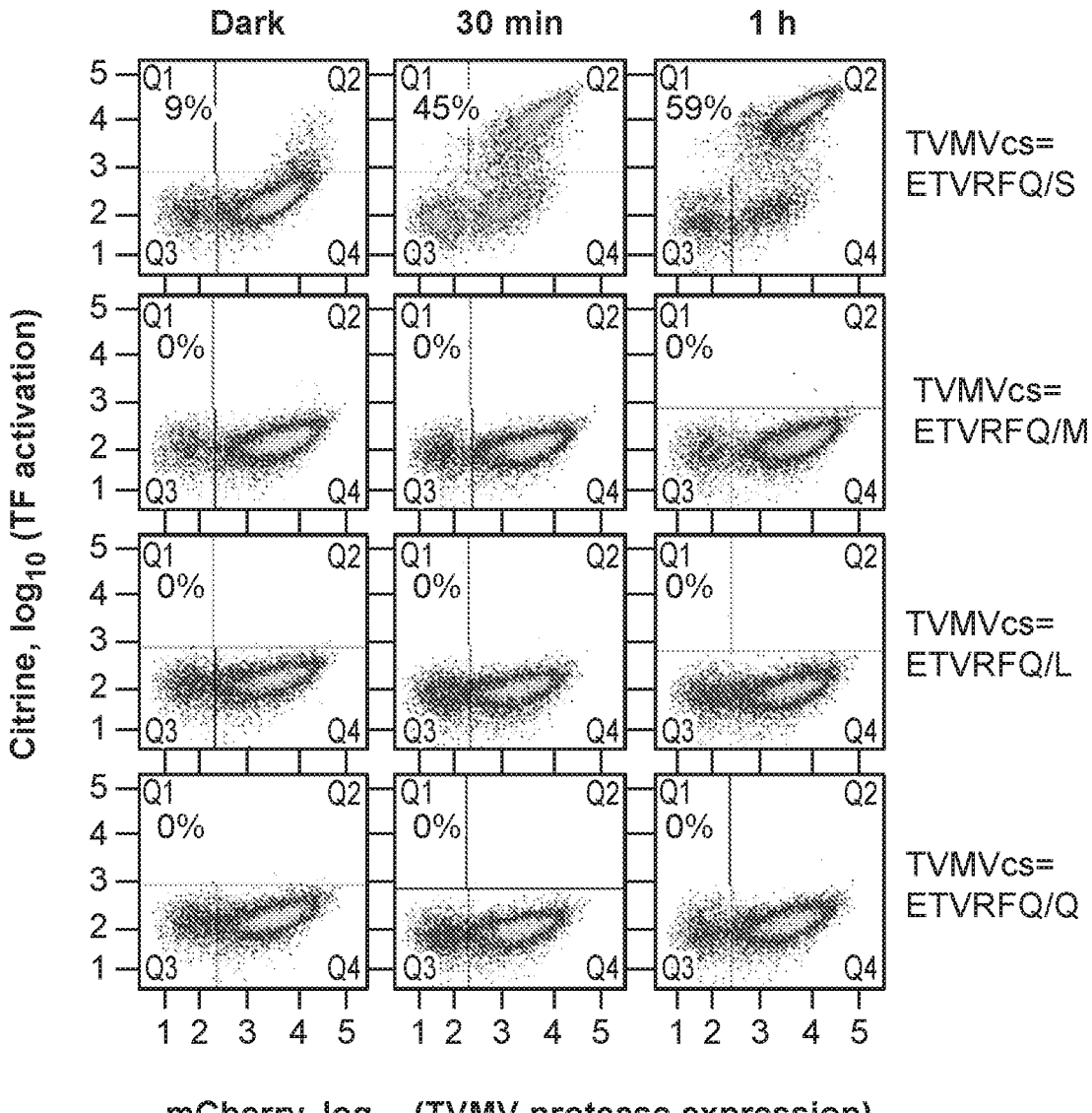

FIG. 27 shows extension of the yeast platform to the TVMV protease. Light and sequence-dependency citrine expression by TVMV protease. Percentage values reflect the fraction of cells with Citrine signal. Each plot represents two replicates, n=20,000 cells. Figure discloses SEQ ID NOS 79-82, respectively, in order of appearance.

Figure 28:
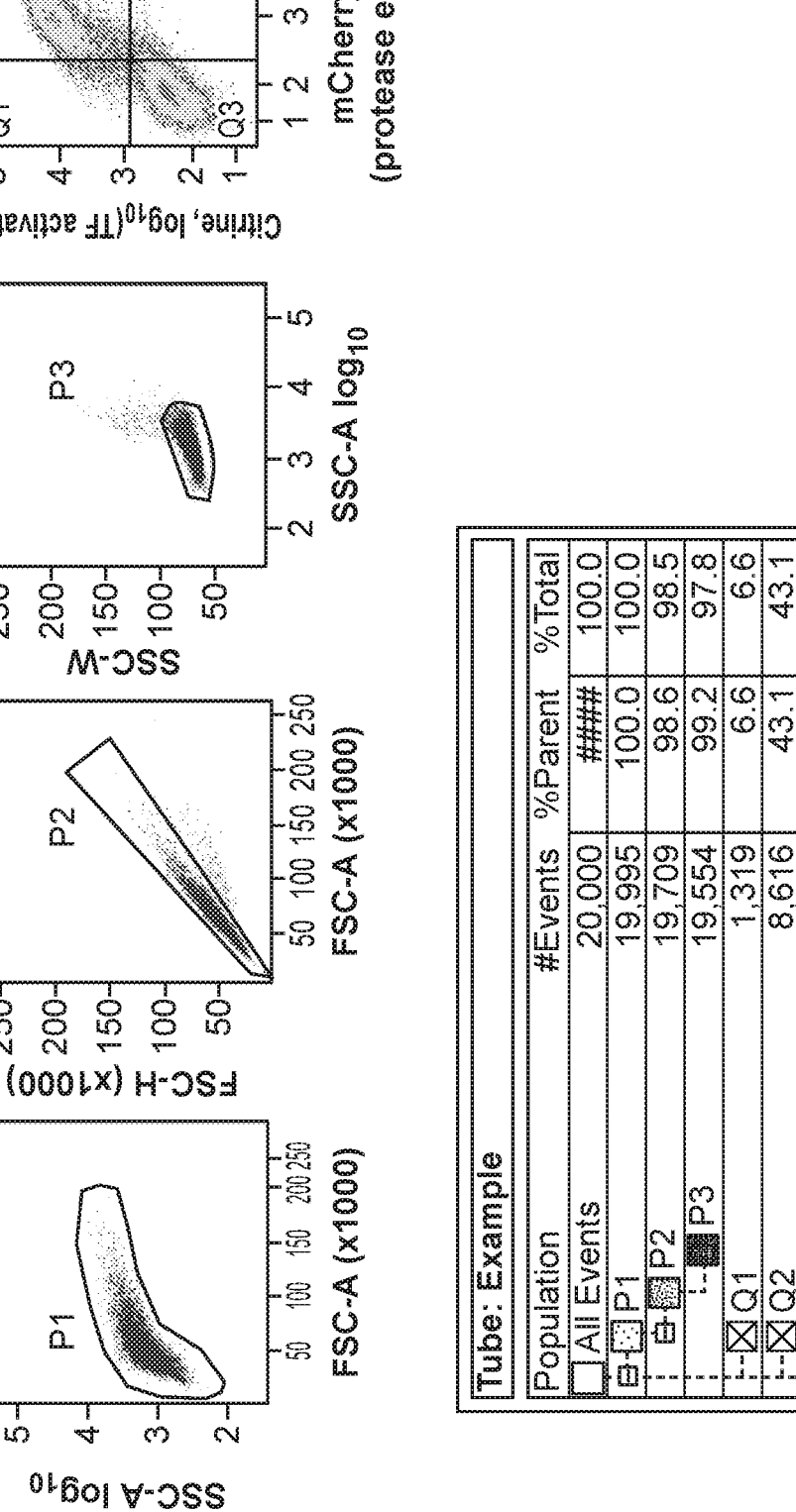

FIG. 28 is a five-panel drawing that shows sample FACS plots showing the gating parameters. Percentage values reflect the fraction of cells with high Citrine intensity, i.e., cells in the upper FACS quadrants Q1+Q2.

DEFINITIONS

As used herein, the term "catalytic efficiency" refers to the rate at which an enzyme, such as a protease, catalyzes a reaction. Catalytic efficiency is typically expressed as Kcat or Kcat/Km.

The term "fusion protein" refers to protein consisting of at least two domains that are encoded by separate genes that have been joined so that they are transcribed and translated as a single unit, producing a single polypeptide.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "Operably linked" refers to a juxtaposition wherein the components so described are in a relationship permitting them to function in their intended manner. For instance, a promoter is operably linked to a coding region of a nucleic acid if the promoter affects transcription or expression of the coding region of a nucleic acid.

A "vector" or "expression vector" is a replicon, such as plasmid, phage, virus, or cosmid, to which another DNA segment, i.e. an "insert", may be attached so as to bring about the replication of the attached segment in a cell.

"Heterologous," as used herein, refers to a nucleotide or polypeptide sequence that is not found in the native (e.g., naturally-occurring) or wild-type nucleic acid or protein, respectively.

As used herein, the term "affinity" refers to the equilibrium constant for the reversible binding of two agents (e.g., a protease and a polypeptide comprising a protease cleavage site) and is expressed as Km. Km is the concentration of peptide at which the catalytic rate of proteolytic cleavage is half of Vmax (maximal catalytic rate). Km is often used in the literature as an approximation of affinity when speaking about enzyme-substrate interactions.

The term "binding" refers to a direct association between two molecules, due to, for example, covalent, electrostatic, hydrophobic, and ionic and/or hydrogen-bond interactions, including interactions such as salt bridges and water bridges. "Specific binding" refers to binding with an affinity of at least about $10^{-7}$ M or greater, e.g., $5\times10^{-7}$ M, $10^{-8}$ M, $5\times10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "modified protease" refers to a protease that differs from a natural or wild-type protease in nucleic acid or amino acid sequence. The term "modified" encompasses proteases having amino acid mutations that are not found in natural or wild-type protease.

The term "mutant," in the context of a modified protease described herein, means a polypeptide, typically recombinant, that comprises one or more amino acid substitutions relative to a corresponding, functional protease.

An amino acid or nucleotide base "position" is denoted by a number that sequentially identifies each amino acid (or nucleotide base) in the reference sequence based on its position relative to the N-terminus (or 5'-end). In general, the amino acid residue number in an amino acid sequence is determined by counting from the N-terminus. However, due to deletions, insertions, truncations, or fusions, the residue number of a mutant protease will not necessarily be the same as the number of its corresponding position in the reference sequence. For example, in a case where a variant has a deletion relative to an aligned reference sequence, there will be no amino acid in the variant that corresponds to a position in the reference sequence at the site of the deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared or aligned with the reference sequence.

The term "substantially similar" refers to a value, measurement, or property that is nearly identical to another reference value, measurement, or property, for example a difference of plus or minus 10%, 9%, 8%, 7%, 6%, 5%, 4%, 3%, 2% or 1% relative to a reference value. In the context of protease substrate specificity, the term "substantially similar" refers to the binding affinity ($K_m$) of a modified protease that is within 1%, 2%, 3%, 4%, 5%, 6%, 7%, 8%, 9% or 10% of the substrate binding affinity of a wild-type or unmodified protease.

The terms "identical," "substantially identical" or percent "identity," in the context of two or more nucleic acids or polypeptide sequences, refer to two or more sequences or subsequences that are the same or have a specified percentage of nucleotides or amino acid residues that are the same (e.g., 60%, 65%, 70%, 75%, 80%, 85%, 90%, 95%, 96%, 97%, 98% or 99% identity over a specified region), when compared and aligned for maximum correspondence over a comparison window, or designated region, as measured using the BLAST and PSI-BLAST algorithms, which are described in Altschul et al. (J. Mol. Biol. 215:403-10, 1990), and Altschul et al. (Nucleic Acids Res., 25:3389-3402, 1997), respectively. Software for performing BLAST analyses is publicly available through the National Center for Biotechnology Information (see the internet at ncbi.nlm.nih-.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, an expectation (E) of 10, and the BLOSUM62 scoring matrix (see Henikoff and Henikoff, Proc. Natl. Acad. Sci. USA 89:10915-10919, 1992).

All nucleic acid and amino acid sequences disclosed herein can include sequences that have at least 60%, 65%, 70%, 75%, 80%, 85%, 90%, 91%, 92%, 93%, 94%, 95%, 96%, 97%, 98% or 99% sequence identity to a sequence or sequence identifier recited herein.

The term "about" when referring to a numerical value or range includes normal variation expected by a person of ordinary skill in the art, and includes a range of plus or minus 0.1%, 0.5%, 1.0%, 2%, 3%, 4%, 5%, 6%, 7%, 8%, 9% or 10% of the recited value or range. Any numerical value or range disclosed herein can be modified by the term about, regardless of whether the term about is expressly recited.

DETAILED DESCRIPTION OF THE INVENTION

Provided herein are fusion proteins, nucleic acids that encode the fusion proteins, recombinant host cells that express the fusion proteins, and methods of using the fusion proteins for selecting proteases with increased catalytic activity using directed evolution. The methods provide the advantage of enabling kinetic selection for fast protease catalysts. Also provided are modified proteases with increased catalytic rates compared to control or wild-type proteases. The improved proteases are useful in various biotechnological techniques, including the FLARE (Fast Light- and Activity-Regulated Expression) and SPARK (Specific Protein Association tool giving transcriptional Readout with rapid Kinetics) tools. For example, the improved proteases increase the signal to background ratio, and allow faster detection of protein-protein interactions (PPIs) in living cells.

Fusion Proteins

In one aspect, provided are fusion proteins that comprise members of a protein interaction pair. In some embodiments, the first fusion protein comprises a protease fused or linked to one member (i.e., a first member) of a protein interaction pair. In some embodiments, the second fusion protein comprises a proteolytically cleavable linker fused or linked to the other member (i.e., a second member) of a protein interaction pair. In some embodiments, the protein interaction pair comprises a photoinducible protein binding pair. In some embodiments, the members of the photoinducible protein binding pair comprise cryptochrome (CRY) and cryptochrome-interacting basic-helix-loop-helix protein (CIB). It will be understood that the terms "first" and "second" can refer to one or the other fusion proteins, depending on the context.

First Fusion Proteins

In some embodiments, the first fusion protein comprises a first member of a protein interaction pair fused to a protease. In some embodiments, the first fusion protein comprises, in order from amino terminus to carboxyl terminus: a) a first member of a protein interaction pair; and b) a protease that cleaves the proteolytically cleavable linker.

In some embodiments, the protein interaction pair is a photoinducible protein binding pair. In some embodiments, the first member of the photoinducible protein binding pair is CRY. In some embodiments, the protease is a TEV protease. Thus, in some embodiments, the first fusion protein comprises, in order from amino terminus to carboxyl terminus: a) CRY; and b) a TEV protease.

TEV Protease

In some embodiments, the protease is a wild-type TEV protease. In some embodiments, wild-type TEV protease comprises the amino acid sequence of SEQ ID NO:1 (EC number 3.4.22.44, CAS number 139946-51-3, see UniProtKB: P04517). In some embodiments, the protease is a low-affinity protease, for example a TEV protease having a carboxy-terminal truncation. In some embodiments, the low affinity protease has a Km of greater than 300 microMolar. In some embodiments, the protease is a C-terminally truncated, low-affinity wild-type TEV (TEVA219, or TEVA) protease. In some embodiments, the TEV protease is a TEVA220-242 protease described in U.S. Patent Publication 2018/0201657. In some embodiments, the C-terminally truncated, low-affinity wild-type TEV protease comprises the amino acid sequence of SEQ ID NO:2. In some embodiments, the TEV protease has increased catalytic activity compared to a wild-type TEV protease (SEQ ID NO:1; EC number 3.4.22.44, CAS number 139946-51-3, see UniProtKB: P04517) or a C-terminally truncated wild-type TEV protease (e.g., TEVA219, or TEVA).

In some embodiments, the improved TEV protease comprises an amino acid sequence differing from wild-type TEV at one or more positions selected from T30, S31, S153, and N177. In some embodiments, the modified TEV protease comprises a sequence having at least 90%, 91%, 92%, 93%, 94%, 95%, 96%, 97%, 98%, or 99% sequence identity to wild-type TEV (SEQ ID NO:1) and comprises one or more mutations selected from T30A, T30I, S31W, S153N, N177Y, or a double T30A/S153N mutation. In some embodiments, the modified TEV protease comprises a sequence having at least 90%, 91%, 92%, 93%, 94%, 95%, 96%, 97%, 98%, or 99% sequence identity to a C-terminally truncated wild-type TEV protease (e.g., TEVA219, or TEVA) and comprises one or more mutations selected from T30A, T30I, S31W, S153N, N177Y, or a double T30A/S153N mutation.

In some embodiments, the first fusion protein comprises a fluorescent reporter molecule. In some embodiments, the first fusion protein comprises a protease fused to a fluorescent reporter molecule. The fluorescent reporter molecule can be fused directly or indirectly to the protease. For example, the protease can be fused to the first member of a photoinducible protein binding pair, such as CRY, and the first member of a photoinducible protein binding pair can be fused to the fluorescent reporter molecule. In some embodiments, the fluorescent reporter molecule is mCherry. In some embodiments, the fluorescent reporter molecule is BFP.

Thus, in some embodiments, the first fusion protein comprises, in order from amino terminus to carboxyl terminus: a) a fluorescent reporter molecule; b) a second member of the protein interaction pair; and c) a protease that cleaves the proteolytically cleavable linker. In some embodiments, the first fusion protein comprises, in order from amino terminus to carboxyl terminus: a) mCherry; b) CRY; and c) a TEV protease or modified TEV protease described herein.

Second Fusion Proteins

In some embodiments, the second fusion protein comprises a proteolytically cleavable linker fused to a first member of a protein interaction pair. In some embodiments, the proteolytically cleavable linker comprises a protease cleavage sequence. In some embodiments, the protease cleavage sequence is a substrate for TEV protease. In some embodiments, the protease cleavage sequence is a TEV cleavage sequence (TEVcs).

In some embodiments, the second fusion protein further comprises a transmembrane domain. In some embodiments, the second fusion protein further comprises a light-oxygen-voltage-sensing (LOV) domain polypeptide. In some embodiments, the second fusion protein further comprises a transcription factor.

In some embodiments, the second fusion protein comprises; in order from amino terminus (N-terminus) to carboxyl terminus (C-terminus): i) a tethering domain (e.g., a transmembrane domain or other tethering domain); ii) a second member of a protein interaction pair; iii) a LOV-domain polypeptide; iv) a proteolytically cleavable linker; and v) a transcription factor.

In some embodiments, the second fusion protein further comprises a fluorescent reporter molecule. In some embodiments, the fluorescent reporter molecule is tethered to the plasma membrane of a host cell. Thus, in some embodiments, the second fusion protein comprises; in order from amino terminus (N-terminus) to carboxyl terminus (C-terminus): i) a tethering domain (e.g., a transmembrane domain or other tethering domain); ii) a fluorescent reporter molecule; (iii) a second member of a protein interaction pair; iv) a LOV-domain polypeptide; v) a proteolytically cleavable linker; and vi) a transcription factor. In some embodiments, the fluorescent reporter molecule is mCherry.

Tethering/Transmembrane Domain

Any of a variety of transmembrane domains (polypeptides) can be used in the second fusion polypeptide described herein. A suitable transmembrane domain is any polypeptide that is thermodynamically stable in a membrane, e.g., a eukaryotic cell membrane such as a mammalian cell membrane. Suitable transmembrane domains include a single alpha helix, a transmembrane beta barrel, or any other structure.

A suitable transmembrane domain can have a length of from about 10 to 50 amino acids, e.g., from about 10 amino acids to about 40 amino acids, from about 20 amino acids to about 40 amino acids, from about 15 amino acids to about 25 amino acids, e.g., from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids.

In some embodiments, the transmembrane domain is a STE2 or a truncated STE2 (STE2A) transmembrane domain as described in Kawada, D. et al. The yeast Arf-GAP Glo3p is required for the endocytic recycling of cell surface proteins. Biochim. Biophys. Acta—Mol. Cell Res. 1853, 144-156 (2015). In some embodiments, the STE2 transmembrane domain has the following sequence:

```
                                    (SEQ ID NO: 9)
MSDAAPSLSNLFYDPTYNPGQSTINYTSIYGNGSTITFDELQGLVNSTVT

QAIMFGVRCGAAALTLIVMWMTSRSRKTPIFIINQVSLFLIILHSALYFK

YLLSNYSSVTYALTGFPQFISRGDVHVYGATNIIQVLLVASIETSLVFQI

KVIFTGDNFKRIGLMLTSISFTLGIATVTMYFVSAVKGMIVTYNDVSATQ

DKYFNASTILLASSINFMSFVLVVKLILAIRSRRFLGLKQFDSFHILLIM

SCQSLLVPSIIFILAYSLKPNQGTDVLTTVATLLAVLSLPLSSMWATAAN

NASKTNTITSDFTTSTDRFYPGTLSSFQTDSINNDAKSSLRSRLYDLYPR

RKETTSDKHSERTFVSETADDIEKNQFYQLPTPTSSKNTRIGPFADASYK

EGEVEPVDMYTPDTAADEEARKFWTEDNMNL.
```

In some embodiments, the truncated-STE2 (STE2A) transmembrane domain has the following sequence:

```
                                   (SEQ ID NO: 10)
MSDAAPSLSNLFYDPTYNPGQSTINYTSIYGNGSTITFDELQGLVNSTVT

QAIMFGVRCGAAALTLIVMWMTSRSRKTPIFIINQVSLFLIILHSALYFK

YLLSNYSSVTYALTGFPQFISRGDVHVYGATNIIQVLLVASIETSLVFQI

KVIFTGDNFKRIGLMLTSISFTLGIATVTMYFVSAVKGMIVTYNDVSATQ

DKYFNASTILLASSINFMSFVLVVKLILAIRSRRFLGLKQFDSFHILLIM

SCQSLLVPSIIFILAYSLKPNQGTDVLTTVATLLAVLSLPLSSMWATAA

N.
```

In some embodiments, the transmembrane domain is fused to a BFP linker. The BFP linker resulted in increased expression of a reporter gene transcribed by the transcription factor, which may be the result of improved membrane targeting of the transcription factor construct.

LOV Domain

The fusion protein can comprise an LOV domain polypeptide that serves to "photocage" the protease cleavage sequence. In some embodiments, the C terminal of the LOV domain comprises an alpha helix into which the protease cleavage sequence, for example, a TEVcs, is inserted. In the absence of blue light, the protease cleavage sequence is sequestered by the LOV domain polypeptide. Under blue-light illumination (450-480 nm), the LOV domain undergoes a conformational change, which makes the protease cleavage sequence more accessible to proteolytic processing by the protease. In some embodiments, the LOV domain light-activated polypeptide can have a length of from about 100 amino acids to about 150 amino acids. For example, a LOV polypeptide can comprise an amino acid sequence having at least 80%, at least 85%, at least 90%, at least 95%, at least 98%, at least 99%, or 100%, amino acid sequence identity to the LOV2 domain of Avena sativa phototropin 1 (AsLOV2).

Enhanced Lov Polypeptide

In some embodiments, the LOV domain comprises an enhanced LOV-domain light-activated polypeptide (also referred to herein as an "enhanced LOV polypeptide" or an "eLOV polypeptide"). A representative eLOV domain is described in Wang, W. et al. "A light- and calcium-gated transcription factor for imaging and manipulating activated neurons" Nat. Biotechnol. 35, 864-871 (2017). Representative examples of eLOV polypeptides are described in U.S. Patent Publication 2018/0201657, which is incorporated by reference herein.

In some cases, an eLOV polypeptide comprises an amino sequence having at least 80%, at least 85%, at least 90%, at least 95%, at least 96%, at least 97%, at least 98%, at least 99%, or 100% amino acid sequence identity to the following amino acid sequence: SLATTLERIEKNFVITDPRLPDN-PIIFASDSFLQLTEYSREEILGRNCRFLQGPETDRATVR KIRDAIDNQTE-VTVQLINYTKSGKKFWNLFHLQPMRDQKGDVQY-FIGVQLDGTEHVRD AAEREAVMLIKKTAEEIDEAAK (SEQ ID NO: 11); and comprises a substitution at one or more of amino acids L2, N12, A28, H117, and 1130, where the numbering is based on the amino acid sequence SLAT-TLERIEKNFVITDPRLPDNPIIFASDSFLQLTEYSREEIL-GRNCRFLQGPETDRATVR KIRDAIDNQTE-VTVQLINYTKSGKKFWNLFHLQPMRDQKGDVQYFI GVQLDGTEHVRD AAEREAVMLIKKTAEEIDEAAK (SEQ ID NO: 12). In some cases, the eLOV polypeptide comprises a substitution selected from an L2R substitution, an L2H substitution, an L2P substitution, and an L2K substitution. In some cases, the eLOV polypeptide comprises a substitution selected from an N12S substitution, an N12T substitution, and an N12Q substitution. In some cases, the eLOV polypeptide comprises a substitution selected from an A28V substitution, an A281 substitution, and an A28L substitution. In some cases, the eLOV polypeptide comprises a substitution selected from an H117R substitution, and an H117K substitution. In some cases, the eLOV polypeptide comprises a substitution selected from an 1130V substitution, an 1130A substitution, and an 1130L substitution. In some cases, the eLOV polypeptide comprises substitutions at amino acids L2, N12, and 1130. In some cases, the eLOV polypeptide comprises substitutions at amino acids L2, N12, H117, and 1130. In some cases, the eLOV polypeptide comprises substitutions at amino acids A28 and H117. In some cases, the eLOV polypeptide comprises substitutions at amino acids N12 and 1130. In some cases, the eLOV polypeptide comprises an L2R substitution, an N12S substitution, and an 1130V substitution. In some cases, the eLOV polypeptide comprises an N12S substitution and an 1130V substitution. In some cases, the eLOV polypeptide comprises an A28V substitution and an H117R substitution. In some cases, the eLOV polypeptide comprises an L2P substitution, an N12S substitution, an 1130V substitution, and an H117R substitution. In some cases, the eLOV polypeptide comprises an L2P substitution, an N12S substitution, an A28V substitution, an H117R substitution, and an 1130V substitution. In some cases, the eLOV polypeptide comprises an L2P substitution, an N12S substitution, an 1130V substitution, and an H117R substitution. In some cases, the eLOV polypeptide comprises an L2R substitution, an N12S substitution, an A28V substitution, an H117R substitution, and an 1130V substitution. In some cases, the eLOV polypeptide has a length of 142 amino acids, 143 amino acids, 144 amino acids, 145 amino acids, 146 amino acids, 147 amino acids, 148 amino acids, 149 amino acids, or 150 amino acids. In some cases, the LOV polypeptide has a length of 142 amino acids.

In some cases, an eLOV polypeptide comprises an amino sequence having at least 80%, at least 85%, at least 90%, at least 95%, at least 96%, %, at least 97%, at least 98%, at least 99%, or 100%, amino acid sequence identity to the following amino acid sequence: SRAT-TLERIEKSFVITDPRLPDNPIIFVSDSFLQLTEYSREEIL-GRNCRFLQGPETDRATVR KIRDAIDNQTE-VTVQLINYTKSGKKFWNLFHLQPMRDQKGDVQYFI GVQLDGTERVRD AAEREAVMLVKKTAEEIDEAAK (SEQ ID NO: 13); and has an Arg at amino acid 2, a Ser at amino acid 12, a Val at amino acid 28, an Arg at amino acid 117, and a Val at amino acid 130, as indicated by bold and underlined letters; and has a length of 142 amino acids, 143 amino acids, 144 amino acids, 145 amino acids, 146 amino acids, 147 amino acids, 148 amino acids, 149 amino acids, or 150 amino acids. In some cases, an eLOV polypeptide comprises the following amino acid sequence: SRAT-TLERIEKSFVITDPRLPDNPIIFVSDSFLQLTEYSREEIL-GRNCRFLQGPETDRATVR KIRDAIDNQTE-VTVQLINYTKSGKKFWNLFHLQPMRDQKGDVQYFI GVQLDGTERVRD AAEREAVMLVKKTAEEIDEAAK (SEQ ID NO: 14); and has a length of 142 amino acids.

In some cases, an eLOV polypeptide comprises an amino sequence having at least 80%, at least 85%, at least 90%, at least 95%, at least 96%, %, at least 97%, at least 98%, at least 99%, or 100%, amino acid sequence identity to the following amino acid sequence: SRAT-TLERIEKSFVITDPRLPDNPVIFVSDSFLQLTEYSREE-ILGRNCRFLQGPETDRATVR KIRDAIDNQTE-VTVQLINYTKSGKKFWNLFHLQPMRDQKGDVQYFI GVQLDGTERVRD AAEREAVMLVKKTAEEIDEAAK (SEQ ID NO: 15); and has an Arg at amino acid 2, a Ser at amino acid 12, a Val at amino acid 25, a Val at amino acid 28, an Arg at amino acid 117, and a Val at amino acid 130, as indicated by bold and underlined letters; and has a length of 142 amino acids, 143 amino acids, 144 amino acids, 145 amino acids, 146 amino acids, 147 amino acids, 148 amino acids, 149 amino acids, or 150 amino acids. In some cases, an eLOV polypeptide comprises the following amino acid sequence: SRATTLERIEKSFVITDPRLPDNPV-IFVSDSFLQLTEYSREEILGRNCRFLQGPETDRATVR KIRDAIDNQTE-VTVQLINYTKSGKKFWNLFHLQPMRDQKGDVQY-FIGVQLDGTERVRD AAEREAVMLVKKTAEEIDEAAK (SEQ ID NO: 15); and has a length of 142 amino acids.

A suitable LOV domain light-activated polypeptide can have a length of from about 100 amino acids to about 150 amino acids. For example, a LOV polypeptide can comprise an amino acid sequence having at least 80%, at least 85%, at least 90%, at least 95%, at least 98%, at least 99%, or 100%, amino acid sequence identity to the LOV2 domain of *Avena sativa* phototropin 1 (AsLOV2).

In some cases, a suitable LOV domain light-activated polypeptide comprises an amino sequence having at least 80%, at least 85%, at least 90%, at least 95%, at least 98%, at least 99%, or 100%, amino acid sequence identity to the following LOV2 amino acid sequence: DLAT-TLERIEKNFVITDPRLPDNPIIFASDSFLQLTEYSREEIL-GRNCRFLQGPETDRATVRKIRDAIDNQTEVTVQL INYTKSGKKFWNLFHLQPMRDQKGDVQY-FIGVQLDGTEHVRDAAEREGVM LIKKTAENIDEAAK (SEQ ID NO: 16); GenBank AF033096.

In some cases, a suitable LOV polypeptide comprises an amino sequence having at least 80%, at least 85%, at least 90%, at least 95%, at least 98%, at least 99%, or 100%, amino acid sequence identity to the following LOV2 amino acid sequence: DLATTLERIEKNFVITDPRLPDNPIIF-ASDSFLQLTEYSREEILGRNCRFLQGPET-DRATVRKIRDAIDNQTEVTVQL INYTKSGKKFWNLFHLQPMRDQKGDVQY-FIGVQLDGTEHVRDAAEREGVM LIKKTAENIDEAAK (SEQ ID NO: 16); and has a length of from 142 amino acids to 150 amino acids.

In some cases, a suitable LOV domain light-activated polypeptide comprises an amino sequence having at least 80%, at least 85%, at least 90%, at least 95%, at least 98%, at least 99%, or 100%, amino acid sequence identity to the following LOV2 amino acid sequence: DLAT-TLERIEKNFVITDPRLPDNPIIFASDSFLQLTEYSREEIL-GRNCRFLQGPETDRATVRKIRDAIDNQTEVTVQL INYTKSGKKFWNLFHLQPMRDQKGDVQY-FIGVQLDGTEHVRDAAEREGVM LIKKTAENIDEAAK (SEQ ID NO: 16); and has a length of 142 amino acids.

In some cases, a suitable LOV domain light-activated polypeptide comprises an amino sequence having at least 80%, at least 85%, at least 90%, at least 95%, at least 98%, at least 99%, or 100%, amino acid sequence identity to the following amino acid sequence:

```
                                    (SEQ ID NO: 12)
SLATTLERIEKNFVITDPRLPDNPIIFASDSFLQLTEYSREEILGRNCRF

LQGPETDRATVRKIRDAIDNQTEVTVQLINYTKSGKKFWNLFHLQPMRDQ

KGDVQYFIGVQLDGTEHVRDAAEREAVMLIKKTAEEIDEAAK.
```

In some cases, a suitable LOV domain light-activated polypeptide comprises an amino sequence having at least 80%, at least 85%, at least 90%, at least 95%, at least 98%, at least 99%, or 100%, amino acid sequence identity to the following amino acid sequence: SLAT-TLERIEKNFVITDPRLPDNPIIFASDSFLQLTEYSREEIL-GRNCRFLQGPETDRATVR KIRDAIDNQTE-VTVQLINYTKSGKKFWNLFHLQPMRDQKGDVQYFI GVQLDGTEHVRD AAEREAVMLIKKTAEEIDEAAK (SEQ ID NO: 11); and has a length of from about 142 amino acids to about 150 amino acids.

In some cases, a suitable LOV domain light-activated polypeptide comprises an amino sequence having at least 80%, at least 85%, at least 90%, at least 95%, at least 98%, at least 99%, or 100%, amino acid sequence identity to the following amino acid sequence: SLAT-TLERIEKNFVITDPRLPDNPIIFASDSFLQLTEYSREEIL-GRNCRFLQGPETDRATVR KIRDAIDNQTE-VTVQLINYTKSGKKFWNLFHLQPMRDQKGDVQYFI GVQLDGTEHVRD AAEREAVMLIKKTAEEIDEAAK (SEQ ID NO: 11); and has a length of 142 amino acids.

In some cases, a suitable LOV domain light-activated polypeptide comprises an amino sequence having at least 80%, at least 85%, at least 90%, at least 95%, at least 98%, at least 99%, or 100%, amino acid sequence identity to the following amino acid sequence: SLAT-TLERIEKNFVITDPRLPDNPIIFASDSFLQLTEYSREEIL-GRNCRFLQGPETDRATVR KIRDAIDNQTE-VTVQLINYTKSGKKFWNLFHLQPMRDQKGDVQYFI GVQLDGTEHVRD AAEREAVMLIKKTAEEIDEAAK (SEQ ID NO: 11); and comprises a substitution at one or more of amino acids L2, N12, A28, H117, and I130, where the numbering is based on the amino acid sequence SLAT-TLERIEKNFVITDPRLPDNPIIFASDSFLQLTEYSREEIL-GRNCRFLQGPETDRATVR KIRDAIDNQTE-VTVQLINYTKSGKKFWNLFHLQPMRDQKGDVQYFI GVQLDGTEHVRD AAEREAVMLIKKTAEEIDEAAK (SEQ ID NO: 12).

Figure 15A:
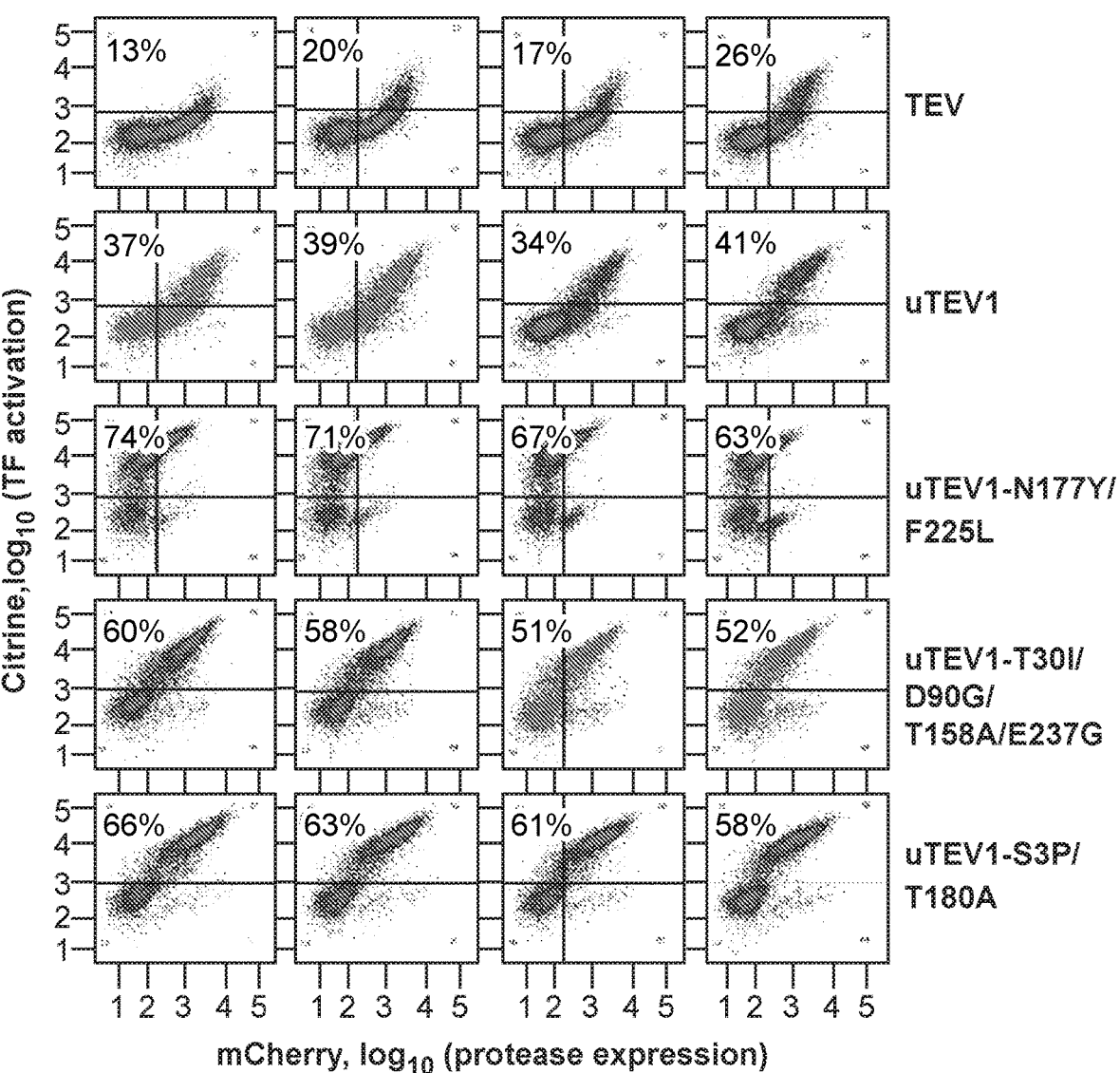
FIGS. 15A and 15B show shows characterization of full-length uTEV clones. Proteases were expressed in a yeast strain bearing 2 LexA boxes and TEVcs=ENLYFQ/S (SEQ ID NO: 5). FACS plots of selected TEV mutants 6 hours after various amounts of blue light exposure (0, 0.5, 2, and 5 min). Configuration of constructs was the same as in FIG. 3A.

In some cases, an eLOV polypeptide of the present disclosure comprises one or more amino acid substitutions relative to the LOV2 amino acid sequence. In some cases, an eLOV polypeptide of the present disclosure comprises one or more amino acid substitutions at positions selected from 1, 2, 12, 25, 28, 91, 100, 117, 118, 119, 120, 126, 128, 135, 136, and 138, relative to the LOV2 amino acid sequence (as shown in FIG. 15A in US2018/0201657, which is incorporated herein by reference). Suitable substitutions include, Asp to Ser at amino acid 1; Asp to Phe at amino acid 1; Leu to Arg at amino acid 2; Asn to Ser at amino acid 12; Ile to Val at amino acid 12; Ala to Val at amino acid 28; Leu to Val at amino acid 91; Gln to Tyr at amino acid 100; His to Arg at amino acid 117; Val to Leu at amino acid 118; Arg to His at amino acid 119; Asp to Gly at amino acid 120; Gly to Ala at amino acid 126; Met to Cys at amino acid 128; Glu to Phe at amino acid 135; Asn to Gln at amino acid 136; Asn to Glu at amino acid 136; and Asp to Ala at amino acid 138, where the amino acid numbering is based on the number of the LOV2 amino acid sequence.

Figure 15B:
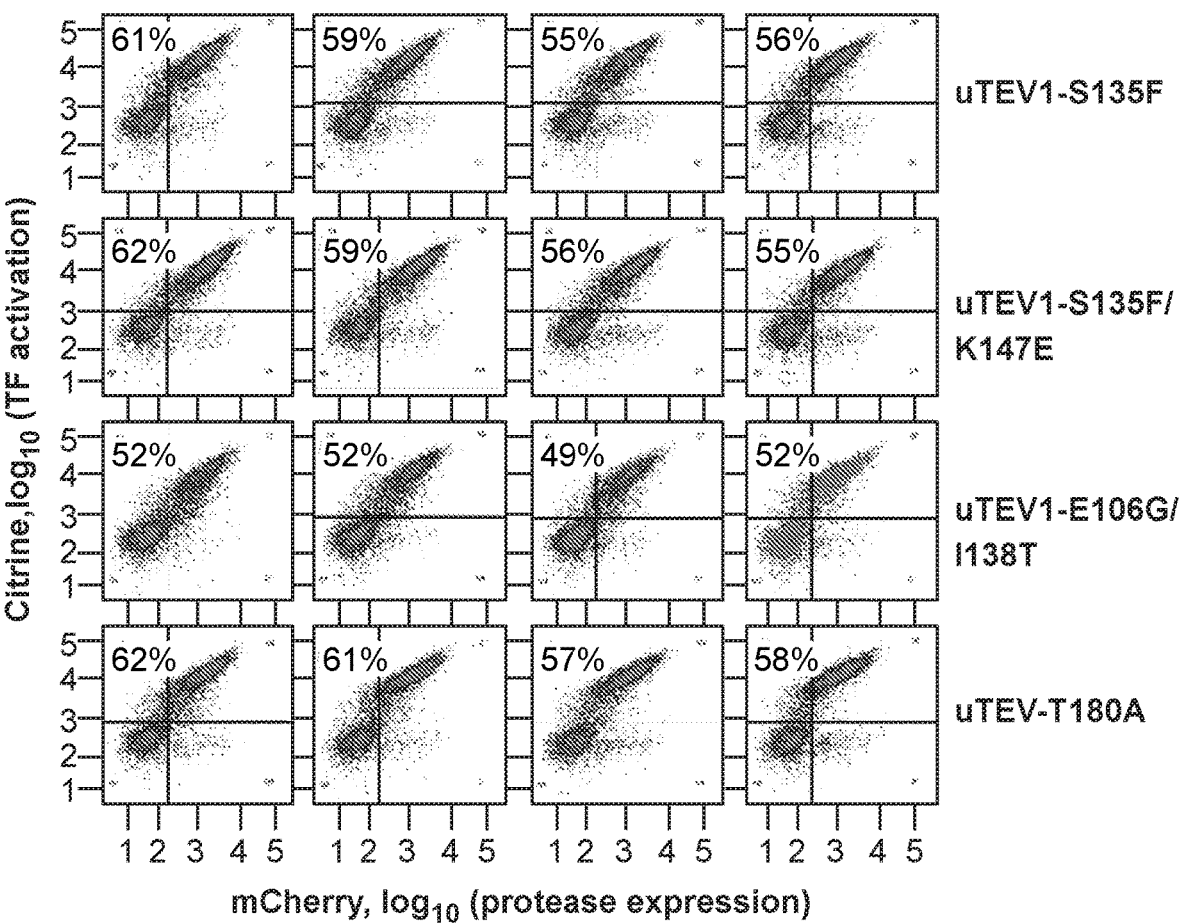

In some cases, an eLOV polypeptide of the present disclosure comprises an amino acid sequence having at least 80%, at least 85%, at least 90%, at least 95%, at least 98%, at least 99%, or 100%, amino acid sequence identity to the amino acid sequence shown in FIG. 15B in US2018/0201657, where amino acid 1 is Ser, amino acid 28 is Ala, amino acid 126 is Ala, and amino acid 136 is Glu. In some case, an eLOV polypeptide of the present disclosure has a length of 142 amino acids.

In some cases, an eLOV polypeptide of the present disclosure comprises an amino acid sequence having at least 80%, at least 85%, at least 90%, at least 95%, at least 98%, at least 99%, or 100%, amino acid sequence identity to the amino acid sequence shown in FIG. 15C in US2018/0201657, where amino acid 1 is Ser; amino acid 2 is Arg; amino acid 12 is Ser; amino acid 28 is Ala; amino acid 117 is Arg; amino acid 126 is Ala; and amino acid 136 is Glu. In some case, an eLOV polypeptide of the present disclosure has a length of 142 amino acids.

In some cases, an eLOV polypeptide of the present disclosure comprises an amino acid sequence having at least 80%, at least 85%, at least 90%, at least 95%, at least 98%, at least 99%, or 100%, amino acid sequence identity to the amino acid sequence shown in FIG. 15D in US2018/0201657, where amino acid 1 is Ser; amino acid 2 is Arg; amino acid 12 is Ser; amino acid 25 is Val; amino acid 28 is Val; amino acid 117 is Arg; amino acid 126 is Ala; amino acid 130 is Val; and amino acid 136 is Glu. In some case, an eLOV polypeptide of the present disclosure has a length of 142 amino acids.

In some cases, an eLOV polypeptide of the present disclosure comprises an amino acid sequence having at least 80%, at least 85%, at least 90%, at least 95%, at least 98%, at least 99%, or 100%, amino acid sequence identity to the amino acid sequence shown in FIG. 15E in US2018/0201657, where amino acid 1 is Ser; amino acid 2 is Arg; amino acid 12 is Ser; amino acid 28 is Ala; amino acid 91 is Val; amino acid 100 is Tyr; amino acid 117 is Arg; amino acid 118 is Leu; amino acid 119 is His; amino acid 120 is Gly; amino acid 126 is Ala; amino acid 128 is Cys; amino acid 130 is Val; amino acid 135 is Phe; amino acid 136 is Gln; and amino acid 138 is Ala. In some case, an eLOV polypeptide of the present disclosure has a length of 142 amino acids.

In some cases, an eLOV polypeptide of the present disclosure comprises an amino acid sequence having at least 80%, at least 85%, at least 90%, at least 95%, at least 98%, at least 99%, or 100%, amino acid sequence identity to the amino acid sequence shown in FIG. 15F in US2018/0201657, where amino acid 1 is Ser; amino acid 2 is Arg; amino acid 12 is Ser; amino acid 28 is Val; amino acid 117 is Arg; amino acid 126 is Ala; amino acid 130 is Val; and amino acid 136 is Glu. In some case, an eLOV polypeptide of the present disclosure has a length of 138 amino acids.

In some cases, an eLOV polypeptide of the present disclosure comprises an amino acid sequence having at least 80%, at least 85%, at least 90%, at least 95%, at least 98%, at least 99%, or 100%, amino acid sequence identity to the amino acid sequence as shown in FIG. 15G in US2018/0201657, where amino acid 1 is Ser; amino acid 2 is Arg; amino acid 12 is Ser; amino acid 28 is Val; amino acid 91 is Val; amino acid 100 is Tyr; amino acid 117 is Arg; amino acid 118 is Leu; amino acid 119 is His; amino acid 120 is Gly; amino acid 126 is Ala; amino acid 128 is Cys; amino acid 130 is Val; amino acid 135 is Phe; amino acid 136 is Gln; and amino acid 138 is Ala. In some case, an eLOV polypeptide of the present disclosure has a length of 138 amino acids.

Representative LOV amino acid sequences are shown in Table 1 below:

TABLE 1

LOV2 domain *Avena sativa*

DLATTLERIEKNFVITDPRLPDNPIIFASDSFLQLTEYSREEILGRNCRF
LQGPETDRATVRKIRDAIDNQTEVTVQLINYTKSGKKFWNLFHLQPMRDQ
KGDVQYFIGVQLDGTEHVRDAAEREGVMLIKKTAENIDEAAK (SEQ ID
NO: 17)

SLATTLERIEKNFVITDPRLPDNPIIFASDSFLQLTEYSREEILGRNCRF
LQGPETDRATVRKIRDAIDNQTEVTVQLINYTKSGKKFWNLFHLQPMRDQ
KGDVQYFIGVQLDGTEHVRDAAEREAVMLIKKTAEEIDEAAK (SEQ ID
NO: 12)

SRATTLERIEKSFVITDPRLPDNPIIFVSDSFLQLTEYSREEILGRNCRF
LQGPETDRATVRKIRDAIDNQTEVTVQLINYTKSGKKFWNLFHLQPMRDQ
KGDVQYFIGVQLDGTERVRDAAEREAVMLVKKTAEEIDEAAK (SEQ ID
NO: 18)

SRATTLERIEKSFVITDPRLPDNPVIFVSDSFLQLTEYSREEILGRNCRF
LQGPEIDRATVRKIRDAIDNQTEVTVQLINYTKSGKKFWNLFHLQPMRDQ
KGDVQYFIGVQLDGTERVRDAAEREAVMLVKKTAEEIDEAAK (SEQ ID
NO: 19)

SRATTLERIEKSFVITDPRLPDNPIIFVSDSFLQL TEYSREEILGRNCR
FLQGPETDRATVRKIRDAIDNQTEVTVQLINYTKSGKKFWNVFHLQPMRD
YKGDVQYFIGVQLDGTERLHGAAEREAVCLVKKTAFQILAEAAK (SEQ
ID NO: 20)

SRATTLERIEKSFVITDPRLPDNPIIFVSDSFLQLTEYSREEILGRNCRF
LQGPETDRATVRKIRDAIDNQTEVTVQLINYTKSGKKFWNLFHLQPMRDQ
KGDVQYFIGVQLDGTERVRDAAEREAVMLVKKTAEEID (SEQ ID NO:
21)

TABLE 1-continued

LOV2 domain *Avena sativa*

```
SRATTLERIEKSFVITDPRLPDNPIIFVSDSFLQLTEYSREEILGRNCRF
LQGPETDRATVRKIRDAIDNQTEVTVQLINYTKSGKKFWNVFHLQPMRDY
KGDVQYFIGVQLDGTERLHGAAEREAVCLVKKTAFQIA (SEQ ID NO:
22)
```

In some cases, a LOV light-activated polypeptide comprises the following amino acid sequence:

```
                                          (SEQ ID NO: 23)
FRATTLERIEKSFVITDPRLPDNPIIFVSDSFLQLTEYSREEILGRN

CRFLQGPETDRATVRKIRDAIDNQTEVTVQLINYTKSGKKFWNVFHL

QPMRDYKGDVQYFIGVCILDGTERLHGAAEREAVCLVKKTAFQIA.
```

In some cases, a LOV light-activated polypeptide comprises the following amino acid sequence:

```
                                          (SEQ ID NO: 21)
SRATTLERIEKSFVITDPRLPDNPIIFVSDSFLQLTEYSREEILGRN

CRFLQGPETDRATVRKIRDAIDNQTEVTVQLINYTKSGKKFWNLFHL

QPMRDQKGDVQYFIGVQLDGTERVRDAAEREAVMLVKKTAEEID.
```

In some cases, a LOV light-activated polypeptide comprises the following amino acid sequence:

```
                                          (SEQ ID NO: 23)
FRATTLERIEKSFVITDPRLPDNPIIFVSDSFLQLTEYSREEILGRN

CRFLQGPETDRATVRKIRDAIDNQTEVTVQLINYTKSGKKFWNVFHL

QPMRDYKGDVQYFIGVQLDGTERLHGAAEREAVCLVKKTAFQIA.
```

In some cases, a LOV light-activated polypeptide comprises the following amino acid sequence:

```
                                          (SEQ ID NO: 24)
SRATTLERIEKSFVITDPRLPDNPIIFVSDSFLQLTEYSREEILGRN

CRFLQGPETDRATVRKIRDAIDNQTEVTVQLINYTKSGKKFWNVFHL

QPMRDYKGDVQYFIGVQLDGTERLHGAAEREAVCLVKKTAFEIDEAAK.
```

In some cases, a LOV light-activated polypeptide comprises the following amino acid sequence:

```
                                          (SEQ ID NO: 18)
SRATTLERIEKSFVITDPRLPDNPIIFVSDSFLQLTEYSREEILGRN

CRFLQGPETDRATVRKIRDAIDNQTEVTVQLINYTKSGKKFWNLFHL

QPMRDQKGDVQYFIGVQLDGTERVRDAAEREAVMLVKKTAEEIDEAAK.
```

When an eLOV polypeptide is present in a fusion polypeptide, e.g., where the fusion polypeptide comprises an eLOV polypeptide and a proteolytically cleavable linker, the eLOV polypeptide cages the proteolytically cleavable linker in the absence of light of an activating wavelength, the proteolytically cleavable linker is substantially not accessible to the protease. Thus, e.g., in the absence of light of an activating wavelength (e.g., in the dark; or in the presence of light of a wavelength other than blue light), the proteolytically cleavable linker is cleaved, if at all, to a degree that is more than 50% less, more than 60% less, more than 70% less, more than 80% less, more than 90% less, more than 95% less, more than 98% less, or more than 99% less, than the degree of cleavage of the proteolytically cleavable linker in the presence of light of an activating wavelength (e.g., blue light, e.g., light of a wavelength in the range of from about 450 nm to about 495 nm, from about 460 nm to about 490 nm, from about 470 nm to about 480 nm, e.g., 473 nm).

Non-limiting examples of suitable polypeptides comprising: a) a LOV light-activated polypeptide; and b) a proteolytically cleavable linker include the following (where the proteolytically cleavable linker is underlined, and where the "/" indicates the cleavage site):

```
                                          (SEQ ID NO: 25)
1) SRATTLERIEKSFVITDPRLPDNPIIFVSDSFLQLTEYSREEILGRN

CRFLQGPETDRATVRKIRDAIDNQTEVTVQLINYTKSGKKFWNLFHL

QPMRDQKGDVQYFIGVQLDGTERVRDAAEREAVMLVKKTAEEIDEAA K

ENLYFQ/M;
```

```
                                          (SEQ ID NO: 26)
2) SRATTLERIEKSFVITDPRLPDNPIIFVSDSFLQLTEYSREEILGRN

CRFLQGPETDRATVRKIRDAIDNQTEVTVQLINYTKSGKKFWNVFHL

QPMRDYKGDVQYFIGVQLDGTERLHGAAEREAVCLVKKTAFEIDEAA K

ENLYFQ/M;
```

```
                                          (SEQ ID NO: 27)
3) FRATTLERIEKSFVITDPRLPDNPIIFVSDSFLQLTEYSREEILGRN

CRFLQGPETDRATVRKIRDAIDNQTEVTVQLINYTKSGKKFWNVFHL

QPMRDYKGDVQYFIGVQLDGTERLHGAAEREAVCLVKKTAFQIA

ENL YFQ/M;
```

```
                                          (SEQ ID NO: 28)
4) SRATTLERIEKSFVITDPRLPDNPIIFVSDSFLQLTEYSREEILGRN

CRFLQGPETDRATVRKIRDAIDNQTEVTVQLINYTKSGKKFWNLFHL

QPMRDQKGDVQYFIGVQLDGTERVRDAAEREAVMLVKKTAEEID

ENLYFQ/G;
and
```

```
                                          (SEQ ID NO: 29)
5) FRATTLERIEKSFVITDPRLPDNPIIFVSDSFLQLTEYSREEILGRN

CRFLQGPETDRATVRKIRDAIDNQTEVTVQLINYTKSGKKFWNVFHL

QPMRDYKGDVQYFIGVQLDGTERLHGAAEREAVCLVKKTAFQIA

ENLYFQ/G.
```

Also provided is a nucleic acid comprising a nucleotide sequence encoding an LOV domain or eLOV domain polypeptide described herein, and a recombinant expression vector comprising the nucleic acid. Also provided is a genetically modified host cell comprising a nucleic acid comprising a nucleotide sequence encoding an LOV domain or eLOV domain polypeptide described herein, or a recombinant expression vector comprising the nucleic acid. In some embodiments, the host cell is a genetically modified yeast cell.

Proteolytically Cleavable Linker

In some embodiments, the proteolytically cleavable linker includes a protease cleavage sequence that is cleaved by a viral protease. In some embodiments, the proteolytically cleavable linker includes a protease cleavage sequence that is cleaved by a tobacco etch virus (TEV) protease. In some embodiments, the proteolytically cleavable linker includes a protease cleavage sequence that is cleaved by low-affinity version of TEV. In some embodiments, the proteolytically cleavable linker includes an amino acid sequence selected from ENLYFQX (SEQ ID NO: 30; where X is any amino acid), ENLYFQS (SEQ ID NO: 5), ENLYFQG (SEQ ID NO: 31), ENLYFQY (SEQ ID NO: 32), ENLYFQL (SEQ ID NO: 33), ENLYFQW (SEQ ID NO: 34), ENLYFQM (SEQ ID NO: 6), ENLYFQH (SEQ ID NO: 35), ENLYFQN (SEQ ID NO: 36), ENLYFQA (SEQ ID NO: 37), or ENLYFQQ (SEQ ID NO: 38).

Transcription Factors

Suitable transcription factors include naturally-occurring transcription factors and recombinant (e.g., non-naturally occurring, engineered, artificial, synthetic) transcription factors. In some cases, the transcription is a transcriptional activator. In some cases, the transcriptional activator is an engineered protein, such as a zinc finger or TALE based DNA binding domain fused to an effector domain such as VP64 (transcriptional activation).

A transcription factor can comprise: i) a DNA binding domain (DBD); and ii) an activation domain (AD). The DBD can be any DBD with a known response element, including synthetic and chimeric DNA binding domains, or analogs, combinations, or modifications thereof. Suitable DNA binding domains include, but are not limited to, a GAL4 DBD, a LexA DBD, a transcription factor DBD, a Group H nuclear receptor member DBD, a steroid/thyroid hormone nuclear receptor superfamily member DBD, a bacterial LacZ DBD, an EcR DBD, a GALA DBD, and a LexA DBD. Suitable ADs include, but are not limited to, a Group H nuclear receptor member AD, a steroid/thyroid hormone nuclear receptor AD, a CJ7 AD, a p65-TA1 AD, a synthetic or chimeric AD, a polyglutamine AD, a basic or acidic amino acid AD, a VP16 AD, a GAL4 AD, an NF-.kappa.B AD, a BP64 AD, a B42 acidic activation domain (B42AD), a p65 transactivation domain (p65AD), SAD, NF-1, AP-2, SP1-A, SP1-B, Oct-1, Oct-2, MTF-1, BTEB-2, and LKLF, or an analog, combination, or modification thereof.

Suitable transcription factors include transcriptional activators, where suitable transcriptional activators include, but are not limited to, GAL4-VP16, GAL5-VP64, Tbx21, tTA-VP16, VP16, VP64, GAL4, p65, LexA-VP16, GAL4-NF.kappa.B, and the like.

In some embodiments, the transcription factor is tethered to the plasma membrane of a host cell by a STE2-based plasma membrane anchor, and a BFP linker.

Reporter Gene Products

Reporter genes described herein encode products including polypeptides that generate a detectable signal. Exemplary polypeptides that generate a detectable signal include, e.g., fluorescent proteins and enzymes that catalyze a reaction that generates a detectable signal as a product.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrapel, mRaspberry, mGrape2, and mPlum (Shaner et al. (2005) Nat. Methods 2:905-909). Any of a variety of fluorescent and colored proteins from Anthozoan species, as described in, e.g., Matz et al. (1999) Nature Biotechnol. 17:969-973, are also suitable for use in the methods described herein.

Protein Interaction Pair

In some embodiments, the protein interaction pair comprises a photoinducible protein binding pair. In some embodiments, the photoinducible protein binding pair comprises a cryptochrome (CRY) and a cryptochrome-interacting basic-helix-loop-helix protein (CIB) (also called calcium and integrin binding) protein pair that dimerize when exposed to blue light. In some embodiments, the photoinducible protein binding pair comprises *Arabidopsis thaliana* cryptochrome 2 and CIB1 that require no exogenous ligands and dimerize on blue light exposure. Thus, in some embodiments, the first member of the photoinducible protein binding pair is CRY, CRY2 (SEQ ID NO: 4), or the PHR domain of CRY2 (CRY2$_{PHR}$, aa 1-498). In some embodiments, the second member of the photoinducible protein binding pair is CIB, Calcium And Integrin Binding 1 (CIB1) protein (e.g., SEQ ID NO:3), or a truncated version of CIB1 referred to as CIBN (aa 1-170, missing the conserved bHLH domain which mediates dimerization and DNA binding), See,e.g., Kennedy, M. J. et al. Rapid blue-light-mediated induction of protein interactions in living cells. Nat. Methods 7, 973-5 (2010).

In some embodiments, a first polypeptide or a second polypeptide of a protein interaction pair is a Cry2 polypeptide (also known as cryptochrome 2). For example, a suitable Cry2 polypeptide can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

```
Cry2 (Arabidopsis thaliana)
                                (SEQ ID NO: 4)
MKMDKKTIVWFRRDLRIEDNPALAAAAHEGSVFPVFIWCPEEEGQF

YPGRASRWWMKQSLAHLSQSLKALGSDLTLIKTHNTISAILDCIRV

TGATKVVFNHLYDPVSLVRDHTVKEKLVERGISVQSYNGDLLYEPW

EIYCEKGKPFTSFNSYWKKCLDMSIESVMLPPPWRLMPITAAAEAI

WACSIEELGLENEAEKPSNALLTRAWSPGWSNADKLLNEFIEKQLI

DYAKNSKKVVGNSTSLLSPYLHFGEISVRHVFQCARMKQIIWARDK

NSEGEESADLFLRGIGLREYSRYICFNFPPFTHEQSLLSHLRFFPWD

ADVDKFKAWRQGRTGYPLVDAGMRELWATGWMHNRIRVIVSSFAVK

FLLLPWKWGMKYFWDTLLDADLECDILGWQYISGSIPDGHELDRLD

NPALQGAKYDPEGEYIRQWLPELARLPTEWIHHPWDAPLTVLKASG
```

-continued

VELGTNYAKPIVDIDTARELLAKAISRTREAQIMIGAAPDEIVADS

FEALGANTIKEPGLCPSVSSNDQQVPSAVRYNGSKRVKPEEEEERD

MKKSRGFDERELFSTAESSSSSSVFFVSQSCSLASEGKNLEGIQDS

SDQITTSLGKNGCK.

In some embodiments, a cryptochrome-2 polypeptide comprises only the conserved photoresponsive region (phytolyase homology domain) of the cryptochrome-2 protein; this polypeptide is referred to as "CRY2 PHR." In some cases, a CRY2 PHR polypeptide is the first member of the protein interaction pair; and a full-length calcium and integrin-binding protein 1 (C1B1) polypeptide is the second member of the protein interaction pair.

In some embodiments, a first polypeptide or a second polypeptide of a protein interaction pair is a CIB1 polypeptide (also known as transcription factor bHLH63). For example, a suitable CIB1 polypeptide can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence:

(SEQ ID NO: 3)

MNGAIGGDLLLNFPDMSVLERQRAHLKYLNPTFDSPLAGFFADSSM

ITGGEMDSYLSTAGLNLPMMYGETTVEGDSRLSISPETTLGTGNFK

KRKFDTETKDCNEKKKKMTMNRDDLVEEGEEEKSKITEQNNGSTKS

IKKMKHKAKKEENNFSNDSSKVTKELEKTDYIHVRARRGQATDSHS

IAERVRREKISERMKFLQDLVPGCDKITGKAGMLDEIINYVQSLQR

QIEFLSMKLAIVNPRPDFDMDDIFAKEVASTPMTVVPSPEMVLSGY

SHEMVHSGYSSEMVNSGYLHVNPMQQVNTSSDPLSCFNNGEAPSMW

DSHVQNLYGNLGV.

In some embodiments, the CIB is from the *Arabidopsis thaliana*. It will be understood that additional CRY-CIBN pairs from other species can be used in the methods described herein. In some embodiments the protein interaction pair comprises PhyB/PIF or BphP1/PpsR2, which are similar to CRY/CIBN but sense red light.

Nucleic Acids and Expression Vectors

Also provided are nucleic acids comprising a nucleotide sequence encoding any of the proteins or polypeptides described herein. In some embodiments, the nucleic acid encodes a first fusion protein described herein, a second fusion protein described herein, or both. In some embodiments, the nucleic acid is operably linked to a transcriptional control element (e.g., a promoter; an enhancer; etc.). In some cases, the transcriptional control element is inducible. In some cases, the transcriptional control element is constitutive. In some cases, the promoters are functional in eukaryotic cells, such as yeast cells. The transcriptional control elements that are operably linked to the fusion proteins described herein can be the same or different.

The nucleic acids can also include expression vectors for expressing nucleic acids encoding any of the proteins or polypeptides described herein in a host cell. In some embodiments, the host cell is a yeast cell. Suitable transcription and translation control elements, including constitutive and inducible promoters, transcription enhancer elements, transcription terminators, may be used in the expression vector (see e.g., Bitter et al. (1987) Methods in Enzymology, 153:516-544).

Suitable promoter and enhancer elements are known in the art. For expression in a yeast cell, suitable promoters include, but are not limited to cytomegalovirus immediate early promoter; herpes simplex virus thymidine kinase promoter; early and late SV40 promoters; or a promoter present in long terminal repeats from a retrovirus. Suitable promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE),and a rous sarcoma virus (RSV) promoter.

In some embodiments, the promoter is selected from pTDH3, pCCW12, pPGK1, pHHF2, pTEF1, pTEF2, pHHF1, pHTB2, pRPL18B, pALD6, pPAB1, pRET2, pRNR1, pPOP6, pRAD27, pPSP2, pREV1, pMFA1, pMFA1, pMFa2, pGAL1, or pCUP1. In some embodiments, the terminator is selected from tENO1, tSSA1, tADH1, tPGK1, tENO2, or tTDH1.

In some embodiments, the promoter is a TDH3 promoter. Suitable promoters for expressing heterologous genes in yeast are described in Peng, B., et al., "Controlling heterologous gene expression in yeast cell factories on different carbon substrates and across the diauxic shift: a comparison of yeast promoter activities." Microb. Cell Fact. 14, 91 (2015); and Partow, S., et al., "Characterization of different promoters for designing a new expression vector in *Saccharomyces cerevisiae*." Yeast 27, 955-964 (2010).

In some embodiments, a nucleic acid of the present disclosure is a recombinant expression vector. In some cases, the recombinant expression vector is a viral construct, e.g., a recombinant adeno-associated virus (AAV) construct, a recombinant adenoviral construct, a recombinant lentiviral construct, or a recombinant retroviral construct. In some cases, a nucleic acid of the present disclosure is a recombinant lentivirus vector. In some cases, a nucleic acid of the present disclosure is a recombinant AAV vector. In some cases, a nucleic acid of the present disclosure is packaged in a viral particle. For example, in some cases, the nucleic acids of the present disclosure are recombinant AAV vectors, and are packaged in recombinant AAV particles. Thus, the present disclosure provides a recombinant viral particle comprising a nucleic acid described herein.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989)

63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

The present disclosure also provides a nucleic acid comprising a nucleotide sequence encoding a fusion protein comprising: a) a member of a protein interaction pair; and b) a protease that cleaves a proteolytically cleavable linker under certain conditions.

The present disclosure provides a nucleic acid comprising: a) a nucleotide sequence encoding a transmembrane domain or other tethering domain; b) an insertion site for a nucleic acid comprising a nucleotide sequence encoding a first member of a protein interaction pair; c) a a nucleotide sequence encoding a light-activated polypeptide comprising a LOV domain; d) a proteolytically cleavable linker; and e) an insertion site for a nucleic acid comprising a nucleotide sequence encoding a transcription factor. In some embodiments, the nucleic acid comprises a nucleotide sequence encoding a fusion protein comprising i) a transmembrane domain (or other tethering domain); ii) a member of a protein-interaction pair; ii) a light-activated polypeptide comprising a LOV domain; iii) a proteolytically cleavable linker that is caged by the light-activated polypeptide in the absence of blue light; and iv) a transcription factor.

In some embodiments, the nucleotide sequence encoding the transcription factor is within 10 nucleotides (nt), within 9 nt, within 8 nt, within 7 nt, within 6 nt, within 5 nt, within 4 nt, within 3 nt, within 2 nt, or 1 nt, of the 3' end of the nucleotide sequence encoding the proteolytically cleavable linker.

In some embodiments, the nucleic acid(s) comprising nucleotide sequences encoding one or more fusion proteins or reporter gene products, as described above, is stably integrated into the genome of the host cell. In some cases, a nucleic acid(s) comprising nucleotide sequences encoding one or one or more fusion proteins or reporter gene products, is present in the host cell episomally.

Genetically Modified Host Cells and Strains

In another aspect, provided are genetically modified eukaryotic host cells. In some embodiments, the eukaryotic host cell is a yeast cell. In some embodiments, the genetically modified yeast cell is a *Saccharomyces cerevisiae* cell.

In some embodiments, the genetically modified host cell is a primary (non-immortalized) cell. In some embodiments, the genetically modified host cell is an immortalized cell line.

In some embodiments, the host cell is a mammalian cell. In some embodiments, the mammalian cell is a human cell line, non-human primate cell line, or rodent (e.g., mouse, rat) cell line. In some embodiments, the mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), or HLHepG2 cells.

Suitable eukaryotic host cells include, but are not limited to, *Pichia pastoris,Pichia finlandica,Pichia trehalophila, Pichia koclamae,Pichia membranaefaciens,Pichia opuntiae,Pichia thermotolerans,Pichia salictaria,Pichia guercuum,Pichia pijperi, Pichia stiptis,Pichia methanolica, Pichia* sp.*,Saccharomyces cerevisiae,Saccharomyces* sp., *Hansenula polymorpha, Kluyveromyces* sp.*,Kluyveromyces lactis,Candida albicans,Aspergillus nidulans,Aspergillus niger, Aspergillus oryzae,Trichoderma reesei, Chrysosporium lucknowense,Fusarium* sp.*,Fusarium gramineum, Fusarium venenatum,Neurospora crassa,*and *Chlamydomonas reinhardtii.*

The genetically modified host cells described herein can be used to screen for proteases with increased catalytic rates compared to parental or wild-type proteases. In one aspect, the genetically modified host strain comprises a fusion protein described herein. For example, the genetically modified host strain can comprise a first fusion protein, a second fusion protein, or both. In some embodiments, the fusion proteins are expressed in the host cell cytosol, for example in a yeast cell cytosol. The reducing environment in the cytosol more closely resembles the environment in which the modified proteases will mostly be used. In some embodiments, the genetically modified host strain comprises a protease fused to one member of a photoinducible protein binding pair, and a protease cleavage sequence fused to another member of a photoinducible protein binding pair. In some embodiments, the photoinducible protein binding pair is CRY and CIBN. Fusion proteins comprising binding members of a photoinducible protein binding pair allow low-affinity versions of proteases, such as TEV, to be used as the starting sequence for selection by directed evolution, because recognition of the protease cleavage sequence by the protease can be induced by blue light activation and binding of the photoinducible protein binding pair. The genetically modified host strain can also comprise a photocaged protease cleavage sequence with an improved LOV domain (eLOV) in order to exert control over the time window the protease has available to cleave the cleavage sequence.

In some embodiments, the genetically modified host cell comprises a first fusion protein described herein. In some embodiments, the genetically modified host cell comprises a second fusion protein described herein. In some embodiments, the genetically modified host cell comprises both the first and second fusion proteins described herein.

In some embodiments, the genetically modified host cell comprises a first fusion protein comprising, in order from amino terminus to carboxyl terminus: a) a first member of a protein interaction pair; and b) a protease that cleaves the proteolytically cleavable linker. In some embodiments, the first fusion protein comprises, in order from amino terminus to carboxyl terminus: a) CRY; and b) a TEV protease. In some embodiments, the genetically modified host cell comprises a first fusion protein comprising, in order from amino terminus to carboxyl terminus: a) a fluorescent reporter molecule; b) a second member of the protein interaction pair; and c) a protease that cleaves the proteolytically cleavable linker. In some embodiments, the first fusion protein comprises, in order from amino terminus to carboxyl terminus: a) mCherry; b) CRY; and c) a TEV protease described herein. In some embodiments, the TEV protease is a low affinity TEV protease, for example a TEV protease having a carboxy-terminal truncation. In some embodiments, the protease is a C-terminally truncated, low-affinity wild-type TEV (TEVA219, or TEVA) protease. In some embodiments, the TEV protease is a modified TEV protease described herein.

In some embodiments, the genetically modified host cell comprises a second fusion protein comprising, in order from amino terminus (N-terminus) to carboxyl terminus (C-terminus): i) a tethering domain (e.g., a transmembrane domain or other tethering domain); ii) a second member of a protein interaction pair; iii) a LOV-domain polypeptide; iv) a proteolytically cleavable linker; and v) a transcription factor. In some embodiments, the genetically modified host cell comprises a second fusion protein comprising; in order from amino terminus (N-terminus) to carboxyl terminus (C-terminus): i) a tethering domain (e.g., a transmembrane domain or other tethering domain); ii) a fluorescent reporter molecule; (iii) a second member of a protein interaction pair; iv) a LOV-domain polypeptide; v) a proteolytically cleavable linker; and vi) a transcription factor. In some embodiments, the fluorescent reporter molecule is mCherry.

In some embodiments, the genetically modified host cell comprises a reporter gene that is transcribed by a transcription factor. In some embodiments, the reporter gene is stably integrated into the yeast cell genome. In some embodiments, the reported gene encodes a fluorescent protein such as Citrine.

In some embodiments, the genetically modified host cell comprises a first fusion protein, a second fusion protein, and a reporter gene described herein.

In some embodiments, the genetically modified host cell comprises a nucleic acid described herein. In some embodiments, the genetically modified host cell comprises a nucleic acid comprising a nucleotide sequence encoding a fusion protein described herein. In some embodiments, the genetically modified host cell comprises a nucleic acid comprising the nucleotide sequence of a reporter gene described herein, along with operably linked transcription regulatory sequences that regulate transcription and/or translation of the reporter gene.

Methods

In one aspect, a method is described that can be used to select modified proteases having increased catalytic efficiency or catalytic rates. After a protease with increased catalytic efficiency is selected, the method is repeated one or more times to select for mutant proteases with progressive increases in catalytic efficiency. This iterative process is referred to as directed evolution. The method is useful for selecting for proteases having high proximity-dependent catalytic activity, such that the rate of cleavage of the protease substrate is increased with each round of selection.

In some embodiments, the method comprises expressing a first and second fusion protein described herein in the cytosol of a yeast cell, for example, a genetically modified yeast cell described herein, contacting the yeast cell with light, and selecting a modified protease having increased catalytic efficiency or catalytic rates compared with a wild-type protease.

In some embodiments, the first fusion protein comprises a protease linked or fused to one member of a photoinducible protein binding pair. In some embodiments, the protease is a TEV protease. In some embodiments, the protease is a low-affinity protease, for example a TEV protease having a carboxy-terminal truncation. In some embodiments, the protease is a C-terminally truncated, low-affinity wild-type TEV (TEVA219, or TEVA) protease. In some embodiments, the second fusion protein is tethered to the plasma membrane. In some embodiments, the second fusion protein comprises a (i) a transmembrane domain, (ii) a second member of a photoinducible protein binding pair; (iii) a light-oxygen-voltage-sensing (LOV) domain sequence; (iv) a proteolytically cleavable linker; and (iv) a transcription factor.

In some embodiments of the method, the first and second fusion proteins comprise members of a protein interaction pair. In some embodiments, the protein interaction pair is a photoinducible protein binding pair. In some embodiments, the photoinducible protein binding pair comprises cryptochrome (CRY) and cryptochrome-interacting basic-helix-loop-helix protein (CIB). In some embodiments, the protease is fused to CRY.

The yeast cell can also comprise a reporter gene that is transcribed by the transcription factor. In some embodiments, the reporter gene is stably integrated into the yeast cell genome. In some embodiments, the reported gene encodes a fluorescent protein such as Citrine.

In some embodiments, the method comprises the following steps:

a) expressing a first fusion protein in the cytosol of a yeast cell, wherein the first fusion protein comprises a TEV protease linked to a first member of a photoinducible protein binding pair;

wherein the yeast cell comprises:

a second fusion protein comprising:

(i) a transmembrane domain, (ii) a second member of a photoinducible protein binding pair;

(iii) a light-oxygen-voltage-sensing (LOV) domain sequence;

(iv) a proteolytically cleavable linker; and (iv) a transcription factor;

wherein the LOV domain sequence prevents cleavage of the protease substrate amino acid sequence by the protease; and a reporter gene that is transcribed by the transcription factor.

b) irradiating the yeast cells with light;

c) selecting yeast cells that express the reporter gene; and d) detecting increased catalytic activity compared to a control protease, thereby producing the modified protease.

In some embodiments, the first fusion protein further comprises a fluorescent molecule, such as mCherry or BFP. In some embodiments, the second fusion protein further comprises a fluorescent molecule, such as mCherry or BFP.

In the above method, irradiating the yeast cells with light produces an intermolecular complex between the first and second members of the photoinducible protein binding pair and induces a conformational change in the LOV domain sequence to expose the protease substrate cleavage sequence to the protease. Cleavage of the protease substrate by the protease releases the transcription factor fused to the proteolytically cleavable linker, allowing the transcription factor to translocate to the nucleus and activate transcription of the reporter gene. Cells that express the reporter gene are then selected, for example by FACS analysis. However, any method for selecting cells that express a reporter gene can be used, including detecting expression of the reporter gene protein product by Western analysis or immunohistochemistry, or detecting expression of the reporter gene RNA product by Northern analysis or RT-PCR. In some embodiments, the cells are selected using auxotrophic complementation or drug resistance.

To select for proteases having increased catalytic rates, genetically modified yeast cells described herein are first transformed with a library of mutant proteases. As will be understood by one of ordinary skill in the art, a single yeast cell is typically transformed with a nucleic acid encoding one mutant protease from the library, and the size of the library is determined by the number of yeast cells that survive selection after transformation. In some embodiments, the size of the library is about $1 \times 10^6$ to about $1 \times 10^8$ transformants. Following transformation with the library of mutant proteases, the yeast and exposed to light for a specified time period. The initial irradiation period is selected to be long enough to allow the photoinducible protein binding pair to interact and induce transcription of the reporter gene. In some embodiments, the irradiation time is between 0.5 and 60 minutes, e.g., 0.5, 1, 5, 10, 15, 20, 25, 30, 35, 40, 45, 50, 55 or 60 minutes. In some embodiments, the irradiation time is one minute or less, e.g., 5, 10, 15, 20, 25, 30, 35, 40, 45, 50, 55, or 60 seconds. In some embodiments, reporter gene activity is determined between 1 and 6 hours after irradiation of the cells. Cells that express a high reporter gene signal-to-background ratio are selected because these cells express a protease with high cleavage activity. The selected cells are typically expanded then irradiated a second time, but the irradiation time is decreased, for example from time X to time Y, where Y is less than X. Cells that express a high reporter gene signal-to-background ratio can again be selected, expanded, and irradiated, where the irradiation time is again decreased, for example from time Y to time Z, where Z is less than Y. The process can be iteratively repeated to select for yeast cells that express higher levels of reporter gene, indicating that the cells comprise a modified protease with increased catalytic activity.

Typically, yeast cells expressing the reporter gene at levels at least one order of magnitude greater than background are selected. Background expression can be determined by the amount of reporter gene expression in the absence of light, or the amount of reporter gene expression in a yeast cell that does express the first member of a photoinducible protein binding pair. In some embodiments, yeast cells are selected that express a high reporter gene to fluorescent molecule signal ratio. In some embodiments, yeast cells are selected that express the reporter gene at saturation levels, for example, when the signal reaches a plateau.

Thus, the methods described herein provide a high signal-to-noise (S/N) or signal-to-background ratio for selecting yeast cells that express a modified protease. In some embodiments, the signal-to-noise (S/N) or signal-to-background ratio is at least 3:1, at least 4:1, at least 5:1, at least 6:1, at least 7:1, at least 8:1, at least 9:1, at least 10:1, from 10:1 to 15:1, from 15:1 to 20:1, or more than 20:1 (e.g., from 20:1 to 50:1, from 50:1 to 100:1, from 100:1 to 150:1, or more than 150:1). For example, the signal produced when the yeast cell is exposed to light of an activating wavelength (e.g., blue light) is at least 2-fold, at lease 3-fold, at least 4-fold, at least 5-fold, at least 6-fold, at least 7-fold, at least 8-fold, at least 9-fold, at least 10-fold, at least 15-fold, at least 20-fold, or more than 20-fold (e.g., more than 25-fold, more than 50-fold, more than 75-fold, more than 100-fold, more than 125-fold, or more than 150-fold), higher than the signal produced by the cell when the cell is: i) not exposed to light of an activating wavelength; or ii) is exposed to light of an activating wavelength, but does not express one member of the protein interaction pair.

Improved TEV Proteases

Also provided herein are improved (modified) TEV proteases having increased catalytic efficiency compared to a wild-type TEV protease (SEQ ID NO:1; EC number 3.4.22.44, CAS number139946-51-3, see UniProtKB: P04517) or a C-terminally truncated wild-type TEV protease (e.g., TEVΔ219, orTEVΔ). In some embodiments, the improved TEV protease comprises an amino acid sequence differing from wild-type TEV at one or more positions corresponding to positions T30, S31, S135, I138, S153, and T180 of SEQ ID NO:1. In some embodiments, the modified TEV protease comprises a sequence having at least 90% sequence identity to wild-type TEV (SEQ ID NO:1) and comprises one or more mutations selected from T30A, T30I, S31W, S135F, I138T, S153N, S153D, T180A, a double T30A/S153N mutation, a triple S135F/I138T/T180A mutation, or a quadruple S135F/I138T/S153N/T180A mutation, wherein the positions are numbered with reference to SEQ ID NO:1. In some embodiments, the modified TEV protease comprises a sequence having at least 90% sequence identity to a C-terminally truncated wild-type TEV protease (e.g., TEVΔ219, or TEVΔ) and comprises one or more mutations corresponding to T30A, T30I, S31W, S135F, I138T, S153N, S153D, T180A, a double T30A/S153N mutation, a triple I138T/S153N/T180A mutation, or a quadruple S135F/I138T/S153N/T180A mutation. It will be understood that the above amino acid mutations can occur at corresponding positions in other TEV proteases.

In some embodiments, the improved TEV proteases comprise the amino acid substitutions shown below:

uTEVΔ1-S153N
uTEVΔ2-T30A/S153N
uTEV1-S153N
uTEV2-T30A/S153N
uTEV3-I138T/S153N/T180A
Δ=a C terminus truncated TEV protease that comprises residues (1-219).

In some embodiments, the TEV variants (in the truncated or full-length form) incorporate the mutation S219V, which enhances stability by reducing the TEV self-cleavage. (Kapust et al Protein Eng. 2001 14(12):993-1000).

Assays to detect increased catalytic efficiency are also provided. In some embodiments, the protease catalytic activity is determined by incubating the modified TEV protease with increasing concentrations of the substrate sequence ENLYFQS (SEQ ID NO: 5) for increasing amounts of time and quantifying the amount of substrate cleaved. In some embodiments, the assay comprises expressing mutant (full-length or truncated versions) and wild-type proteases with Histidine tags in bacteria, purifying the proteases by affinity chromatography, and contacting the purified proteases with a substrate protein. In some embodiments, the substrate protein comprises maltose binding protein (MBP) fused to a TEV cleavage sequence (for example ENLYFQS (SEQ ID NO: 5)). In some embodiments, the substrate protein comprises a MBP-TEVcs-eGFP fusion protein. After incubation at 30° C. for various times and at various substrate concentrations, cleavage of the substrate protein is determined by quenching the reactions and separating the cleaved protein products using SDS-PAGE gels. Michaelis-Menten analysis is used to determine protease activity. A representative assay is shown in FIG. 15.

In some embodiments, the improved full-length mutant TEV proteases described herein are at least 2-fold, 3-fold, 4-fold, or 5-fold more active that wild-type TEV (SEQ ID NO:1). In some embodiments, the improved truncated versions of mutant TEV proteases described herein have kcat values at least 2-fold, 3-fold, 4-fold, or 5-fold greater than truncated wild-type TEVΔ. Protease activity can be determined, for example, by Michaelis-Menten analysis.

In some embodiments, the modified protease has a substrate specificity or substrate affinity substantially similar to wild-type TEV protease (SEQ ID NO: 1). In some embodiments, the protease substrate amino acid sequence comprises ENLYFQS (SEQ ID NO: 5).

In another embodiment, the modified TEV protease has increased binding affinity for the protease cleavage sequence. In one embodiment, the modified TEV protease having increased binding affinity for the protease cleavage sequence comprises a substitution at amino acid N177 of wild-type TEV protease, or an amino acid corresponding to position N177 of wild-type TEV protease (SEQ ID NO1). In some embodiments, the modified TEV protease comprises a N177Y mutation, or an Asparagine (N) to Tyrosine (Y) mutation at an amino acid corresponding to position N177 of wild-type TEV protease. In some embodiments, the modified TEV protease comprises a N177Y mutation and is truncated at a position corresponding to position 219 of wild-type TEV.

The modified TEV protease can include one or more of the following amino acid substitutions relative to an unmodified or wild-type TEV protease (SEQ ID NO:1): T301, S31W, L56S, D90G, S135F, S153D, or N177Y.

Improved FLARE2 and SPARK2 Reporters

The modified TEV proteases described herein can be used to improve existing biotechnology tools. For example, two such tools are FLARE and SPARK, which comprise caged transcription factors that are activated by the coincidence of blue light and a second stimulus—for FLARE, that stimulus is elevated cytosolic calcium, while for SPARK, it is a protein-protein interaction (PPI) (see FIGS. 3A and 3B). Both tools strive to convert transient cellular events into long-lasting signals that can enable microscopy, manipulation, or genetic selection. How transient an event can be recorded by FLARE or SPARK depends on how many TF molecules can be released per unit time, which is in turn is limited by protease catalytic rate. FLARE requires a minimum of 10-15 minutes of light+calcium to give sufficient signal/noise in neuron culture. Similarly, SPARK requires a 10-15 minute "recording" time window to capture a cellular PPI event. The modified TEV proteases described herein provide faster response time and increased signal to noise ratios compared to wild-type TEV or wild-type truncated TEV (TEVA).

For example, when modified TEV proteases comprising a S153N mutation, or both a S153N and T30A mutation, were introduced into the FLARE and SPARK tools, an increase in reporter gene expression was observed compared to wild-type TEV or wild-type TEVA. In addition, the increase in reporter gene expression occurred with a significantly decreased irradiation time, and the signal-to-background ratio and signal to noise ratios were substantially increased (as described in the Examples).

Kits

In another aspect, a kit is provided comprising a fusion protein described herein, or a nucleic acid encoding one or more polypeptides of a fusion protein described herein. In some embodiments, the kit comprises a modified yeast cell described herein. In some embodiments, the kit comprises a genetically modified yeast cell comprising a reporter gene described herein. In some embodiments, the kit comprises a genetically modified yeast cell comprising one or more fusion proteins described herein. In some embodiments, the kit comprises a genetically modified yeast cell comprising one or more fusion proteins described herein and a reporter gene described herein. The kit can also include instructions for using the genetically modified yeast cell to select for proteases having increased catalytic activity.

In some embodiments, the kit comprises a modified protease described herein. In some embodiments, the kit comprises a modified TEV protease comprising a sequence having at least 90% sequence identity to wild-type TEV (SEQ ID NO:1) and comprising one or more mutations selected from T30A, T301, S31W, S153N, N177Y, or a double T30A/S153N mutation. In some embodiments, the kit comprises a modified TEV protease comprising a sequence having at least 90% sequence identity to a C-terminally truncated wild-type TEV protease (e.g., TEVA219, or TEVA) and comprising one or more mutations selected from T30A, T301, S31W, S153N, N177Y, or a double T30A/S153N mutation.

EXAMPLES

Example 1

This example describes methods for producing yeast strains described herein.

Cloning

See the Plasmid table for a list of genetic constructs used in this Example, with detailed description of construct features such as promoters, linkers, auxotrophic markers, epitope and fluorescence tags.

For cloning, PCR fragments were amplified using Q5© polymerase (New England BioLabs (NEB)). The vectors were double-digested and ligated to gel-purified PCR products by T4 ligation or Gibson Assembly®, a molecular cloning method that allows for the joining of multiple DNA fragments in a single, isothermal reaction. Ligated plasmid products were introduced by heat shock transformation into competent XL1-Blue bacteria.

Yeast Strains Construction

All strains were derived from *Saccharomyces cerevisiae* BY4741 (Euroscarf, Johann Wolfgang Goethe-University Frankfurt, Germany). Plasmid transformation or integration in yeast was performed using the Frozen E-Z Yeast Transformation II kit (Zymoprep) according to manufacturer protocols.

*S. cerevisiae* strains were produced step-wise and propagated at 30° C. in supplemented minimal medium, (SMM; 6.7 g/L Difco nitrogen base without amino acids, 20 g/L dextrose, 0.54 g/L CSM-Ade-His-Leu-Lys-Trp-Ura (Sunrise Science Products). Transformants were isolated in appropriate selective SD medium by auxotrophy complementation. For yeast strain transformation, we grew cells at 30° C. in YPD, containing 10 g/L yeast extract (BD Biosciences, Germany), 20 g/L peptone (BD Biosciences, Germany) and 20 g/L dextrose.

The yeast strain containing the reporter gene was produced by integrating (lexA-box)4-PminCYC1-Citrine-TCYC1 plasmid, (addgene plasmid #58434 or FRP793) into BY4741. [38] For integration, plasmid was linearized with Pacl. Transformed cells containing the URA3 gene were selected on SMM plates (SMM with 20 g/L agar) and propagated in SMM at 30° C. supplemented with 20 mg/L histidine and 100 mg/L Leucine, producing BY4741-ura3Δ0::(lexA-box)4-PminCYC1-Citrine-tCYC1.

Next, different pRS-derived constructs bearing the membrane-anchored transcription factors were integrated into the plasmids. STE2 (addgene #32171), promoters/terminators and different TFs (addgene plasmids #58434, #58431, #58438, and #64511) were integrated. [38] For integration, plasmids were digested with Ascl. Transformed cells containing the LEU2 gene were selected on SMM plates (SMM with 20 g/L agar) and propagated in SMM at 30° C. supplemented with 20 mg/L histidine.

Plasmids bearing different TEV protease versions were episomally introduced in a pRSII413 vector (Addgene non-profit plasmid depository #35450). Transformed cells containing the HIS3 gene were selected on SMM plates (SMM with 20 g/L agar) and propagated in SMM at 30° C.

For the sequence specificity protease profiling in yeast, BY4741-ura3Δ0::(lexA-box)4-PminCYC1-Citrine-tCYC1 was also used. In this case, wild type and evolved proteases in full length or truncated versions (fussed to mtagBFPll to detect protease expression) were integrated into the Leu2A1 locus after digestion with Ascl. Transformed cells containing the LEU2 gene were selected on SMM plates (SMM with 20 g/L agar) and propagated in SMM at 30° C. supplemented with 20 mg/L histidine.

Plasmids bearing mutations on the TEV recognition site were episomally introduced in a pRS11413. Transformed cells containing the HIS3 gene were selected on SMM plates (SMM with 20 g/L agar) and propagated in SMM at 30° C.

Yeast Cell Culture

Single colonies of transformed cells containing the 3 components (reporter gene, membrane-anchored TF and TEV-protease) were inoculated in 5 mL SSM media and cultured at 30° C. and 220 r.p.m. The fresh saturated culture was diluted 1:20 in fresh media of identical composition and allowed to grow for approximately 6-9 h more until reaching OD600 ~0.6.

TEV protease expression was induced by inoculating 0.25 mL of a non-saturated yeast culture (OD600 ~0.6) into 4.75 mL of 10% D/G SMM (SMM medium with 90% of dextrose replaced with galactose) at 30° C. and 220 r.p.m. for 12 h. An aliquot of this culture (around 0.2 mL) was placed in a cuvette and illuminated with MaestroGen UltraBright® LED transilluminator (470 nm) at different time points. After irradiation, samples were transferred to an Eppendorf tube containing 0.040 mL of the volume of fresh 10% D/G SMM and incubated in a rotator for 6 hours in the darkness at 30° C.

TDH3 promoter activity could decrease with time and saturation conditions, which reduce the quantity of transcription factor available to be released from the plasma membrane by the protease, potentially reducing the signal of the reporter gene. [39]

Constructs displaying altered TEV peptide substrates were expressed in the same way as the ones bearing the TEV protease. After expression, yeast were illuminated at indicated time points under the same settings and incubated in the same conditions.

FACS Analysis.

After incubation for 6 h in the conditions detailed above, yeast samples were transferred to a 5 mL polystyrene round-bottom tube with 1 mL of DBPS.

For two-dimensional FACS analysis, a LSRII-UV flow cytometer (BD Biosciences) was used to analyze yeast with 488-nm and 561 nm-nm lasers and 525/50 (for citrine) and 610/20 (for mCherry) emission filters. To analyze and sort single yeast cells, cells were plotted by a forward-scatter area (FSC-A) and side-scatter area (SSC-A) and a gate was drawn around cells clustered between 10e4-10e5 FSC-A, 10e3-10e5 SSC-A to give population P1. Cells from population P1 were then plotted by side-scatter width (SSC-W) and side-scatter height (SSC-H) and a gate was drawn around cells clustered between 10-100 SSC-W and 10e3-10e5 SSC-H to give population P2. Cells from population P2 were then plotted by forward-scatter width (FSC-W) and forward-scatter height (FSC-H) and a gate was drawn around cells clustered between 10-100 FSC-W and 10e3-10e5 FSC-H to give population P3. Population P3 often represented >90% of the total population analyzed. From population P3, was analyzed to show in the x-axis, the mCherry signal associated to TEV protease or peptide substrate expression (561 nm and 610/20 emission filters) and in the y-axis, the citrine signal related with the turn on of the expression gene (488 nm and 525/50 emission filters).

To sort yeast populations, a BD FACSAria™ II cell sorter (BD Biosciences) with the same parameters described above was used. From population P3, gates were drawn to collect yeast with the highest activity/expression ratio, i.e., positive for citrine signal (reflects the extension of transcription factor released) that also had high mCherry signal (to measure TEV protease or peptide substrate expression levels).

BD FACSDiva™ image analysis software was used to analyze all data from FACS sorting and analysis. Summaries of all yeast-display directed evolution, resulting mutants and TEV protease sequence profiling are shown in FIG. 1 and FIGS. 4-11.

Directed Evolution of TEVA and Transformation in Yeast.

For the directed evolution of TEVA, which comprises amino acids 1-219 of the wild type TEV protease, three libraries were generated using TEVA-S219V as starting template using error prone PCR as described below. The TEV gene corresponds to addgene #8827.

To perform error-prone PCR, 100 ng of the template plasmid (GalP-mCherry-CRY2 PHR-TEVA-S219V in pRS11413) was combined with 0.4 μM forward and reverse primers that anneal to the sequences just outside the 5' and 3' ends of the gene encoding TEVA-S219V, 2 mM MgCl2, 10 units of Taq polymerase (NEB), 0.2 mM of regular dNTPs, 1×Taq polymerase buffer (NEB) and 2 μM or 20 μM each of the mutagenic nucleotide analogs 8-oxo-2'-deoxyguanosine-5'-triphosphate (8-oxo-dGTP) and 2'-deoxy-p-nucleoside-5'-triphosphate (dPTP) in a total volume of 100 μL.

The following conditions were used to produce varying levels of mutagenesis:

Library 1: 2 μM 8-oxo-dGTP, 2 μM dPTP, 10 PCR cycles
    Library 2: 2 μM 8-oxo-dGTP, 2 μM dPTP, 20 PCR cycles
    Library 3: 20 μM 8-oxo-dGTP, 20 μM dPTP, 10 PCR cycles

```
Forward primer:
                                     (SEQ ID NO: 39)
5'- ggtggaagtggatcaggcagcggtggatctggcagcggaaagcttg gttccggg -3'

Reverse primer:
                                     (SEQ ID NO: 40)
5'-ggagggcgtgaatgtaagcgtgacataactaattacatgactcgagc tatta-3'
```

The PCR was run for 20 or 10 cycles (depending on the library) with an annealing temperature of 58° C. per cycle. The PCR product was gel-purified, and re-amplified in regular conditions for another 30 cycles with 0.4 μM forward and reverse primers that introduce ~45 bp of overlap with both ends of the vector.

In a parallel experiment, the pIIRS-413:GalP-mCherry-CRY2 PHR-TEVA-S219V-tCYC1 plasmid was linearized by digesting with HindIII-HF and XhoI restriction enzymes overnight at 37° C. These enzymes digest the gene just upstream and downstream of the gene TEVA-S219V. The linearized plasmid was purified by gel extraction. 1 µg of linearized vector was combined with 4 µg of mutagenized TEVA PCR product from above, and concentrated using Pellet Paint® Co-Precipitant, MilliporeSigma (a visible dye-labeled carrier formulated specifically for use in alcohol precipitation of nucleic acids) according to the manufacturer's protocols. The DNA was precipitated with ethanol and sodium acetate, and resuspended in 10 µL ddH2O.

Fresh electrocompetent strain BY4741 with the reporter gene (lexA-box)4-PminCYC1-Citrine-tCYC1 integrated in the ura3Δ0 locus, and cells containing the optimized TF TDH3:STE2Δ-CIBN-BFP-eLOV-TEVcs-LexAVP16-tCYC1 in the Leu2Δ1 locuswere prepared. Yeast were passaged at least two times before this procedure to ensure that yeast were healthy. 2-3 mL of an overnight grown culture was used to inoculate 100 mL of YPD media. The culture was grown with shaking at 220 r.p.m. at 30° C. for 6-8 h until the OD600 reached 1.5-1.8. Yeast were then harvested by centrifugation for 3 min at 3,000 r.p.m. and resuspended in 50 mL of sterile 100 mM lithium acetate in water by vigorous shaking. Fresh sterile DTT (1 M stock solution, made on the same day) was added to the yeast cells to a final concentration of 10 mM. The cells were incubated with shaking at 220 r.p.m. for 12 min at 30° C. (necessary to ensure adequate oxygenation). Then yeast were pelleted at 4° C. by centrifugation at 3,000 r.p.m. for 3 min and washed once with 25 mL ice-cold sterile water, pelleted again, and resuspended in 1 mL ice-cold sterile water.

The concentrated mixed DNA from above was combined with 250 µL of electrocompetent yeast placed into a Gene Pulser® electroporation cuvette (BIO-RAD Laboratories, catalog 3165-2086) prechilled in ice and then electroporated using a Bio-Rad Gene pulser XCell with the following settings: 500-V, 15-ms pulse duration, one pulse only, 2-mm cuvette. The electroporated cells were immediately rescued with 2 mL pre-warmed YPD media and then incubated at 30° C. for 2 h without shaking. Cells were vortexed briefly, and 1.99 mL of the rescued cell suspension was transferred to 100 mL of SMM medium supplemented with 50 units/mL penicillin and 50 µg/mL streptomycin and grown for 2 days at 30° C. The remaining 10 µL of the rescued cell suspension was diluted 100×, 1000×, 10000×, and 100000×; 20 µL of each dilution was plated on SDCAA plates and incubated at 30° C. for 3 days. After 3 days, each colony observed in the 100×, 1000×, 10000×, or 100000× segments of plates will correspond to 104, 105, 106, or 107 transformants in the library, respectively. The culture was grown at 30° C. with shaking at 220 r.p.m. for 1 d, before induction of protein expression and positive selection as described below ("Yeast display selection").

The transformation efficiency of the TEVA-S219V library into BY4741-ura3Δ0::(lexA-box)4-PminCYC1-Citrine-tCYC1/Leu2Δ1::TDH3:STE2Δ-CIBN-BFP-eLOV-TEVcs-LexAVP16-tCYC1 pRSII413-HIS3::GalP-mCherry-CRY-TEVΔ-S219V(library)-tCYC1 was determined to be ~4×107.

DNA sequencing of 24 individual clones showed that each clone had 0-8 amino acids changed relative to the original TEVΔ-S219V template.

Example 2

This example describes a representative method for producing improved proteases using directed evolution.
Directed Evolution of uTEV3

The directed evolution of uTEV3 was performed in the same manner described above, but with the following differences: full-length uTEV1 (S153N/S219V) was our starting template and we have used the following primers to generate the library:

```
Forward primer:
                                    (SEQ ID NO: 41)
5'- gtggaggcggtagcggaggcggagggtcggctagcggcagcggaaa gcttggttccggg -3'

Reverse primer:
                                    (SEQ ID NO: 40)
5'- ggagggcgtgaatgtaagcgtgacataactaattacatgactcgag ctatta -3'
```

The transformation efficiency of our TEV-S153N/S219V library into BY4741-ura3Δ0::(lexA-box)2-PminCYC1-Citrine-tCYC1/Leu2Δ1::TDH3:STE2Δ-CIBN-BFP-eLOV-TEVcs(ENLYFQ/S)-LexAVP16-tCYC1 pRSII413-HIS3::GalP-mCherry-TEV-S153N/S219V (library)-tCYC1 was determined to be ~31×10e7. DNA sequencing of 24 individual clones (showed that each clone had 0-7 amino acids changed relative to the original template.
Directed Evolution of TEV with Altered Substrate Recognition.

The directed evolution of full-length TEV(S219V) was performed in the same manner described above but TEV (S219) was our starting template and we have used the following primers to generate the library:

```
Forward primer:
                                    (SEQ ID NO: 41)
5'- gtggaggcggtagcggaggcggagggtcggctagcggcagcggaaa gcttggttccggg -3'

Reverse primer:
                                    (SEQ ID NO: 40)
5'- ggagggcgtgaatgtaagcgtgacataactaattacatgactcgag ctatta -3'
```

The transformation efficiency of the TEV(S219) library into BY4741-ura3Δ0::(lexA-box)4-PminCYC1-Citrine-tCYC1/Leu2Δ1::TDH3:STE2Δ-CIBN-BFP-eLOV-TEVcs (ENLXFO/S)-LexAVP16-tCYC1 (X=His orTrp) pRSII413-HIS3::GalP-mCherry-TEV-S219V (library)-tCYC1 was determined to be ~10×10e7. DNA sequencing of 24 individual clones (showed that each clone had 0-9 amino acids changed relative to the original template.
Yeast Display Selection For each round of evolution (FIG. 8A, FIG. 15 and FIG. 21), the input was 10-fold more yeast cells than the estimated library size. For the first round, library size was estimated by the transformation efficiency of the initial ligase library. For subsequent rounds, library size was taken to be the number of yeast cells collected during the previous sort.

Yeast cells transformed with the TEVΔ-S219V library in pRSII413, as described above ("Directed evolution of TEVA and transformation in yeast"), were induced by transferring them to 1:10 SMM-D/G media, and growing the cells for 12 at 30° C. with shaking at 220 r.p.m. For the first round of selection, 10 mL of yeast culture (at OD600 ~1.5; note that OD600 ~1 corresponds to roughly $3\times10^7$ yeast cells/mL) were placed in cuvettes and illuminated with MaestroGen UltraBright® LED transilluminator (470 nm) for 8 min.

After irradiation, samples were transferred to two culture tube with fresh 1 mL D/G SMM and incubated for 6 h at 30° C. with shaking at 220 r.p.m. Culture was spin down at 3,000 r.p.m. for 3 min and resuspended with 5 mL of PBS-B (sterile phosphate-buffered saline supplemented with 0.1% BSA).

To sort more active mutants, gates were drawn to collect yeast with the highest activity/expression ratio, i.e., positive for citrine signal and for mCherry signal as explained in FACS analysis section. Cells retained during sorting were immediately put to a 30° C. incubator with shaking at 220 r.p.m in SSM+1% pen-strep were grown until saturation (1-2 d). Yeast cells were passaged in this manner at least two times prior to the next round of selection.

For subsequent rounds of selection (rounds 2-3), 1 mL of a saturated culture was blue-light irradiated for 4 min and 30 sec subsequently. The size of sorted yeast populations were at least 10-fold more of the sorted population in the previous sort.

Round 1: 1.5% of cells collected (6×10e6 cells)
Round 2: 1% of cells collected (6×10e5 cells)
Round 3: 0.5% of cells collected (3×10e4 cells)

After the third sort, yeast were collected as described above and 1 mL of the growing culture was removed for DNA extraction using the Zymoprep™ yeast Plasmid Miniprep II (Zymo Research) purification kit according to manufacturer protocols. After plasmid transformation in XL1B bacteria, single colonies were grown overnight at 37° C. with shaking at 220 r.p.m. Bacteria cultures were spin down at 6000 rpm for 6 min and plasmid was extracted with QIAprep® Spin Miniprep DNA preparation Kit according to manufacturer protocols.

Mutants were Analyzed by Sanger Sequencing..

```
Sequencing Primer:
                              (SEQ ID NO: 42)
5'-cgcagattatgatcggagcagcgccg -3'
```

The same procedure was used to select active mutants in "Directed evolution of uTEV1 against TEVcs (ENLYFQ/ S)" ("ENLYFQ/S" disclosed as (SEQ ID NO: 5) and "Directed evolution of TEV with altered substrate recognition (ENLHFQ/S) or (ENLWFQ/S) (SEQ ID NOS:7 and 8).

```
Sequencing Primer:
                              (SEQ ID NO: 43)
5'- ggtcaaggtctgcaggctagtggtg -3'
```

Sequence Specificity Protease Profiling in Yeast

Plasmid pRSII413:GaIP-STE2Δ-mCherry-CIBN-PIF6-eLOV-ENLYFQ/Met-LexAVP16-tCYC1 was digested overnight with BamHI-HF and HindIII-HF overnight at 37 C and the linearize vector was gel purified.

In a separate experiment, PRC reactions were carried out with primers bearing degenerated nucleotides to randomized single positions in the TEV peptide substrate. PCR reactions were gel purified and digested with BamHI-HF and HindIII-HF for 3 hours and purified with QIAprep® Spin Miniprep DNA preparation Columns according to manufacturer protocols.

```
F:
                              (SEQ ID NO: 44)
5'-GTTGGAAAGCAATAAACATGTTGACGGGGGATCC-3'

R-P6:
                              (SEQ ID NO: 45)
5'-GCCTGGCCGTTAACGCTTTCATAAGCTTCCCGCCCATCTGGAAGTA

GAGATTNNNCTTAGCGGCTTC-3'

R-P5:
                              (SEQ ID NO: 46)
5'-GCCTGGCCGTTAACGCTTTCATAAGCTTCCCGCCCATCTGGAAGTA

GAGNNNTTCCTTAGCG-3'

R-P4:
                              (SEQ ID NO: 47)
5'-GCCTGGCCGTTAACGCTTTCATAAGCTTCCCGCCCATCTGGAAGTA

NNNATTTTCCTTAGC-3'

R-P3:
                              (SEQ ID NO: 48)
5'-GCCTGGCCGTTAACGCTTTCATAAGCTTCCCGCCCATCTGGAANNN

GAGATTTTCCTTAG-3'

R-P2:
                              (SEQ ID NO: 49)
5'-GCCTGGCCGTTAACGCTTTCATAAGCTTCCCGCCCATCTGNNNGTA

GAGATTTTCC-3'

R-P1:
                              (SEQ ID NO: 50)
5'-GCCTGGCCGTTAACGCTTTCATAAGCTTCCCGCCCATNNNGAAG

TAGAGATTTTC-3'

R-P1':
                              (SEQ ID NO: 51)
5'-GCCTGGCCGTTAACGCTTTCATAAGCTTCCCGCCNNNCTGGAAGTA

GAG-3'
```

Digested vectors and inserts were treated with T4 ligase and transformed into competent XL1-Blue bacteria. After 20 h, colonies were harvested with 5 mL of in Lysogeny Broth (LB) supplemented with 100 μg/mL ampicillin and grown overnight at 37° C. with shaking at 220 r.p.m. Bacteria cultures were spin down at 6000 rpm for 6 min and plasmid was extracted with QIAprep® Spin Miniprep DNA preparation Kit according to manufacturer protocols.

Yeast strains with integrated reporter gene and TEV proteases were transformed according to the protocols described in explained in the Yeast strains construction section. After 48 h, single colonies appear in SMM-plates and were harvested with 5 mL of SMM and grown overnight at 30° C. with shaking at 220 r.p.m.

Yeast cells transformed with randomize single positions in TEV peptide substrate in pRSII413, were induced by transferring them to 1:10 SMM-D/G media, and growing the cells for 12 at 30° C. with shaking at 220 r.p.m. 1 mL of yeast culture (at OD600 ~1.5; note that OD600 ~1 corresponds to roughly $3\times107$ yeast cells/mL) were placed in cuvettes and illuminated with MaestroGen UltraBright LED transilluminator (470 nm) at indicated times (supporting FIG. X).

After irradiation, samples were transferred to two culture tubes with fresh 0.1 mL D/G SMM and incubated for 6 h at 30° C. with shaking at 220 r.p.m. Culture was spun down at 3,000 r.p.m. for 3 min and resuspended with 1 mL of PBS-B (sterile phosphate-buffered saline supplemented with 0.1% BSA).

To sort peptide substrates bearing mutations processable by TEV evolved proteases, gates were drawn to collect yeast with the highest activity/expression ratio, i.e., positive for citrine signal and for mCherry signal as explained in FACS analysis section.

Cells retained during sorting were immediately put to a 30° C. incubator with shaking at 220 r.p.m in SSM+1% pen-strep were grown until saturation (it takes 1-2 d). When saturated, 1 mL of the growing culture was removed for DNA extraction using the Zymoprep™ yeast Plasmid Mini-prep II (Zymo Research) kit according to manufacturer protocols. After plasmid transformation in XL1B bacteria, single colonies were grown overnight at 37° C. with shaking at 220 r.p.m. Bacteria cultures were spun down at 6000 rpm for 6 min and plasmid was extracted with QIAprep® Spin Miniprep XL1 DNA preparation Kit according to manufacturer protocols.

Amino acid identity was analyzed by Sanger sequencing. Sequencing Primer: 5'-ggtgccatcacaaatctcggggacacgc-3' (SEQ ID NO: 52).

Example 3

This example describes representative methods for analyzing, tranfecting, and culturing cells.

Fluorescence Microscopy of Cultured Cells

Confocal imaging was performed on a Zeiss AxioObserver inverted confocal microscope with 10× air and 40× oil-immersion objectives, outfitted with a Yokogawa spinning disk confocal head, a Quad-band notch dichroic mirror (405/488/568/647), and 405 (diode), 491 (DPSS), 561 (DPSS) and 640-nm (diode) lasers (all 50 mW). The following combinations of laser excitation and emission filters were used for various fluorophores: eGFP/citrine (491 laser excitation; 528/38 emission), mCherry (561 laser excitation; 617/73 emission), and differential interference contrast (DIC). Acquisition times ranged from 100 to 500 ms. All images were collected and processed using SlideBook (Intelligent Imaging Innovations).

HEK 293T Cell Culture and Transfection

HEK293T cells from ATCC with fewer than 20 passages were cultured as monolayers in media composed of a 1:1 mixture of DMEM (Dulbecco's Modified Eagle medium, Gibco) and MEM (Minimum Essential Medium Eagle) supplemented with 10% (v/v) FBS (Fetal Bovine Serum, Sigma) and +1% (v/v) pen-strep (Fisher Scientific cat #: MT3002C1.), at 37° C. under 5% CO2. For imaging at 10× magnification, the cells were grown in plastic 48-well plates that were pretreated with 50 μg/mL human fibronectin (Millipore) for at least 10 min at 37° C. before cell plating (to improve adherence of HEK cells). For imaging at 40× magnification, the cells were grown on 7×7 mm glass cover slips placed inside 48-well plates. The coverslips were also pretreated with 50 μg/mL human fibronectin for at least 10 min at 37° C. before cell plating. Cells were transfected at 60-90% confluence with 1 mg/mL PEI MAX® transfection reagent (polyethylenimine HCl Max pH 7.3).

For transfection for FLARE and SPARK experiments in a single well in a 48-well plate, a mix of DNA (20 ng of UAS-mCherry plasmid; 20 ng of protease plasmid; and 50-100 ng of TF plasmid) was incubated with 0.8 μL PEI MAX® transfection reagent in 10 μL serum-free MEM media for 15 min at room temperature. DMEM/MEM with 10% FBS (100 μL) was then mixed with the DNA-PEI max solution and added to the HEK 293T cells and incubated for 15-18 h before further processing. After 15-18 h post-transfection, HEK 293T cells were subjected to four different conditions. Procedures for high-calcium, low-calcium, light, and dark conditions were identical to those described above.

HEK 293T Cell Stimulation, Imaging, and Data Analysis for FLARE and SPARK Experiments HEK 293T cells expressing FLARE constructs were processed 15 h post-transfection. To elevate cytosolic calcium, 100 μL of ionomycin and $CaCl_2$) in complete growth media was added gently to the top of the media in a 48-well plate to final concentrations of 2 μM and 6 mM, respectively. For low Ca2+ conditions, 200 μL complete growth media was added. After a 30 sec incubation, the solution in the 48-well plates was removed and the cells were washed once and then incubated with 200 μL complete growth media. When Ca2+ stimulation is coincident with light illumination, one 48-well plate of HEK 293T cells was placed on top of a custom-built LED light box that delivers 467-nm blue light at 60 mW/cm2 intensity and 33% duty cycle (2 s of light every 6 s). Cells were irradiated on the blue LED light box for 30 sec total. For the dark condition, HEK 293T cells were wrapped in aluminum foil. Afterwards, media in each well was removed, and the cells were washed once and then incubated with 250 μL complete growth media. HEK 293T cells were then incubated in the dark at 37° C. for 8 h and imaged right away. (see FIG. 4E and FIG. 23).

HEK 293T cells expressing SPARK constructs were processed 15 h post-transfection. To promote agonist interaction, complete growth media containing isoproterenol was added gently to the top of the media in a 48-well plate to final concentrations of 10 μM. For no agonist interaction, 200 μL complete growth media was added. After a 30 sec incubation, the solution in the 48-well plates was removed and the cells were washed once and then incubated with 200 μL complete growth media. When agonist stimulation is coincident light irradiation, selected plates were expose to blue light in the same conditions as describe before. For the dark condition, HEK 293T cells were wrapped in aluminum foil. Afterwards, media in each well was removed, and the cells were washed once and then incubated with 250 μL complete growth media. HEK 293T cells were then incubated in the dark at 37° C. for 8 h and imaged immediately.

Figure 4D:
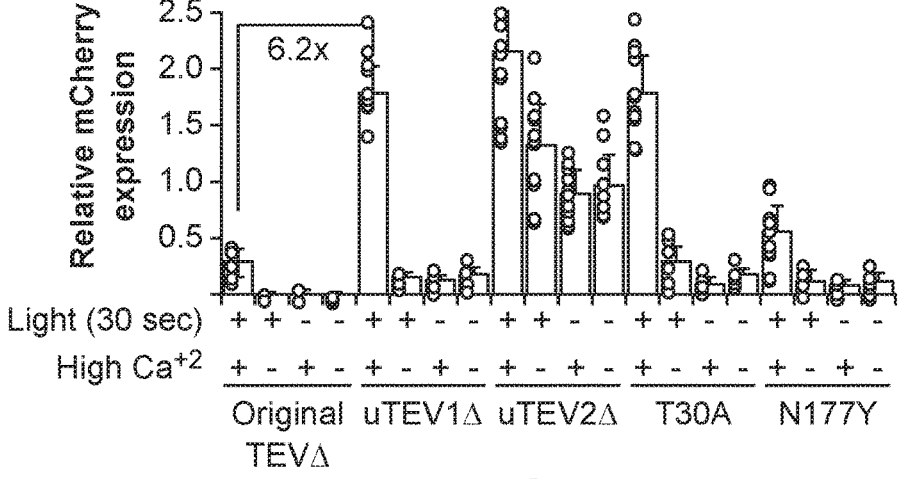
Figures 4E, 4F:
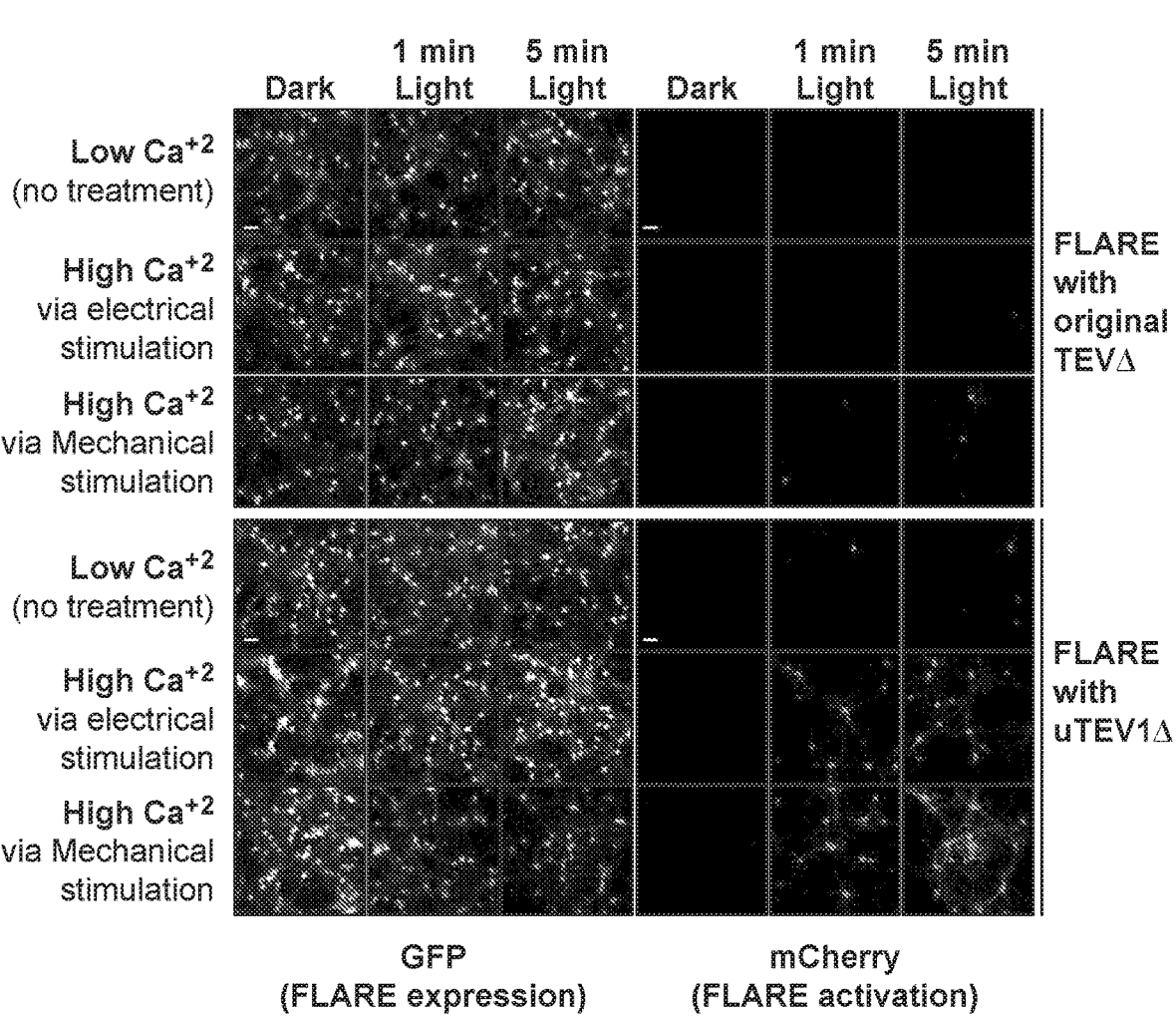
Figures 4G, 4H:
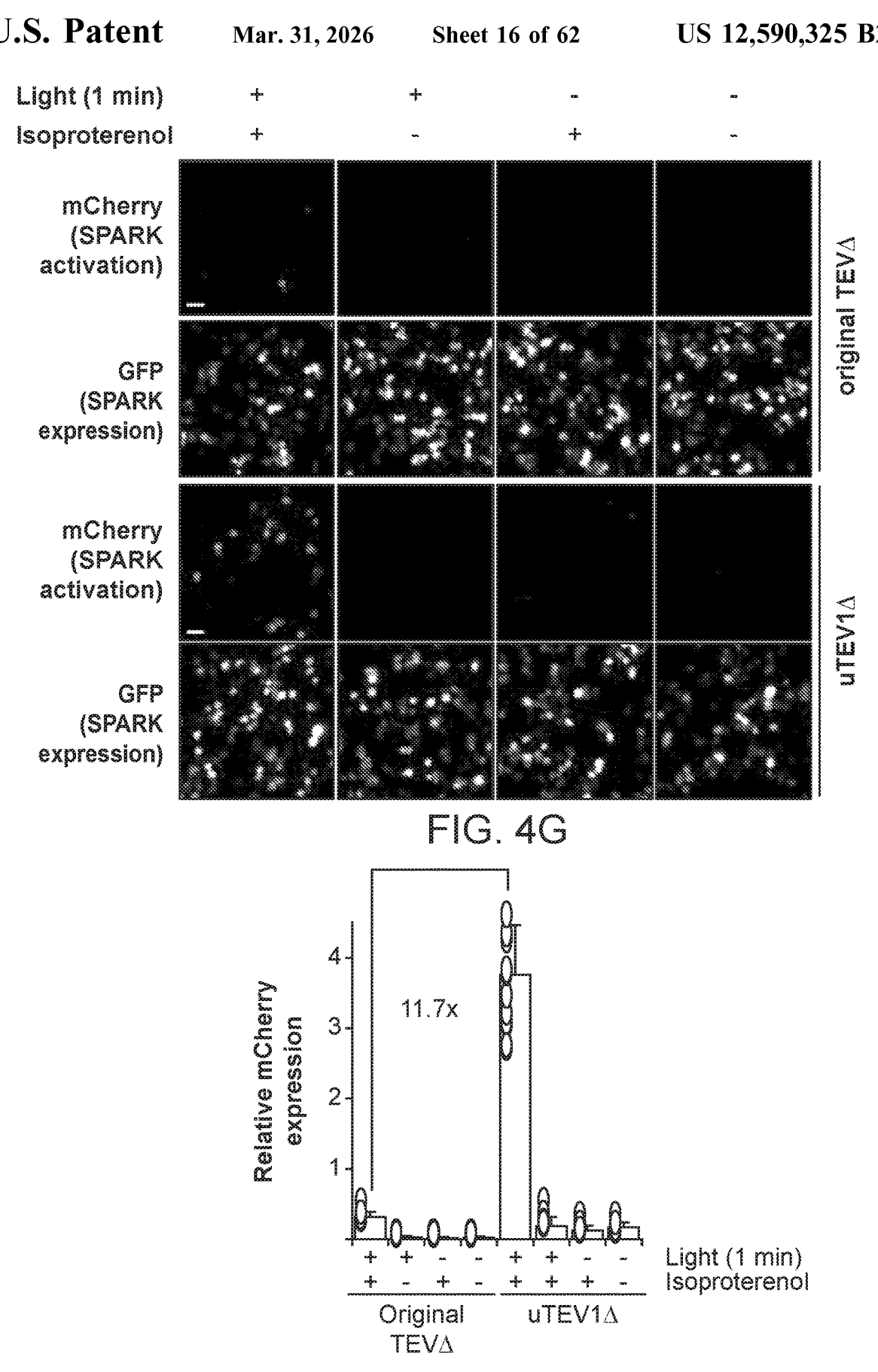
Figure 5A:
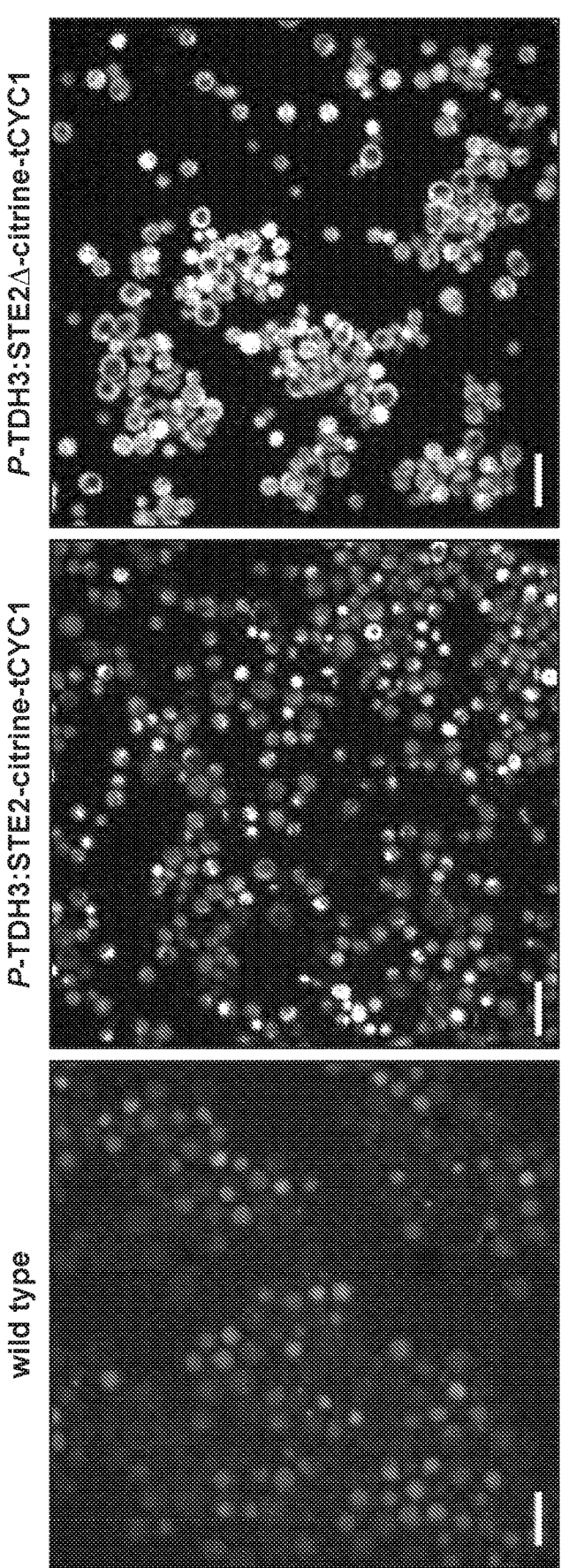
FIGS. 5A, 5B, and 5C show optimization of membrane-anchored transcription factor for yeast directed evolution. FACS plots used to generate the plot in FIG. 1C.
Figure 5B:
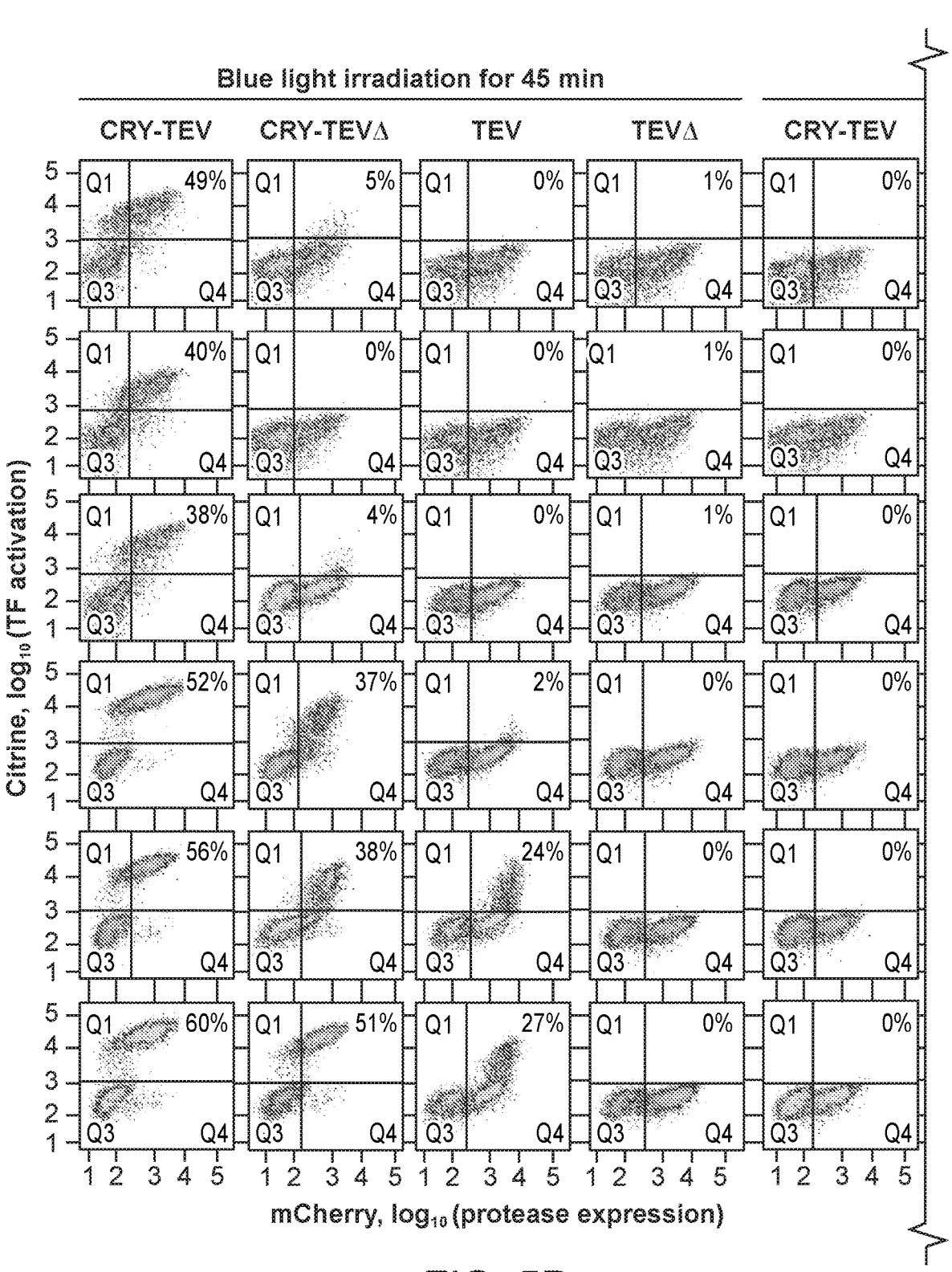
Figure 5C:
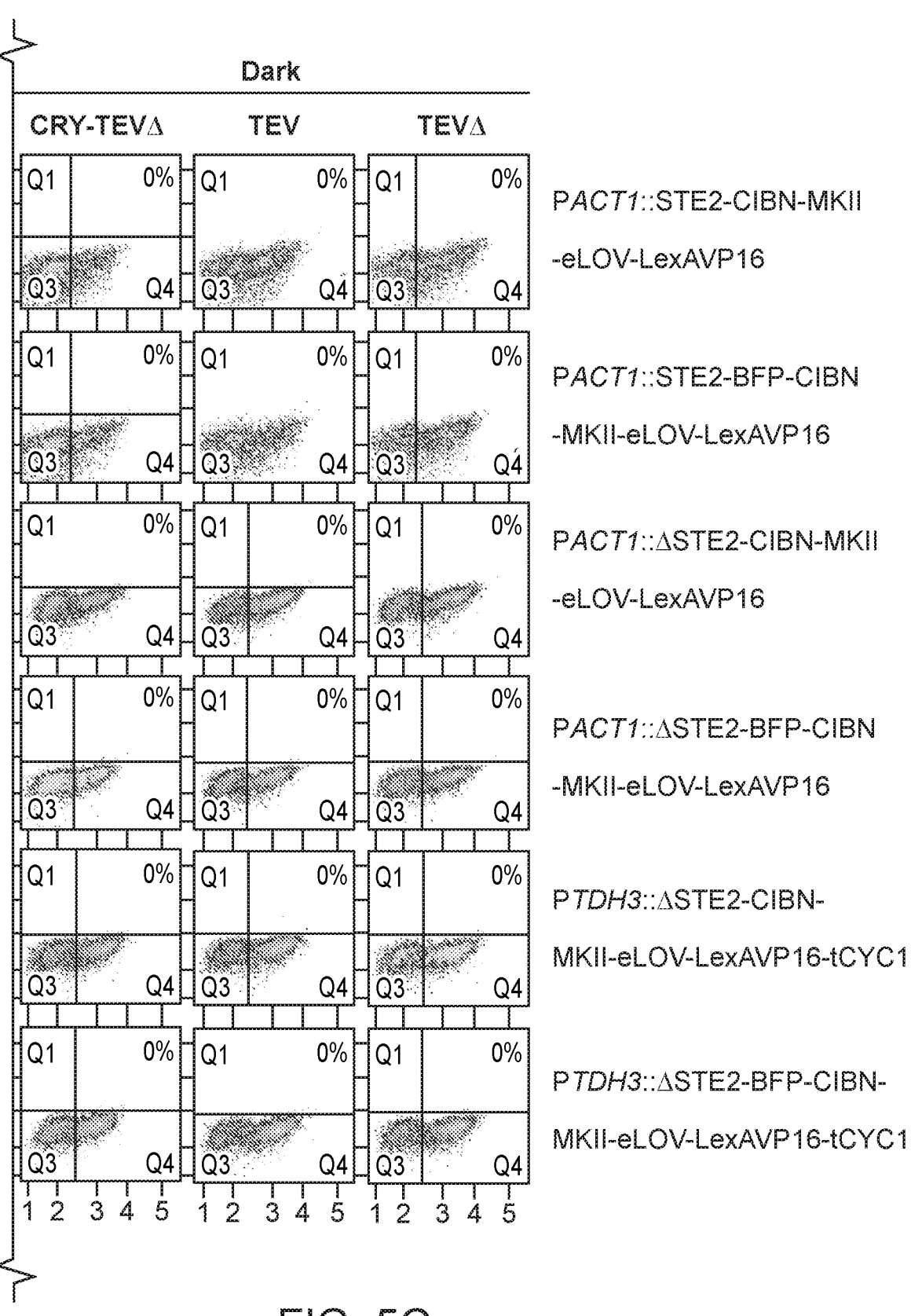

HEK 293T cells directly plated into 48-well plates were imaged with the 10× air objective on the Zeiss AxioObserver inverted confocal microscope (described in the section Fluorescence microscopy of cultured cells). Normally, more than ten fields of view were acquired for each condition. A mask was defined according to eGFP (expression of the FLARE protease component). Within this mask, the mean mCherry intensity (=Intensity 1) was calculated. A second mask was drawn in the area outside of eGFP and mean mCherry intensity here was calculated as Intensity 2 (background). Intensity 1 was subtracted from Intensity 2 for each field of view. Background-corrected mean mCherry intensities from ≥10 fields of view were averaged together and reported for each condition (FIG. 4G and FIG. 26).

AAV Virus Supernatant Production

AAV virus supernatant was used for neuron culture experiments. To generate viruses, HEK 293T cells were transfected at 70-90%. For each well of HEK cells in a T25 plate, we combined 1.04 μg viral DNA (plasmid P67, P68, P69, or P70 from Plasmid Table), 0.87 μg AAV1 serotype plasmid (plasmid P77), 0.87 μg AAV2 serotype plasmid (plasmid P78), and 2.08 μg helper plasmid pDF6 (plasmid P79)) were combined with 26 μL PEI max and 100 μL serum-free DMEM. [40] This mixture was incubated for 15 min at r.t. The media in the T25 flask was then removed by aspiration and replaced with 5 mL of complete growth media plus the DNA mixture.

HEK293T cells were incubated for 48 h at 37° C. After this time, the supernatant (containing secreted AAV virus) was collected and filtered through a 0.45-μm syringe filter (VWR). AAV virus was aliquoted into sterile Eppendorf tubes (0.5 mL/tube), flash frozen in liquid nitrogen and stored at −80° C.

Rat Cortical Neuron Culture

Cortical neurons were harvested from rat embryos euthanized at embryonic day 18 and plated in 24-well plates as previously described [41], but without glass cover slips. At DIV4, 300 μL media was removed from each well and replaced with 500 μL complete neurobasal media (neurobasal supplemented with 2% (v/v) B27 supplement (Life Technologies), 1% (v/v) GlutaMAX® medium supplement (Life Technologies), and 1% (v/v) penicillin-streptomycin (VWR, 5,000 units/ml of penicillin and 5,000 μg/mL streptomycin), supplemented with 10 μM 5-fluorodexoyuridine (FUDR, Sigma-Aldrich) to inhibit glial cell growth. Subsequently, approximately 30% of the media in each well was replaced with fresh complete neurobasal media every 3 d. Neurons were maintained at 37° C. under 5% CO2.

Viral Transduction of Cortical Neuron Cultures, Stimulation and Data Analysis

A mixture of AAV viruses, harvested from HEK 293T supernatant as described above, was added to cultured neurons between DIV11-12 and incubated for 3 d at 37° C. before 30% of the media in the well was replaced with fresh complete neurobasal media. Typical viral supernatant quantities used were 100 μL of each viral component, added in combination to each well of a 24-well plate dish, already containing 1,500 μL of complete neurobasal media.

After viral transduction, neurons were grown in the dark, wrapped in aluminum foil, and all subsequent manipulations were performed in a dark room with red light illumination to prevent unwanted activation of the LOV domain. Six days post-transduction (DIV 18-19), neurons were subjected to four conditions: light+high Ca2+; light+low Ca2+; dark+ high Ca2+; and dark +low Ca2+. To elevate cytosolic Ca2+, two methods were used: mechanical or field stimulation. Electrical stimulation did not give as robust a FLARE turn-on as mechanical stimulation (media change), because the latter produces sustained high Ca2+, whereas the former gives transient Ca2+ spikes.

Mechanical stimulation: To elevate cytosolic calcium [8], 50% of the media in the well was replaced with fresh complete neurobasal media of identical composition. After this treatment for 60 sec or 5 min, the saved old culture media was returned to the wells, which improved the health of the neurons. For the low-calcium condition, neurons were not treated (no media change). For light stimulation, neurons in a 24-well plate were placed on top of the custom-built LED light box described above ("HEK 293T cell stimulation, imaging, and data analysis for FLARE and SPARK experiments") and irradiated with 467-nm blue light at 60 mW/cm2 and 10-33% duty cycle, 0.5 s of light every 5 s. For the dark condition, neurons were wrapped in aluminum foil. Imaging was performed 18 hours later Field Stimulation: To elevate cytosolic calcium by field stimulation, a Master 8 device (AMPI) was used to induce trains of electric stimuli; a stimulator isolator unit (Warner Instrument, SIU-102b) was used to provide constant current output ranging from 10-100 mA. Platinum iridium alloy (70:30) wire from Alfa-Aesar was folded into a pair of rectangles (0.7 cm×1.5 cm) and placed right above the neurons on the edge of the well to act as electrodes. 3-second trains, each consistng of 32 1-ms 48 mA pulses at 20 Hz, were used, lasting for a total of 60 sec or 5 min. For blue-light irradiation, the same settings explained before were used. For the dark condition, neurons were wrapped in aluminum foil. Imaging was performed 18 hours later. Note that prior to treating of FLARE-expressing neurons, the equipment and protocol were tested on neurons expressing GCaMP5f.

For each experimental condition and time point, ten fields of view were collected. For each field of view, a mask was created to encompass regions with eGFP expression, associated with FLARE protease expression. In these masked regions, the mean mCherry fluorescence intensity was calculated, and background was subtracted (mean mCherry intensity in a eGFP region). These mean mCherry intensity values were calculated individually for 10 fields of view per condition and plotted in a bar plot. Mean of the means shown as horizontal bars in FIG. 4F and FIG. 25.

Photostimulation Device for Cultured HEK Cells and Neurons

In vitro light stimulation of cultured HEK cells and neurons was performed with a custom-built light box, as described previously [8]

Example 4

This example describes representative methods for producing TEV proteases.

Cloning, Expression, and Purification of TEV Proteases

For kinetic characterization of TEV proateases, the wild type (S219) and evolved proteases in truncated form were cloned into the ppRK793 vector (addgene #8827) while the full length forms were cloned into the pYFJ16 plasmid for its expression in E. coli.

TEV protease expression was performed by following the protocol described by Tropea et al. [42]. Competent BL21-CodonPlus™ (DE3)-RIPL E. coli were transformed with evolved TEV protease expression plasmids by heat shock transformation. Cells were grown in TB media (1L) with 100 mg/L ampicillin at 37° C. and 220 r.p.m. until OD600 0.6. Protein expression was then induced with 1 mM (Cf) IPTG. Cultures were shifted from 37C to 30C during induction to maximize the yield of soluble TEV protease and grown for 6 h at 220 r.p.m. Bacteria were pelleted by centrifugation at 6,000 r.p.m. for 6 min at room temperature, the supernatant was discarded, and the pellet kept at−80C.

The frozen pellet was thawed on ice in 50 mL of lysis buffer (50 mM sodium phosphate (pH 8.0), 200 mM NaCl, 10% Glycerol, and 25 mM imidazole) with one cOmplete™ protease inhibitor tablet (Roche). Then, the pellet was pipetted to homogeneity and transferred to a small metal beaker pre-chilled on ice and sonicated 2× using a sonicator (20 s on, 60 s off, 3 min on). The lysate was clarified for 15 min at 11.000 rpm and the supernatant transferred into a falcon tube, where it was incubated with Ni-NTA agarose beads (QIAGEN) in lysis buffer for 10 min. The slurry was placed in a gravity column and washed with 50 mL of lysis buffer. The protein was eluted with elution buffer (50 mM sodium phosphate (pH 8.0), 200 mM NaCl, 10% Glycerol, and 250 mM imidazole). The purity was analyzed by SDS-PAGE and the gel was stained with Coomassie Blue. (FIG. 9)

The eluted samples were dialyzed overnight (40 mM Tris-HCl (pH 7.5), 200 mM NaCl, 2 mM EDTA, 0.2% Triton X-100 and 4 mM BME) at 4C in a Slide-A-Lyzer™ Dialysis Cassette (Extra Strength) 10,000 MWCO (Thermo Fisher Scientific). The dialyzed sample was concentrated using Amicon® Ultra-15 Centrifugal Filter Units-10,000 NMWL. After concentration, 20% v/v of glycerol was added, and the samples were flash frozen and stored at–80C.

For kinetic characterization of full-length TEV proteases, we cloned the evolved protease genes into the vector backbone pYFJ16 for expression in *E. coli*. This vector bears an MBP and a His6 tags (SEQ ID NO: 53) in the N-terminus. Protease purification was carried out following exactly the same conditions as describe before.

Cloning, Expression, and Purification of MBP-TEVcs(EN-LYFQ/S)-eGFP

The protease substrate MBP-TEVcs-eGFP was cloned into a pYFJ16 vector for expression in *E. coli*. Competent BL21-CodonPlus™ (DE3)-RIPL *E. coli* were transformed with evolved TEV protease expression plasmids by heat shock transformation. Cells were grown in TB media (1L) with 100 mg/L ampicillin at 37° C. and 220 r.p.m. until OD600 0.6. Protein expression was then induced with 1 mM (Cf) IPTG. Cultures were shifted from 37C to 30C during induction to maximize protein expression.

The lysis and elution was carried out in the same conditions explained before. Bright yellow protein fractions were collected and transferred to an Amicon® Ultra-15 centrifugal filter, and exchanged 3 times into ice-cold 50 mM Tris-HCl buffer (pH 8.0), 10% glycerol containing 1 mM EDTA and 2 mM of DTT.

TEV Kinetics Assays

Figures 9A, 9B:
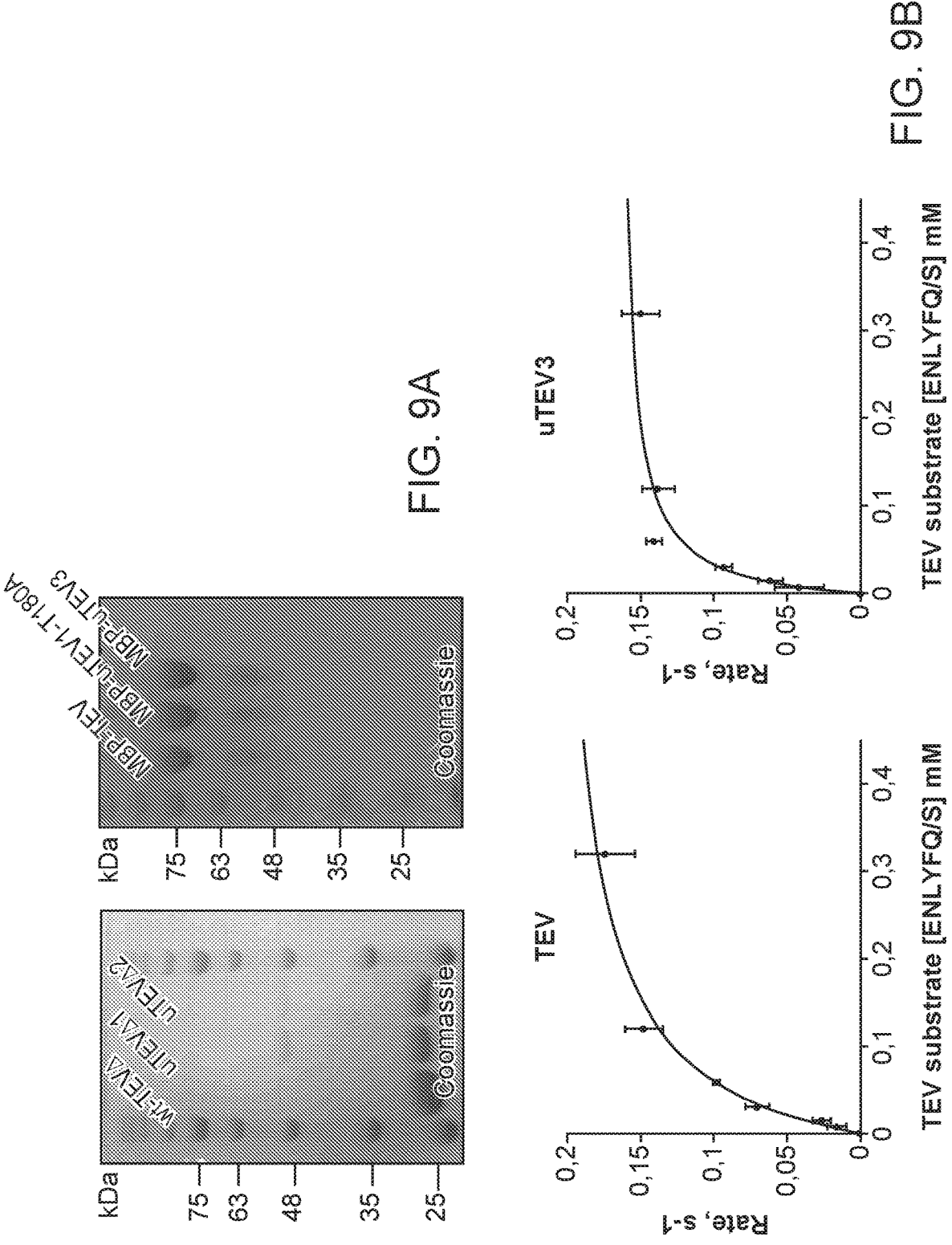
FIGS. 9A and 9B show TEV expression and kinetics.

Protein fusion substrate MBP-TEVcs(ENLYFQ/S)-eGFP at different concentrations, was incubated in 50 mM Tris-HCl buffer (pH 8.0), 10% Glycerol containing 1 mM EDTA and 2 mM of DTT (freshly prepared) at 30C for different times in the presence of 100 nM of selected protease (TEV(S219) or uTEV3). Digestion reactions were terminated at different time points [5 to 30 min] by the addition of sodium dodecyl sulfate-polyacrylamide gel electrophoresis (SDS-PAGE) sample buffer and immediately flash-frozen. [43] The reaction products were separated by SDS-PAGE at 4° C. The band intensities of the product were quantified by in-gel fluorescence with a Typhoon™ 9410. Quantitation of gels was performed using ImageJ on raw images under non-saturating conditions. Initial velocities were calculated under conditions of less than 25% substrate hydrolysis. Peak integrations were tabulated, converted into product concentrations using the standard curves. Data was fit to a Michaelis-Menten enzyme kinetics model with center values representing the mean and error bars representing the standard deviation of three technical replicates (FIG. 9B).

To study the kinetics of TEVΔ, TEV1Δ and TEV2Δ we used, the same protocol but with the protein fusion substrate MBP-TEVcs(ENLYFQ/M)-eGFP.

Removal of Affinity Tags: MBP-TEVcs(ENLEYFQ/S)-eGFP Digestion.

The substrate concentration was 0.72 mg/ml (10 uM), which is typical for the digestion of a fusion protein substrate. The enzyme concentration was 60 nM (MBP-TEV or MBP-uTEV3). Reactions were initiated by adding the enzymes to reaction buffer containing the substrates. Aliquots were taken after different time points and the reaction was terminated by the addition of protein loading buffer containing sodium dodecyl sulfate and immediately flash-frozen. The reaction products were separated by SDS-PAGE and analyzed by in-gel fluorescence with a Typhoon™ 9410. We observed that substrate digestion is much more efficient with uTEV3, which is able to digest the starting material until completion. (FIG. 19) Please note that at higher protease or substrate concentration the differences are much less obvious.

Example 5

This example describes the results of using the methods described herein to produce proteases having increased catalytic activity.

Results

A yeast-based platform for evolving protease catalysis

Yeast are attractive as a platform for directed evolution because they can be easily transformed with large mutant libraries, they naturally compartmentalize chemical reactions, and they can be sorted by FACS instruments over a large dynamic range. The inventors previously used yeast-based directed evolution to improve the properties of APEX [18], promiscuous biotin ligase [19], split horseradish peroxidase [20], and split APEX [21]. Iverson et al. developed a yeast display platform to alter the sequence-specificity of TEV [17]. In their approach, a TEV mutant library was co-expressed in the yeast ER lumen with an HA-tagged reporter linked by a TEVcs sequence to an ER retention motif. An active TEV mutant could remove the ER retention motif and free the reporter to traffic to the cell surface, where it could be detected by a fluorescent antibody specific for 6×His (SEQ ID NO:53) and enriched by FACS. While this scheme was very effective at identifying TEV variants that could recognize alternative TEVcs sequences, it was not able to distinguish highly active catalysts from moderately active ones. This is because the time window for TEV action on TEVcs was not controlled; TEV mutants could act on TEVcs over >8 hours (the time window for co-expression), enabling even low-activity mutants to be enriched.

To devise a platform that could be used to enrich faster proteases over moderately-active ones, the following modifications were implemented: (1) the system was moved into the yeast cytosol, since this reducing environment more closely resembles the eventual context in which evolved TEVs will mostly be used; (2) the TEV activity was coupled to release of a membrane-anchored transcription factor (TF) which in turn drives the expression of a fluorescent protein reporter, in order to increase sensitivity and dynamic range of the protease activity readout; (3) TEV and TEVcs were fused to the photoinducible protein binding pair CRY and CIBN, respectively, so that selection could be performed on truncated, low-affinity versions of TEV that are utilized in FLARE and SPARK tools. Despite their low affinity, recognition of TEVcs by TEV can be induced via blue light activation of the CRY-CIBN interaction. The TEVcs sequence was photocaged with an improved LOV domain (eLOV [8]) in order to exert control over the time window TEV has available to cleave TEVcs.

Figures 1A, 1B:
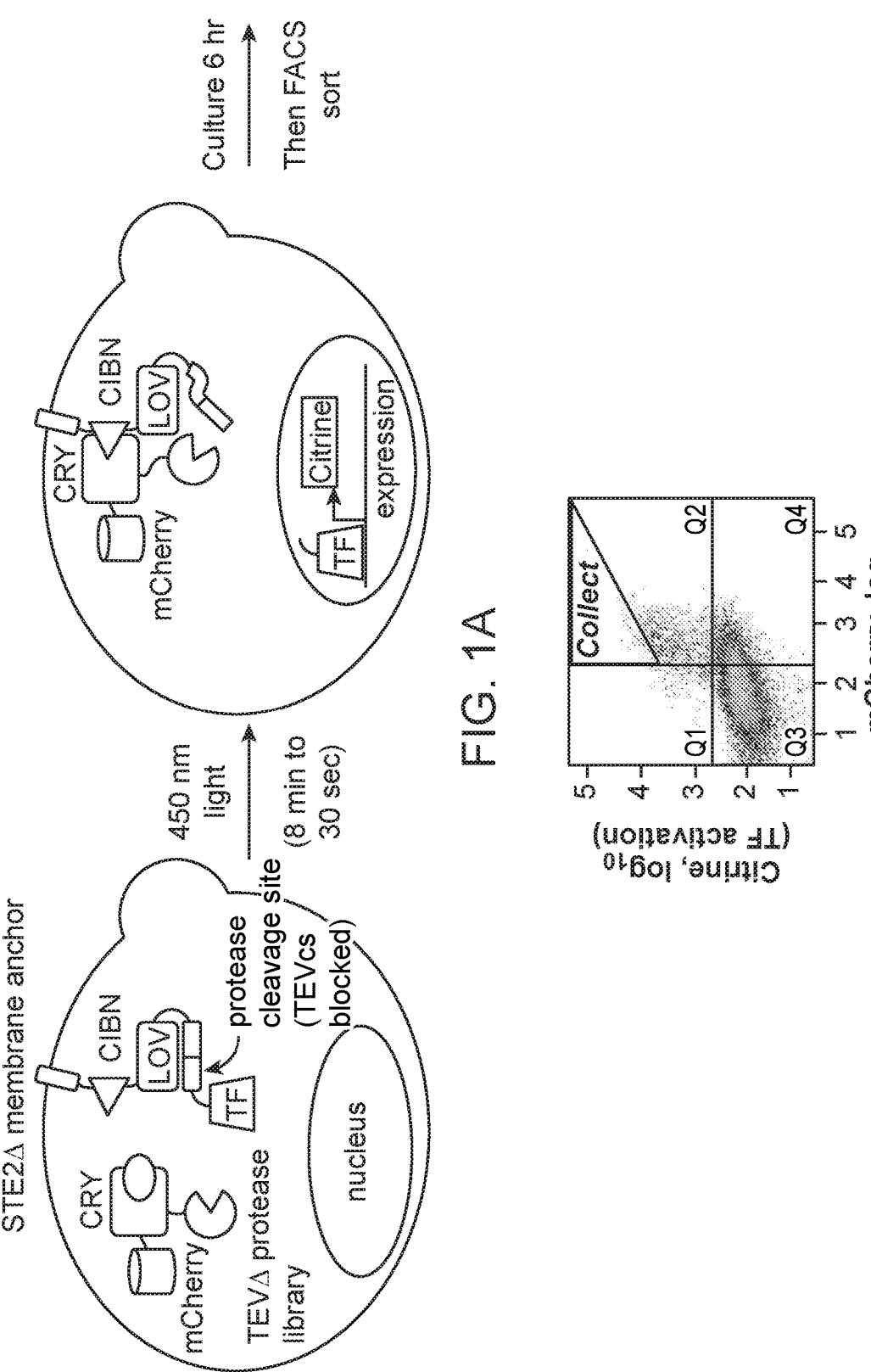
FIGS. 1A to 1G show a representative yeast platform for directed evolution of high-turnover, low-affinity proteases.

FIG. 1A shows an exemplary design of the protease evolution platform in the yeast cytosol. The TEV mutant library was expressed in yeast as a fusion to CRY and mCherry. The transcription factor (TF) used to read out TEV activity was linked to a plasma membrane anchor via CIBN and LOV-caged TEVcs. Upon irradiation of the cell population with blue light, CRY and CIBN form an intermolecular complex, driving TEV into proximity of TEVcs. In addition, the LOV domain undergoes a conformational change, exposing TEVcs. Active TEV mutants will then cleave TEVcs, releasing the TF for translocation to the nucleus and transcription of the reporter gene (Citrine). Six hours later (to allow time for Citrine transcription, translation, and maturation) FACS is used to enrich yeast cells with high Citrine/mCherry signal ratio, indicative of high TEV cleavage activity (FIG. 1B). The platform design allows selection stringency to be increased simply by decreasing the time of blue light irradiation. With less time available to sterically access TEVcs, only the most active TEV mutants will produce Citrine signal over background.

Figures 1C, 1D:
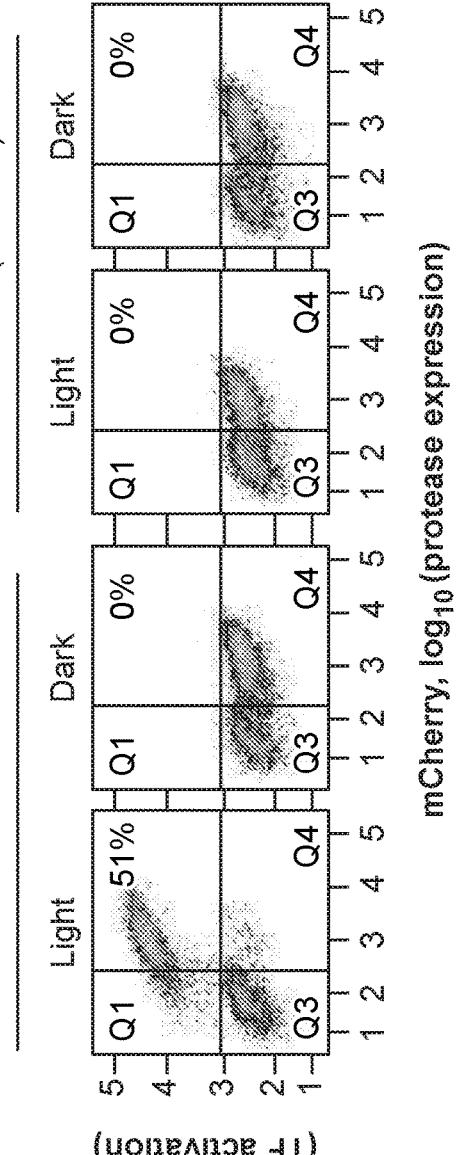
Figure 6A:
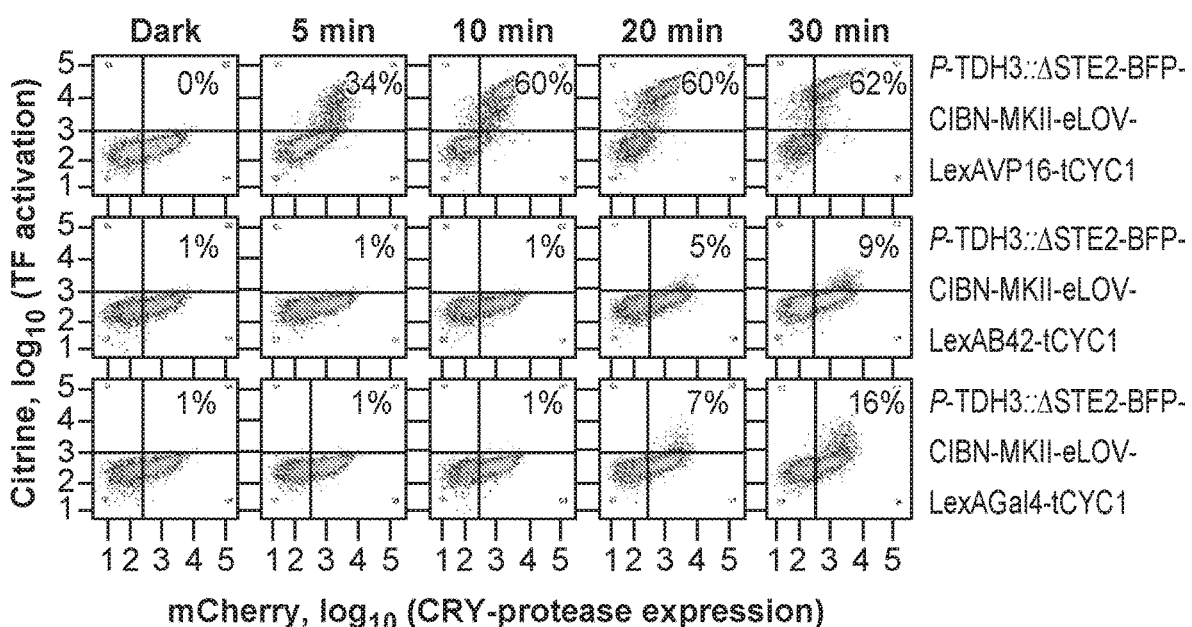
FIGS. 6A and 6B show further optimization of membrane-anchored transcription factor for yeast 1036 directed evolution and optimization of reporter gene expression time window. Related to FIG. 1C.
Figure 6B:
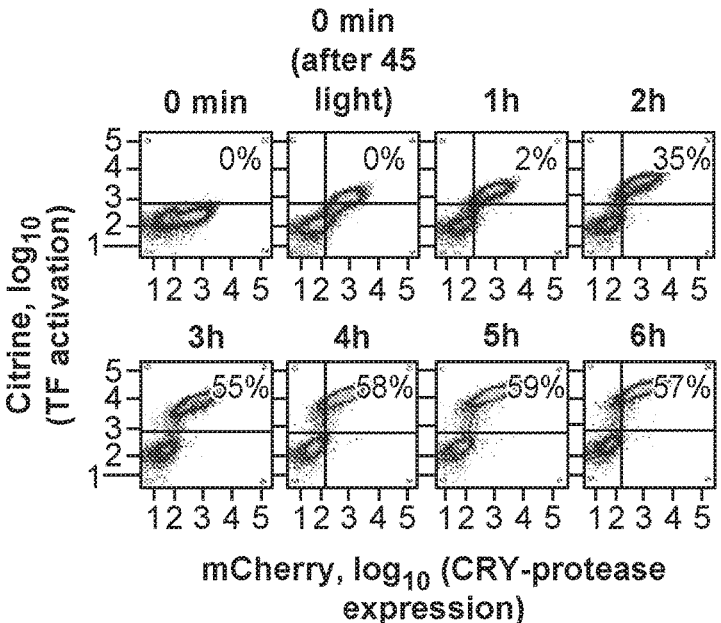

Using C-terminally truncated, low-affinity wild-type TEV (TEVΔ219, or TEVΔ[22]) as the starting template, we optimized a number of features of the platform. We found that truncation of the STE2-based plasma membrane anchor (FIG. 5A) [23] and incorporation of a BFP linker both increased Citrine signal, likely because of improved membrane trafficking of the TF construct. We also increased expression of the membrane-anchored TF by optimizing its promoter [24] (FIG. 1C), incorporated a terminator [25] (FIG. 1C), and tested alternative activation domains (FIG. 6A). By performing a time course, we determined that 6 hours was sufficient to reach maximal Citrine expression post light-induction of TF release (FIG. 6B). Omission of either light or CRY abolished the Citrine signal (FIG. 1D). Using these optimized constructs and conditions, we observed increasing Citrine signal as the blue light irradiation time was increased from 5 minutes to 30 minutes (FIG. 1E), suggesting that selection stringency of this platform is tunable by modulating the light time.

Figures 1E, 1F:
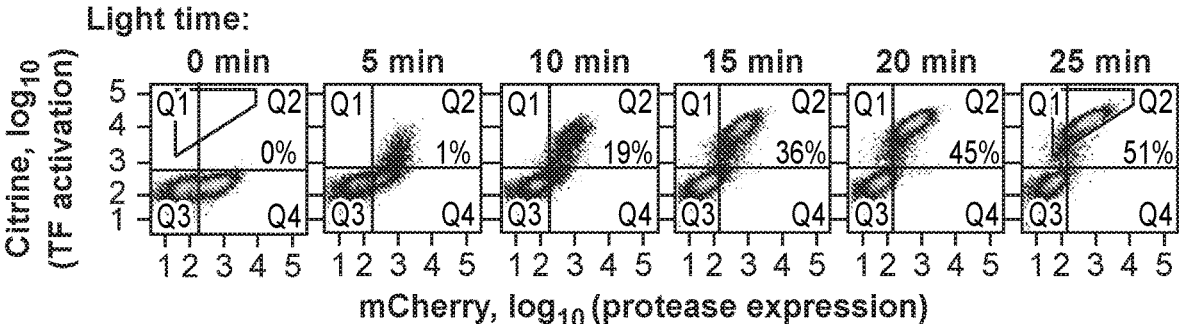
Figure 7A:
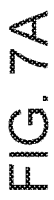
Figures 8A, 8B:
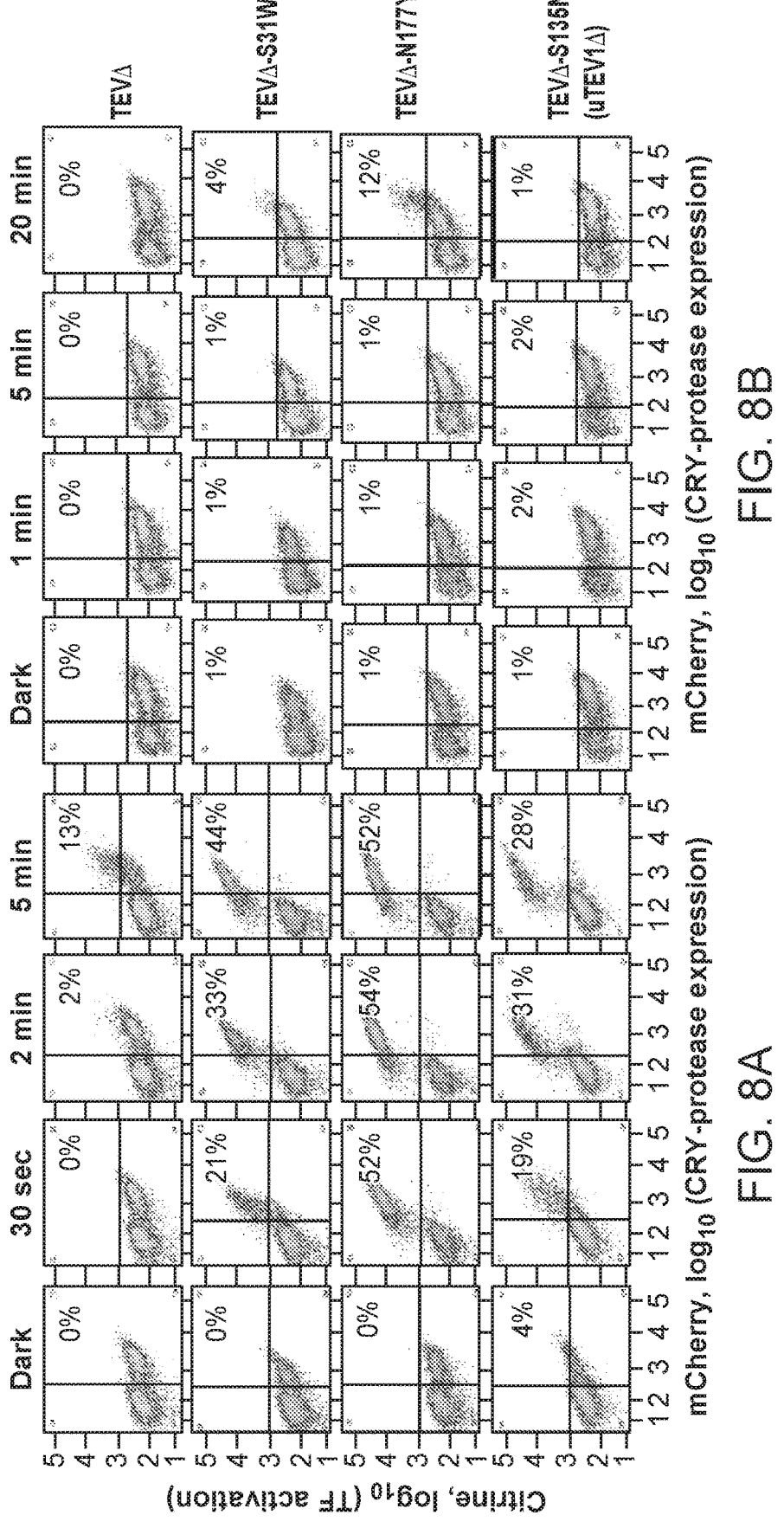
FIGS. 8A and 8B show the characterization of evolved single, double, and triple TEVA mutants in yeast. FACS plots used to generate the plot are as in FIG. 2A.

To implement the directed evolution, we first generated a library of TEVA mutants using error-prone PCR. Sequencing indicated an average mutation rate of 4 amino acids per gene. The library was transformed into yeast cells along with a membrane-anchored TF bearing a low-affinity TEVcs sequence (ENLYFQ/M (SEQ ID NO: 6)), and we performed three successive rounds of selection. Eight minutes of blue light irradiation was used for the first round of selection, and we enriched cells with high Citrine/mCherry signal ratio using the red sorting gate depicted in FIG. 1A. The second and third rounds of selection used 4 minutes and 30 seconds of blue light, respectively. Yeast pools collected after each round were amplified and compared side by side under matched conditions. FIG. 1F shows that the post-round 3 population is much more active than both the original library and the wild-type TEVA template. As much Citrine signal is seen in the post-round 3 population after 30 seconds of blue light as original TEVA produces after 30 minutes of light (FIG. 1F and FIG. 7).

Characterization of Evolved TEV Mutants

Figure 1G:
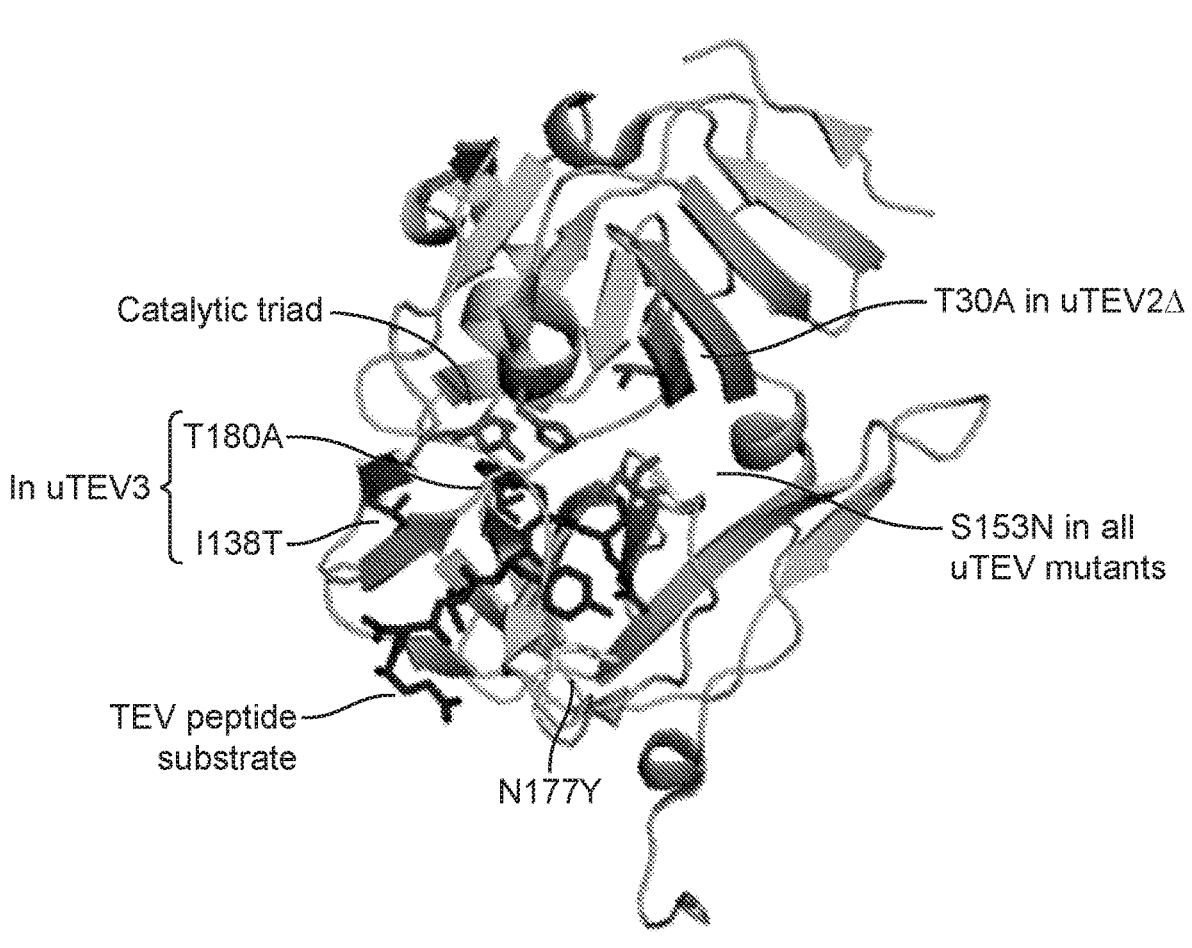

Sequencing after round 3 showed that specific mutations were enriched by the selection. Several of these mutations (T30A, T30I, S31W and S153N) surround the catalytic triad (FIG. 1G) in the wild-type TEV structure (PDB: 1LVM) [26], and might reasonably be expected to lower the energy of the transition state, improving catalysis (FIG. 1G). An additional enriched mutation, N117Y, interacts directly with the bound TEVcs. Without being limited by mechanism, N117Y may be enriched because it enhanced binding to TEVcs instead of improving kcat (also supported by data in FIG. 2A).

Figure 2A:
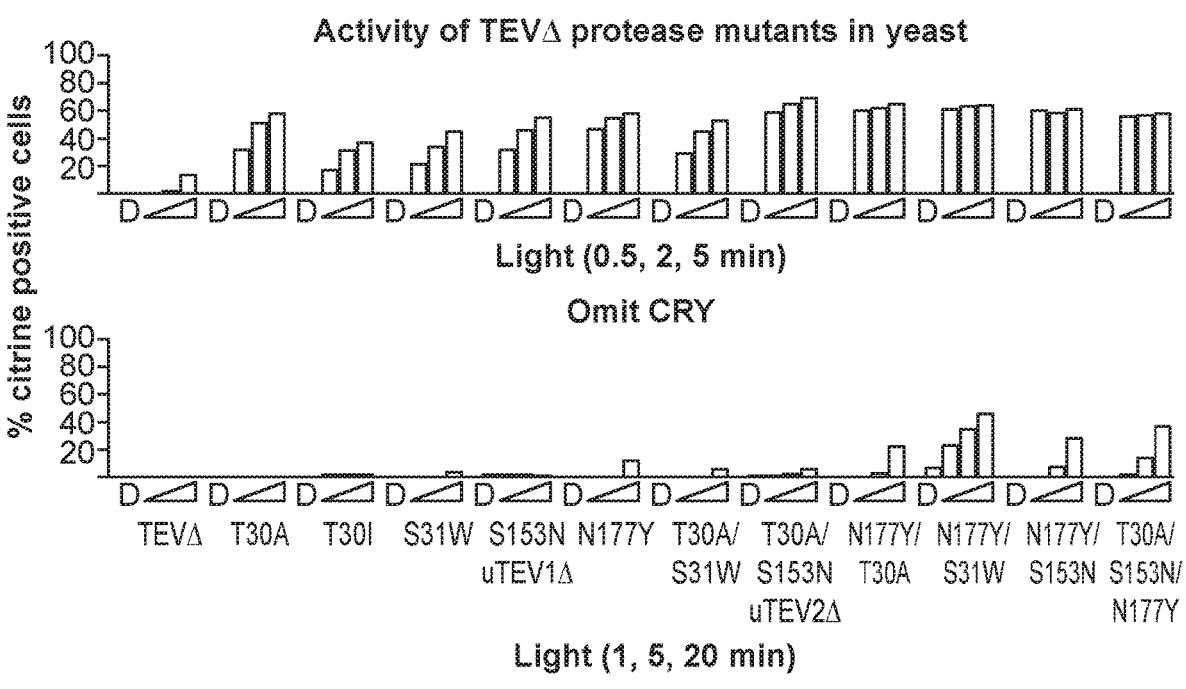

To evaluate the activities of evolved TEV mutants, individual clones were amplified and irradiated with blue light for various lengths of time before FACS analysis of the yeast 6 hours later. FIG. 2A shows that all evolved clones are significantly more active than wild-type TEVΔ, producing greater Citrine expression at all time points. To check for interaction-dependence of the cleavage activity, the assay was repeated with TEV mutants fused to mCherry only and not mCherry-CRY ("omit CRY" control, FIG. 2A). Whereas most of these lost Citrine signal, the mutants containing the N177Y mutation still exhibited activity. The ability of these N177Y mutants (which are all truncated at position 219) to cleave TEVcs even when the CRY-CIBN pair is not present to bring protease and substrate together under blue light, is consistent with the hypothesis that N177Y may increase the affinity of TEVA for TEVcs.

Figure 2B:
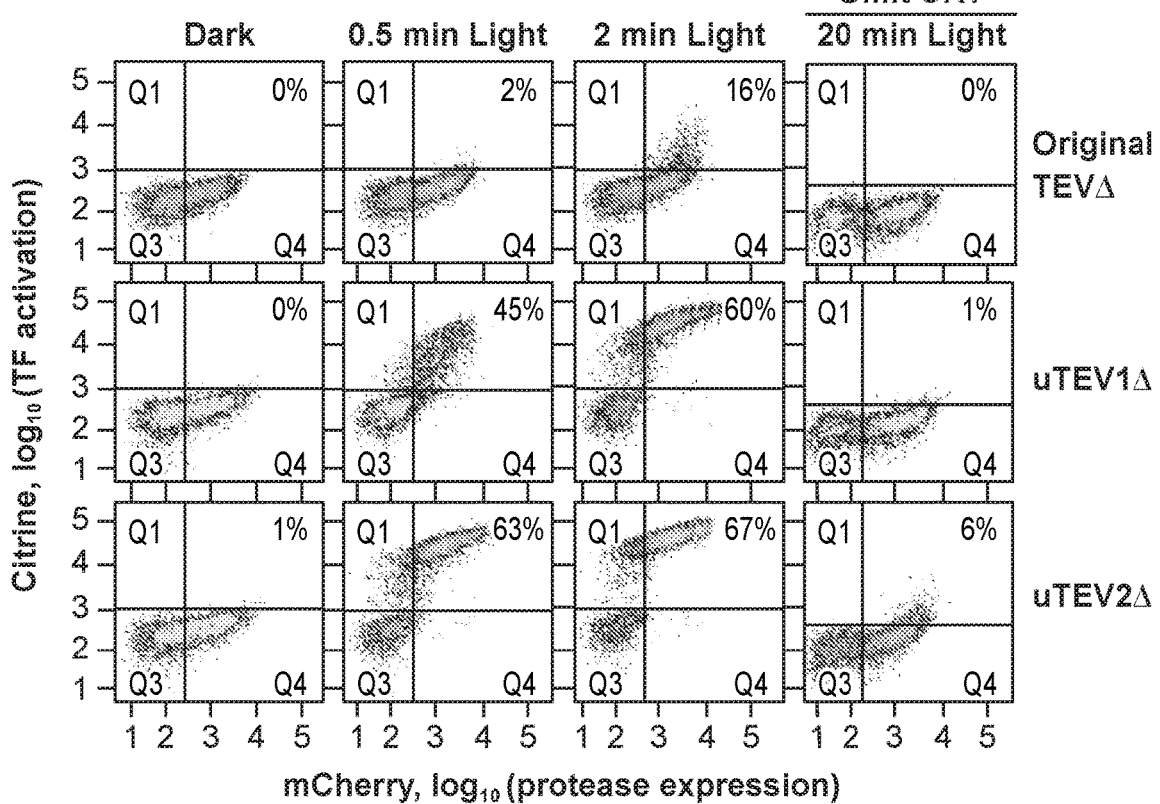

Based on the analysis in yeast, the two TEV mutants with the highest proximity-dependent activity were S153N ("uTEVΔ") and the T30A/S153N double mutant ("uTEV2Δ"). Their yeast FACS plots are shown in FIG. 2B and FIG. 8 under different blue light irradiation times.

Next, we characterized these evolved TEV mutants using an in vitro assay of catalytic activity. uTEV1Δ and uTEV2Δ, along with wild-type TEVΔ, were expressed and purified with His6 tags (SEQ ID NO: 53) from bacteria (FIG. 9) and then combined with the substrate protein MBP-TEVcs-eGFP, where MBP is maltose binding protein and TEVcs is the low-affinity substrate sequence ENLYFQ/M (SEQ ID NO: 6) used in the original selection. Due to protein solubility limits, the MBP-TEVcs-eGFP concentration was 360 μM, likely far below the concentration required to saturate the active site (for comparison, wild-type TEVA has a Km of 448 μM for the high-affinity TEVcs ENLYFQ/S (SEQ ID NO: 5) [22]; its Km for the low-affinity TEVcs used here has never been measured but is likely to be much higher). After incubation for various times, we evaluated the cleavage extent by running the reactions out on SDS-PAGE and performing in-gel fluorescence imaging 147 and quantitation (FIG. 2C) [27].

Based on measurements of initial reaction velocities, wild-type TEVA gave a turnover rate (kapp) of $10 \times 10^{-3}$/sec under these conditions, while the evolved proteases uTEV1Δ and uTEVΔ2 gave rates of $54 \times 10^{-3}$/sec and $62 \times 10^{-3}$/sec, respectively, 5.4- and 6.2-fold higher than wild-type. The actual differences in kcat may be even greater, but could not be measured due to our inability to saturate the active sites (to reach Vmax). Our results, combined with the yeast-based characterization in FIG. 2B (showing proximity-dependence) suggest that our directed evolution achieved the goal of increasing the catalytic efficiency of TEV while retaining low substrate affinity.

Characterization of Protease Sequence-Specificity

Figure 2F:
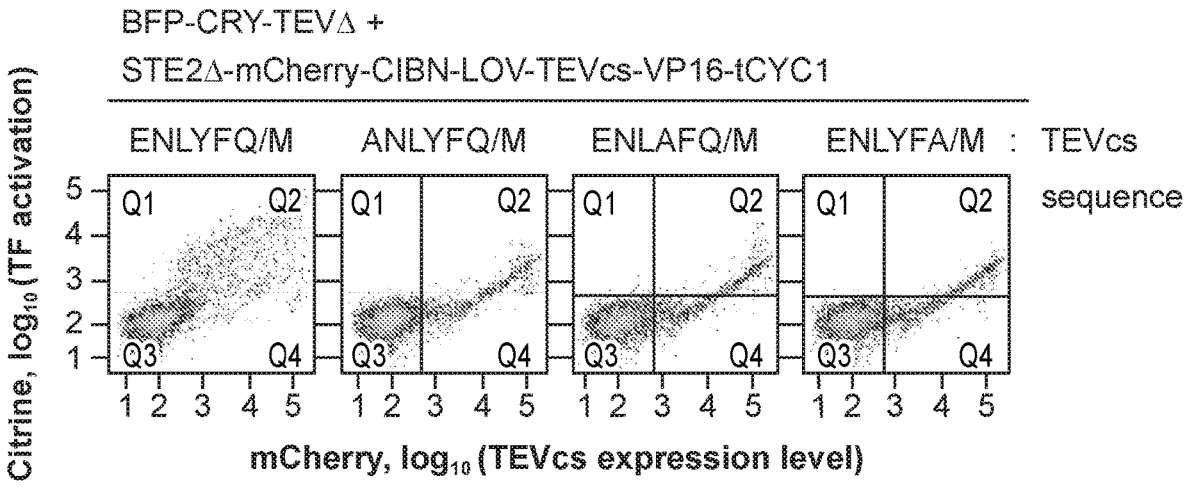
Figure 2G:
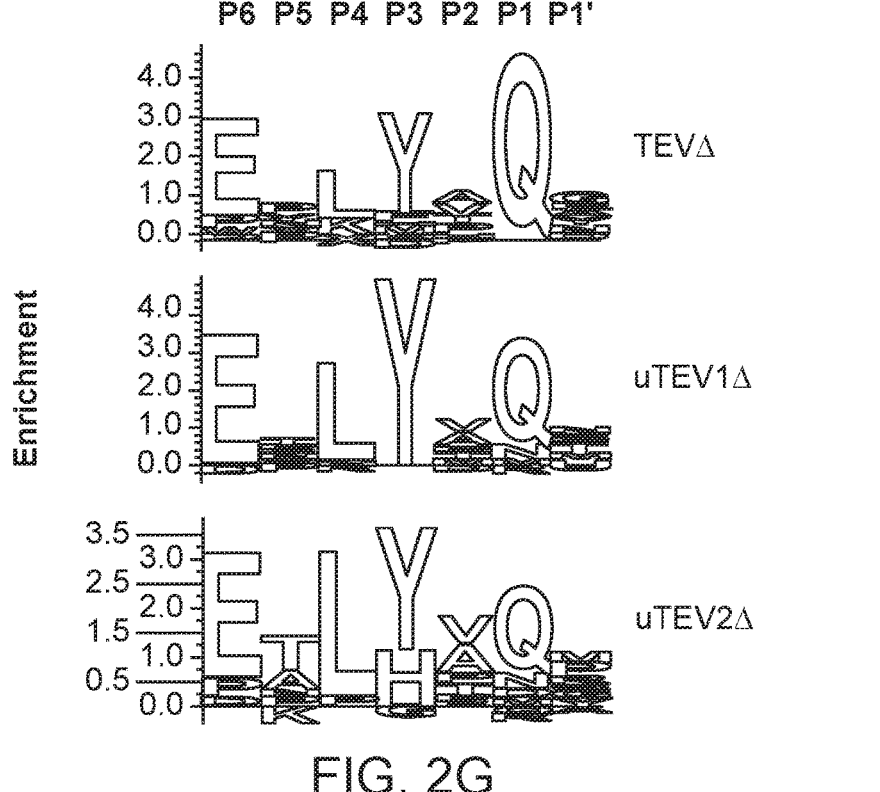
Figures 10A, 10B:
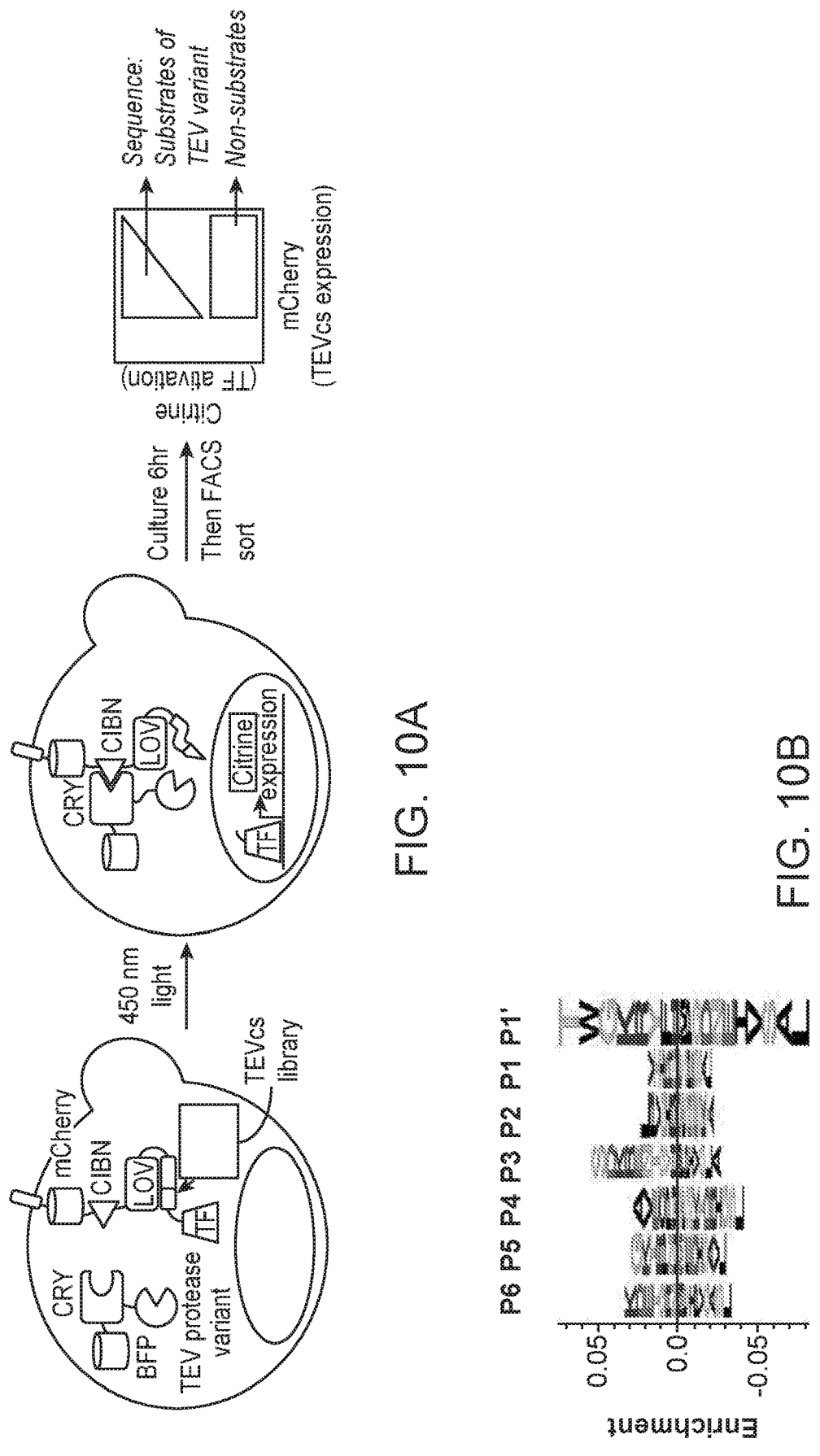
FIGS. 10A, 10B, and 10C show profiling the sequence specificity of TEVA variants in yeast. Related to FIG. 2F.
Figure 10C:
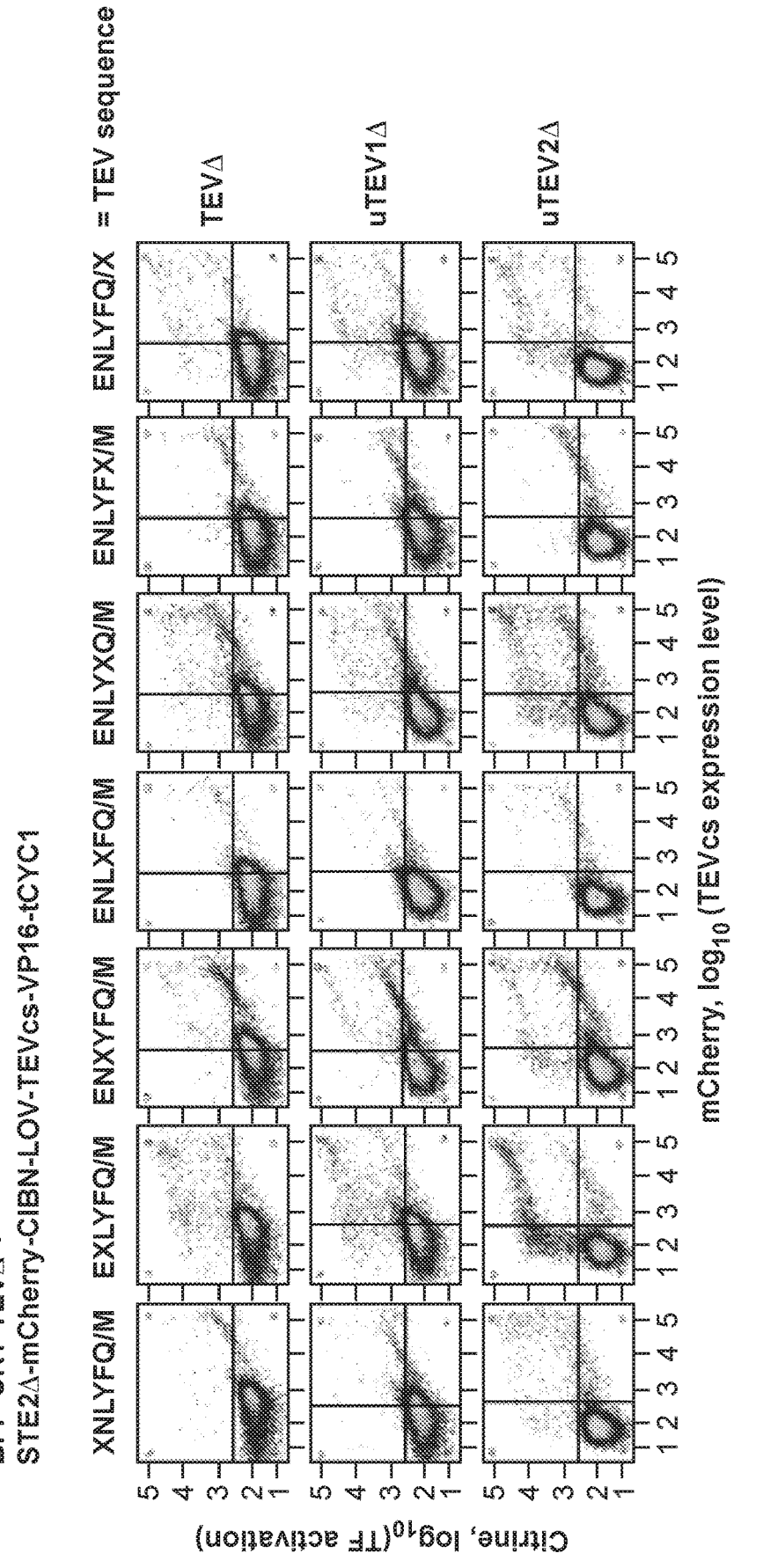

The mutations in uTEV and uTEV2 border the catalytic triad and are distal to the substrate binding pocket, making them unlikely to affect the valuable and useful property of sequence-specificity of TEV. To evaluate sequence-specificity, the yeast platform was coupled with sequencing analysis. Yeast strains expressing TEVcs libraries, caged by LOV and tethered to a transcription factor (as shown in FIG. 10) were prepared. The query protease was co-expressed as a fusion to BFP and CRY. After blue light irradiation for 30 minutes, FACS was used to enrich the cells with high Citrine expression. Sequencing of these cells revealed the collection of TEVcs sequences that are competent for cleavage by the protease variant of interest. As proof of concept, specific positions in TEVcs were mutated to alanine. Positions P6 (the 6th amino acid N-terminal to the cut site), P3, and P1 were selected because previous studies have shown that TEV is most sensitive to amino acid identity changes at these sites [25, 28, 29] FIG. 2F shows that Ala-mutation of P6, P3, or P1 largely abolishes recognition by TEV.

uTEV1Δ, uTEVΔ2, and wild-type TEVA were evaluated using seven TEVcs libraries, each with randomization at one of the positions P6-P1 or P1' (the residue immediatelyC-terminal to the cut site) [30]. Analysis of the libraries post-FACS (FIG. 10) revealed that the sequence preferences of uTEV1Δ and uTEVΔ2were largely unchanged from that of wild-type TEV (FIG. 2G). [31]

Figure 11:
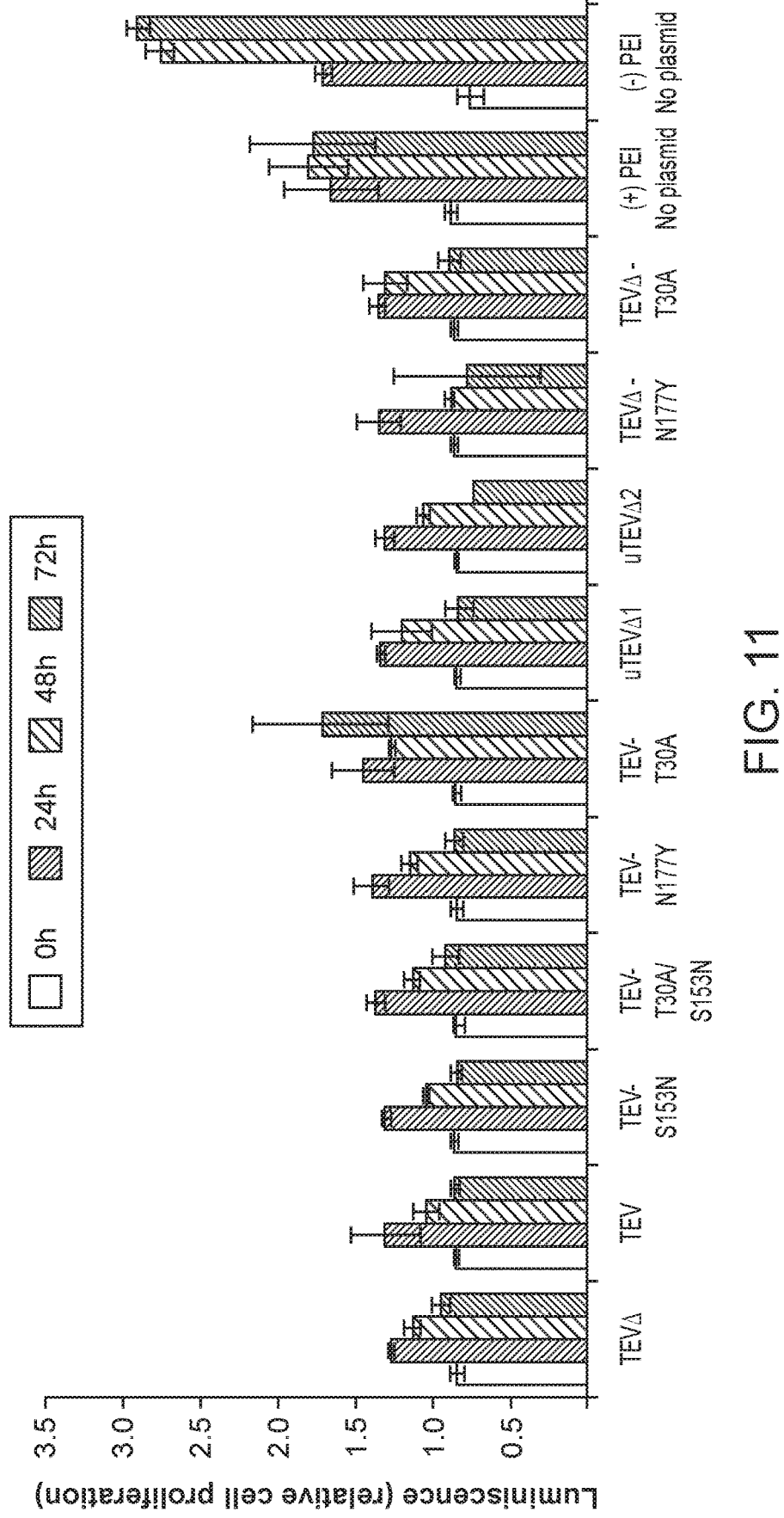
FIG. 11 shows viability assays in HEK 293T cells expressing evolved TEV proteases in full length or truncated forms. Cells, including untransfected HEK 293T controls, were plated in triplicate in matched 96-well plates. At each time point, a plate was removed and processed with the Cell-Titer Glo assay (Promega) to quantify viable cells. This experiment was performed once with three biological replicates per sample. Data plotted as mean±standard deviation of relative cell proliferation (three biological replicates are shown).

In addition, as a further indirect measure of possible sequence promiscuity, the viability of HEK cells expressing each of the TEV proteases was evaluated over 3 days. Overexpression of the evolved TEVs (both truncated and full-length) did not negatively impact cell health compared to overexpression of wild-type TEV (FIG. 11). Based on the above results, uTEV1Δ and uTEVΔ2should be useful for cellular applications for which protease orthogonality is a requirement.

Directed Evolution of Full-Length, High-Affinity TEV Protease

Figure 12A:
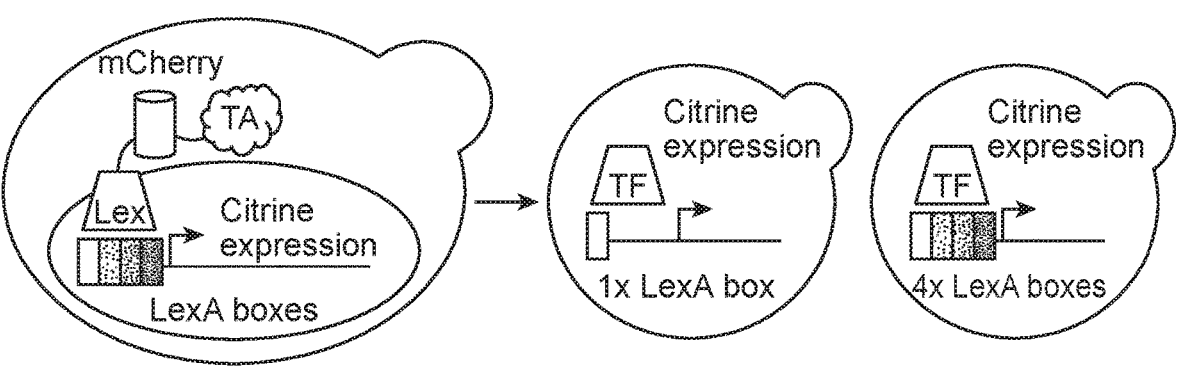
FIGS. 12A and 12B show tuning the dynamic range of the yeast evolution platform. Related to FIG. 3B.
Figure 12B:
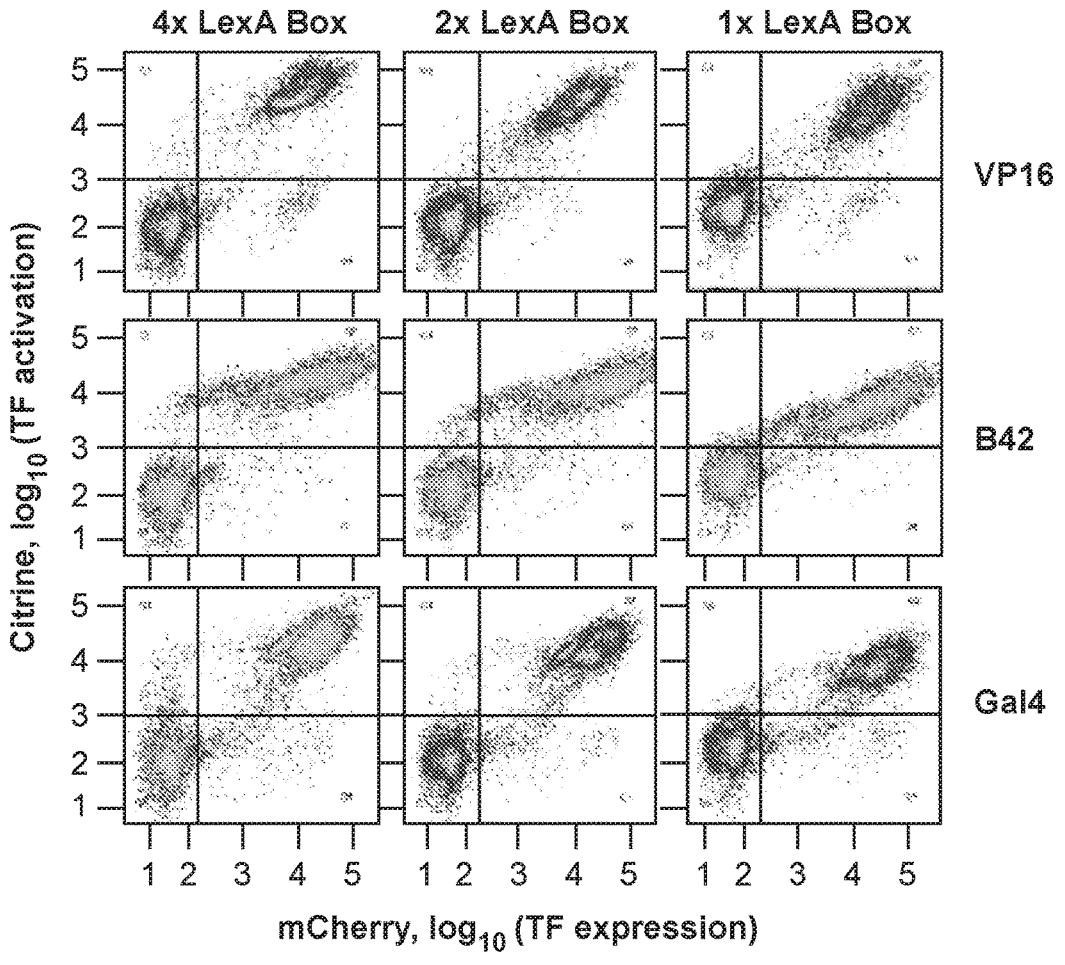
Figure 13A:
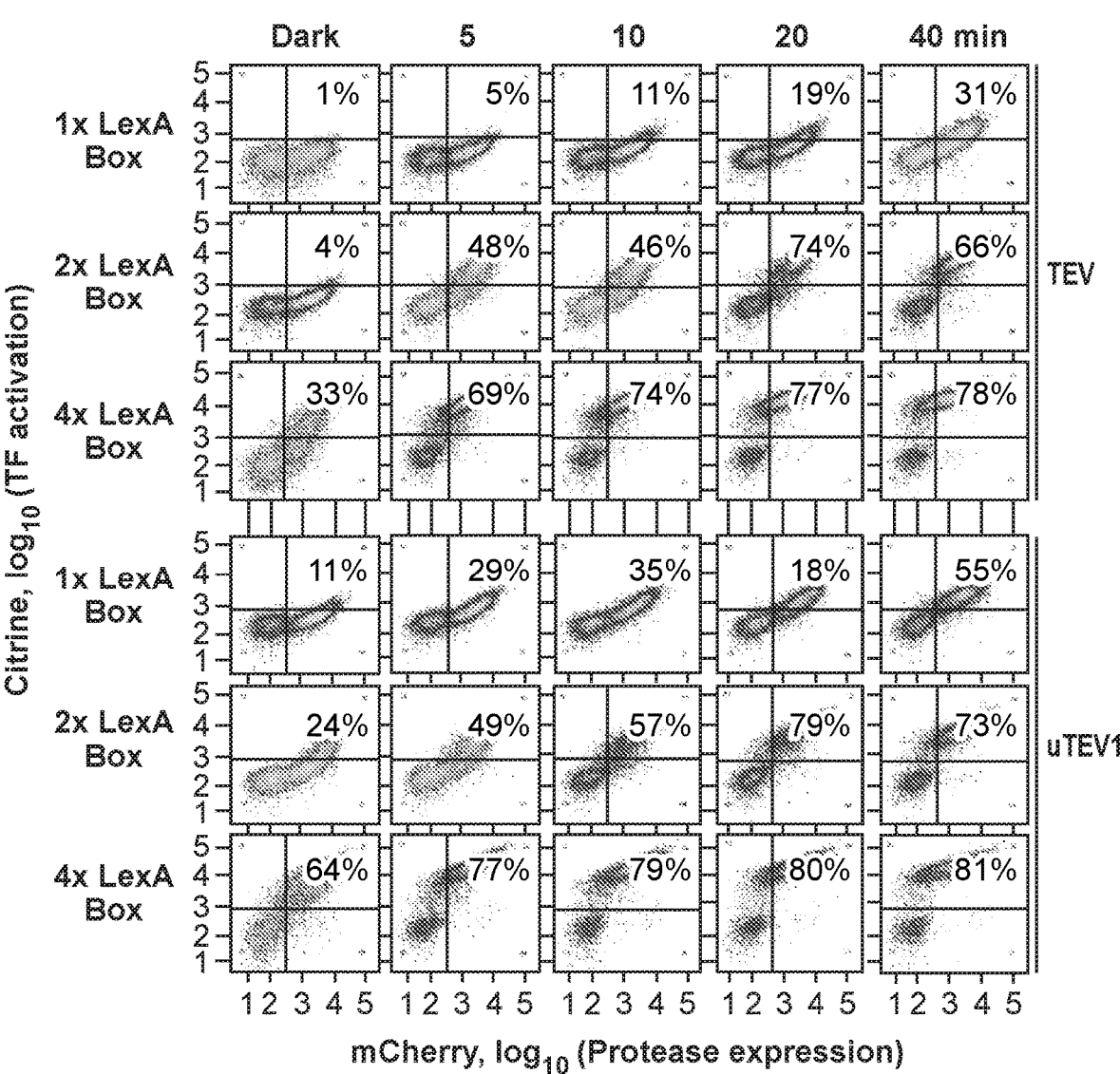
FIGS. 13A and 13B show activity of full-length TEV proteases in yeast strains bearing different numbers of LexA boxes with the high-affinity TEVcs (ENLYFQ/S (SEQ ID NO: 5)). FACS plots used to generate the plot in FIG. 3B. Sample FACS plots 6 hours after blue light exposure for the indicated times (5, 10, 20 and 40 min). Each plot represents one replicate, n=20,000 cells.
Figure 13B:
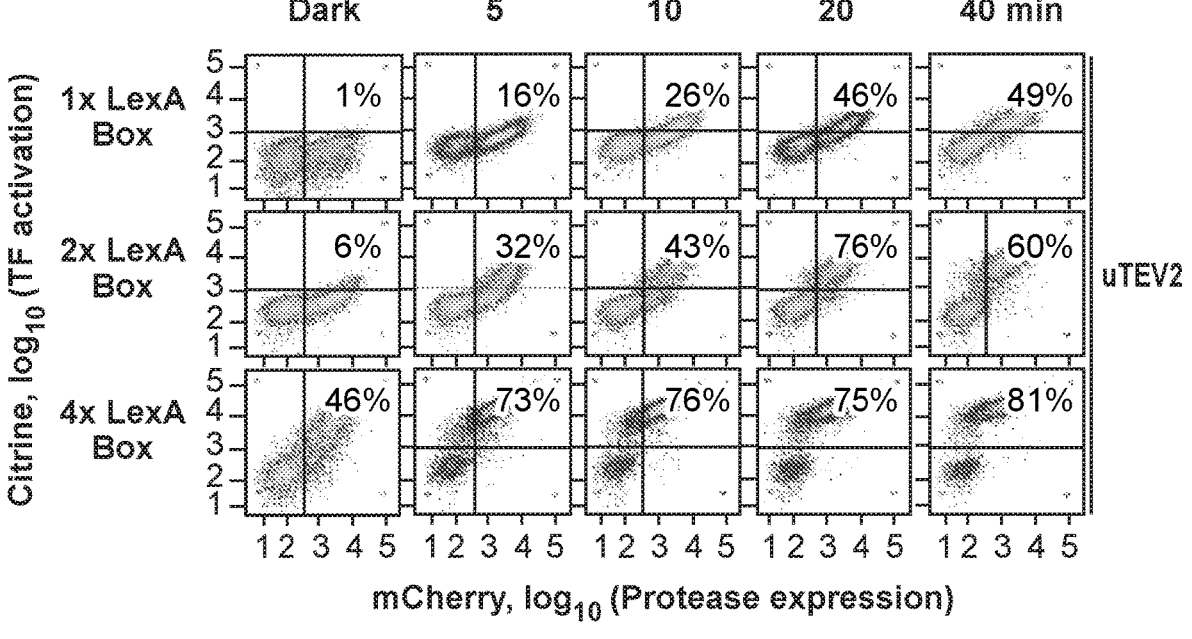

While proximity-dependent TEVs are necessary for transcriptional reporters such as FLARE, SPARK, TANGO, and Cal-Light, other applications in biotechnology could benefit from improved high-affinity TEVs (e.g., removal of affinity tags, bottom-up proteomics, etc.). We explored whether our yeast platform could also be used for evolving better (higher kcat/Km) full-length TEV variants. The selection scheme in FIG. 3A differs from the original setup in that (1) the CRY domain is omitted and (2) the TEVcs is the high-affinity sequence ENLYFQ/S (SEQ ID NO: 5) rather than the low-affinity sequence ENLYFQ/M (SEQ ID NO: 6) used earlier. In our preliminary tests (FIG. 3B), we observed signal saturation due to the high affinity between wild-type full-186 length TEV and its TEVcs. To reduce the sensitivity, and thereby increase the dynamic range of our platform, we experimented with alternative TFs and promoters (FIG. 12). We found that by reducing the number of LexA boxes in the promoter of the reporter gene, we could diminish the Citrine response to wild-type TEV. We then tested the mutations enriched in our previous selection (FIG. 3B and FIG. 13) in the context of full-length TEV. We found that the S153N mutation (from uTEV1Δ) improved activity and selected this as the template ("uTEV1") for our new selections.

Figure 3A:
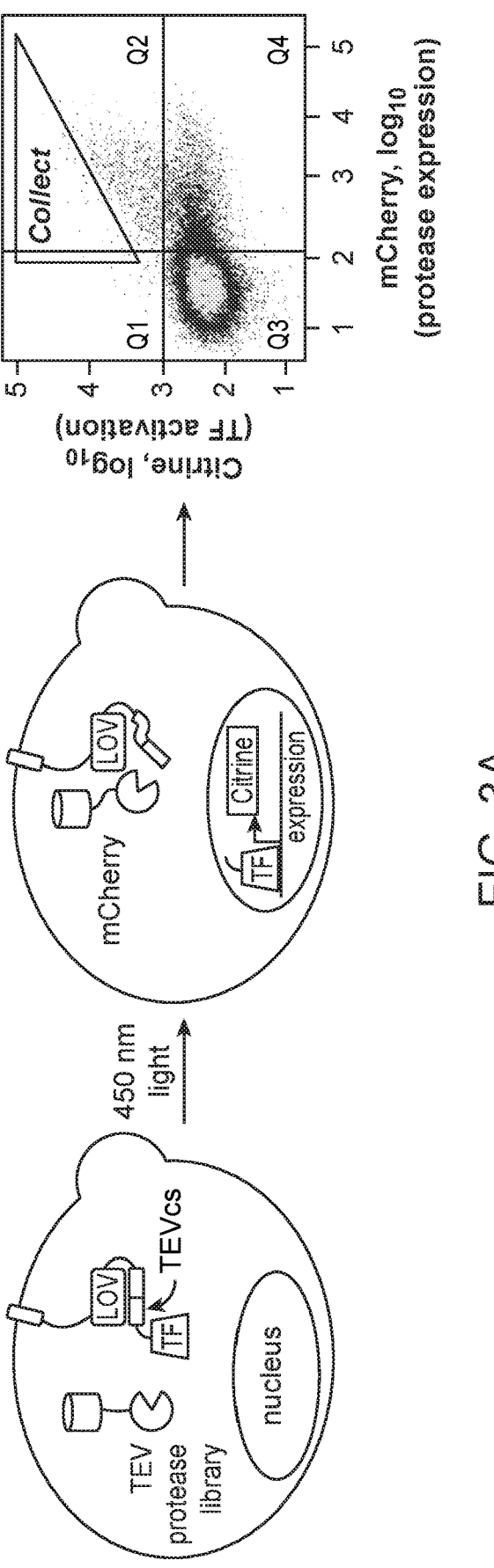
FIGS. 3A to 3H show evolution of full-length TEV protease.
Figure 3B:
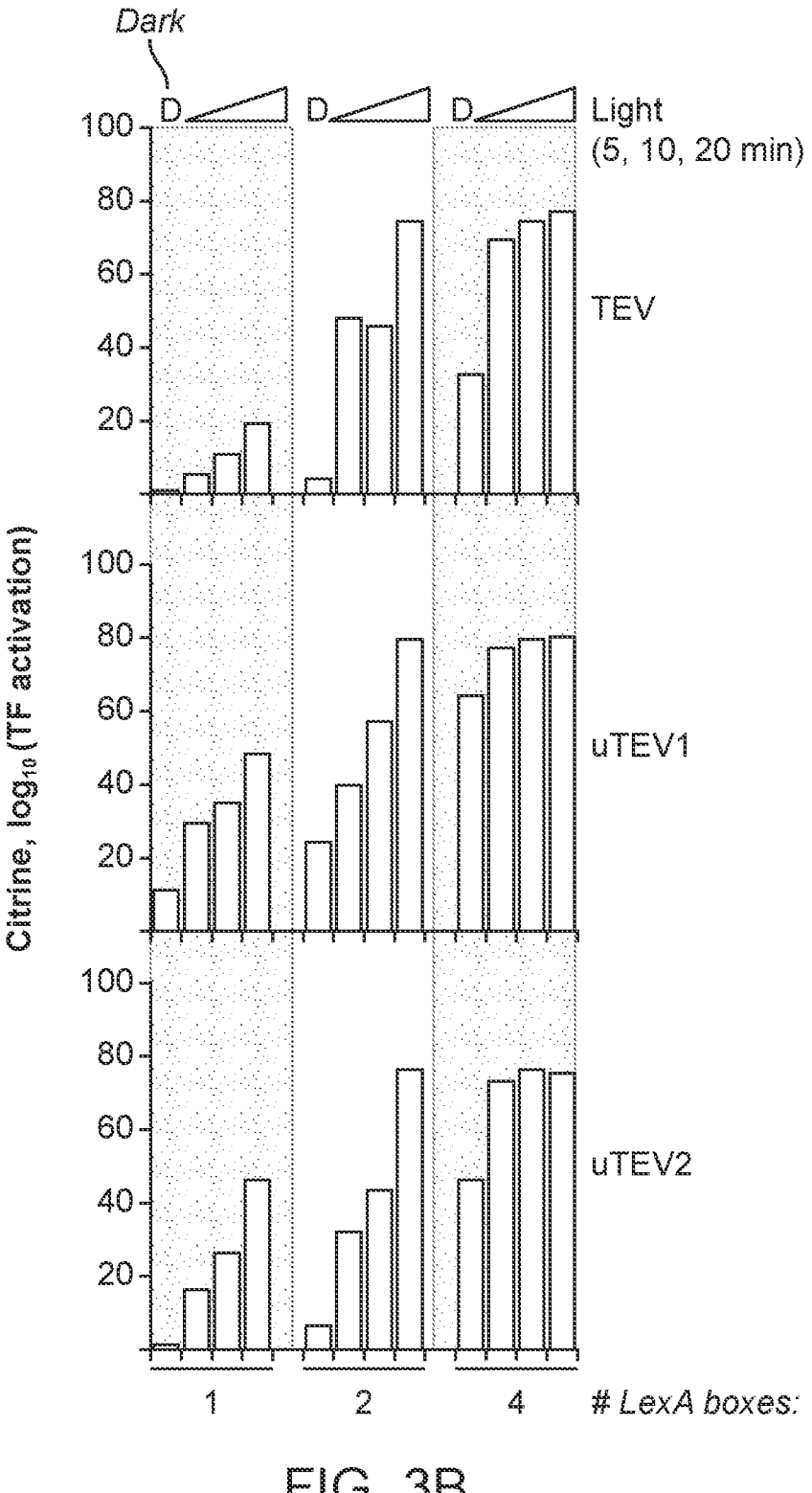
Figure 3C:
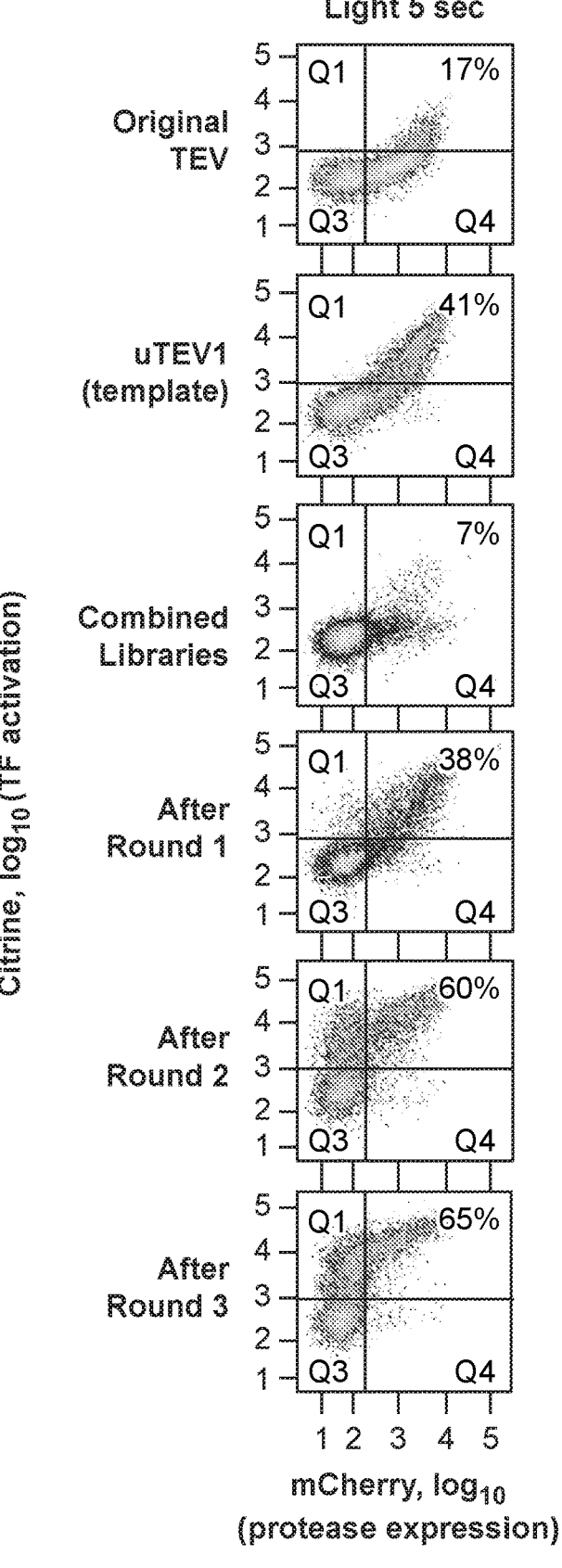
Figure 14A:
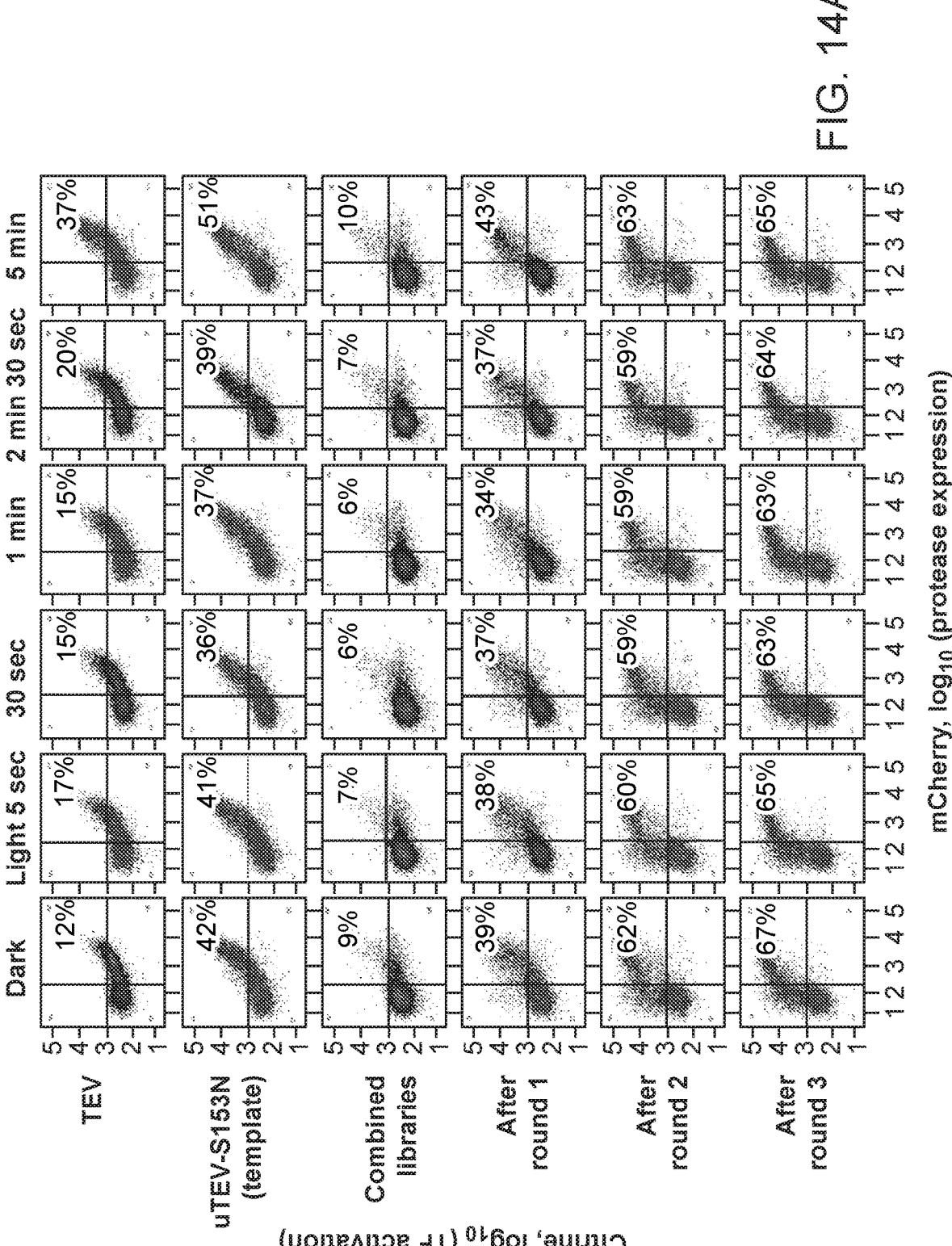
FIGS. 14A and 14B show FACS plots summarizing the progress of the selections. Analysis of full-length uTEV1 libraries after 3 rounds of sorting (Related to FIG. 3C).
Figure 14B:
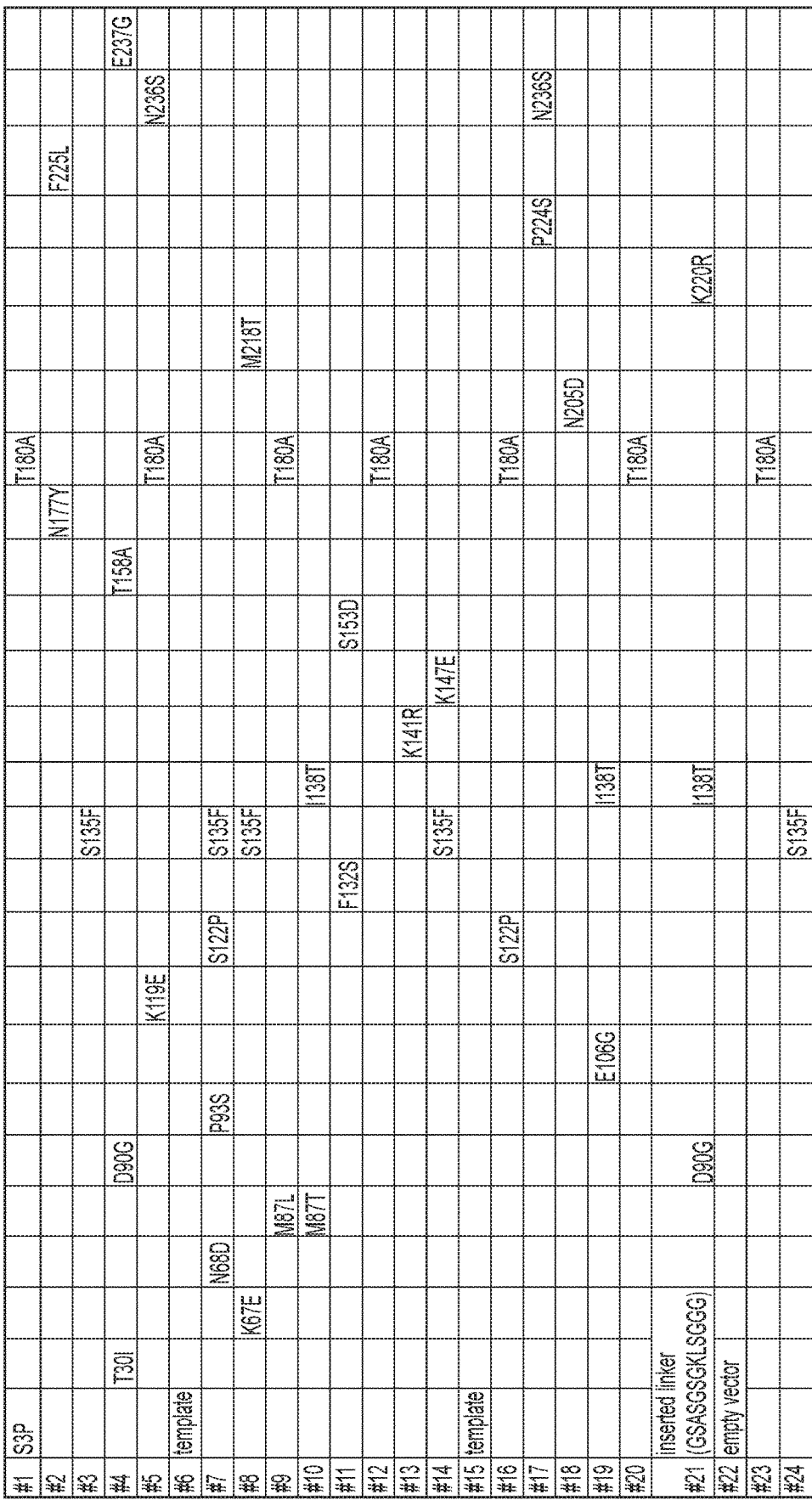
Figure 16A:
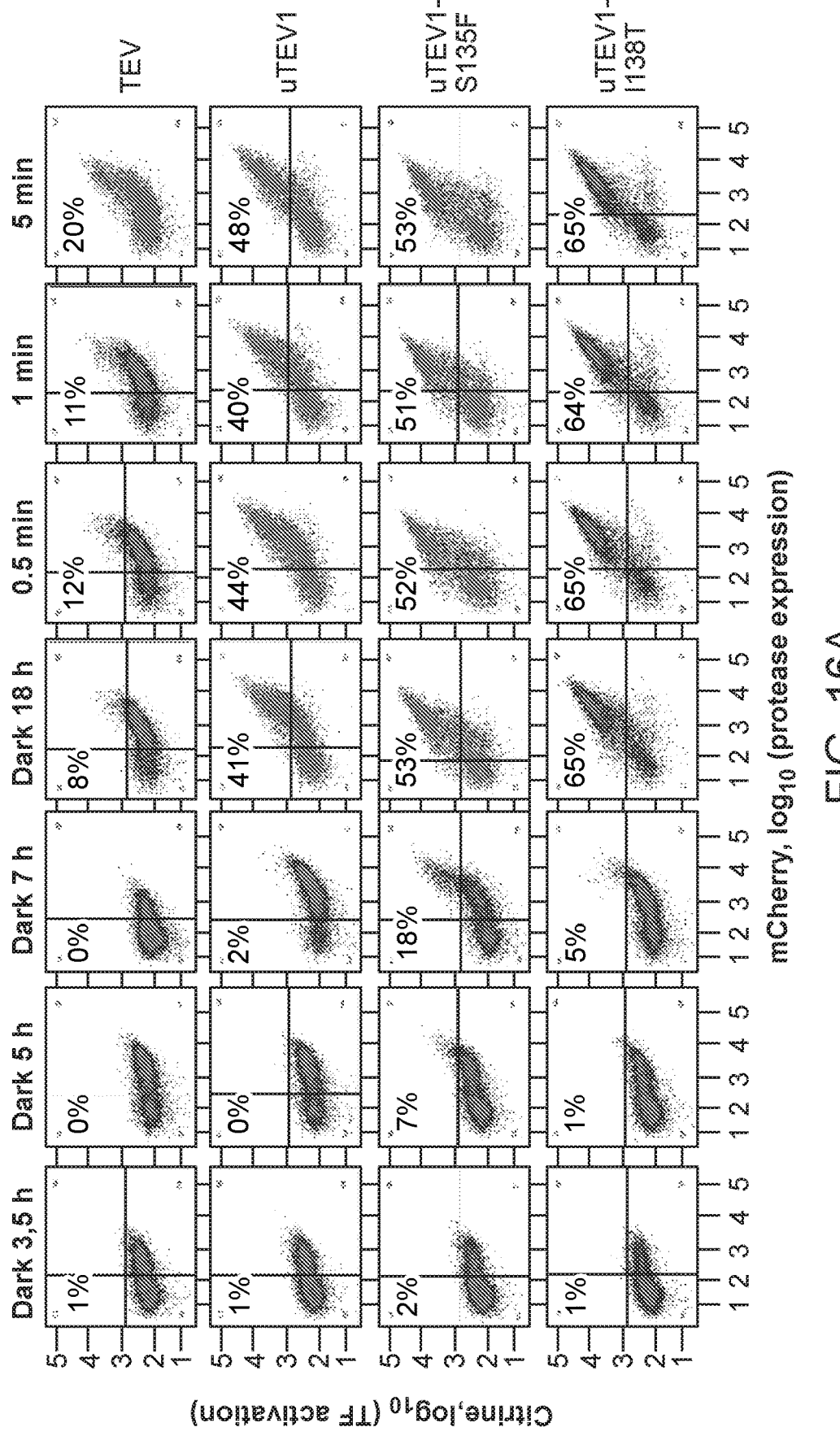
FIGS. 16A and 16B show shows characterization of full-length TEV clones with combined mutations. FACS plots used to generate plot in FIG. 3D. FACS plots of selected TEV mutants 6 hours after blue light exposure for the indicated times (0, 0.5, 2, and 5 min) and shorter protein induction times (3.5 to 7 hours instead of 18). Each plot represents two replicates, n=20,000 cells.
Figure 16B:
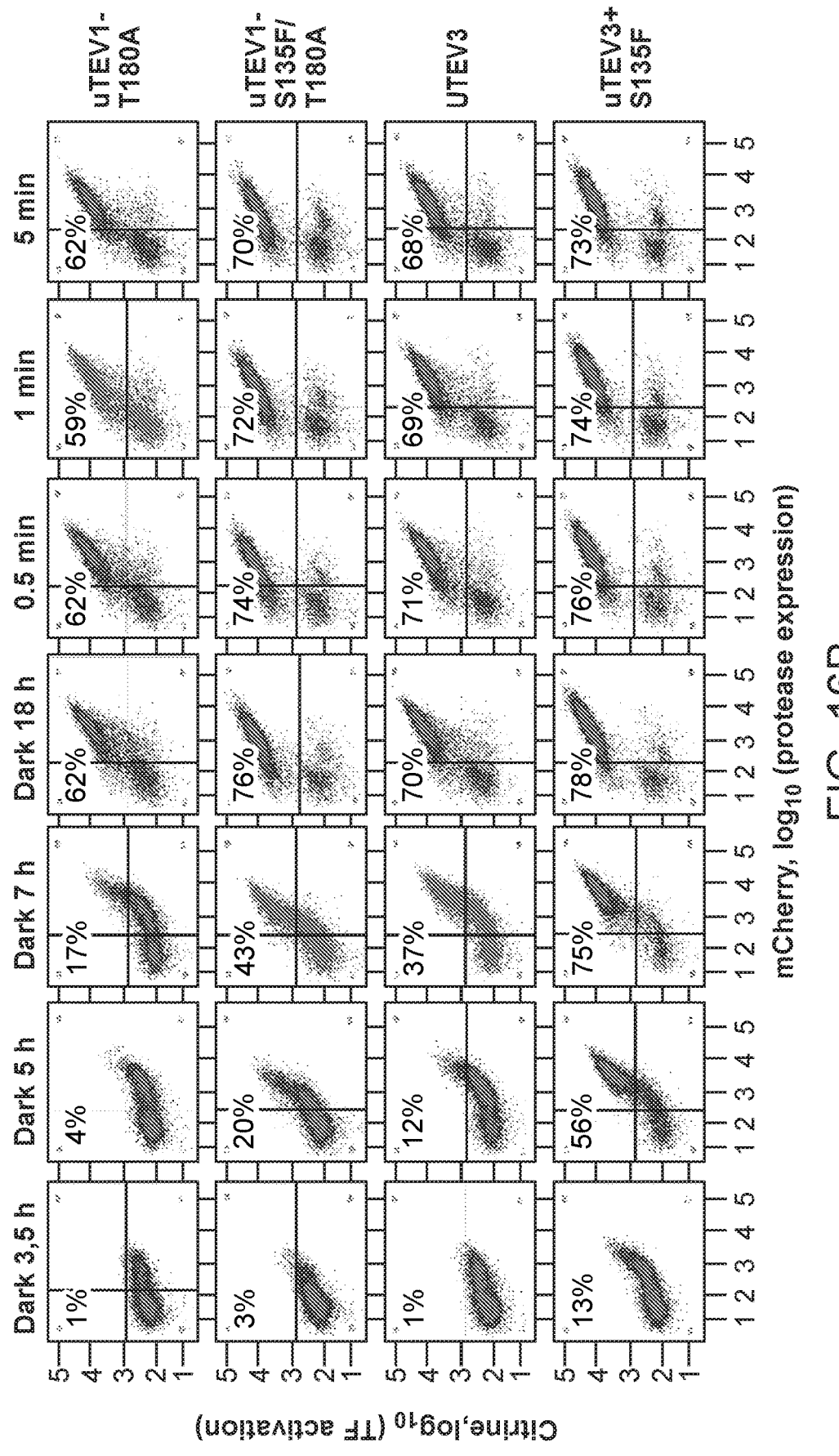

An error-prone PCR library of uTEV1 variants was fused to mCherry and transformed into yeast cells co-expressing the membrane-anchored TF as shown in FIG. 3A. Protease expression was induced with galactose for 12 hours prior to blue light irradiation for 45 seconds (round 1), 30 seconds (round 2), or 5 195 seconds (round 3). The yeast populations after each of three rounds of selection were compared to each other, and to the template, in FIG. 3C. The evolution clearly enriched the activity of the pool, but there was little difference between light and dark conditions (FIG. 3C and FIG. 14A), suggesting that eLOV does not effectively cage the high-affinity TEVcs from full-length TEV under these conditions. Even without the advantage of light-based kinetic selection as in FIG. 1A, however, we nevertheless enriched mutations that improved the catalytic efficiency of full-length TEV. Sequencing of round 3 showed that the mutations S135F, I138T and T180A had been enriched (FIG. 14B). Assays on individual mutants in yeast showed that all three mutations contributed to improved TEV activity (FIG. 15), and combining the mutations had an additive effect (FIG. 16).

Figure 17:
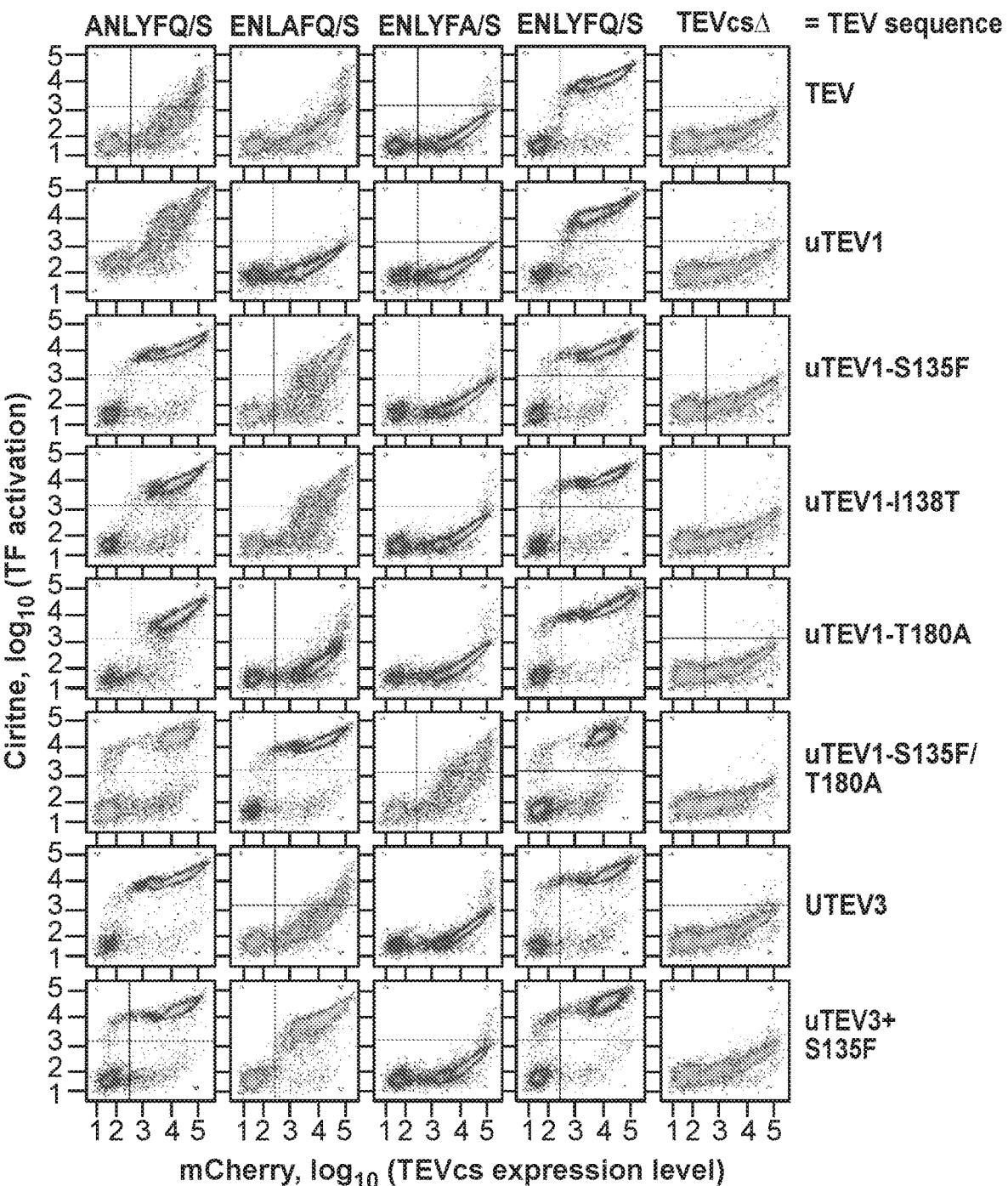
FIG. 17 shows profiling the sequence specificity of full-length uTEV clones in yeast. Same assay as in FIG. 2F. FACS plots shown after 12 hours. Each plot represents one replicate, n=20,000 cells. SEQ ID NOS: 76, 77, 78, and 5 in order of appearance.

Since mutations near the TEV active site could also impact sequence specificity, we further evaluated our evolved mutants using the substrate profiling assay shown in FIG. 2F. FIG. 17 shows that the mutations I138T and T180A maintain the highly-specific substrate profile of wild-type TEV and uTEV1, while the S135F/T180A mutation increases promiscuity at position P1. Based on this data, we selected I138T/S153N/T180A (uTEV3) because this clone balances improved kinetics with high sequence-specificity.

Figures 3D, 3E:
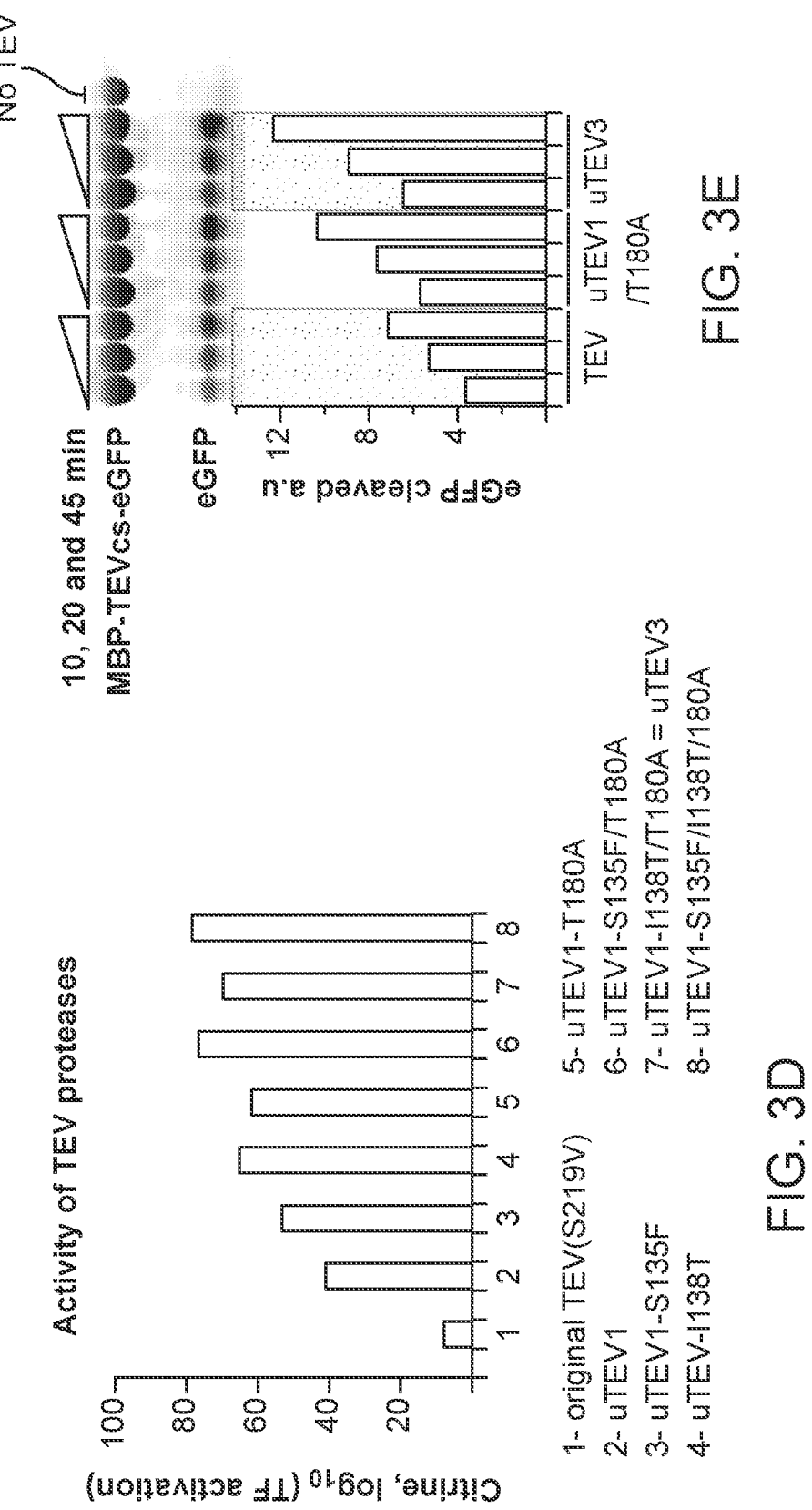
Figures 3F, 3G:
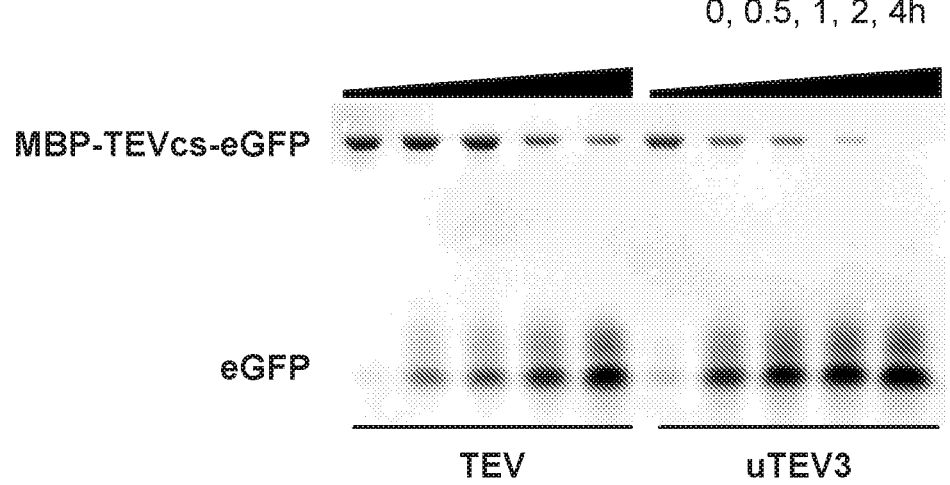

To characterize uTEV3 in vitro, we expressed and purified the enzyme from bacteria (FIG. 9), and combined it with the substrate protein MBP-TEVcs-eGFP (TEVcs=ENLYFQ/S (SEQ ID NO: 5), 320 uM) for various lengths of time. Fluorescence imaging of the SDS-PAGE gels in FIG. 3E shows that uTEV3 cleaves the substrate to a greater extent than wild-type TEV or the double mutant S153N/T180A. By titrating the substrate concentration, we were able to measure kcat and Km values for both wild-type TEV and uTEV3 (FIG. 3F). Our selection did not appear to increase kcat in this case, but Km improved by 3-fold, leading to a 2.8-fold increase in kcat/Km (FIG. 9).

Figure 18A:
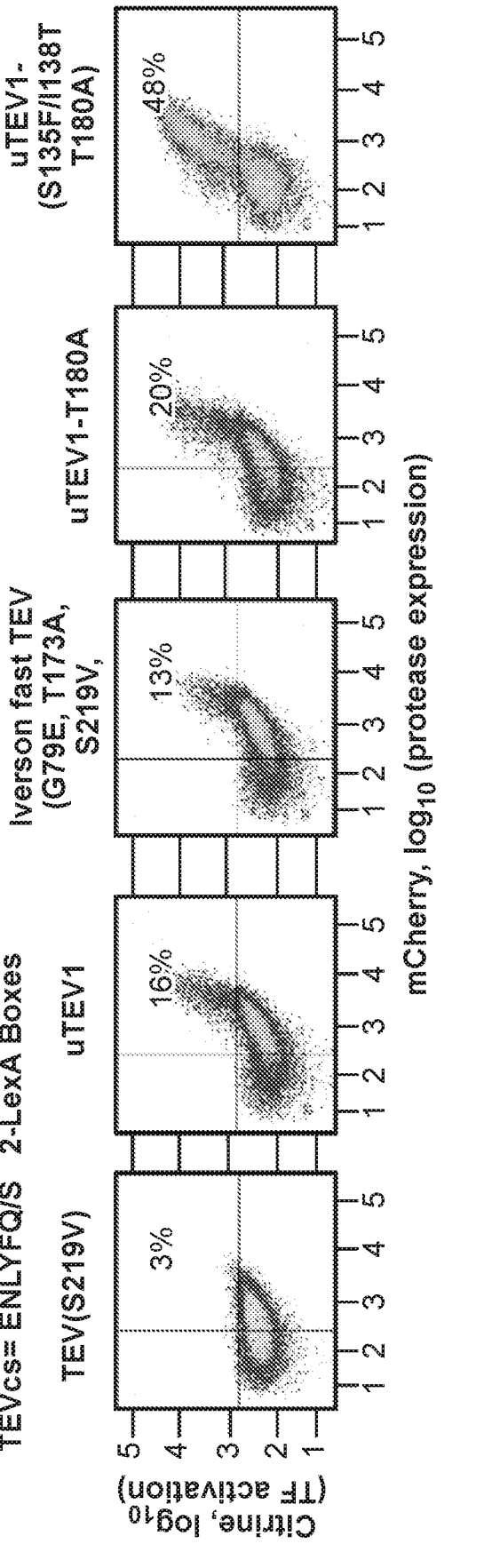
FIGS. 18A, 18B and 18C show shows a comparison of evolved proteases with Iverson's fast TEV.
Figure 18B:
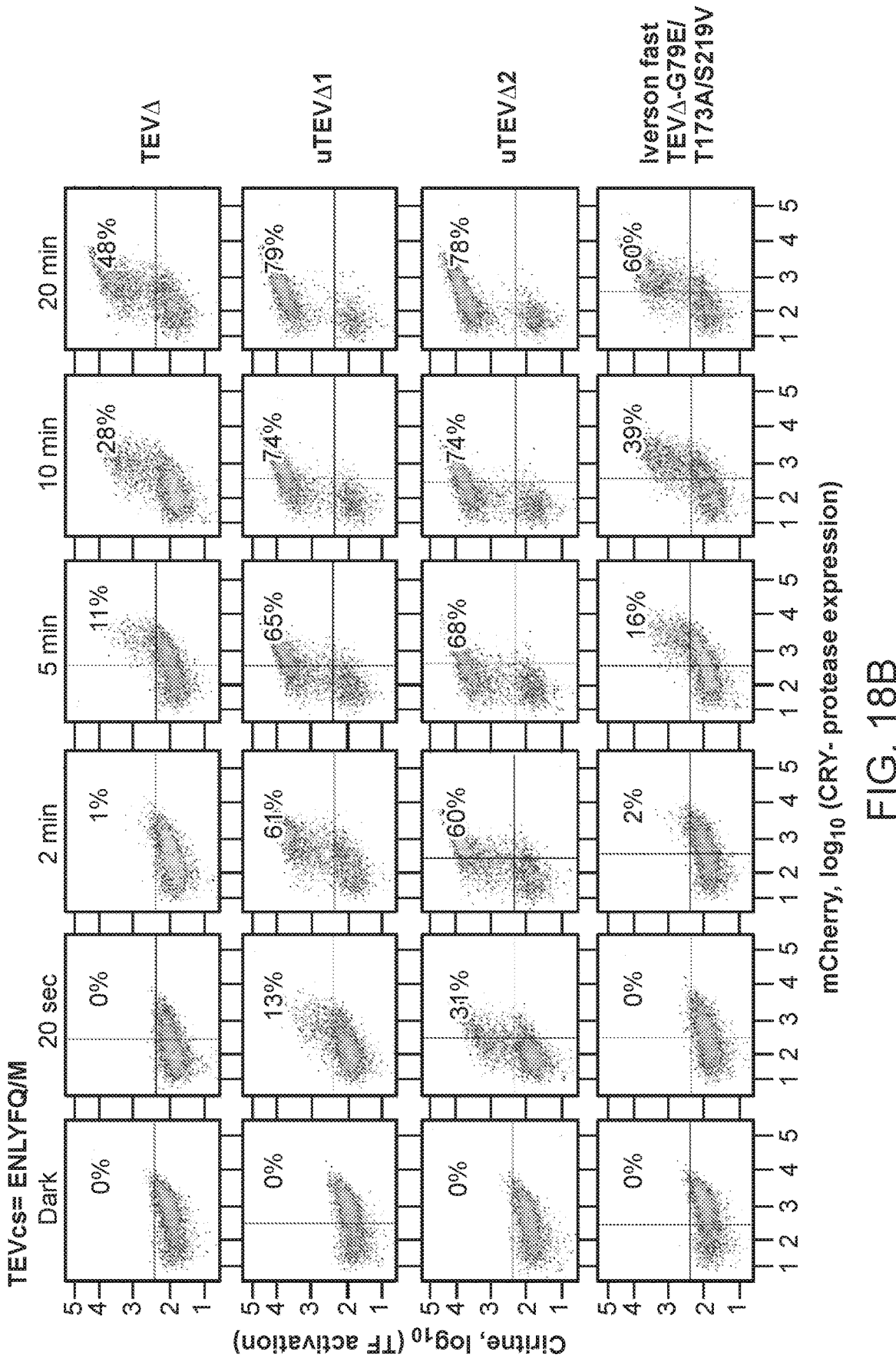
Figure 18C:
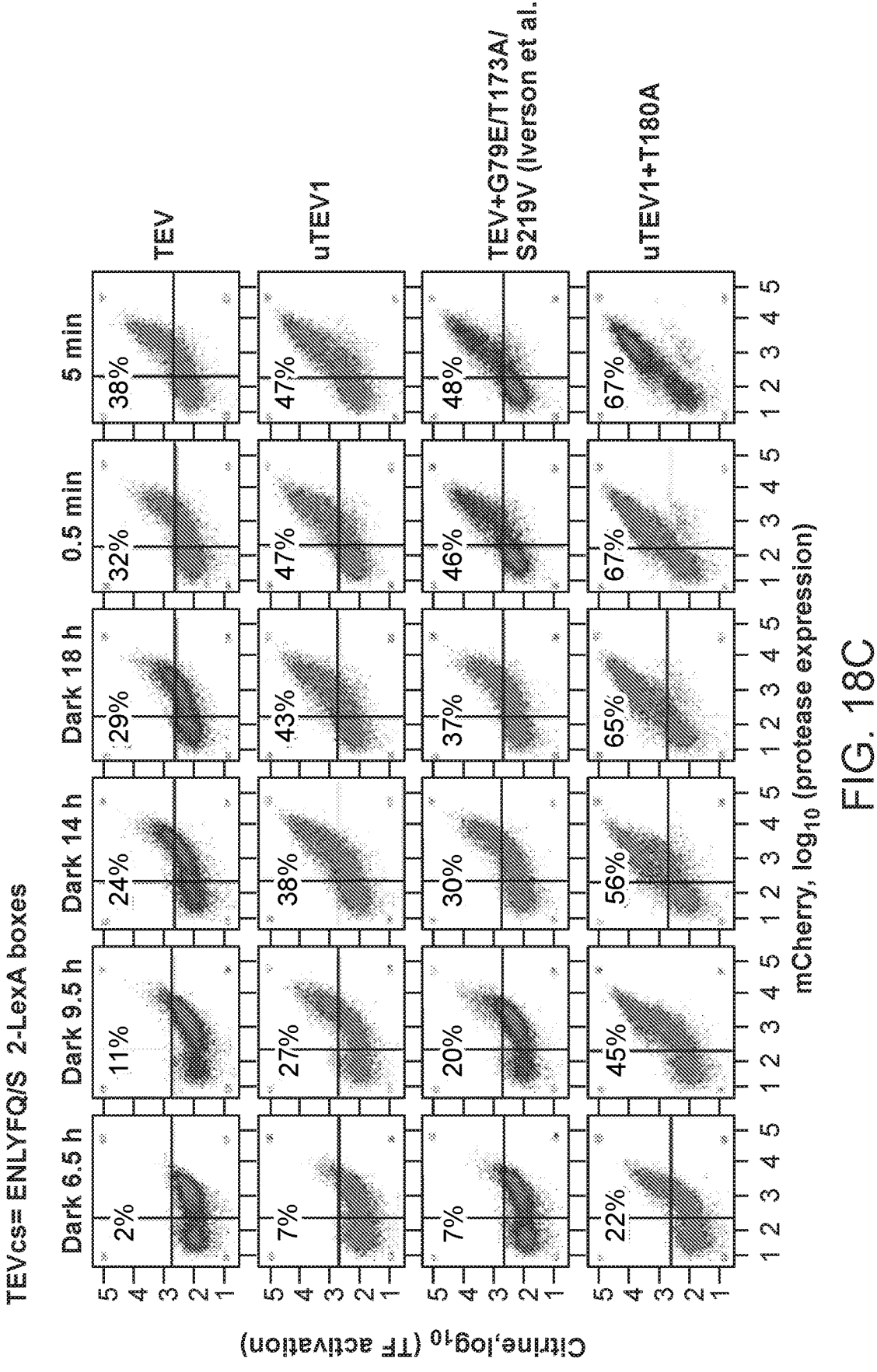
Figure 18C:
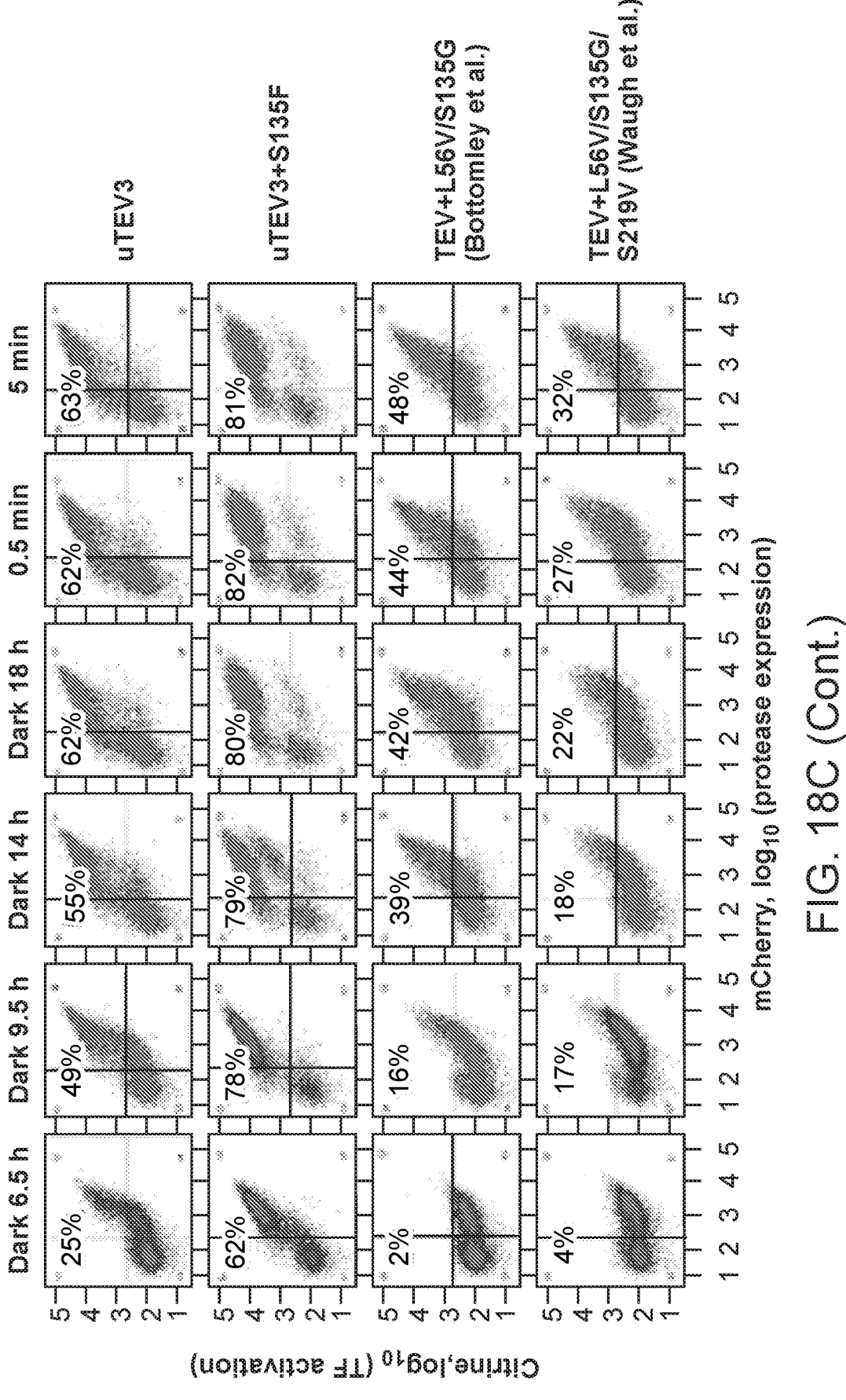

Previously, Iverson et al. used directed evolution in the yeast secretory pathway to evolve a full-length TEV mutant (G79E/T173Δ/S219V) with higher activity than wild-type TEV[17]. We compared this Iverson mutant with our evolved TEV mutants in the yeast cytosol (FIG. 18A). We found that the quadruple mutant S135F/I138T/S153N/T180A (which incorporates all three mutations found in uTEV3) was the most active, while the activities of uTEV1 and the Iverson mutant were comparable. Wild-type TEV was the least active. We also tested the Iverson mutations in the context of truncated TEVΔ for proximity-dependent cleavage. FIG. 18A shows that uTEV2Δ was the most active (against the low-affinity TEVcs ENLYFQ/M (SEQ ID NO: 6)), while IversonΔ and wild-type TEVΔ were comparable in activity. Without being bound by theory, we hypothesize that IversonΔ has lower kcat for the low-affinity TEVcs than does uTEV2Δ in the context of FLARE (vide infra). Also, the IversonΔ mutant also gave poorer performance than uTEV1Δ (FIG. 24).

Figure 19:
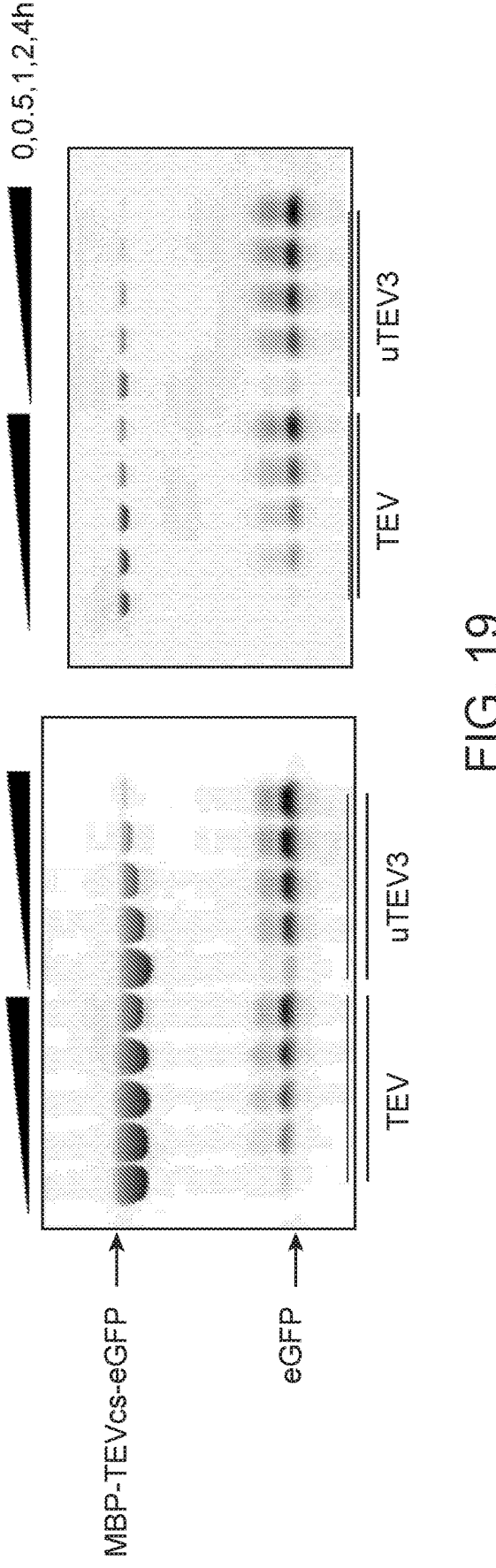
FIG. 19 shows uTEV3 more efficiently catalyzes the removal of affinity tags. Related to FIG. 3G. (A) Protein substrate MBP-TEVcs-GFP (10 µM) was incubated with the indicated full-length proteases (MBP-TEV(S219V) and MBP-uTEV3) at 60 nM and incubated at 30° C. in TrisHCl 50 mM, pH8 EDTA 1 mM, 10% Glycerol and 1 mM of DTT. MBP=maltose binding protein, TEVcs=ENLYFQ/S (SEQ ID NO: 5). Aliquots were taken at different time points (0, 0.5, 1, 2 and 4 h) and reactions terminated by addition of sodium dodecyl sulfate-polyacrylamide gel electrophoresis (SDS-PAGE) sample buffer and immediately flash-frozen. The reaction products were separated by SDS-PAGE at 4° C. and analyzed by in-gel fluorescence with a Thyphoon 9410.

A higher-affinity variant of TEV protease could be useful for removal of affinity tags during recombinant protein production. To test this, we generated MBP-TEVcs-eGFP and used TEV to remove the maltose binding protein tag. FIG. 3G and FIG. 19 show that the evolved uTEV3 does this more rapidly and more completely than does wild-type TEV.

Figure 3H:
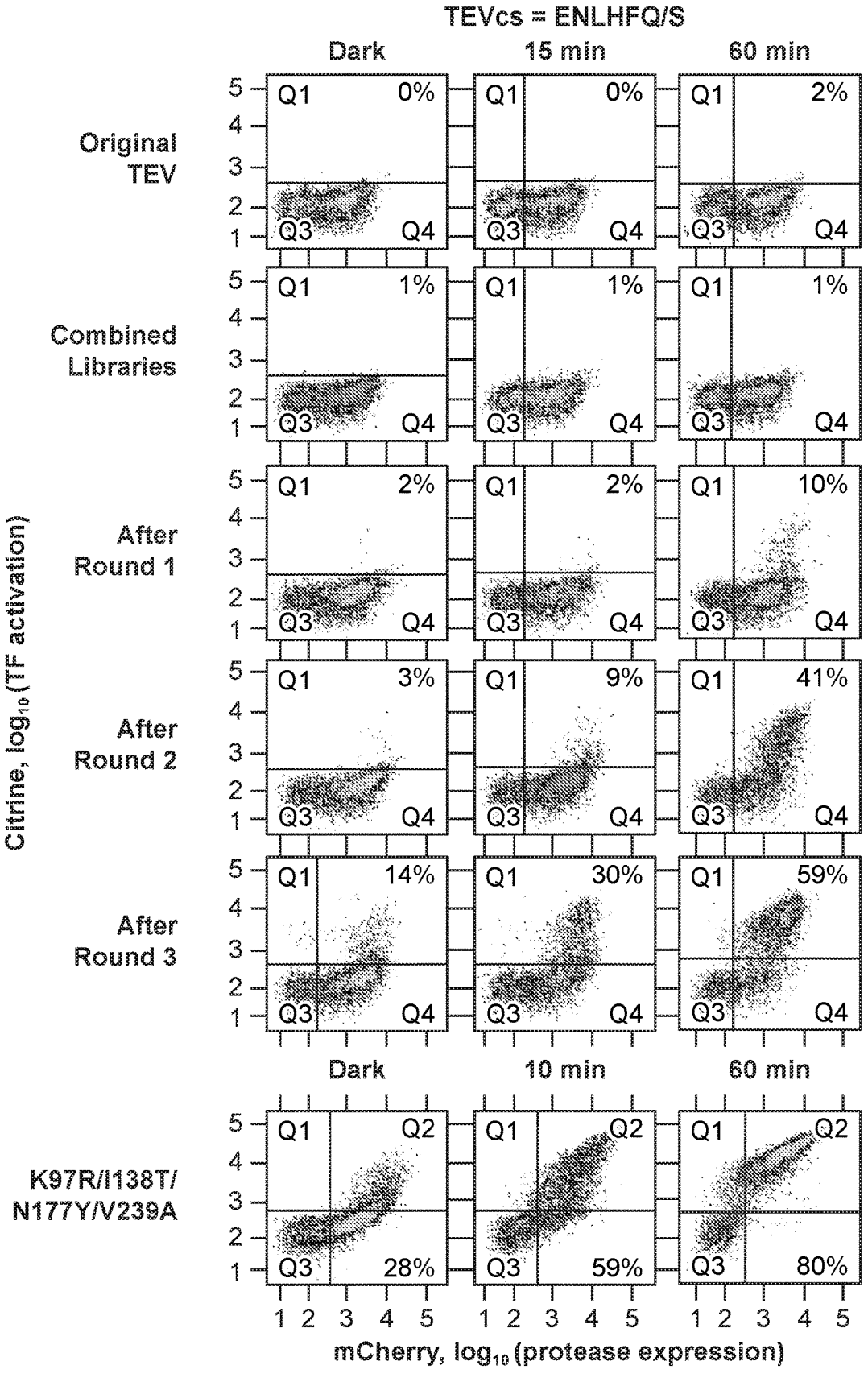

Apart from kinetics, we tested whether our yeast-based evolution platform could also be used to re-engineer the sequence specificity of full-length TEV. This has previously been achieved by evolution in the yeast secretory pathway [17] and by PACE in bacteria [16]. Here, we started by mutating TEVcs so that it would no longer be recognized by wild-type TEV. Both P3(Tyr→His) and P3(Tyr→Trp) exhibited minimal recognition by full-length wild-type TEV even after 1 hour of blue-light illumination (FIG. 3H). We co-expressed each of these substrates along with a library of full-length TEV variants in yeast, and performed three successive rounds of selection (FIG. 3H and FIG. 20). As before, the light irradiation time was gradually reduced from 45 minutes (round 1) to 30 minutes (round 2) to 15 minutes (round 3). FIG. 3H and FIG. 20 show that the post-round 3 populations are much more active toward the mutated substrate sequences than both the original library or wild-type TEV. Sequencing showed that 96% of the enriched clones contained the mutation N177Y for both substrates (FIG. 21 and FIG. 22). Interestingly, this same mutation was enriched in our earlier selections (FIG. 7B), and mutations at N177 were enriched in previous TEV evolution studies by Liu et al.[16] and Iverson et al [17]. Our analysis in yeast suggests that N177 mutants have increased TEVcs affinity and decreased sequence specificity (i.e., greater promiscuity). Thus, our yeast platform is able to relax TEV sequence specificity.

uTEV1Δ Improves the Performance of FLARE and SPARK Tools

TEV is utilized in a wide range of biotechnological tools, some of which could benefit from faster protease catalysis. Two such tools are FLARE and SPARK, which are caged transcription factors that are activated by the coincidence of blue light and a second stimulus—for FLARE, that stimulus is elevated cytosolic calcium, while for SPARK, it is a protein-protein interaction (PPI) (FIGS. 4A and 4B). Both tools strive to convert transient cellular events into long-lasting signals that can enable microscopy, manipulation, or genetic selection. How transient an event can be recorded by FLARE or SPARK depends on how many TF molecules can be released per unit time; this in turn is limited by protease catalytic rate. For example, FLARE requires a minimum of 10-15 minutes of light+calcium to give sufficient signal/noise in neuron culture. Similarly, SPARK requires a 10-15 minute "recording" time window to capture a cellular PPI event. The following results show that uTEV1Δ and uTEV2Δ improve the temporal resolution of FLARE and SPARK tools.

The uTEV1Δ, uTEVΔ2, and two other truncated TEV variants were introduced into FLARE, and the constructs were tested in HEK 293T cells. Cells were treated with 6 mM CaCl₂) and 2 μM ionomycin to elevate cytosolic calcium, while blue light was delivered for just 30 seconds. Reporter gene (mCherry) expression was then detected by confocal microscopy 8 hours later. FIG. 4D shows that all evolved proteases exhibited increased mCherry expression compared to wild-type TEVΔ. However, uTEV2Δ was accompanied by high background in the no-light and low-calcium conditions (FIG. 4D), perhaps because the eLOV domain is no longer sufficient to fully cage TEVcs against this highly active protease. FLARE with uTEV1Δ gave the best signal-to-background ratio (12.2), a 6.2-fold improvement over original FLARE with wild-type TEVΔ1. Also, the truncated form of Iverson's protease yields a poor signal (FIG. 4D, 4E, FIG. 23 and FIG. 24).

uTEV was then tested in neuron culture, which allows elevation of cytosolic calcium in a more physiological manner by using either electrical field stimulation or media replacement, which mechanically stimulates the neurons while providing fresh glutamate. The cells were concurrently irradiated with blue light at 60 mW/cm2 for either 5 minutes or 60 seconds. FIG. 4F shows that original FLARE with wild-type TEVΔ gives minimal reporter gene (mCherry) expression, consistent with previous observations. By contrast, FLARE incorporating uTEVΔ shows calcium- and light-dependent reporter gene expression at both 5 minute and 60-second time points. Quantitation showed signal-to-noise ratios 27-fold and 16-fold higher, for FLARE containing uTEVΔ compared to FLARE containing wild-type TEVΔ, at 60 sec and 5 min time points, respectively (electrical stimulation conditions). uTEVΔ therefore improves the performance and temporal resolution of FLARE in neuron culture. (FIG. 25).

To test uTEV1Δ in SPARK, beta-2-adrenergic receptor (B2AR) and beta-arrestin were used as the protein-protein interaction pair. Isoproterenol stimulates this interaction, and arrestin is recruited to the GPCR as part of its desensitization pathway [32]. Previously, SPARK required at least 10 minutes of light stimulation to give detectable reporter gene expression in HEK 293T cells. FIG. 3G shows that with just 1 minute of isoproterenol+light, mCherry is robustly detected by confocal microscopy. By contrast, original SPARK with uTEVΔ gives mCherry signal that is 11.7-fold lower (FIG. 4G, 4H and FIG. 26). Thus, uTEV1 also improves the temporal resolution of the PPI transcriptional tool SPARK.

54

DISCUSSION

The inventors have developed a new yeast-based platform for evolution of protease catalytic rate. The platform was used to improve kcat for both full-length TEV protease and its truncated, low affinity variant. The latter was then incorporated into the cellular transcriptional reporters FLARE and SPARK to improve the temporal resolution of calcium and protein-protein interaction detection, respectively.

The directed evolution platform has features that distinguish it from previous platforms used to evolve enzyme catalytic function. In contrast to selections on the yeast cell surface (used for APEX, TurboID, split HRP [18, 19, 20], and Iverson's TEV[17]), the selection described herein takes place in the yeast cytosol, which is more physiologically relevant, and allows protease catalytic activity to be linked to transcription of a fluorescent protein reporter. As a consequence, the signal is amplified, and each selection step is very simple to perform, not requiring any antibody staining. A second major feature of the platform is the use of the photosensory LOV domain to cage the TEV cleavage sequence (TEVcs). This allows a user to modulate the time window available for TEV action on TEVcs, and progressively increase selection stringency (by decreasing the light irradiation time). Third, the light-sensitive CRY-CIBN interaction [33] was used to recruit TEV to its peptide substrate, which allowed selection of low affinity (high Km) proteases, which are required for TANGO, FLARE, Cal-Light and SPARK tools.

The simplicity and modularity of the yeast evolution platform suggest that it could be adapted for other engineering or analysis goals. As demonstrated herein, with some small modifications, the system could be used to characterize protease sequence-specificity via sequencing of FACS-enriched clones (FIG. 2F). Alternative strategies for characterizing protease sequence-specificity, using synthetic peptide libraries [34] or N-terminal capture with subtiligase [35], require expensive peptide synthesis or mass spectrometry. Potentially, this platform could also be used to improve catalytic efficiency of other proteases (substitution of TEV with TVMV protease is shown in FIG. 27).

Directed evolution on truncated TEVΔ produced mutations at two residues bordering the catalytic triad: T30A and S153N. Based on examination of the wild-type TEV crystal structure [26], the S153N mutation may finely re-shape the active site, lowering the energy of the tetrahedral transition state, while the T30A mutation could decrease a steric clash between the enzyme and Met at the P1' position of the TEVcs substrate. In addition, selection enriched N177Y, which makes contact with the P1 position of the bound TEVcs. Characterization in yeast suggests that this mutation increases TEV affinity for TEVcs rather than improving kcat. Interestingly, the N177 mutation was also enriched in previous studies that used directed evolution to redirect TEV towards different TEVcs sequences [17, 16].

Wild-type TEVΔ was replaced with uTEV1Δ in FLARE and SPARK tools to increase the rate of transcription factor proteolysis and consequently improve temporal resolution. Given the extensive use of TEV protease in biotechnological tools as well as protein purification, the faster evolved variants presented here could be beneficial across a range of applications.

Plasmid Tables

| ID | Plasmid name | Plasmid Vecor/ Backbone | Promoter | Terminator | Expression in | Tags | More Details | Antibiotic R. |
|---|---|---|---|---|---|---|---|---|
| p1 | STE2-V5-CIBN-M13-eLOV-TEVcs(ENLYFQM)-LexAVP16 | pRS-derived | ACT1 | | Yeast/ApaI digestion to integrate | V5 | HIS3 selectable marker | Amp |
| p2 | STE2-V5-BFP-CIBN-M13-eLOV-TEVcs(ENLYFQM)-LexAVP16 | pRS-derived | ACT1 | | Yeast/ApaI digestion to integrate | V5/BFP | HIS3 selectable marker | Amp |
| p3 | STE2Δ-BFP-CIBN-MKII-eLOV-TEVcs(ENLYFQM)-LexAVP16-tCpRS-derived | pRS-derived | TDH3 | tCYC1 | Yeast/AscI digestion to integrate | flag/BFP | LEU2 selectable marker | Amp |
| p4 | STE2Δ-CIBN-MKII-eLOV-TEVcs(ENLYFQM)-LexAVP16-tCYC | pRS-derived | TDH3 | tCYC1 | Yeast/AscI digestion to integrate | flag/BFP | LEU2 selectable marker | Amp |
| p5 | STE2Δ-V5-CIBN-M13-eLOV(ENLYFQM)-TEVcs-LexAVP16 | pRS-derived | ACT1 | | Yeast/AscI digestion to integrate | V5 | LEU2 selectable marker | Amp |
| p6 | STE2Δ-V5-BFP-CIBN-M13-eLOV(ENLYFQM)-TEVcs-LexAVP16pRS-derived | pRS-derived | ACT1 | | Yeast/AscI digestion to integrate | V5/BFP | LEU2 selectable marker | Amp |
| p7 | mCherry-CRY-TEV | pRSII415 | Gal | tCYC1 | Yeast/episomally | mCherry | LEU2 selectable marker | Amp |
| p8 | mCherry-CRY-TEVΔ/S219V | pRSII415 | Gal | tCYC1 | Yeast/episomally | mCherry | LEU2 selectable marker | Amp |

| ID | Plasmid name | Plasmid Vecor/ Backbone | Promoter | Terminator | Expression in | Tags | More Details | Antibiotic R. |
|---|---|---|---|---|---|---|---|---|
| p9 | mCherry-TEV | pRSII415 | Gal | tCYC1 | Yeast/episomally | mCherry | LEU2 selectable marker | Amp |
| p10 | mCherry-TEVΔ-S219V | pRSII415 | Gal | tCYC1 | Yeast/episomally | mCherry | LEU2 selectable marker | Amp |
| p11 | mCherry-CRY-TEV | pRSII413 | Gal | tCYC1 | Yeast/episomally | mCherry | HIS3 selectable marker | Amp |
| p12 | mCherry-CRY-TEVΔ/S219V | pRSII413 | Gal | tCYC1 | Yeast/episomally | mCherry | HIS3 selectable marker | Amp |
| p13 | mCherry-TEV | pRSII413 | Gal | tCYC1 | Yeast/episomally | mCherry | HIS3 selectable marker | Amp |
| p14 | mCherry-TEVΔ/S219V | pRSII413 | Gal | tCYC1 | Yeast/episomally | mCherry | HIS3 selectable marker | Amp |
| p15 | STE2Δ-BFP-CIBN-MKII-eLOV-TEVcs-LexAB42 | pRS-derived | ACT1 | tCYC1 | Yeast/AscI digestion to integrate | V5/BFP | LEU2 selectable marker | Amp |
| p16 | STE2Δ-BFP-CIBN-MKII-eLOV-TEVcs-LexAGal4 | pRS-derived | ACT1 | tCYC1 | Yeast/AscI digestion to integrate | V5/BFP | LEU2 selectable marker | Amp |
| p17 | mCherry-CRY-TEVΔ/S219V + S31W | pRSII413 | Gal | tCYC1 | Yeast/episomally | mCherry | HIS3 selectable marker | Amp |
| p18 | mCherry-CRY-TEVΔ/S219V + S153N | pRSII413 | Gal | tCYC1 | Yeast/episomally | mCherry | HIS3 selectable marker | Amp |
| p19 | mCherry-CRY-TEVΔ/S219V + T30A + S153N | pRSII413 | Gal | tCYC1 | Yeast/episomally | mCherry | HIS3 selectable marker | Amp |
| p20 | mCherry-CRY-TEVΔ/S219V + T30I | pRSII413 | Gal | tCYC1 | Yeast/episomally | mCherry | HIS3 selectable marker | Amp |

| ID | Plasmid name | Plasmid Vecor/ Backbone | Promoter | Terminator | Expression in | Tags | More Details | Antibiotic R. |
|---|---|---|---|---|---|---|---|---|
| p21 | mCherry-CRY-TEVΔ/S219V + N177Y | pRSII413 | Gal | tCYC1 | Yeast/ episomally | mCherry | HIS3 selectable marker | Amp |
| p22 | mCherry-CRY-TEVΔ/S219V + T30A | pRSII413 | Gal | tCYC1 | Yeast/ episomally | mCherry | HIS3 selectable marker | Amp |
| p23 | mCherry-TEVΔ/S219V + S31W | pRSII413 | Gal | tCYC1 | Yeast/ episomally | mCherry | HIS3 selectable marker | Amp |
| p24 | mCherry-TEVΔ/S219V + S153N | pRSII413 | Gal | tCYC1 | Yeast/ episomally | mCherry | HIS3 selectable marker | Amp |
| p25 | mCherry-TEVΔ/S219V + T30A + S153N | pRSII413 | Gal | tCYC1 | Yeast/ episomally | mCherry | HIS3 selectable marker | Amp |
| p26 | mCherry-TEVΔ/S219V + T30I | pRSII413 | Gal | tCYC1 | Yeast/ episomally | mCherry | HIS3 selectable marker | Amp |
| p27 | mCherry-TEVΔ/S219V + N177Y | pRSII413 | Gal | tCYC1 | Yeast/ episomally | mCherry | HIS3 selectable marker | Amp |
| p28 | mCherry-TEVΔ/S219V + T30A | pRSII413 | Gal | tCYC1 | Yeast/ episomally | mCherry | HIS3 selectable marker | Amp |
| p29 | mCherry-CRY-TEVΔ/S219V + T30A + N177Y | pRSII413 | Gal | tCYC1 | Yeast/ episomally | mCherry | HIS3 selectable marker | Amp |
| p30 | mCherry-CRY-TEVΔ/S219V + S153N + N177Y | pRSII413 | Gal | tCYC1 | Yeast/ episomally | mCherry | HIS3 selectable marker | Amp |
| p31 | mCherry-CRY-TEVΔ/S219V + S31W + N177Y | pRSII413 | Gal | tCYC1 | Yeast/ episomally | mCherry | HIS3 selectable marker | Amp |
| p32 | mCherry-CRY-TEVΔ-S219V-T30A- S153N + Asn177Tyr-tCYC1 | pRSII413 | Gal | tCYC1 | Yeast/ episomally | mCherry | HIS3 selectable marker | Amp |
| p33 | mCherry-CRY-TEVΔ-S219V-Thr30Ala + Ser31Trp-tCYC1 | pRSII413 | Gal | tCYC1 | Yeast/ episomally | mCherry | HIS3 selectable marker | Amp |

| ID | Plasmid name | Plasmid Vecor/ Backbone | Promoter | Terminator | Expression in | Tags | More Details | Antibiotic R. |
|---|---|---|---|---|---|---|---|---|
| p34 | mCherry-TEVΔ/S219V + T30A + N177Y | pRSII413 | Gal | tCYC1 | Yeast/ episomally | mCherry | HIS3 selectable marker | Amp |
| p35 | mCherry-TEVΔ/S219V + S153N + N177Y | pRSII413 | Gal | tCYC1 | Yeast/ episomally | mCherry | HIS3 selectable marker | Amp |
| p36 | mCherry-TEVΔ/S219V + S31W + N177Y | pRSII413 | Gal | tCYC1 | Yeast/ episomally | mCherry | HIS3 selectable marker | Amp |
| p37 | mCherry-TEVΔ/S219V + T30A + S153N + N177Y | pRSII413 | Gal | tCYC1 | Yeast/ episomally | mCherry | HIS3 selectable marker | Amp |
| p38 | mCherry-TEVΔ/S219V + T30A + S31W | pRSII413 | Gal | tCYC1 | Yeast/ episomally | mCherry | HIS3 selectable marker | Amp |
| p39 | mCherry-CRY-TEVΔ/G79E + T173A + S219V | pRSII413 | Gal | tCYC1 | Yeast/ episomally | mCherry | HIS3 selectable marker | Amp |
| p40 | mCherry-TEV/S219V | pRSII413 | Gal | tCYC1 | Yeast/ episomally | mCherry | HIS3 selectable marker | Amp |

-continued

| ID | Plasmid name | Plasmid Vecor/ Backbone | Promoter | Terminator | Expression in | Tags | More Details | Antibiotic R. |
|---|---|---|---|---|---|---|---|---|
| p41 | mCherry-TEV/S153N + S219V | pRSII413 | Gal | tCYC1 | Yeast/ episomally | mCherry | HIS3 selectable marker | Amp |
| p42 | mCherry-TEV/T30A + S153N + S219V | pRSII413 | Gal | tCYC1 | Yeast/ episomally | mCherry | HIS3 selectable marker | Amp |
| p43 | mCherry-TEV/G79E + T173A + S219V | pRSII413 | Gal | tCYC1 | Yeast/ episomally | mCherry | HIS3 selectable marker | Amp |
| p44 | mtagBFPII-CRY-TEVΔ | pRS-derived | TDH3 | tCYC1 | Yeast/AscI digestion to integrate | mtagBFPII | LEU2 selectable marker | Amp |
| p45 | mtagBFPII-CRY-TEVΔ/S219V + S153N | pRS-derived | TDH3 | tCYC1 | Yeast/AscI digestion to integrate | mtagBFPII | LEU2 selectable marker | Amp |
| p46 | mtagBFPII-CRY-TEVΔ/s219V + T30A + S153N | pRS-derived | TDH3 | tCYC1 | Yeast/AscI digestion to integrate | mtagBFPII | LEU2 selectable marker | Amp |

| ID | Plasmid name | Plasmid Vecor/ Backbone | Promoter | Terminator | Expression in | Tags | More Details | Antibiotic R. |
|---|---|---|---|---|---|---|---|---|
| p47 | STE2Δ-mCherry-CIBN-PIF6-eLOV-TEVcs-LexAVP16 | pRSII413 | Gal | tCYC1 | Yeast/ episomally | mCherry | HIS3 selectable marker | Amp |
| p48 | STE2Δ-mCherry-CIBN-PIF6-eLOV-TEVcs-Ala P6-LexAVP16 | pRSII413 | Gal | tCYC1 | Yeast/ episomally | mCherry | HIS3 selectable marker | Amp |
| p49 | STE2Δ-mCherry-CIBN-PIF6-eLOV-TEVcs-Ala P3-LexAVP16 | pRSII413 | Gal | tCYC1 | Yeast/ episomally | mCherry | HIS3 selectable marker | Amp |
| p50 | STE2Δ-mCherry-CIBN-PIF6-eLOV-TEVcs-Ala P1-LexAVP16 | pRSII413 | Gal | tCYC1 | Yeast/ episomally | mCherry | HIS3 selectable marker | Amp |
| p51 | MBP-TEVcs-7xHis-TEVΔ/S219V | pRK793 | tac P | | E. coli | | | Amp |
| p52 | MBP-TEVcs-7xHis-TEVΔ/S219V + S153N | pRK793 | tac P | | E. coli | | | Amp |
| p53 | MBP-TEVcs-7xHis-TEVΔ/S219V + T30A + S153N | pRK793 | tac P | | E. coli | | | Amp |
| p54 | MBP-TEVcs(ENLYFQ/ S)-eGFP | pYFJ16 | tac P | | E. coli | | | Amp |
| p55 | UAS-mCherry | AAV | UAS | WPRE/PolyA | mammalian/ HEK | | | Amp |
| p56 | CD4-HA-CIBN-2xMKII-NNES-heLOV-GAL4 | AAV | CMV | PolyA | mammalian/ HEK | HA | | Amp |

| ID | Plasmid name | Plasmid Vecor/ Backbone | Promoter | Terminator | Expression in | Tags | More Details | Antibiotic R. |
|---|---|---|---|---|---|---|---|---|
| p57 | CMV-eGFP-CaM-TEVΔ/S219V | AAV | CMV | PolyA | mammalian/ HEK | V5/eGFP | | Amp |
| p58 | CMV-eGFP-CaM-TEVΔ/S219V + S153N | AAV | CMV | PolyA | mammalian/ HEK | V5/eGFP | | Amp |
| p59 | CMV-eGFP-CaM-TEVΔ/S219V + T30A + S153N | AAV | CMV | PolyA | mammalian/ HEK | V5/eGFP | | Amp |
| p60 | CMV-eGFP-CaM-TEVΔ/S219V + N177Y | AAV | CMV | PolyA | mammalian/ HEK | V5/eGFP | | Amp |
| p61 | CMV-eGFP-CaM-TEVΔ/S219V + T30A | AAV | CMV | PolyA | mammalian/ HEK | V5/eGFP | | Amp |
| p62 | TRE-mCherry | AAV | TRE | WPRE/PolyA | mammalian/ Neuron | | | Amp |
| p63 | tNeu-CIBN-2xMKII-heLOV-tTA | AAV | Syn | PolyA | mammalian/ Neuron | HA/ flag/VP16 | | Amp |
| p64 | AAV-EGFP-CaM5f-V5-TEVΔ/S219V | AAV | Syn | WPRE/PolyA | Neuron mammalian/ | V5/eGFP | | Amp |
| p65 | AAV-eGFP-CaM5f-V5-TEVΔ/S219V + S153N | AAV | Syn | WPRE/PolyA | Neuron mammalian/ | V5/eGFP | | Amp |
| p66 | AAV-EGFP-(CaM5f-V5-TEVΔ/S219V + T30A + S153N | AAV | Syn | WPRE/PolyA | Neuron mammalian/ | V5/eGFP | | Amp |
| p67 | AAV-EGFP-CaM5f-V5-TEVΔ/S219V + N177Y | AAV | Syn | WPRE/PolyA | Neuron mammalian/ | V5/eGFP | | Amp |
| p68 | AAV-EGFP-CaM5f-V5-TEVΔ/S219V + T30A | AAV | Syn | WPRE/PolyA | Neuron mammalian/ | V5/eGFP | | Amp |

| ID | Plasmid name | Plasmid Vecor/ Backbone | Promoter | Terminator | Expression in | Tags | More Details | Antibiotic R. |
|---|---|---|---|---|---|---|---|---|
| p69 | B2Ar-heLOV-TEVcs-Gal4-V5 | plx208 | CMV | | mammalian/ HEK | HA/eGFP | Hygromycin gene deleted | Amp |
| p70 | EGFP-p2a-HA-arrestin-TEVΔ/S219V | plx208 | CMV | | mammalian/ HEK | HA/eGFP | Hygromycin gene deleted | Amp |
| p71 | EGFP-p2a-HA-arrestin-TEVΔ/S153N | plx208 | CMV | | mammalian/ HEK | HA/eGFP | Hygromycin gene deleted | Amp |
| p72 | pAAV1 | | | | | | | Amp |
| p73 | pAAV2 | | | | | | | Amp |
| p74 | pDF6 | | | | | | | Amp |
| p75 | mCherry-TEV/S153N + T180A + S219V | pRSII413 | Gal | tCYC1 | Yeast/ episomally | mCherry | HIS3 selectable marker | Amp |
| p76 | mCherry-TEV/S135F + S153N + T180A + S219V | pRSII413 | Gal | tCYC1 | Yeast/ episomally | mCherry | HIS3 selectable marker | Amp |
| p77 | mCherry-TEV/I138T + S153N + T180A + S219V | pRSII413 | Gal | tCYC1 | Yeast/ episomally | mCherry | HIS3 selectable marker | Amp |

-continued

| ID | Plasmid name | Plasmid Vecor/ Backbone | Promoter | Terminator | Expression in | Tags | More Details | Antibiotic R. |
|---|---|---|---|---|---|---|---|---|
| p78 | mCherry-TEV/S135F + I138T + S153N + T180A + S219V | pRSII413 | Gal | tCYC1 | Yeast/ episomally | mCherry | HIS3 selectable marker | Amp |
| p79 | mCherry-TEV/I138T + S153N + S219V | pRSII413 | Gal | tCYC1 | Yeast/ episomally | mCherry | HIS3 selectable marker | Amp |
| p80 | mtagBFPII-TEV/S153N + T180A + S219V | pRS-derived | TDH3 | tCYC1 | Yeast/AscI digestion to integrate | mtagBFPII | HIS3 selectable marker | Amp |
| p81 | mtagBFPII-TEV/S135F + S153N + T180A + S219V | pRS-derived | TDH3 | tCYC1 | Yeast/AscI digestion to integrate | mtagBFPII | HIS3 selectable marker | Amp |
| p82 | mtagBFPII-TEV/I138T + S153N + T180A + S219V | pRS-derived | TDH3 | tCYC1 | Yeast/AscI digestion to integrate | mtagBFPII | HIS3 selectable marker | Amp |

| ID | Plasmid name | Plasmid Vecor/ Backbone | Promoter | Terminator | Expression in | Tags | More Details | Antibiotic R. |
|---|---|---|---|---|---|---|---|---|
| p83 | mtagBFPII-TEV/S135F + I138T + S153N + T180A + S219V | pRS-derived | TDH3 | tCYC1 | Yeast/AscI digestion to integrate | mtagBFPII | HIS3 selectable marker | Amp |
| p84 | mtagBFPII-TEV/I138T + S153N + S219V | pRS-derived | TDH3 | tCYC1 | Yeast/AscI digestion to integrate | mtagBFPII | HIS3 selectable marker | Amp |
| p85 | mtagBFPII-TEV/I153F + S153N + S219V | pRS-derived | TDH3 | tCYC1 | Yeast/AscI digestion to integrate | mtagBFPII | HIS3 selectable marker | Amp |
| p86 | STE2Δ-mCherry-CIBN-PIF6-eLOV-TEVcs-Ala P6-LexAVP16 | pRSII413 | Gal | tCYC1 | Yeast/ episomally | mCherry | HIS3 selectable marker | Amp |
| p87 | STE2Δ-mCherry-CIBN-PIF6-eLOV-TEVcs-Ala P3-LexAVP16 | pRSII413 | Gal | tCYC1 | Yeast/ episomally | mCherry | HIS3 selectable marker | Amp |
| p88 | STE2Δ-mCherry-CIBN-PIF6-eLOV-TEVcs-Ala P1-LexAVP16 | pRSII413 | Gal | tCYC1 | Yeast/ episomally | mCherry | HIS3 selectable marker | Amp |
| p89 | STE2Δ-mCherry-CIBN-PIF6-eLOV-TEVcs-LexAVP16 | pRSII413 | Gal | tCYC1 | Yeast/ episomally | mCherry | HIS3 selectable marker | Amp |
| p90 | mCherry-TEV/L56V + S135G | pRSII413 | Gal | tCYC1 | Yeast/ episomally | mCherry | HIS3 selectable marker | Amp |
| p91 | mCherry-TEV/L56V + S135G + S219V | pRSII413 | Gal | tCYC1 | Yeast/ episomally | mCherry | HIS3 selectable marker | Amp |
| p92 | HIS6-MBP-TEV | pYFJ16 | tac P | | *E. coli* | MBP/ His6 | S219V | Amp |

| ID | Plasmid name | Plasmid Vecor/ Backbone | Promoter | Terminator | Expression in | Tags | More Details | Antibiotic R. |
|---|---|---|---|---|---|---|---|---|
| p93 | HIS6-MBP-TEV I138T S153N T180A | pYFJ16 | tac P | | *E. coli* | MBP/ His6 | S219V | Amp |
| p94 | mCherry-TVMV-tCYC1 | pRSII413 | Gal | | Yeast/ episomally | mCherry | HIS3 selectable marker | Amp |
| p95 | STE2Δ-BFP-CIBN-MKII-eLOV-TVMV (ETVRFQS)-LexAVP16 | pRS-derived | TDH3 | tCYC1 | Yeast/AscI digestion to integrate | BFP | LEU2 selectable marker | Amp |
| p96 | STE2Δ-BFP-CIBN-MKII-eLOV-TVMV(P1' = M)-LexAVP16 | pRS-derived | TDH3 | tCYC1 | Yeast/AscI digestion to integrate | BFP | LEU2 selectable marker | Amp |
| p97 | STE2Δ-BFP-CIBN-MKII-eLOV-TVMV(P1' = L)-LexAVP16 | pRS-derived | TDH3 | tCYC1 | Yeast/AscI digestion to integrate | BFP | LEU2 selectable marker | Amp |
| p98 | STE2Δ-BFP-CIBN-MKII-eLOV-TVMV(P1' = Q)-LexAVP16 | pRS-derived | TDH3 | tCYC1 | Yeast/AscI digestion to integrate | BFP | LEU2 selectable marker | Amp |
| p99 | LexA-mCherry-VP16 | pRSII413 | Gal | tCYC1 | Yeast/ episomally | mCherry | HIS3 selectable marker | Amp |
| p100 | LexA-mCherry-B42 | pRSII414 | Gal | tCYC1 | Yeast/ episomally | mCherry | HIS3 selectable marker | Amp |
| p101 | LexA-mCherry-Gal4 | pRSII415 | Gal | tCYC1 | Yeast/ episomally | mCherry | HIS3 selectable marker | Amp |
| p102 | MBP-TEVcs(ENLYFQ/ M)-eGFP | pYFJ16 | tac P | | *E. coli* | MBP/ eGFP | | Amp |
| p103 | STE2-citrine | pRS-derived | TDH3 | tCYC1 | Yeast/AscI digestion to integrate | citrine | LEU2 selectable marker | Amp |

40

| ID | Plasmid name | Plasmid Vecor/ Backbone | Promoter | Terminator | Expression in | Tags | More Details | Antibiotic R. |
|---|---|---|---|---|---|---|---|---|
| p104 | STE2Δ-citrine | pRS-derived | TDH3 | tCYC1 | Yeast/AscI digestion to integrate | citrine | LEU2 selectable marker | Amp |
| p105 | STE2Δ-BFP-CIBN-eLOV-TEVcs (ENLHFQS, P3 = H)-LexAVP16 | pRS-derived | TDH3 | tCYC1 | Yeast/AscI digestion to integrate | BFP/flag | LEU2 selectable marker | Amp |
| p106 | STE2Δ-BFP-CIBN-eLOV-TEVcs (ENLWFQS, P3 = W)-LexAVP16pRS-derived | | TDH3 | tCYC1 | Yeast/AscI digestion to integrate | BFP/flag | LEU2 selectable marker | Amp |
| p107 | STE2Δ-BFP-CIBN-eLOV-TEVcs (ENLYFQS)-LexAVP16 | pRS-derived | TDH3 | tCYC1 | Yeast/AscI digestion to integrate | BFP/flag | LEU2 selectable marker | Amp |
| p108 | mCherry-TEVΔ | AAV | CMV | PolyA | mammalian/ HEK | mCherry | | Amp |

| ID | Plasmid name | Plasmid Vecor/ Backbone | Promoter | Terminator | Expression in | Tags | More Details | Antibiotic R. |
|---|---|---|---|---|---|---|---|---|
| p109 | mCherry-TEV | AAV | CMV | PolyA | mammalian/ HEK | mCherry | | Amp |
| p110 | mCherry-TEV/S31W + S219V | AAV | CMV | PolyA | mammalian/ HEK | mCherry | | Amp |
| p111 | mCherry-TEV/S153N + S219V | AAV | CMV | PolyA | mammalian/ HEK | mCherry | | Amp |
| p112 | mCherry-TEV/T30A + S153N + S219V | AAV | CMV | PolyA | mammalian/ HEK | mCherry | | Amp |
| p113 | mCherry-TEV-T301 + S219V | AAV | CMV | PolyA | mammalian/ HEK | mCherry | | Amp |
| p114 | mCherry-TEV/N177Y + S219V | AAV | CMV | PolyA | mammalian/ HEK | mCherry | | Amp |
| p115 | CMS817-CMV-mCherry-TEV/T30A S219V | AAV | CMV | PolyA | mammalian/ HEK | mCherry | | Amp |

| ID | Plasmid name | Plasmid Vecor/ Backbone | Promoter | Terminator | Expression in | Tags | More Details | Antibiotic R. |
|---|---|---|---|---|---|---|---|---|
| p116 | mCherry-TEV/N177Y + T30A + S219V | AAV | CMV | PolyA | mammalian/ HEK | mCherry | | Amp |
| p117 | mCherry-TEV/N177Y + S153N + S219V | AAV | CMV | PolyA | mammalian/ HEK | mCherry | | Amp |
| p118 | mCherry-TEV/N177Y + S31W + S219V | AAV | CMV | PolyA | mammalian/ HEK | mCherry | | Amp |
| p119 | mCherry-TEV/T30A + S153N + N177Y + S219V | AAV | CMV | PolyA | mammalian/ HEK | mCherry | | Amp |
| p120 | mCherry-TEV/T30A + S31W + S219V | AAV | CMV | PolyA | mammalian/ HEK | mCherry | | Amp |
| p121 | mCherry-TEVΔ/S31W + S219V | AAV | CMV | PolyA | mammalian/ HEK | mCherry | | Amp |
| p122 | mCherry-TEVΔ/S153N + S219V | AAV | CMV | PolyA | mammalian/ HEK | mCherry | | Amp |
| p123 | mCherry-TEVΔ/T30A + S153N + S219V | AAV | CMV | PolyA | mammalian/ HEK | mCherry | | Amp |
| p124 | mCherry-TEVΔ/T301 + S219V | AAV | CMV | PolyA | mammalian/ HEK | mCherry | | Amp |
| p125 | mCherry-TEVΔ/N177Y + S219V | AAV | CMV | PolyA | mammalian/ HEK | mCherry | | Amp |
| p126 | mCherry-TEVΔ/T30A + S219V | AAV | CMV | PolyA | mammalian/ HEK | mCherry | | Amp |

Yeast Tables

The original strain used is BY4741. Genotype: MATa his3Δ1 leu2Δ0 met15Δ0 ura3Δ0. Description: S288C-derivative laboratory strain

| ID | Plasmid used | Auxotrophic selection marker |
|---|---|---|
| YS-FRP791 | Addgene plasmid # 58432 (FRP791) | URA3 |
| YS-FRP792 | Addgene plasmid # 58433 (FRP792) | URA3 |
| YS-FRP793 | Addgene plasmid # 58434 (FRP793) | URA3 |
| YS1 | P3-pTDH3-STE2Δ-BFP-CIBN-MKII-eLOV-TEVcs(ENLYFQ/M)-LexAVP16-tCYC | URA3/LEU2 |
| YS2 | P105-pTDH3-STE2Δ-BFP-CIBN-MKII-eLOV-TEVcs(ENLHFQ/S P3 = H)-LexAVP16-tCYC | URA3/LEU2 |
| YS3 | P106-pTDH3-STE2Δ-BFP-CIBN-MKII-eLOV-TEVcs(ENLWFQ/S P3 = W)-LexAVP16-tCYC | URA3/LEU2 |
| YS4 | P107-pTDH3-STE2Δ-BFP-CIBN-MKII-eLOV-TEVcs(ENLYFQ/S)-LexAVP16-tCYC.ape | URA3/LEU2 |
| YS5 | P44-mtagBFPII-CRY-TEVΔ/S219V | URA3/LEU2 |
| YS6 | P45-mtagBFPII-CRY-TEVΔ/S153N + S219V | URA3/LEU2 |
| YS7 | P46-mtagBFPII-CRY-TEVΔ/T30A + S153N + S219V | URA3/LEU2 |
| YS8 | P79-mtagBFPII-TEV/S153N + T180A + S219V | URA3/LEU2 |
| YS9 | P80-mtagBFPII-TEV/S135F + S153N + T180A + S219V | URA3/LEU2 |
| YS10 | P81-mtagBFPII-TEV/I138T + S153N + T180A + S219V | URA3/LEU2 |
| YS11 | P82-mtagBFPII-TEV/S135F + I138T + S153N + T180A + S219V | URA3/LEU2 |
| YS12 | P83-mtagBFPII-TEV/I138T + S153N + S219V | URA3/LEU2 |
| YS13 | P84-mtagBFPII-TEV/I153F + S153N + S219V | URA3/LEU2 |
| YS14 | P94-STE2Δ-BFP-CIBN-MKII-eLOV-TVMVcs(ETVRFQ/S)-LexAVP16 | URA3/LEU2 |
| YS15 | P95-STE2Δ-BFP-CIBN-MKII-eLOV-TVMVcs(ETVRFQ/M P1' = M)-LexAVP16 | URA3/LEU2 |
| YS16 | P96-STE2Δ-BFP-CIBN-MKII-eLOV-TVMVcs(ETVRFQ/L P1' = L)-LexAVP16 | URA3/LEU2 |
| YS17 | P97-STE2Δ-BFP-CIBN-MKII-eLOV-TVMVcs(ETVRFQ/Q P1' = Q)-LexAVP16 | URA3/LEU2 |

| ID | Genetic Background |
|---|---|
| YS-FRP791 | BY4741::insul-(lexA-box)1-PminCYC1-Citrine-TCYC1 (URA3) |
| YS-FRP792 | BY4741::insul-(lexA-box)2-PminCYC1-Citrine-TCYC1 (URA3) |
| YS-FRP793 | BY4741::insul-(lexA-box)4-PminCYC1-Citrine-TCYC1 (URA3) |
| YS1 | BY4741::insul-(lexA-box)4-PminCYC1-Citrine-TCYC1 (URA3), pTDH3-STE2Δ-BFP-CIBN-MKII-eLOV-TEVcs(ENLYFQM)-LexAVP16-tCYC (LEU2) |
| YS2 | BY4741::insul-(lexA-box)4-PminCYC1-Citrine-TCYC1 (URA3), pTDH3-STE2Δ-BFP-CIBN-MKII-eLOV-TEVcs(ENLHFQS)-LexAVP16-tCYC (LEU2) |
| YS3 | BY4741::insul-(lexA-box)4-PminCYC1-Citrine-TCYC1 (URA3), pTDH3-STE2Δ-BFP-CIBN-MKII-eLOV-TEVcs(ENLWFQS)-LexAVP16-tCYC (LEU2) |
| YS4 | BY4741::insul-(lexA-box)2-PminCYC1-Citrine-TCYC1 (URA3), pTDH3-STE2Δ-BFP-CIBN-MKII-eLOV-TEVcs(ENLYFQS)-LexAVP16-tCYC (LEU2) |
| YS5 | BY4741::insul-(lexA-box)4-PminCYC1-Citrine-TCYC1 (URA3), pTDH3-mtagBFPII-TEVΔ/S219V (LEU2) |
| YS6 | BY4741::insul-(lexA-box)4-PminCYC1-Citrine-TCYC1 (URA3), pTDH3-mtagBFPII-TEVΔ/S153N + S219V (LEU2) |
| YS7 | BY4741::insul-(lexA-box)4-PminCYC1-Citrine-TCYC1 (URA3), pTDH3-mtagBFPII-TEVΔ/T30A + S153N + S219V (LEU2) |
| YS8 | BY4741::insul-(lexA-box)4-PminCYC1-Citrine-TCYC1 (URA3), pTDH3-mtagBFPII-TEVΔ/S153N + T180A + S219V (LEU2) |
| YS9 | BY4741::insul-(lexA-box)4-PminCYC1-Citrine-TCYC1 (URA3), pTDH3-mtagBFPII-TEVΔ/S135F + S153N + T180A + S219V (LEU2) |
| YS10 | BY4741::insul-(lexA-box)4-PminCYC1-Citrine-TCYC1 (URA3), pTDH3-mtagBFPII-TEVΔ/I138T + S153N + T180A + S219V (LEU2) |
| YS11 | BY4741::insul-(lexA-box)4-PminCYC1-Citrine-TCYC1 (URA3), pTDH3-mtagBFPII-TEVΔ/S135F + I138T + S153N + T180A + S219V (LEU2) |
| YS12 | BY4741::insul-(lexA-box)4-PminCYC1-Citrine-TCYC1 (URA3), pTDH3-mtagBFPII-TEVΔ/I138T + S153N + S219V (LEU2) |
| YS13 | BY4741::insul-(lexA-box)4-PminCYC1-Citrine-TCYC1 (URA3), pTDH3-mtagBFPII-TEVΔ/I153F + S153N + S219V (LEU2) |
| YS14 | BY4741::insul-(lexA-box)4-PminCYC1-Citrine-TCYC1 (URA3), pTDH3-STE2Δ-BFP-CIBN-MKII-eLOV-TEVcs(ETVRFQ/S)-LexAVP16-tCYC (LEU2) |
| YS15 | BY4741::insul-(lexA-box)4-PminCYC1-Citrine-TCYC1 (URA3), pTDH3-STE2Δ-BFP-CIBN-MKII-eLOV-TEVcs(ETVRFQ/M P1' = M)-LexAVP16-tCYC (LEU2) |
| YS16 | BY4741::insul-(lexA-box)4-PminCYC1-Citrine-TCYC1 (URA3), pTDH3-STE2Δ-BFP-CIBN-MKII-eLOV-TEVcs(ETVRFQ/L P1' = L)-LexAVP16-tCYC (LEU2) |
| YS17 | BY4741::insul-(lexA-box)4-PminCYC1-Citrine-TCYC1 (URA3), pTDH3-STE2Δ-BFP-CIBN-MKII-eLOV-TEVcs(ETVRFQ/Q P1' = Q)-LexAVP16-tCYC (LEU2) |

REFERENCES

1. Forler, D. et al. An efficient protein complex purification method for functional proteomics in higher eukaryotes. Nat. Biotechnol. 21, 89-92 (2003).
2. Liu, Q. et al. A Photoactivatable Botulinum Neurotoxin for Inducible Control of Neurotransmission. Neuron (2019). doi:10.1016/j.neuron.2019.01.002
3. Smart, A. D. et al. Engineering a light-activated caspase-3 for precise ablation of neurons in vivo. Proc. Natl. Acad. Sci. U.S.A 114, E8174-E8183 (2017).
4. Lin, M. Z., Glenn, J. S. & Tsien, R. Y. A drug-controllable tag for visualizing newly synthesized proteins in cells and whole animals. Proc. Natl. Acad. Sci. 105, 7744-7749 (2008).
5. Schuster, B. S. et al. Controllable protein phase separation and modular recruitment to form responsive membrane-less organelles. Nat. Commun. 9, 2985 (2018).
6. Gao, X. J., Chong, L. S., Kim, M. S. & Elowitz, M. B. Programmable protein circuits in living cells. Science 361, 1252-1258 (2018).
7. Fink, T. et al. Design of fast proteolysis-based signaling and logic circuits in mammalian cells. Nat. Chem. Biol. 15, 115-122 (2019).
8. Wang, W. et al. A light- and calcium-gated transcription factor for imaging and manipulating activated neurons. Nat. Biotechnol. 35, 864-871 (2017).
9. Lee, D., Hyun, J. H., Jung, K., Hannan, P. & Kwon, H.-B. A calcium- and light-gated switch to induce gene expression in activated neurons. Nat. Biotechnol. 35, 858-863 (2017).
10. Barnea, G. et al. The genetic design of signaling cascades to record receptor activation. Proc. Natl. Acad. Sci. U.S.A 105, 64-9 (2008).
11. Kim, M. W. et al. Time-gated detection of protein-protein interactions with transcriptional readout. Elife 6, (2017).
12. Copeland, M. F., Politz, M. C., Johnson, C. B., Markley, A. L. & Pfleger, B. F. A transcription activator-like effector (TALE) induction system mediated by proteolysis. Nat. Chem. Biol. 12, 254-260 (2016).
13. Parks, T. D., Howard, E. D., Wolpert, T. J., Arp, D. J. & Dougherty, W. G. Expression and Purification of a Recombinant Tobacco Etch Virus NIa Proteinase: Biochemical Analyses of the Full-Length and a Naturally Occurring Truncated Proteinase Form. Virology 210, 194-201 (1995).
14. Evnin, L. B., Vasquez, J. R. & Craik, C. S. Substrate specificity of trypsin investigated by using a genetic selection. Proc. Natl. Acad. Sci. U.S.A 87, 6659-63 (1990).
15. Estell, D. A., Graycar, T. P. & Wells, J. A. Engineering an enzyme by site-directed mutagenesis to be resistant to chemical oxidation. J. Biol. Chem. 260, 6518-21 (1985).
16. Packer, M. S., Rees, H. A. & Liu, D. R. Phage-assisted continuous evolution of proteases with altered substrate specificity. Nat. Commun. 8, 956 (2017).
17. Yi, L. et al. Engineering of TEV protease variants by yeast ER sequestration screening (YESS) of combinatorial libraries. Proc. Natl. Acad. Sci. U.S.A 110, 7229-34 (2013).
18. Lam, S. S. et al. Directed evolution of APEX2 for electron microscopy and proximity labeling. Nat. Methods 12, 51-54 (2015).
19. Branon, T. C. et al. Efficient proximity labeling in living cells and organisms with TurboID. Nat. Biotechnol. 36, 880-887 (2018).
20. Martell, J. D. et al. A split horseradish peroxidase for the detection of intercellular protein-protein interactions and sensitive visualization of synapses. Nat. Biotechnol. 34, 774-780 (2016).
21. Han, Y. et al. Directed Evolution of Split APEX2 Peroxidase. ACS Chem. Biol. acschembio.8b00919 (2019). doi:10.1021/acschembio.8b00919
22. Kawada, D. et al. The yeast Arf-GAP Glo3p is required for the endocytic recycling of cell surface proteins. Biochim. Biophys. Acta—Mol. Cell Res. 1853, 144-156 (2015).
23. Peng, B., Williams, T. C., Henry, M., Nielsen, L. K. & Vickers, C. E. Controlling heterologous gene expression in yeast cell factories on different carbon substrates and across the diauxic shift: a comparison of yeast promoter activities. Microb. Cell Fact. 14, 91 (2015).
24. Curran, K. A., Karim, A. S., Gupta, A. & Alper, H. S. Use of expression-enhancing terminators in *Saccharomyces cerevisiae* to increase mRNA half-life and improve gene expression control for metabolic engineering applications. Metab. Eng. 19, 88-97 (2013).
25. Phan, J. et al. Structural Basis for the Substrate Specificity of Tobacco Etch Virus Protease. J. Biol. Chem. 277, 50564-50572 (2002).
26. Raran-Kurussi, S., Tözsér, J., Cherry, S., Tropea, J. E. & Waugh, D. S. Differential temperature dependence of tobacco etch virus and rhinovirus 3C proteases. Anal. Biochem. 436, 142-144 (2013).
27. Kapust, R. B. et al. Tobacco etch virus protease: mechanism of autolysis and rational design of stable mutants with wild-type catalytic proficiency. Protein Eng. 14, 993-1000 (2001).
28. Kostallas, G., Löfdahl, P.-A. & Samuelson, P. Substrate profiling of tobacco etch virus protease using a novel fluorescence-assisted whole-cell assay. PLoS One 6, e16136 (2011).
29. Li, Q. et al. Profiling Protease Specificity: Combining Yeast ER Sequestration Screening (YESS) with Next Generation Sequencing. ACS Chem. Biol. 12, 510-518 (2017).
30. Kapust, R. B., Tözsér, J., Copeland, T. D. & Waugh, D. S. The P1' specificity of tobacco etch virus protease. Biochem. Biophys. Res. Commun. 294, 949-955 (2002).
31. Thomsen, M. C. F. & Nielsen, M. Seq2Logo: a method for construction and visualization of amino acid binding motifs and sequence profiles including sequence weighting, pseudo counts and two-sided representation of amino acid enrichment and depletion. Nucleic Acids Res. 40, W281-W287 (2012).
32. Sente, A. et al. Molecular mechanism of modulating arrestin conformation by GPCR phosphorylation. Nat. Struct. Mol. Biol. 25, 538-545 (2018).
33. Kennedy, M. J. et al. Rapid blue-light-mediated induction of protein interactions in living cells. Nat. Methods 7, 973-5 (2010).
34. Turk, B. E., Huang, L. L., Piro, E. T. & Cantley, L. C. Determination of protease cleavage site motifs using mixture-based oriented peptide libraries. Nat. Biotechnol. 19, 661-667 (2001).
35. Wiita, A. P., Seaman, J. E. & Wells, J. A. Global analysis of cellular proteolysis by selective enzymatic labeling of protein N-termini. Methods Enzymol. 544, 327-58 (2014).
36. Seifert, S. & Brakmann, S. LOV Domains in the Design of Photoresponsive Enzymes. ACS Chem. Biol. 13, 1914-1920 (2018).

37. Kim, J. H. et al. High Cleavage Efficiency of a 2A Peptide Derived from Porcine Teschovirus-1 in Human Cell Lines, Zebrafish and Mice. PLoS One 6, e18556 (2011).

38. Ottoz, D. S. M., Rudolf, F. & Stelling, J. Inducible, tightly regulated and growth condition-independent transcription factor in *Saccharomyces cerevisiae*. Nucleic Acids Res. 42, e130-e130 (2014).

39. Partow, S., Siewers, V., Bjorn, S., Nielsen, J. & Maury, J. Characterization of different promoters for designing a new expression vector in *Saccharomyces cerevisiae*. Yeast 27, 955-964 (2010).

40. Swiech, L. et al. In vivo interrogation of gene function in the mammalian brain using CRISPR-Cas9. Nat. Biotechnol. 33, 102-106 (2015).

41. Loh, K. H. et al. Proteomic Analysis of Unbounded Cellular Compartments: Synaptic Clefts. Cell 166, 1295-1307.e21 (2016).

42. Tropea, J. E., Cherry, S. & Waugh, D. S. Expression and Purification of Soluble His6-Tagged TEV Protease, in Methods in molecular biology (Clifton, N.J.) 498, 297-307 (2009).

43. Raran-Kurussi, S., T6zser, J., Cherry, S., Tropea, J. E. & Waugh, D. S. Differential temperature dependence of tobacco etch virus and rhinovirus 3C proteases. Anal. Biochem. 436, 142-4 (2013).

44. Swiech, L. et al. In vivo interrogation of gene function in the mammalian brain using CRISPR-1002 Cas9. Nat. Biotechnol. 33, 102-106 (2015).

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

SEQUENCES IN THE ACCOMPANYING SEQUENCE LISTING

```
SEQ ID NO: 1:
sp|P04517|POLG_TEV Genome polyprotein OS = Tobacco
etch virus OX = 12227 PE = 1 SV = 1.

SEQ ID NO: 2: Amino acid sequence of the truncated
TEV:

SEQ ID NO: 3
Transcription factor bHLH63 from Arabidopsis
thaliana.
>sp|Q8GY61|BH063_ARATH Transcription factor bHLH63
OS = Arabidopsis thaliana OX = 3702 GN = BHLH63
PE = 1 SV = 1

Sequence of the STE2 transmembrane domain (SEQ ID
NO: 9)

Sequence of the truncated-STE2 (STE2Δ) transmem-
brane domain (SEQ ID NO: 10)

uTEV1 (SEQ ID NO: 54):

UTEV2 (SEQ ID NO: 55):

UTEV3 (SEQ ID NO: 56):

truncated uTEV1delta (SEQ ID NO: 57)

truncated uTEV2 delta (SEQ ID NO: 58):

>STE2 YFL026W SGDID: S000001868 (SEQ ID NO: 59)

TEVΔ-S219V (SEQ ID NO: 60)

TEV1ΔA-(S135N/S219V) (SEQ ID NO: 61)

TEV2ΔA-(T30A/S135N/S219V) (SEQ ID NO: 62)

TEV-S219V (SEQ ID NO: 63)

uTEV3-(I138T/S153N/T180A/S219V)(SEQ ID NO: 65)
```

What is claimed is:

1. A library of yeast cells for selecting a modified Tobacco Etch Virus (TEV) protease having altered catalytic properties consequent to directed evolution of a TEV protease template, wherein the library comprises yeast cells that each contain the following:

(a) a first fusion protein comprising:
  (i) a first member of a photoinducible protein binding pair;
  (ii) a TEV protease variant that cleaves a proteolytically cleavable linker;

(b) a second fusion protein comprising:
  (i) a transmembrane domain;
  (ii) a second member of a photoinducible protein binding pair;
  (iii) a light-oxygen-voltage-sensing (LOV) domain sequence;
  (iv) said proteolytically cleavable linker, comprising a TEV cleavage sequence (TEVcs);
  (v) a transcription factor; and (c) a reporter gene that is transcribed by the transcription factor;

wherein different yeast cells in the library contain different TEV protease variants as part of the first fusion protein;

wherein the different TEV protease variants each contain one or more amino acid changes compared with a C-terminally truncated wild-type TEV protease having SEQ ID NO: 2; and wherein when the yeast cells are irradiated in culture with a light that induces binding of component (a) to component (b), then as a consequence, component (c) is expressed in at least some of the yeast cells as an indication of protease activity of the respective TEV protease variant contained therein.

2. The yeast cell library of claim 1, wherein the first member of the photoinducible protein binding pair is a cryptochrome (CRY) and the second member of the pho-toinducible protein binding pair is a cryptochrome-interacting basic-helix-loop-helix protein (CIB).

3. The yeast cell library of claim 1, wherein the LOV domain sequence comprises a C-terminal alpha helix fused to the TEV cleavage sequence.

4. The yeast cell library of claim 1, wherein the transmembrane domain comprises an amino acid sequence from pheromone alpha factor receptor (STE2) or a truncated STE2.

5. The yeast cell library of claim 1, wherein the first fusion protein, the second fusion protein, or both further comprise a fluorescent protein.

6. The yeast cell library of claim 1, wherein the TEV protease variant in each yeast cell in the library is a C-terminally truncated TEV protease.

7. The yeast cell library of claim 1, wherein the transcription factor comprises transactivating tegument protein VP16.

8. The yeast cell library of claim 1, wherein the TEV protease variant in the first fusion protein of each cell in the library has been generated by error-prone polymerase chain reaction (PCR).

9. A method for identifying a modified TEV protease having altered catalytic properties, the method comprising:
  (a) obtaining a library of yeast cells according to claim 1,
  (b) irradiating yeast cells from the library in culture with light that induces binding of the first and the second member of the photoinducible protein binding pair to each other in individual yeast cells in the library;
  (c) selecting yeast cells that express the reporter gene; and
  (d) determining altered catalytic properties in the yeast cells selected in step (c) compared to a control protease, thereby identifying said modified TEV protease.

10. The method of claim 9, wherein the irradiating produces an intermolecular complex between the first and second members of the photoinducible protein binding pair and induces a conformational change in the LOV domain sequence to expose a protease substrate cleavage sequence to the TEV protease variant in each yeast cell.

11. The method of claim 9, wherein the first member of the photoinducible protein binding pair is a cryptochrome (CRY) and the second member of the photoinducible protein binding pair is a cryptochrome-interacting basic-helix-loop-helix protein (CIB).

12. The method of claim 9, wherein the selecting in step (c) comprises selecting yeast cells that express the reporter gene at levels at least one order of magnitude greater than yeast cells that do not express component (a).

13. The method of claim 8, wherein the irradiating step (b) and selecting of step (c) are repeated one or more times.

14. The method of claim 13, wherein the irradiating step (b) is done for a period of time, and the period of time is decreased when step (b) is repeated.

15. The method of claim 14, wherein a percentage of cells expressing the reporter gene increases each time the period of time in step (b) is decreased.

16. The method of claim 9, wherein step (a) comprises:
(i) generating a library of polynucleotide vectors that each encode a TEV protease variant by error-prone polymerase chain reaction (PCR) of a TEV protease template;
(ii) integrating a plurality of vectors from said library of polynucleotide vectors into plasmids encoding said first fusion protein; and (iii) transforming a plurality of said plasmids into separate yeast cells to be expressed as part of an assembly of said first fusion protein, said second fusion protein, and said reporter gene;
thereby forming said yeast cell library.

17. The method of claim 16, wherein said TEV protease template is a low affinity TEV protease characterized as having a Km that is greater than 300 microMolar.

18. The method of claim 9, wherein the TEV protease variants identified in step (d) increased catalytic efficiency compared with C-terminally truncated wild-type TEV protease having SEQ ID NO:2, wherein catalytic efficiency is defined as the rate of proteolytic cleavage ($k_{cat}$).

19. The method of claim 9, wherein the TEV protease variants identified in step (d) have relaxed TEV sequence specificity compared with C-terminally truncated wild-type TEV protease having SEQ ID NO:2.

20. The method of claim 9, wherein one or more of the TEV protease variants identified in step (d) comprise a mutation or combination thereof selected from T30A, T301, S31W, S135F, 1138T, S153N, S153D, T180A, a double T30A/S153N mutation, atriple 1138T/S153N/T180A mutation, and a quadruple S135F/1138T/S153N/T180A mutation.

* * * * *

SEQUENCE LISTING

```
<160> NUMBER OF SEQ ID NOS: 82

<210> SEQ ID NO 1
<211> LENGTH: 3054
<212> TYPE: PRT
<213> ORGANISM: Tobacco etch virus

<400> SEQUENCE: 1

Met Ala Leu Ile Phe Gly Thr Val Asn Ala Asn Ile Leu Lys Glu Val
1               5                   10                  15

Phe Gly Gly Ala Arg Met Ala Cys Val Thr Ser Ala His Met Ala Gly
                20                  25                  30

Ala Asn Gly Ser Ile Leu Lys Lys Ala Glu Glu Thr Ser Arg Ala Ile
            35                  40                  45

Met His Lys Pro Val Ile Phe Gly Glu Asp Tyr Ile Thr Glu Ala Asp
        50                  55                  60

Leu Pro Tyr Thr Pro Leu His Leu Glu Val Asp Ala Glu Met Glu Arg
65                  70                  75                  80

Met Tyr Tyr Leu Gly Arg Arg Ala Leu Thr His Gly Lys Arg Arg Lys
                85                  90                  95

Val Ser Val Asn Asn Lys Arg Asn Arg Arg Arg Lys Val Ala Lys Thr
                100                 105                 110
```

```
Tyr Val Gly Arg Asp Ser Ile Val Glu Lys Ile Val Pro His Thr
            115                 120                 125

Glu Arg Lys Val Asp Thr Thr Ala Ala Val Glu Asp Ile Cys Asn Glu
    130                 135                 140

Ala Thr Thr Gln Leu Val His Asn Ser Met Pro Lys Arg Lys Lys Gln
145                 150                 155                 160

Lys Asn Phe Leu Pro Ala Thr Ser Leu Ser Asn Val Tyr Ala Gln Thr
                165                 170                 175

Trp Ser Ile Val Arg Lys Arg His Met Gln Val Glu Ile Ile Ser Lys
            180                 185                 190

Lys Ser Val Arg Ala Arg Val Lys Arg Phe Glu Gly Ser Val Gln Leu
            195                 200                 205

Phe Ala Ser Val Arg His Met Tyr Gly Glu Arg Lys Arg Val Asp Leu
    210                 215                 220

Arg Ile Asp Asn Trp Gln Gln Glu Thr Leu Leu Asp Leu Ala Lys Arg
225                 230                 235                 240

Phe Lys Asn Glu Arg Val Asp Gln Ser Lys Leu Thr Phe Gly Ser Ser
                245                 250                 255

Gly Leu Val Leu Arg Gln Gly Ser Tyr Gly Pro Ala His Trp Tyr Arg
            260                 265                 270

His Gly Met Phe Ile Val Arg Gly Arg Ser Asp Gly Met Leu Val Asp
            275                 280                 285

Ala Arg Ala Lys Val Thr Phe Ala Val Cys His Ser Met Thr His Tyr
    290                 295                 300

Ser Asp Lys Ser Ile Ser Glu Ala Phe Phe Ile Pro Tyr Ser Lys Lys
305                 310                 315                 320

Phe Leu Glu Leu Arg Pro Asp Gly Ile Ser His Glu Cys Thr Arg Gly
                325                 330                 335

Val Ser Val Glu Arg Cys Gly Glu Val Ala Ala Ile Leu Thr Gln Ala
            340                 345                 350

Leu Ser Pro Cys Gly Lys Ile Thr Cys Lys Arg Cys Met Val Glu Thr
            355                 360                 365

Pro Asp Ile Val Glu Gly Glu Ser Gly Glu Ser Val Thr Asn Gln Gly
    370                 375                 380

Lys Leu Leu Ala Met Leu Lys Glu Gln Tyr Pro Asp Phe Pro Met Ala
385                 390                 395                 400

Glu Lys Leu Leu Thr Arg Phe Leu Gln Gln Lys Ser Leu Val Asn Thr
                405                 410                 415

Asn Leu Thr Ala Cys Val Ser Val Lys Gln Leu Ile Gly Asp Arg Lys
            420                 425                 430

Gln Ala Pro Phe Thr His Val Leu Ala Val Ser Glu Ile Leu Phe Lys
            435                 440                 445

Gly Asn Lys Leu Thr Gly Ala Asp Leu Glu Glu Ala Ser Thr His Met
    450                 455                 460

Leu Glu Ile Ala Arg Phe Leu Asn Asn Arg Thr Glu Asn Met Arg Ile
465                 470                 475                 480

Gly His Leu Gly Ser Phe Arg Asn Lys Ile Ser Ser Lys Ala His Val
                485                 490                 495

Asn Asn Ala Leu Met Cys Asp Asn Gln Leu Asp Gln Asn Gly Asn Phe
            500                 505                 510

Ile Trp Gly Leu Arg Gly Ala His Ala Lys Arg Phe Leu Lys Gly Phe
            515                 520                 525

Phe Thr Glu Ile Asp Pro Asn Glu Gly Tyr Asp Lys Tyr Val Ile Arg
```

-continued

```
        530              535              540
Lys His Ile Arg Gly Ser Arg Lys Leu Ala Ile Gly Asn Leu Ile Met
545              550              555              560

Ser Thr Asp Phe Gln Thr Leu Arg Gln Gln Ile Gln Gly Glu Thr Ile
                 565              570              575

Glu Arg Lys Glu Ile Gly Asn His Cys Ile Ser Met Arg Asn Gly Asn
             580              585              590

Tyr Val Tyr Pro Cys Cys Val Thr Leu Glu Asp Gly Lys Ala Gln
             595              600              605

Tyr Ser Asp Leu Lys His Pro Thr Lys Arg His Leu Val Ile Gly Asn
         610              615              620

Ser Gly Asp Ser Lys Tyr Leu Asp Leu Pro Val Leu Asn Glu Glu Lys
625              630              635              640

Met Tyr Ile Ala Asn Glu Gly Tyr Cys Tyr Met Asn Ile Phe Phe Ala
             645              650              655

Leu Leu Val Asn Val Lys Glu Glu Asp Ala Lys Asp Phe Thr Lys Phe
             660              665              670

Ile Arg Asp Thr Ile Val Pro Lys Leu Gly Ala Trp Pro Thr Met Gln
             675              680              685

Asp Val Ala Thr Ala Cys Tyr Leu Leu Ser Ile Leu Tyr Pro Asp Val
         690              695              700

Leu Arg Ala Glu Leu Pro Arg Ile Leu Val Asp His Asp Asn Lys Thr
705              710              715              720

Met His Val Leu Asp Ser Tyr Gly Ser Arg Thr Thr Gly Tyr His Met
             725              730              735

Leu Lys Met Asn Thr Thr Ser Gln Leu Ile Glu Phe Val His Ser Gly
             740              745              750

Leu Glu Ser Glu Met Lys Thr Tyr Asn Val Gly Gly Met Asn Arg Asp
             755              760              765

Val Val Thr Gln Gly Ala Ile Glu Met Leu Ile Lys Ser Ile Tyr Lys
             770              775              780

Pro His Leu Met Lys Gln Leu Leu Glu Glu Glu Pro Tyr Ile Ile Val
785              790              795              800

Leu Ala Ile Val Ser Pro Ser Ile Leu Ile Ala Met Tyr Asn Ser Gly
             805              810              815

Thr Phe Glu Gln Ala Leu Gln Met Trp Leu Pro Asn Thr Met Arg Leu
             820              825              830

Ala Asn Leu Ala Ala Ile Leu Ser Ala Leu Ala Gln Lys Leu Thr Leu
             835              840              845

Ala Asp Leu Phe Val Gln Gln Arg Asn Leu Ile Asn Glu Tyr Ala Gln
         850              855              860

Val Ile Leu Asp Asn Leu Ile Asp Gly Val Arg Val Asn His Ser Leu
865              870              875              880

Ser Leu Ala Met Glu Ile Val Thr Ile Lys Leu Ala Thr Gln Glu Met
             885              890              895

Asp Met Ala Leu Arg Glu Gly Gly Tyr Ala Val Thr Ser Glu Lys Val
             900              905              910

His Glu Met Leu Glu Lys Asn Tyr Val Lys Ala Leu Lys Asp Ala Trp
             915              920              925

Asp Glu Leu Thr Trp Leu Glu Lys Phe Ser Ala Ile Arg His Ser Arg
         930              935              940

Lys Leu Leu Lys Phe Gly Arg Lys Pro Leu Ile Met Lys Asn Thr Val
945              950              955              960
```

```
Asp Cys Gly Gly His Ile Asp Leu Ser Val Lys Ser Leu Phe Lys Phe
            965               970                 975

His Leu Glu Leu Leu Lys Gly Thr Ile Ser Arg Ala Val Asn Gly Gly
            980               985                 990

Ala Arg Lys Val Arg Val Ala Lys  Asn Ala Met Thr Lys  Gly Val Phe
            995             1000                 1005

Leu Lys  Ile Tyr Ser Met Leu  Pro Asp Val Tyr Lys  Phe Ile Thr
            1010            1015              1020

Val Ser  Ser Val Leu Ser Leu  Leu Leu Thr Phe Leu  Phe Gln Ile
            1025            1030              1035

Asp Cys  Met Ile Arg Ala His  Arg Glu Ala Lys Val  Ala Ala Gln
            1040            1045              1050

Leu Gln  Lys Glu Ser Glu Trp  Asp Asn Ile Ile Asn  Arg Thr Phe
            1055            1060              1065

Gln Tyr  Ser Lys Leu Glu Asn  Pro Ile Gly Tyr Arg  Ser Thr Ala
            1070            1075              1080

Glu Glu  Arg Leu Gln Ser Glu  His Pro Glu Ala Phe  Glu Tyr Tyr
            1085            1090              1095

Lys Phe  Cys Ile Gly Lys Glu  Asp Leu Val Glu Gln  Ala Lys Gln
            1100            1105              1110

Pro Glu  Ile Ala Tyr Phe Glu  Lys Ile Ile Ala Phe  Ile Thr Leu
            1115            1120              1125

Val Leu  Met Ala Phe Asp Ala  Glu Arg Ser Asp Gly  Val Phe Lys
            1130            1135              1140

Ile Leu  Asn Lys Phe Lys Gly  Ile Leu Ser Ser Thr  Glu Arg Glu
            1145            1150              1155

Ile Ile  Tyr Thr Gln Ser Leu  Asp Asp Tyr Val Thr  Thr Phe Asp
            1160            1165              1170

Asp Asn  Met Thr Ile Asn Leu  Glu Leu Asn Met Asp  Glu Leu His
            1175            1180              1185

Lys Thr  Ser Leu Pro Gly Val  Thr Phe Lys Gln Trp  Trp Asn Asn
            1190            1195              1200

Gln Ile  Ser Arg Gly Asn Val  Lys Pro His Tyr Arg  Thr Glu Gly
            1205            1210              1215

His Phe  Met Glu Phe Thr Arg  Asp Thr Ala Ala Ser  Val Ala Ser
            1220            1225              1230

Glu Ile  Ser His Ser Pro Ala  Arg Asp Phe Leu Val  Arg Gly Ala
            1235            1240              1245

Val Gly  Ser Gly Lys Ser Thr  Gly Leu Pro Tyr His  Leu Ser Lys
            1250            1255              1260

Arg Gly  Arg Val Leu Met Leu  Glu Pro Thr Arg Pro  Leu Thr Asp
            1265            1270              1275

Asn Met  His Lys Gln Leu Arg  Ser Glu Pro Phe Asn  Cys Phe Pro
            1280            1285              1290

Thr Leu  Arg Met Arg Gly Lys  Ser Thr Phe Gly Ser  Ser Pro Ile
            1295            1300              1305

Thr Val  Met Thr Ser Gly Phe  Ala Leu His His Phe  Ala Arg Asn
            1310            1315              1320

Ile Ala  Glu Val Lys Thr Tyr  Asp Phe Val Ile Ile  Asp Glu Cys
            1325            1330              1335

His Val  Asn Asp Ala Ser Ala  Ile Ala Phe Arg Asn  Leu Leu Phe
            1340            1345              1350
```

-continued

```
Glu His Glu Phe Glu Gly Lys Val Leu Lys Val Ser Ala Thr Pro
    1355                1360                1365

Pro Gly Arg Glu Val Glu Phe Thr Thr Gln Phe Pro Val Lys Leu
    1370                1375                1380

Lys Ile Glu Glu Ala Leu Ser Phe Gln Glu Phe Val Ser Leu Gln
    1385                1390                1395

Gly Thr Gly Ala Asn Ala Asp Val Ile Ser Cys Gly Asp Asn Ile
    1400                1405                1410

Leu Val Tyr Val Ala Ser Tyr Asn Asp Val Asp Ser Leu Gly Lys
    1415                1420                1425

Leu Leu Val Gln Lys Gly Tyr Lys Val Ser Lys Ile Asp Gly Arg
    1430                1435                1440

Thr Met Lys Ser Gly Gly Thr Glu Ile Ile Thr Glu Gly Thr Ser
    1445                1450                1455

Val Lys Lys His Phe Ile Val Ala Thr Asn Ile Ile Glu Asn Gly
    1460                1465                1470

Val Thr Ile Asp Ile Asp Val Val Val Asp Phe Gly Thr Lys Val
    1475                1480                1485

Val Pro Val Leu Asp Val Asp Asn Arg Ala Val Gln Tyr Asn Lys
    1490                1495                1500

Thr Val Val Ser Tyr Gly Glu Arg Ile Gln Lys Leu Gly Arg Val
    1505                1510                1515

Gly Arg His Lys Glu Gly Val Ala Leu Arg Ile Gly Gln Thr Asn
    1520                1525                1530

Lys Thr Leu Val Glu Ile Pro Glu Met Val Ala Thr Glu Ala Ala
    1535                1540                1545

Phe Leu Cys Phe Met Tyr Asn Leu Pro Val Thr Thr Gln Ser Val
    1550                1555                1560

Ser Thr Thr Leu Leu Glu Asn Ala Thr Leu Leu Gln Ala Arg Thr
    1565                1570                1575

Met Ala Gln Phe Glu Leu Ser Tyr Phe Tyr Thr Ile Asn Phe Val
    1580                1585                1590

Arg Phe Asp Gly Ser Met His Pro Val Ile His Asp Lys Leu Lys
    1595                1600                1605

Arg Phe Lys Leu His Thr Cys Glu Thr Phe Leu Asn Lys Leu Ala
    1610                1615                1620

Ile Pro Asn Lys Gly Leu Ser Ser Trp Leu Thr Ser Gly Glu Tyr
    1625                1630                1635

Lys Arg Leu Gly Tyr Ile Ala Glu Asp Ala Gly Ile Arg Ile Pro
    1640                1645                1650

Phe Val Cys Lys Glu Ile Pro Asp Ser Leu His Glu Glu Ile Trp
    1655                1660                1665

His Ile Val Val Ala His Lys Gly Asp Ser Gly Ile Gly Arg Leu
    1670                1675                1680

Thr Ser Val Gln Ala Ala Lys Val Val Tyr Thr Leu Gln Thr Asp
    1685                1690                1695

Val His Ser Ile Ala Arg Thr Leu Ala Cys Ile Asn Arg Arg Ile
    1700                1705                1710

Ala Asp Glu Gln Met Lys Gln Ser His Phe Glu Ala Ala Thr Gly
    1715                1720                1725

Arg Ala Phe Ser Phe Thr Asn Tyr Ser Ile Gln Ser Ile Phe Asp
    1730                1735                1740

Thr Leu Lys Ala Asn Tyr Ala Thr Lys His Thr Lys Glu Asn Ile
```

-continued

```
        1745                1750                1755

Ala Val Leu Gln Gln Ala Lys  Asp Gln Leu Leu Glu  Phe Ser Asn
    1760                1765                1770

Leu Ala Lys Asp Gln Asp Val  Thr Gly Ile Ile Gln  Asp Phe Asn
    1775                1780                1785

His Leu Glu Thr Ile Tyr Leu  Gln Ser Asp Ser Glu  Val Ala Lys
    1790                1795                1800

His Leu Lys Leu Lys Ser His  Trp Asn Lys Ser Gln  Ile Thr Arg
    1805                1810                1815

Asp Ile Ile Ile Ala Leu Ser  Val Leu Ile Gly Gly  Gly Trp Met
    1820                1825                1830

Leu Ala Thr Tyr Phe Lys Asp  Lys Phe Asn Glu Pro  Val Tyr Phe
    1835                1840                1845

Gln Gly Lys Lys Asn Gln Lys  His Lys Leu Lys Met  Arg Glu Ala
    1850                1855                1860

Arg Gly Ala Arg Gly Gln Tyr  Glu Val Ala Ala Glu  Pro Glu Ala
    1865                1870                1875

Leu Glu His Tyr Phe Gly Ser  Ala Tyr Asn Asn Lys  Gly Lys Arg
    1880                1885                1890

Lys Gly Thr Thr Arg Gly Met  Gly Ala Lys Ser Arg  Lys Phe Ile
    1895                1900                1905

Asn Met Tyr Gly Phe Asp Pro  Thr Asp Phe Ser Tyr  Ile Arg Phe
    1910                1915                1920

Val Asp Pro Leu Thr Gly His  Thr Ile Asp Glu Ser  Thr Asn Ala
    1925                1930                1935

Pro Ile Asp Leu Val Gln His  Glu Phe Gly Lys Val  Arg Thr Arg
    1940                1945                1950

Met Leu Ile Asp Asp Glu Ile  Glu Pro Gln Ser Leu  Ser Thr His
    1955                1960                1965

Thr Thr Ile His Ala Tyr Leu  Val Asn Ser Gly Thr  Lys Lys Val
    1970                1975                1980

Leu Lys Val Asp Leu Thr Pro  His Ser Ser Leu Arg  Ala Ser Glu
    1985                1990                1995

Lys Ser Thr Ala Ile Met Gly  Phe Pro Glu Arg Glu  Asn Glu Leu
    2000                2005                2010

Arg Gln Thr Gly Met Ala Val  Pro Val Ala Tyr Asp  Gln Leu Pro
    2015                2020                2025

Pro Lys Asn Glu Asp Leu Thr  Phe Glu Gly Glu Ser  Leu Phe Lys
    2030                2035                2040

Gly Pro Arg Asp Tyr Asn Pro  Ile Ser Ser Thr Ile  Cys His Leu
    2045                2050                2055

Thr Asn Glu Ser Asp Gly His  Thr Thr Ser Leu Tyr  Gly Ile Gly
    2060                2065                2070

Phe Gly Pro Phe Ile Ile Thr  Asn Lys His Leu Phe  Arg Arg Asn
    2075                2080                2085

Asn Gly Thr Leu Leu Val Gln  Ser Leu His Gly Val  Phe Lys Val
    2090                2095                2100

Lys Asn Thr Thr Thr Leu Gln  Gln His Leu Ile Asp  Gly Arg Asp
    2105                2110                2115

Met Ile Ile Ile Arg Met Pro  Lys Asp Phe Pro Pro  Phe Pro Gln
    2120                2125                2130

Lys Leu Lys Phe Arg Glu Pro  Gln Arg Glu Glu Arg  Ile Cys Leu
    2135                2140                2145
```

-continued

```
Val Thr  Thr Asn Phe Gln Thr  Lys Ser Met Ser Ser  Met Val Ser
    2150             2155         2160

Asp Thr  Ser Cys Thr Phe Pro  Ser Ser Asp Gly Ile  Phe Trp Lys
    2165             2170         2175

His Trp  Ile Gln Thr Lys Asp  Gly Gln Cys Gly Ser  Pro Leu Val
    2180             2185         2190

Ser Thr  Arg Asp Gly Phe Ile  Val Gly Ile His Ser  Ala Ser Asn
    2195             2200         2205

Phe Thr  Asn Thr Asn Asn Tyr  Phe Thr Ser Val Pro  Lys Asn Phe
    2210             2215         2220

Met Glu  Leu Leu Thr Asn Gln  Glu Ala Gln Gln Trp  Val Ser Gly
    2225             2230         2235

Trp Arg  Leu Asn Ala Asp Ser  Val Leu Trp Gly Gly  His Lys Val
    2240             2245         2250

Phe Met  Ser Lys Pro Glu Glu  Pro Phe Gln Pro Val  Lys Glu Ala
    2255             2260         2265

Thr Gln  Leu Met Asn Glu Leu  Val Tyr Ser Gln Gly  Glu Lys Arg
    2270             2275         2280

Lys Trp  Val Val Glu Ala Leu  Ser Gly Asn Leu Arg  Pro Val Ala
    2285             2290         2295

Glu Cys  Pro Ser Gln Leu Val  Thr Lys His Val Val  Lys Gly Lys
    2300             2305         2310

Cys Pro  Leu Phe Glu Leu Tyr  Leu Gln Leu Asn Pro  Glu Lys Glu
    2315             2320         2325

Ala Tyr  Phe Lys Pro Met Met  Gly Ala Tyr Lys Pro  Ser Arg Leu
    2330             2335         2340

Asn Arg  Glu Ala Phe Leu Lys  Asp Ile Leu Lys Tyr  Ala Ser Glu
    2345             2350         2355

Ile Glu  Ile Gly Asn Val Asp  Cys Asp Leu Leu Glu  Leu Ala Ile
    2360             2365         2370

Ser Met  Leu Val Thr Lys Leu  Lys Ala Leu Gly Phe  Pro Thr Val
    2375             2380         2385

Asn Tyr  Ile Thr Asp Pro Glu  Glu Ile Phe Ser Ala  Leu Asn Met
    2390             2395         2400

Lys Ala  Ala Met Gly Ala Leu  Tyr Lys Gly Lys Lys  Lys Glu Ala
    2405             2410         2415

Leu Ser  Glu Leu Thr Leu Asp  Glu Gln Glu Ala Met  Leu Lys Ala
    2420             2425         2430

Ser Cys  Leu Arg Leu Tyr Thr  Gly Lys Leu Gly Ile  Trp Asn Gly
    2435             2440         2445

Ser Leu  Lys Ala Glu Leu Arg  Pro Ile Glu Lys Val  Glu Asn Asn
    2450             2455         2460

Lys Thr  Arg Thr Phe Thr Ala  Ala Pro Ile Asp Thr  Leu Leu Ala
    2465             2470         2475

Gly Lys  Val Cys Val Asp Asp  Phe Asn Asn Gln Phe  Tyr Asp Leu
    2480             2485         2490

Asn Ile  Lys Ala Pro Trp Thr  Val Gly Met Thr Lys  Phe Tyr Gln
    2495             2500         2505

Gly Trp  Asn Glu Leu Met Glu  Ala Leu Pro Ser Gly  Trp Val Tyr
    2510             2515         2520

Cys Asp  Ala Asp Gly Ser Gln  Phe Asp Ser Ser Leu  Thr Pro Phe
    2525             2530         2535
```

-continued

```
Leu Ile  Asn Ala Val Leu Lys  Val Arg Leu Ala Phe  Met Glu Glu
    2540             2545            2550

Trp Asp  Ile Gly Glu Gln Met  Leu Arg Asn Leu Tyr  Thr Glu Ile
    2555             2560            2565

Val Tyr  Thr Pro Ile Leu Thr  Pro Asp Gly Thr Ile  Ile Lys Lys
    2570             2575            2580

His Lys  Gly Asn Asn Ser Gly  Gln Pro Ser Thr Val  Val Asp Asn
    2585             2590            2595

Thr Leu  Met Val Ile Ile Ala  Met Leu Tyr Thr Cys  Glu Lys Cys
    2600             2605            2610

Gly Ile  Asn Lys Glu Glu Ile  Val Tyr Tyr Val Asn  Gly Asp Asp
    2615             2620            2625

Leu Leu  Ile Ala Ile His Pro  Asp Lys Ala Glu Arg  Leu Ser Arg
    2630             2635            2640

Phe Lys  Glu Ser Phe Gly Glu  Leu Gly Leu Lys Tyr  Glu Phe Asp
    2645             2650            2655

Cys Thr  Thr Arg Asp Lys Thr  Gln Leu Trp Phe Met  Ser His Arg
    2660             2665            2670

Ala Leu  Glu Arg Asp Gly Met  Tyr Ile Pro Lys Leu  Glu Glu Glu
    2675             2680            2685

Arg Ile  Val Ser Ile Leu Glu  Trp Asp Arg Ser Lys  Glu Pro Ser
    2690             2695            2700

His Arg  Leu Glu Ala Ile Cys  Ala Ser Met Ile Glu  Ala Trp Gly
    2705             2710            2715

Tyr Asp  Lys Leu Val Glu Glu  Ile Arg Asn Phe Tyr  Ala Trp Val
    2720             2725            2730

Leu Glu  Gln Ala Pro Tyr Ser  Gln Leu Ala Glu Glu  Gly Lys Ala
    2735             2740            2745

Pro Tyr  Leu Ala Glu Thr Ala  Leu Lys Phe Leu Tyr  Thr Ser Gln
    2750             2755            2760

His Gly  Thr Asn Ser Glu Ile  Glu Glu Tyr Leu Lys  Val Leu Tyr
    2765             2770            2775

Asp Tyr  Asp Ile Pro Thr Thr  Glu Asn Leu Tyr Phe  Gln Ser Gly
    2780             2785            2790

Thr Val  Asp Ala Gly Ala Asp  Ala Gly Lys Lys Lys  Asp Gln Lys
    2795             2800            2805

Asp Asp  Lys Val Ala Glu Gln  Ala Ser Lys Asp Arg  Asp Val Asn
    2810             2815            2820

Ala Gly  Thr Ser Gly Thr Phe  Ser Val Pro Arg Ile  Asn Ala Met
    2825             2830            2835

Ala Thr  Lys Leu Gln Tyr Pro  Arg Met Arg Gly Glu  Val Val Val
    2840             2845            2850

Asn Leu  Asn His Leu Leu Gly  Tyr Lys Pro Gln Gln  Ile Asp Leu
    2855             2860            2865

Ser Asn  Ala Arg Ala Thr His  Glu Gln Phe Ala Ala  Trp His Gln
    2870             2875            2880

Ala Val  Met Thr Ala Tyr Gly  Val Asn Glu Glu Gln  Met Lys Ile
    2885             2890            2895

Leu Leu  Asn Gly Phe Met Val  Trp Cys Ile Glu Asn  Gly Thr Ser
    2900             2905            2910

Pro Asn  Leu Asn Gly Thr Trp  Val Met Met Asp Gly  Glu Asp Gln
    2915             2920            2925

Val Ser  Tyr Pro Leu Lys Pro  Met Val Glu Asn Ala  Gln Pro Thr
```

```
          2930                2935                2940

Leu Arg  Gln Ile Met Thr His  Phe Ser Asp Leu Ala  Glu Ala Tyr
    2945                2950                2955

Ile Glu  Met Arg Asn Arg Glu  Arg Pro Tyr Met Pro  Arg Tyr Gly
    2960                2965                2970

Leu Gln  Arg Asn Ile Thr Asp  Met Ser Leu Ser Arg  Tyr Ala Phe
    2975                2980                2985

Asp Phe  Tyr Glu Leu Thr Ser  Lys Thr Pro Val Arg  Ala Arg Glu
    2990                2995                3000

Ala His  Met Gln Met Lys Ala  Ala Ala Val Arg Asn  Ser Gly Thr
    3005                3010                3015

Arg Leu  Phe Gly Leu Asp Gly  Asn Val Gly Thr Ala  Glu Glu Asp
    3020                3025                3030

Thr Glu  Arg His Thr Ala His  Asp Val Asn Arg Asn  Met His Thr
    3035                3040                3045

Leu Leu  Gly Val Arg Gln
    3050

<210> SEQ ID NO 2
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Glu Ser Leu Phe Lys Gly Pro Arg Asp Tyr Asn Pro Ile Ser Ser
1                   5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Val
    210                 215
```

-continued

<210> SEQ ID NO 3
<211> LENGTH: 335
<212> TYPE: PRT
<213> ORGANISM: Arabidopsis thaliana

<400> SEQUENCE: 3

```
Met Asn Gly Ala Ile Gly Gly Asp Leu Leu Leu Asn Phe Pro Asp Met
1               5                   10                  15

Ser Val Leu Glu Arg Gln Arg Ala His Leu Lys Tyr Leu Asn Pro Thr
                20                  25                  30

Phe Asp Ser Pro Leu Ala Gly Phe Phe Ala Asp Ser Ser Met Ile Thr
                35                  40                  45

Gly Gly Glu Met Asp Ser Tyr Leu Ser Thr Ala Gly Leu Asn Leu Pro
        50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Lys Arg Lys Phe
                85                  90                  95

Asp Thr Glu Thr Lys Asp Cys Asn Glu Lys Lys Lys Met Thr Met
                100                 105                 110

Asn Arg Asp Asp Leu Val Glu Glu Gly Glu Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Val Arg Ala Arg Arg
                165                 170                 175

Gly Gln Ala Thr Asp Ser His Ser Ile Ala Glu Arg Val Arg Arg Glu
                180                 185                 190

Lys Ile Ser Glu Arg Met Lys Phe Leu Gln Asp Leu Val Pro Gly Cys
        195                 200                 205

Asp Lys Ile Thr Gly Lys Ala Gly Met Leu Asp Glu Ile Ile Asn Tyr
    210                 215                 220

Val Gln Ser Leu Gln Arg Gln Ile Glu Phe Leu Ser Met Lys Leu Ala
225                 230                 235                 240

Ile Val Asn Pro Arg Pro Asp Phe Asp Met Asp Asp Ile Phe Ala Lys
                245                 250                 255

Glu Val Ala Ser Thr Pro Met Thr Val Val Pro Ser Pro Glu Met Val
                260                 265                 270

Leu Ser Gly Tyr Ser His Glu Met Val His Ser Gly Tyr Ser Ser Glu
        275                 280                 285

Met Val Asn Ser Gly Tyr Leu His Val Asn Pro Met Gln Gln Val Asn
    290                 295                 300

Thr Ser Ser Asp Pro Leu Ser Cys Phe Asn Asn Gly Glu Ala Pro Ser
305                 310                 315                 320

Met Trp Asp Ser His Val Gln Asn Leu Tyr Gly Asn Leu Gly Val
                325                 330                 335
```

<210> SEQ ID NO 4
<211> LENGTH: 612
<212> TYPE: PRT
<213> ORGANISM: Arabidopsis thaliana

<400> SEQUENCE: 4

-continued

```
Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
                20              25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
            195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
    275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
```

```
              420              425              430

Trp Leu Pro Glu Leu Ala Arg Leu Pro Thr Glu Trp Ile His His Pro
        435              440              445

Trp Asp Ala Pro Leu Thr Val Leu Lys Ala Ser Gly Val Glu Leu Gly
    450              455              460

Thr Asn Tyr Ala Lys Pro Ile Val Asp Ile Asp Thr Ala Arg Glu Leu
465              470              475              480

Leu Ala Lys Ala Ile Ser Arg Thr Arg Glu Ala Gln Ile Met Ile Gly
                485              490              495

Ala Ala Pro Asp Glu Ile Val Ala Asp Ser Phe Glu Ala Leu Gly Ala
            500              505              510

Asn Thr Ile Lys Glu Pro Gly Leu Cys Pro Ser Val Ser Ser Asn Asp
        515              520              525

Gln Gln Val Pro Ser Ala Val Arg Tyr Asn Gly Ser Lys Arg Val Lys
    530              535              540

Pro Glu Glu Glu Glu Arg Asp Met Lys Lys Ser Arg Gly Phe Asp
545              550              555              560

Glu Arg Glu Leu Phe Ser Thr Ala Glu Ser Ser Ser Ser Ser Val
            565              570              575

Phe Phe Val Ser Gln Ser Cys Ser Leu Ala Ser Glu Gly Lys Asn Leu
            580              585              590

Glu Gly Ile Gln Asp Ser Ser Asp Gln Ile Thr Thr Ser Leu Gly Lys
        595              600              605

Asn Gly Cys Lys
    610

<210> SEQ ID NO 5
<211> LENGTH: 7
<212> TYPE: PRT
<213> ORGANISM: Tobacco etch virus

<400> SEQUENCE: 5

Glu Asn Leu Tyr Phe Gln Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 6

Glu Asn Leu Tyr Phe Gln Met
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 7

Glu Asn Leu His Phe Gln Ser
1               5

<210> SEQ ID NO 8
```

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Asn Leu Trp Phe Gln Ser
1               5

<210> SEQ ID NO 9
<211> LENGTH: 431
<212> TYPE: PRT
<213> ORGANISM: Saccharomyces cerevisiae

<400> SEQUENCE: 9

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
                20                  25                  30

Gly Ser Thr Ile Thr Phe Asp Glu Leu Gln Gly Leu Val Asn Ser Thr
            35                  40                  45

Val Thr Gln Ala Ile Met Phe Gly Val Arg Cys Gly Ala Ala Ala Leu
        50                  55                  60

Thr Leu Ile Val Met Trp Met Thr Ser Arg Ser Arg Lys Thr Pro Ile
65                  70                  75                  80

Phe Ile Ile Asn Gln Val Ser Leu Phe Leu Ile Ile Leu His Ser Ala
                85                  90                  95

Leu Tyr Phe Lys Tyr Leu Leu Ser Asn Tyr Ser Ser Val Thr Tyr Ala
                100                 105                 110

Leu Thr Gly Phe Pro Gln Phe Ile Ser Arg Gly Asp Val His Val Tyr
                115                 120                 125

Gly Ala Thr Asn Ile Ile Gln Val Leu Leu Val Ala Ser Ile Glu Thr
        130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                165                 170                 175

Thr Val Thr Met Tyr Phe Val Ser Ala Val Lys Gly Met Ile Val Thr
                180                 185                 190

Tyr Asn Asp Val Ser Ala Thr Gln Asp Lys Tyr Phe Asn Ala Ser Thr
                195                 200                 205

Ile Leu Leu Ala Ser Ser Ile Asn Phe Met Ser Phe Val Leu Val Val
        210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                245                 250                 255

Val Pro Ser Ile Ile Phe Ile Leu Ala Tyr Ser Leu Lys Pro Asn Gln
                260                 265                 270

Gly Thr Asp Val Leu Thr Thr Val Ala Thr Leu Leu Ala Val Leu Ser
        275                 280                 285

Leu Pro Leu Ser Ser Met Trp Ala Thr Ala Ala Asn Asn Ala Ser Lys
        290                 295                 300

Thr Asn Thr Ile Thr Ser Asp Phe Thr Thr Ser Thr Asp Arg Phe Tyr
305                 310                 315                 320
```

-continued

```
Pro Gly Thr Leu Ser Ser Phe Gln Thr Asp Ser Ile Asn Asn Asp Ala
            325                 330             335

Lys Ser Ser Leu Arg Ser Arg Leu Tyr Asp Leu Tyr Pro Arg Arg Lys
            340                 345             350

Glu Thr Thr Ser Asp Lys His Ser Glu Arg Thr Phe Val Ser Glu Thr
            355                 360             365

Ala Asp Asp Ile Glu Lys Asn Gln Phe Tyr Gln Leu Pro Thr Pro Thr
    370                 375             380

Ser Ser Lys Asn Thr Arg Ile Gly Pro Phe Ala Asp Ala Ser Tyr Lys
385                 390             395                 400

Glu Gly Glu Val Glu Pro Val Asp Met Tyr Thr Pro Asp Thr Ala Ala
            405                 410             415

Asp Glu Glu Ala Arg Lys Phe Trp Thr Glu Asp Asn Asn Asn Leu
            420                 425             430

<210> SEQ ID NO 10
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ser Asp Ala Ala Pro Ser Leu Ser Asn Leu Phe Tyr Asp Pro Thr
1               5               10              15

Tyr Asn Pro Gly Gln Ser Thr Ile Asn Tyr Thr Ser Ile Tyr Gly Asn
            20              25              30

Gly Ser Thr Ile Thr Phe Asp Glu Leu Gln Gly Leu Val Asn Ser Thr
            35              40              45

Val Thr Gln Ala Ile Met Phe Gly Val Arg Cys Gly Ala Ala Ala Leu
    50              55              60

Thr Leu Ile Val Met Trp Met Thr Ser Arg Ser Arg Lys Thr Pro Ile
65              70              75              80

Phe Ile Ile Asn Gln Val Ser Leu Phe Leu Ile Ile Leu His Ser Ala
            85              90              95

Leu Tyr Phe Lys Tyr Leu Leu Ser Asn Tyr Ser Ser Val Thr Tyr Ala
            100             105             110

Leu Thr Gly Phe Pro Gln Phe Ile Ser Arg Gly Asp Val His Val Tyr
            115             120             125

Gly Ala Thr Asn Ile Ile Gln Val Leu Leu Val Ala Ser Ile Glu Thr
    130             135             140

Ser Leu Val Phe Gln Ile Lys Val Ile Phe Thr Gly Asp Asn Phe Lys
145             150             155             160

Arg Ile Gly Leu Met Leu Thr Ser Ile Ser Phe Thr Leu Gly Ile Ala
            165             170             175

Thr Val Thr Met Tyr Phe Val Ser Ala Val Lys Gly Met Ile Val Thr
            180             185             190

Tyr Asn Asp Val Ser Ala Thr Gln Asp Lys Tyr Phe Asn Ala Ser Thr
            195             200             205

Ile Leu Leu Ala Ser Ser Ile Asn Phe Met Ser Phe Val Leu Val Val
    210             215             220

Lys Leu Ile Leu Ala Ile Arg Ser Arg Arg Phe Leu Gly Leu Lys Gln
225             230             235             240

Phe Asp Ser Phe His Ile Leu Leu Ile Met Ser Cys Gln Ser Leu Leu
```

```
                245             250             255
Val Pro Ser Ile Ile Phe Ile Leu Ala Tyr Ser Leu Lys Pro Asn Gln
            260             265             270

Gly Thr Asp Val Leu Thr Thr Val Ala Thr Leu Leu Ala Val Leu Ser
        275             280             285

Leu Pro Leu Ser Ser Met Trp Ala Thr Ala Ala Asn
    290             295             300

<210> SEQ ID NO 11
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Leu Ala Thr Thr Leu Glu Arg Ile Glu Lys Asn Phe Val Ile Thr
1               5               10              15

Asp Pro Arg Leu Pro Asp Asn Pro Ile Ile Phe Ala Ser Asp Ser Phe
            20              25              30

Leu Gln Leu Thr Glu Tyr Ser Arg Glu Glu Ile Leu Gly Arg Asn Cys
        35              40              45

Arg Phe Leu Gln Gly Pro Glu Thr Asp Arg Ala Thr Val Arg Lys Ile
    50              55              60

Arg Asp Ala Ile Asp Asn Gln Thr Glu Val Thr Val Gln Leu Ile Asn
65              70              75              80

Tyr Thr Lys Ser Gly Lys Lys Phe Trp Asn Leu Phe His Leu Gln Pro
                85              90              95

Met Arg Asp Gln Lys Gly Asp Val Gln Tyr Phe Ile Gly Val Gln Leu
            100             105             110

Asp Gly Thr Glu His Val Arg Asp Ala Ala Glu Arg Glu Ala Val Met
        115             120             125

Leu Ile Lys Lys Thr Ala Glu Glu Ile Asp Glu Ala Ala Lys
    130             135             140

<210> SEQ ID NO 12
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Leu Ala Thr Thr Leu Glu Arg Ile Glu Lys Asn Phe Val Ile Thr
1               5               10              15

Asp Pro Arg Leu Pro Asp Asn Pro Ile Ile Phe Ala Ser Asp Ser Phe
            20              25              30

Leu Gln Leu Thr Glu Tyr Ser Arg Glu Glu Ile Leu Gly Arg Asn Cys
        35              40              45

Arg Phe Leu Gln Gly Pro Glu Thr Asp Arg Ala Thr Val Arg Lys Ile
    50              55              60

Arg Asp Ala Ile Asp Asn Gln Thr Glu Val Thr Val Gln Leu Ile Asn
65              70              75              80

Tyr Thr Lys Ser Gly Lys Lys Phe Trp Asn Leu Phe His Leu Gln Pro
                85              90              95

Met Arg Asp Gln Lys Gly Asp Val Gln Tyr Phe Ile Gly Val Gln Leu
```

```
              100                 105                 110

Asp Gly Thr Glu His Val Arg Asp Ala Ala Glu Arg Glu Ala Val Met
        115                 120                 125

Leu Ile Lys Lys Thr Ala Glu Glu Ile Asp Glu Ala Ala Lys
    130                 135                 140

<210> SEQ ID NO 13
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Arg Ala Thr Thr Leu Glu Arg Ile Glu Lys Ser Phe Val Ile Thr
1                   5                   10                  15

Asp Pro Arg Leu Pro Asp Asn Pro Ile Ile Phe Val Ser Asp Ser Phe
                20                  25                  30

Leu Gln Leu Thr Glu Tyr Ser Arg Glu Glu Ile Leu Gly Arg Asn Cys
            35                  40                  45

Arg Phe Leu Gln Gly Pro Glu Thr Asp Arg Ala Thr Val Arg Lys Ile
        50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu Arg Val Arg Asp Ala Ala Glu Arg Glu Ala Val Met
        115                 120                 125

Leu Val Lys Lys Thr Ala Glu Glu Ile Asp Glu Ala Ala Lys
    130                 135                 140

<210> SEQ ID NO 14
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ala Thr Thr Leu Glu Arg Ile Glu Lys Ser Phe Val Ile Thr
1                   5                   10                  15

Asp Pro Arg Leu Pro Asp Asn Pro Ile Ile Phe Val Ser Asp Ser Phe
                20                  25                  30

Leu Gln Leu Thr Glu Tyr Ser Arg Glu Glu Ile Leu Gly Arg Asn Cys
            35                  40                  45

Arg Phe Leu Gln Gly Pro Glu Thr Asp Arg Ala Thr Val Arg Lys Ile
        50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu Arg Val Arg Asp Ala Ala Glu Arg Glu Ala Val Met
```

-continued

```
        115              120              125
Leu Val Lys Lys Thr Ala Glu Glu Ile Asp Glu Ala Ala Lys
    130              135              140

<210> SEQ ID NO 15
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser Arg Ala Thr Thr Leu Glu Arg Ile Glu Lys Ser Phe Val Ile Thr
1               5                   10                  15

Asp Pro Arg Leu Pro Asp Asn Pro Val Ile Phe Val Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu Arg Val Arg Asp Ala Ala Glu Arg Glu Ala Val Met
        115                 120                 125

Leu Val Lys Lys Thr Ala Glu Glu Ile Asp Glu Ala Ala Lys
    130              135              140

<210> SEQ ID NO 16
<211> LENGTH: 142
<212> TYPE: PRT
<213> ORGANISM: Avena sativa

<400> SEQUENCE: 16

Asp Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
        115                 120                 125

Leu Ile Lys Lys Thr Ala Glu Asn Ile Asp Glu Ala Ala Lys
    130              135              140
```

<210> SEQ ID NO 17
<211> LENGTH: 142
<212> TYPE: PRT
<213> ORGANISM: Avena sativa

<400> SEQUENCE: 17

Asp Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
        115                 120                 125

Leu Ile Lys Lys Thr Ala Glu Asn Ile Asp Glu Ala Ala Lys
    130                 135                 140

<210> SEQ ID NO 18
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu Arg Val Arg Asp Ala Ala Glu Arg Glu Ala Val Met
        115                 120                 125

Leu Val Lys Lys Thr Ala Glu Glu Ile Asp Glu Ala Ala Lys
    130                 135                 140

<210> SEQ ID NO 19
<211> LENGTH: 142
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Ser Arg Ala Thr Thr Leu Glu Arg Ile Glu Lys Ser Phe Val Ile Thr
1               5                   10                  15

Asp Pro Arg Leu Pro Asp Asn Pro Val Ile Phe Val Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Ile Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu Arg Val Arg Asp Ala Ala Glu Arg Glu Ala Val Met
        115                 120                 125

Leu Val Lys Lys Thr Ala Glu Glu Ile Asp Glu Ala Ala Lys
    130                 135                 140

<210> SEQ ID NO 20
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Val Phe His Leu Gln Pro
                85                  90                  95

Met Arg Asp Tyr Lys Gly Asp Val Gln Tyr Phe Ile Gly Val Gln Leu
            100                 105                 110

Asp Gly Thr Glu Arg Leu His Gly Ala Ala Glu Arg Glu Ala Val Cys
        115                 120                 125

Leu Val Lys Lys Thr Ala Phe Gln Ile Leu Ala Glu Ala Ala Lys
    130                 135                 140

<210> SEQ ID NO 21
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

-continued

```
Ser Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu Arg Val Arg Asp Ala Ala Glu Arg Glu Ala Val Met
        115                 120                 125

Leu Val Lys Lys Thr Ala Glu Glu Ile Asp
    130                 135
```

```
<210> SEQ ID NO 22
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

```
Ser Arg Ala Thr Thr Leu Glu Arg Ile Glu Lys Ser Phe Val Leu Thr
1               5                   10                  15

Asp Pro Arg Leu Pro Asp Asn Pro Ile Ile Phe Val Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Val Phe His Leu Gln Pro
                85                  90                  95

Met Arg Asp Tyr Lys Gly Asp Val Gln Tyr Phe Ile Gly Val Gln Leu
            100                 105                 110

Asp Gly Thr Glu Arg Leu His Gly Ala Ala Glu Arg Glu Ala Val Cys
        115                 120                 125

Leu Val Lys Lys Thr Ala Phe Gln Ile Ala
    130                 135
```

```
<210> SEQ ID NO 23
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23
```

```
Phe Arg Ala Thr Thr Leu Glu Arg Ile Glu Lys Ser Phe Val Ile Thr
1               5                   10                  15
```

-continued

```
Asp Pro Arg Leu Pro Asp Asn Pro Ile Ile Phe Val Ser Asp Ser Phe
        20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Val Phe His Leu Gln Pro
                85                  90                  95

Met Arg Asp Tyr Lys Gly Asp Val Gln Tyr Phe Ile Gly Val Gln Leu
            100                 105                 110

Asp Gly Thr Glu Arg Leu His Gly Ala Ala Glu Arg Glu Ala Val Cys
        115                 120                 125

Leu Val Lys Lys Thr Ala Phe Gln Ile Ala
    130                 135
```

<210> SEQ ID NO 24
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Ser Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
        20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Val Phe His Leu Gln Pro
                85                  90                  95

Met Arg Asp Tyr Lys Gly Asp Val Gln Tyr Phe Ile Gly Val Gln Leu
            100                 105                 110

Asp Gly Thr Glu Arg Leu His Gly Ala Ala Glu Arg Glu Ala Val Cys
        115                 120                 125

Leu Val Lys Lys Thr Ala Phe Glu Ile Asp Glu Ala Ala Lys
    130                 135                 140
```

<210> SEQ ID NO 25
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Ser Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
        20                  25                  30
```

-continued

```
Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
                100                 105                 110

Asp Gly Thr Glu Arg Val Arg Asp Ala Ala Glu Arg Glu Ala Val Met
        115                 120                 125

Leu Val Lys Lys Thr Ala Glu Glu Ile Asp Glu Ala Ala Lys Glu Asn
    130                 135                 140

Leu Tyr Phe Gln Met
145
```

```
<210> SEQ ID NO 26
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26
```

```
Ser Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
                20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Val Phe His Leu Gln Pro
                85                  90                  95

Met Arg Asp Tyr Lys Gly Asp Val Gln Tyr Phe Ile Gly Val Gln Leu
                100                 105                 110

Asp Gly Thr Glu Arg Leu His Gly Ala Ala Glu Arg Glu Ala Val Cys
        115                 120                 125

Leu Val Lys Lys Thr Ala Phe Glu Ile Asp Glu Ala Ala Lys Glu Asn
    130                 135                 140

Leu Tyr Phe Gln Met
145
```

```
<210> SEQ ID NO 27
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

```
Phe Arg Ala Thr Thr Leu Glu Arg Ile Glu Lys Ser Phe Val Ile Thr
1               5                   10                  15
```

-continued

```
Asp Pro Arg Leu Pro Asp Asn Pro Ile Ile Phe Val Ser Asp Ser Phe
            20                  25                  30

Leu Gln Leu Thr Glu Tyr Ser Arg Glu Glu Ile Leu Gly Arg Asn Cys
            35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Val Phe His Leu Gln Pro
                85                  90                  95

Met Arg Asp Tyr Lys Gly Asp Val Gln Tyr Phe Ile Gly Val Gln Leu
            100                 105                 110

Asp Gly Thr Glu Arg Leu His Gly Ala Ala Glu Arg Glu Ala Val Cys
            115                 120                 125

Leu Val Lys Lys Thr Ala Phe Gln Ile Ala Glu Asn Leu Tyr Phe Gln
    130                 135                 140

Met
145

<210> SEQ ID NO 28
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
            20                  25                  30

Leu Gln Leu Thr Glu Tyr Ser Arg Glu Glu Ile Leu Gly Arg Asn Cys
            35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu Arg Val Arg Asp Ala Ala Glu Arg Glu Ala Val Met
            115                 120                 125

Leu Val Lys Lys Thr Ala Glu Glu Ile Asp Glu Asn Leu Tyr Phe Gln
    130                 135                 140

Gly
145

<210> SEQ ID NO 29
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

-continued

```
Phe Arg Ala Thr Thr Leu Glu Arg Ile Glu Lys Ser Phe Val Ile Thr
1               5                   10                  15

Asp Pro Arg Leu Pro Asp Asn Pro Ile Ile Phe Val Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Val Phe His Leu Gln Pro
                85                  90                  95

Met Arg Asp Tyr Lys Gly Asp Val Gln Tyr Phe Ile Gly Val Gln Leu
            100                 105                 110

Asp Gly Thr Glu Arg Leu His Gly Ala Ala Glu Arg Glu Ala Val Cys
        115                 120                 125

Leu Val Lys Lys Thr Ala Phe Gln Ile Ala Glu Asn Leu Tyr Phe Gln
    130                 135                 140

Gly
145

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 30

Glu Asn Leu Tyr Phe Gln Xaa
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Asn Leu Tyr Phe Gln Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Asn Leu Tyr Phe Gln Tyr
1               5

<210> SEQ ID NO 33
```

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Asn Leu Tyr Phe Gln Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Asn Leu Tyr Phe Gln Trp
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Asn Leu Tyr Phe Gln His
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Asn Leu Tyr Phe Gln Asn
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Asn Leu Tyr Phe Gln Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

-continued

Glu Asn Leu Tyr Phe Gln Gln
1               5

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggtggaagtg gatcaggcag cggtggatct ggcagcggaa agcttggttc cggg          54

<210> SEQ ID NO 40
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggagggcgtg aatgtaagcg tgacataact aattacatga ctcgagctat ta          52

<210> SEQ ID NO 41
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtggaggcgg tagcggaggc ggagggtcgg ctagcggcag cggaaagctt ggttccggg          59

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgcagattat gatcggagca gcgccg          26

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggtcaaggtc tgcaggctag tggtg          25

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

-continued

```
gttggaaagc aataaacatg ttgacggggg atcc                                 34

<210> SEQ ID NO 45
<211> LENGTH: 67
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (53)..(55)
<223> OTHER INFORMATION: a, c, t, g, unknown or other

<400> SEQUENCE: 45
gcctggccgt taacgctttc ataagcttcc cgcccatctg gaagtagaga ttnnncttag     60
cggcttc                                                               67

<210> SEQ ID NO 46
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (50)..(52)
<223> OTHER INFORMATION: a, c, t, g, unknown or other

<400> SEQUENCE: 46
gcctggccgt taacgctttc ataagcttcc cgcccatctg gaagtagagn nnttccttag     60
cg                                                                    62

<210> SEQ ID NO 47
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (47)..(49)
<223> OTHER INFORMATION: a, c, t, g, unknown or other

<400> SEQUENCE: 47
gcctggccgt taacgctttc ataagcttcc cgcccatctg gaagtannna ttttccttag     60
c                                                                     61

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (44)..(46)
<223> OTHER INFORMATION: a, c, t, g, unknown or other

<400> SEQUENCE: 48
gcctggccgt taacgctttc ataagcttcc cgcccatctg gaannngaga ttttccttag     60

<210> SEQ ID NO 49
<211> LENGTH: 56
```

<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (41)..(43)
<223> OTHER INFORMATION: a, c, t, g, unknown or other

<400> SEQUENCE: 49
gcctggccgt taacgctttc ataagcttcc cgcccatctg nnngtagaga ttttcc            56

<210> SEQ ID NO 50
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (38)..(40)
<223> OTHER INFORMATION: a, c, t, g, unknown or other

<400> SEQUENCE: 50
gcctggccgt taacgctttc ataagcttcc cgcccatnnn gaagtagaga ttttc             55

<210> SEQ ID NO 51
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(37)
<223> OTHER INFORMATION: a, c, t, g, unknown or other

<400> SEQUENCE: 51
gcctggccgt taacgctttc ataagcttcc cgccnnnctg gaagtagag                    49

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggtgccatca caaatctcgg ggacacgc                                           28

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 53

His His His His His His
1               5

<210> SEQ ID NO 54
<211> LENGTH: 242
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 54

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Ile Phe Trp Lys His Trp Ile
    130                 135                 140

Gln Thr Lys Asp Gly Gln Cys Gly Asn Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
            195                 200                 205

Val Leu Trp Gly Gly His Lys Val Phe Met Val Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 55
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Ala Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80
```

-continued

```
Asp Met Ile Ile Ile Arg Met Pro Lys Asp Phe Pro Pro Phe Pro Gln
             85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Ile Phe Trp Lys His Trp Ile
        130                 135                 140

Gln Thr Lys Asp Gly Gln Cys Gly Asn Pro Leu Val Ser Thr Arg Asp
145                 150                 155                 160

Gly Phe Ile Val Gly Ile His Ser Ala Ser Asn Phe Thr Asn Thr Asn
            165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
            195                 200                 205

Val Leu Trp Gly Gly His Lys Val Phe Met Val Lys Pro Glu Glu Pro
        210                 215                 220

Phe Gln Pro Val Lys Glu Ala Thr Gln Leu Met Asn Glu Leu Val Tyr
225                 230                 235                 240

Ser Gln

<210> SEQ ID NO 56
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
             85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Thr Phe Trp Lys His Trp Ile
        130                 135                 140

Gln Thr Lys Asp Gly Gln Cys Gly Asn Pro Leu Val Ser Thr Arg Asp
145                 150                 155                 160

Gly Phe Ile Val Gly Ile His Ser Ala Ser Asn Phe Thr Asn Thr Asn
            165                 170                 175

Asn Tyr Phe Ala Ser Val Pro Lys Asn Phe Met Glu Leu Leu Thr Asn
            180                 185                 190
```

-continued

```
Gln Glu Ala Gln Gln Trp Val Ser Gly Trp Arg Leu Asn Ala Asp Ser
        195                 200                 205

Val Leu Trp Gly Gly His Lys Val Phe Met Val Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 57
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
            85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Ile Phe Trp Lys His Trp Ile
        130                 135                 140

Gln Thr Lys Asp Gly Gln Cys Gly Asn Pro Leu Val Ser Thr Arg Asp
145                 150                 155                 160

Gly Phe Ile Val Gly Ile His Ser Ala Ser Asn Phe Thr Asn Thr Asn
            165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Val
    210                 215

<210> SEQ ID NO 58
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Glu Ser Leu Phe Lys Gly Pro Arg Asp Tyr Asn Pro Ile Ser Ser
1               5                   10                  15
```

-continued

```
Thr Ile Cys His Leu Thr Asn Glu Ser Asp Gly His Thr Ala Ser Leu
            20                  25                  30

Tyr Gly Ile Gly Phe Gly Pro Phe Ile Ile Thr Asn Lys His Leu Phe
            35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Ile Phe Trp Lys His Trp Ile
    130                 135                 140

Gln Thr Lys Asp Gly Gln Cys Gly Asn Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
                180                 185                 190

Gln Glu Ala Gln Gln Trp Val Ser Gly Trp Arg Leu Asn Ala Asp Ser
            195                 200                 205

Val Leu Trp Gly Gly His Lys Val Phe Met Val
    210                 215
```

```
<210> SEQ ID NO 59
<211> LENGTH: 1296
<212> TYPE: DNA
<213> ORGANISM: Saccharomyces cerevisiae

<400> SEQUENCE: 59
atgtctgatg cggctccttc attgagcaat ctattttatg atccaacgta taatcctggt      60
caaagcacca ttaactacac ttccatatat gggaatggat ctaccatcac tttcgatgag     120
ttgcaaggtt tagttaacag tactgttact caggccatta tgtttggtgt cagatgtggt     180
gcagctgctt tgactttgat tgtcatgtgg atgacatcga gaagcagaaa aacgccgatt     240
ttcattatca accaagtttc attgttttta atcattttgc attctgcact ctattttaaa     300
tatttactgt ctaattactc ttcagtgact tacgctctca ccggatttcc tcagttcatc     360
agtagaggtg acgttcatgt ttatggtgct acaaatataa ttcaagtcct tcttgtggct     420
tctattgaga cttcactggt gtttcagata aaagtttattt tcacaggcga caacttcaaa     480
aggataggtt tgatgctgac gtcgatatct ttcactttag ggattgctac agttaccatg     540
tattttgtaa gcgctgttaa aggtatgatt gtgacttata atgatgttag tgccacccaa     600
gataaatact tcaatgcatc cacaatttta cttgcatcct caataaactt tatgtcattt     660
gtcctggtag ttaaattgat tttagctatt agatcaagaa gattccttgg tctcaagcag     720
ttcgatagtt tccatattt actcataatg tcatgtcaat ctttgttggt tccatcgata     780
atattcatcc tcgcatacag tttgaaacca accagggaa cagatgtctt gactactgtt     840
gcaacattac ttgctgtatt gtctttacca ttatcatcaa tgtgggccac ggctgctaat     900
aatgcatcca aacaaacac aattacttca gactttacaa catccacaga taggttttat     960
```

-continued

```
ccaggcacgc tgtctagctt tcaaactgat agtatcaaca acgatgctaa aagcagtctc    1020
agaagtagat tatatgacct atatcctaga aggaaggaaa caacatcgga taaacattcg    1080
gaaagaactt ttgtttctga gactgcagat gatatagaga aaaatcagtt ttatcagttg    1140
cccacaccta cgagttcaaa aaatactagg ataggaccgt ttgctgatgc aagttacaaa    1200
gagggagaag ttgaacccgt cgacatgtac actcccgata cggcagctga tgaggaagcc    1260
agaaagttct ggactgaaga taataataat ttatga                              1296
```

<210> SEQ ID NO 60
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
ggagaatcct tgtttaaggg accacgtgat tacaacccga tatcgagcac catttgtcat      60
ttgacgaatg aatctgatgg gcacacaaca tcgttgtatg gtattggatt tggtcccttc     120
atcattacaa acaagcactt gtttagaaga aataatggaa cactgttggt ccaatcacta     180
catggtgtat tcaaggtcaa gaacaccacg actttgcaac aacacctcat tgatgggagg     240
gacatgataa ttattcgcat gcctaaggat ttcccaccat ttcctcaaaa gctgaaattt     300
agagagccac aaagggaaga gcgcatatgt cttgtgacaa ccaacttcca aactaagagc     360
atgtctagca tggtgtcaga cactagttgc acattccctt catctgatgg catattctgg     420
aagcattgga ttcaaaccaa ggatgggcag tgtggcagtc cattagtatc aactagagat     480
gggttcattg ttggtataca ctcagcatcg aatttcacca acacaaacaa ttatttcaca     540
agcgtgccga aaaacttcat ggaattgttg acaaatcagg aggcgcagca gtgggttagt     600
ggttggcgat aaatgctga ctcagtattg tggggggggcc ataaagtttt catggtg        657
```

<210> SEQ ID NO 61
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
ggagaatcct tgtttaaggg accacgtgat tacaacccga tatcgagcac catttgtcat      60
ttgacgaatg aatctgatgg gcacacaaca tcgttgtatg gtattggatt tggtcccttc     120
atcattacaa acaagcactt gtttagaaga aataatggaa cactgttggt ccaatcacta     180
catggtgtat tcaaggtcaa gaacaccacg actttgcaac aacacctcat tgatgggagg     240
gacatgataa ttattcgcat gcctaaggat ttcccaccat ttcctcaaaa gctgaaattt     300
agagagccac aaagggaaga gcgcatatgt cttgtgacaa ccaacttcca aactaagagc     360
atgtctagca tggtgtcaga cactagttgc acattccctt catctgatgg catattctgg     420
aagcattgga ttcaaaccaa ggatgggcag tgtggcaatc cattagtatc aactagagat     480
gggttcattg ttggtataca ctcagcatcg aatttcacca acacaaacaa ttatttcaca     540
agcgtgccga aaaacttcat ggaattgttg acaaatcagg aggcgcagca gtgggttagt     600
ggttggcgat aaatgctga ctcagtattg tggggggggcc ataaagtttt catggtg        657
```

```
<210> SEQ ID NO 62
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ggagaatcct tgtttaaggg accacgtgat tacaacccga tatcgagcac catttgtcat        60
ttgacgaatg aatctgatgg gcacacagca tcgttgtatg gtattggatt tggtcccttc       120
atcattacaa acaagcactt gtttagaaga aataatggaa cactgttggt ccaatcacta       180
catggtgtat tcaaggtcaa gaacaccacg actttgcaac aacacctcat tgatgggagg       240
gacatgataa ttattcgcat gcctaaggat ttcccaccat ttcctcaaaa gctgaaattt       300
agagagccac aaagggaaga gcgcatatgt cttgtgacaa ccaacttcca aactaagagc       360
atgtctagca tggtgtcaga cactagttgc acattccctt catctgatgg catattctgg       420
aagcattgga ttcaaaccaa ggatgggcag tgtggcaatc cattagtatc aactagagat       480
gggttcattg ttggtataca ctcagcatcg aatttcacca acacaaacaa ttatttcaca       540
agcgtgccga aaaacttcat ggaattgttg acaaatcagg aggcgcagca gtgggttagt       600
ggttggcgat taaatgctga ctcagtattg tggggggggcc ataaagtttt catggtg        657

<210> SEQ ID NO 63
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ggagaatcct tgtttaaggg accacgtgat tacaacccga tatcgagcac catttgtcat        60
ttgacgaatg aatctgatgg gcacacaaca tcgttgtatg gtattggatt tggtcccttc       120
atcattacaa acaagcactt gtttagaaga aataatggaa cactgttggt ccaatcacta       180
catggtgtat tcaaggtcaa gaacaccacg actttgcaac aacacctcat tgatgggagg       240
gacatgataa ttattcgcat gcctaaggat ttcccaccat ttcctcaaaa gctgaaattt       300
agagagccac aaagggaaga gcgcatatgt cttgtgacaa ccaacttcca aactaagagc       360
atgtctagca tggtgtcaga cactagttgc acattccctt catctgatgg catattctgg       420
aagcattgga ttcaaaccaa ggatgggcag tgtggcagtc cattagtatc aactagagat       480
gggttcattg ttggtataca ctcagcatcg aatttcacca acacaaacaa ttatttcaca       540
agcgtgccga aaaacttcat ggaattgttg acaaatcagg aggcgcagca gtgggttagt       600
ggttggcgat taaatgctga ctcagtattg tggggggggcc ataaagtttt catggttaaa       660
cctgaagagc cttttcagcc agttaaggaa gcgactcaac tcatgaatga attggtctac       720
agccag                                                                  726

<210> SEQ ID NO 64
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64
```

```
Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
            165                 170                 175

Asn Tyr Phe Thr Ser Val Pro Lys Asn Phe Met Glu Leu Leu Thr Asn
        180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Val Lys Pro Glu Glu Pro
    210                 215                 220

Phe Gln Pro Val Lys Glu Ala Thr Gln Leu Met Asn Glu Leu Val Tyr
225                 230                 235                 240

Ser Gln
```

<210> SEQ ID NO 65
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
ggagaatcct tgtttaaggg accacgtgat tacaacccga tatcgagcac catttgtcat      60
ttgacgaatg aatctgatgg gcacacaaca tcgttgtatg gtattggatt tggtcccttc     120
atcattacaa acaagcactt gtttagaaga ataatggaa cactgttggt ccaatcacta      180
catggtgtat tcaaggtcaa gaacaccacg actttgcaac aacacctcat tgatgggagg     240
gacatgataa ttattcgcat gcctaaggat ttcccaccat ttcctcaaaa gctgaaattt     300
agagagccac aaagggaaga gcgcatatgt cttgtgacaa ccaacttcca aactaagagc     360
atgtctagca tggtgtcaga cactagttgc acattccctt catctgatgg cacattctgg     420
aagcattgga ttcaaaccaa ggatgggcag tgtggcaatc cattagtatc aactagagat     480
gggttcattg ttggtataca ctcagcatcg aatttcacca acacaaacaa ttatttcgca     540
agcgtgccga aaaacttcat ggaattgttg acaaatcagg aggcgcagca gtgggttagt     600
```

-continued

```
ggttggcgat taaatgctga ctcagtattg tgggggggcc ataaagtttt catggtgaaa        660
cctgaagagc cttttcagcc agttaaggaa gcgactcaac tcatgaatga attggtctac        720
agccag                                                                   726
```

```
<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Asn Leu Tyr Phe Gln Met
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Asn Leu Ala Phe Gln Met
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Asn Leu Tyr Phe Ala Met
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 69

Xaa Asn Leu Tyr Phe Gln Met
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
```

```
<400> SEQUENCE: 70

Glu Xaa Leu Tyr Phe Gln Met
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 71

Glu Asn Xaa Tyr Phe Gln Met
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 72

Glu Asn Leu Xaa Phe Gln Met
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 73

Glu Asn Leu Tyr Xaa Gln Met
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 74

Glu Asn Leu Tyr Phe Xaa Met
1               5

<210> SEQ ID NO 75
```

-continued

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Ala Ser Gly Ser Gly Lys Leu Ser Gly Gly Gly
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Asn Leu Tyr Phe Gln Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Asn Leu Ala Phe Gln Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Asn Leu Tyr Phe Ala Ser
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Thr Val Arg Phe Gln Ser
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80
```

-continued

```
Glu Thr Val Arg Phe Gln Met
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Glu Thr Val Arg Phe Gln Leu
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Thr Val Arg Phe Gln Gln
1               5
```